United States Patent
Benenson et al.

(10) Patent No.: US 9,458,509 B2
(45) Date of Patent: Oct. 4, 2016

(54) MULTIPLE INPUT BIOLOGIC CLASSIFIER CIRCUITS FOR CELLS

(75) Inventors: Yaakov Benenson, Basel (CH); Ron Weiss, Newton, MA (US); Liliana Wroblewska, Arlington, MA (US); Zhen Xie, Malden, MA (US)

(73) Assignees: PRESIDENT AND FELLOWS OF HARVARD COLLEGE, Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 385 days.

(21) Appl. No.: 13/811,126

(22) PCT Filed: Jul. 22, 2011

(86) PCT No.: PCT/US2011/045038
§ 371 (c)(1),
(2), (4) Date: Apr. 5, 2013

(87) PCT Pub. No.: WO2012/012739
PCT Pub. Date: Jan. 26, 2012

(65) Prior Publication Data
US 2013/0202532 A1 Aug. 8, 2013

Related U.S. Application Data

(60) Provisional application No. 61/366,787, filed on Jul. 22, 2010.

(51) Int. Cl.
C12Q 1/68 (2006.01)
C12N 15/63 (2006.01)
G06F 19/20 (2011.01)
G06F 19/24 (2011.01)

(52) U.S. Cl.
CPC ............ *C12Q 1/6886* (2013.01); *C12N 15/63* (2013.01); *C12Q 1/6897* (2013.01); *G06F 19/20* (2013.01); *G06F 19/24* (2013.01)

(58) Field of Classification Search
None
See application file for complete search history.

(56) References Cited

FOREIGN PATENT DOCUMENTS

WO    WO 2008134593 A1 * 11/2008

OTHER PUBLICATIONS

"Encode" definition; Oxford dictionary; http://www.oxford-dictionaries.com/us/definition/american_english/encode; accessed Apr. 27, 2015; pp. 5-6.*

* cited by examiner

*Primary Examiner* — Antonio Galisteo Gonzalez
(74) *Attorney, Agent, or Firm* — Nath, Goldberg & Meyer; Tanya E. Harkins

(57) ABSTRACT

Provided herein are high-input detector modules and multi-input biological classifier circuits and systems that integrate sophisticated sensing, information processing, and actuation in living cells and permit new directions in basic biology, biotechnology and medicine. The multi-input biological classifier circuits described herein comprise synthetic, scaleable transcriptional/post-transcriptional regulatory circuits that are designed to interrogate the status of a cell by simultaneously sensing expression levels of multiple endogenous inputs, such as microRNAs. The classifier circuits then compute whether to trigger a desired output or response if the expression levels match a pre-determined profile of interest.

21 Claims, 22 Drawing Sheets

SEQUENCE LISTING

<160> NUMBER OF SEQ ID NOS: 873

<210> SEQ ID NO 1
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 1
gcatgctccc tatcagtgat agagattgac atccctatca gtgatagaga tactgagcac    60
atcagcagga cgcactgacc agga    84

<210> SEQ ID NO 2
<211> LENGTH: 286
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 2

```
aagaaaccaa ttgtccatat tgcatcagac attgccgtca ctgcgtcttt tactggctct    60
tctcgctaac caaaccggta accccgctta ttaaaagcat tctgtaacaa agcgggacca   120
aagccatgac aaaaacgcgt aacaaaagtg tctataatca cggcagaaaa gtccacattg   180
attatttgca cggcgtcaca ctttgctatg ccatagcatt tttatccata agattagcgg   240
atcctacctg acgcttttta tcgcaactct ctactgtttc tccata                  286
```

<210> SEQ ID NO 3
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3

```
ccatcgaatg gctgaaatga gctgttgaca attaatcatc cggctcgtat aatgtgtgga    60
attgtgagcg gataacaatt tcacacagga                                    90
```

<210> SEQ ID NO 4
<211> LENGTH: 74
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4

```
ataaatgtga gcggataaca ttgacattgt gagcggataa caagatactg agcactcagc    60
aggacgcact gacc                                                     74
```

<210> SEQ ID NO 5
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5

```
aaaatttatc aaaaagagtg ttgacttgtg agcggataac aatgatactt agattcaatt    60
gtgagcggat aacaatttca caca                                          84
```

<210> SEQ ID NO 6
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6

```
catagcattt ttatccataa gattagcgga tcctaagctt tacaattgtg agcgctcaca    60
attatgatag attcaattgt gagcggataa caatttcaca ca                     102
```

<210> SEQ ID NO 7

```
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7
gcatgcacag ataaccatct gcggtgataa attatctctg gcggtgttga cataaatacc    60
actggcggtt ataatgagca catcagcagg gtatgcaaag ga                      102

<210> SEQ ID NO 8
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
gtttatacat aggcgagtac tctgttatgg                                     30

<210> SEQ ID NO 9
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
agaggttcca actttcacca taatgaaaca                                     30

<210> SEQ ID NO 10
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
taaacaacta acggacaatt ctacctaaca                                     30

<210> SEQ ID NO 11
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
acatcaagcc aaattaaaca ggattaacac                                     30

<210> SEQ ID NO 12
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 12
gaggtaaaat agtcaacacg cacggtgtta                                    30

<210> SEQ ID NO 13
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
caggccggaa taactcccta taatgcgcca                                    30

<210> SEQ ID NO 14
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ggctagctca gtcctaggta cagtgctagc                                    30

<210> SEQ ID NO 15
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
agctagctca gtcctaggta ttatgctagc                                    30

<210> SEQ ID NO 16
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
agctagctca gtcctaggta ctgtgctagc                                    30

<210> SEQ ID NO 17
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
agctagctca gtcctaggga ttatgctagc                                    30

<210> SEQ ID NO 18
<211> LENGTH: 30
<212> TYPE: DNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
agctagctca gtcctaggta ttgtgctagc                                          30

<210> SEQ ID NO 19
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ggctagctca gtcctaggta ctatgctagc                                          30

<210> SEQ ID NO 20
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
ggctagctca gtcctaggta tagtgctagc                                          30

<210> SEQ ID NO 21
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ggctagctca gccctaggta ttatgctagc                                          30

<210> SEQ ID NO 22
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
agctagctca gtcctaggta taatgctagc                                          30

<210> SEQ ID NO 23
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
agctagctca gtcctaggga ctgtgctagc                                          30
```

<210> SEQ ID NO 24
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
ggctagctca gtcctaggta caatgctagc                                      30

<210> SEQ ID NO 25
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
ggctagctca gtcctaggta tagtgctagc                                      30

<210> SEQ ID NO 26
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 26
agctagctca gtcctaggga ttatgctagc                                      30

<210> SEQ ID NO 27
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 27
ggctagctca gtcctaggga ttatgctagc                                      30

<210> SEQ ID NO 28
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 28
ggctagctca gtcctaggta caatgctagc                                      30

<210> SEQ ID NO 29
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 29
agctagctca gcccttggta caatgctagc                    30

<210> SEQ ID NO 30
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
agctagctca gtcctaggga ctatgctagc                    30

<210> SEQ ID NO 31
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
agctagctca gtcctaggga ttgtgctagc                    30

<210> SEQ ID NO 32
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
ggctagctca gtcctaggta ttgtgctagc                    30

<210> SEQ ID NO 33
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
agctagctca gtcctaggta taatgctagc                    30

<210> SEQ ID NO 34
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
ggctagctca gtcctaggta ttatgctagc                    30

<210> SEQ ID NO 35
<211> LENGTH: 30

-continued

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
ggctagctca gtcctaggta caatgctagc                                          30

<210> SEQ ID NO 36
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
aaagtgtgac gccgtgcaaa taatcaatgt                                          30

<210> SEQ ID NO 37
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
gacgaatact taaaatcgtc atacttattt                                          30

<210> SEQ ID NO 38
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
aaacctttcg cggtatggca tgatagcgcc                                          30

<210> SEQ ID NO 39
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
tgatagcgcc cggaagagag tcaattcagg                                          30

<210> SEQ ID NO 40
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
ttatttaccg tgacgaacta attgctcgtg                                              30

<210> SEQ ID NO 41
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
catacgccgt tatacgttgt ttacgctttg                                              30

<210> SEQ ID NO 42
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ttatgcttcc ggctcgtatg ttgtgtggac                                              30

<210> SEQ ID NO 43
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
ttatgcttcc ggctcgtatg gtgtgtggac                                              30

<210> SEQ ID NO 44
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
atatatatat atatataatg gaagcgtttt                                              30

<210> SEQ ID NO 45
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
atatatatat atatataatg gaagcgtttt                                              30

<210> SEQ ID NO 46
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
ccccgaaagc ttaagaatat aattgtaagc                                      30

<210> SEQ ID NO 47
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
ccccgaaagc ttaagaatat aattgtaagc                                      30

<210> SEQ ID NO 48
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
tgacaatata tatatatata taatgctagc                                      30

<210> SEQ ID NO 49
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
acaatatata tatatatata taatgctagc                                      30

<210> SEQ ID NO 50
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
aatatatata tatatatata taatgctagc                                      30

<210> SEQ ID NO 51
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
tatatatata tatatatata taatgctagc                                      30

<210> SEQ ID NO 52

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
tatatatata tatatatata taatgctagc                              30

<210> SEQ ID NO 53
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
aaaaaaaaaa aaaaaaaata taatgctagc                              30

<210> SEQ ID NO 54
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
aaaaaaaaaa aaaaaaaata taatgctagc                              30

<210> SEQ ID NO 55
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
caccttcggg tgggcctttc tgcgtttata                              30

<210> SEQ ID NO 56
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
caccttcggg tgggcctttc tgcgtttata                              30

<210> SEQ ID NO 57
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
```

```
caccttcggg tgggcctttc tgcgtttata                                    30
```

<210> SEQ ID NO 58
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58

```
caccttcggg tgggcctttc tgcgtttata                                    30
```

<210> SEQ ID NO 59
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59

```
ggctagctca gtcctaggta cagtgctagc                                    30
```

<210> SEQ ID NO 60
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60

```
tgctagctac tagagattaa agaggagaaa                                    30
```

<210> SEQ ID NO 61
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61

```
cctgttttta tgttattctc tctgtaaagg                                    30
```

<210> SEQ ID NO 62
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62

```
aaatatttgc ttatacaatc ttcctgtttt                                    30
```

<210> SEQ ID NO 63
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 63
gctgataaac cgatacaatt aaaggctcct                              30

<210> SEQ ID NO 64
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ctcttctcag cgtcttaatc taagctatcg                              30

<210> SEQ ID NO 65
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
atgagccagt tcttaaaatc gcataaggta                              30

<210> SEQ ID NO 66
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
ctattgattg tgacaaaata aacttattcc                              30

<210> SEQ ID NO 67
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
gtttcgcgct tggtataatc gctggggtc                               30

<210> SEQ ID NO 68
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
ctttgcttct gactataata gtcagggtaa                              30
```

<210> SEQ ID NO 69
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
aaaccgatac aattaaaggc tcctgctagc                                    30

<210> SEQ ID NO 70
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
gccggaataa ctccctataa tgcgccacca                                    30

<210> SEQ ID NO 71
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
gccggaataa ctccctataa tgcgccacca                                    30

<210> SEQ ID NO 72
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
ttgacaagct tttcctcagc tccgtaaact                                    30

<210> SEQ ID NO 73
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
ttgacagcta gctcagtcct aggtataatg ctagc                              35

<210> SEQ ID NO 74
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 74
ttgacggcta gctcagtcct aggtacagtg ctagc                              35

<210> SEQ ID NO 75
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
tttacagcta gctcagtcct aggtattatg ctagc                              35

<210> SEQ ID NO 76
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
ttgacagcta gctcagtcct aggtactgtg ctagc                              35

<210> SEQ ID NO 77
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
ctgatagcta gctcagtcct agggattatg ctagc                              35

<210> SEQ ID NO 78
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
ttgacagcta gctcagtcct aggtattgtg ctagc                              35

<210> SEQ ID NO 79
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
tttacggcta gctcagtcct aggtactatg ctagc                              35

<210> SEQ ID NO 80
<211> LENGTH: 35
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 80
tttacggcta gctcagtcct aggtatagtg ctagc                              35

<210> SEQ ID NO 81
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
tttacggcta gctcagccct aggtattatg ctagc                              35

<210> SEQ ID NO 82
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
ctgacagcta gctcagtcct aggtataatg ctagc                              35

<210> SEQ ID NO 83
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
tttacagcta gctcagtcct agggactgtg ctagc                              35

<210> SEQ ID NO 84
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
tttacggcta gctcagtcct aggtacaatg ctagc                              35

<210> SEQ ID NO 85
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
ttgacggcta gctcagtcct aggtatagtg ctagc                              35
```

<210> SEQ ID NO 86
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
ctgatagcta gctcagtcct agggattatg ctagc                              35

<210> SEQ ID NO 87
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
ctgatggcta gctcagtcct agggattatg ctagc                              35

<210> SEQ ID NO 88
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
tttatggcta gctcagtcct aggtacaatg ctagc                              35

<210> SEQ ID NO 89
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
tttatagcta gctcagccct tggtacaatg ctagc                              35

<210> SEQ ID NO 90
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
ttgacagcta gctcagtcct agggactatg ctagc                              35

<210> SEQ ID NO 91
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
ttgacagcta gctcagtcct agggattgtg ctagc        35

<210> SEQ ID NO 92
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
ttgacggcta gctcagtcct aggtattgtg ctagc        35

<210> SEQ ID NO 93
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
ggtttcaaaa ttgtgatcta tatttaacaa        30

<210> SEQ ID NO 94
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
ggtttcaaaa ttgtgatcta tatttaacaa        30

<210> SEQ ID NO 95
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
tctattccaa taaagaaatc ttcctgcgtg        30

<210> SEQ ID NO 96
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
aaaaatgggc tcgtgttgta caataaatgt        30

<210> SEQ ID NO 97
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
aaaaaaagcg cgcgattatg taaaatataa                                       30

<210> SEQ ID NO 98
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
atccttatcg ttatgggtat tgtttgtaat                                       30

<210> SEQ ID NO 99
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
taaaagaatt gtgagcggga atacaacaac                                       30

<210> SEQ ID NO 100
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
aaaaaaagcg cgcgattatg taaaatataa                                       30

<210> SEQ ID NO 101
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
tacaaaataa ttcccctgca aacattatca                                       30

<210> SEQ ID NO 102
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
tacaaaataa ttcccctgca aacattatcg                                       30
```

<210> SEQ ID NO 103
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
agggaataca agctacttgt tcttttttgca                              30

<210> SEQ ID NO 104
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
taatacgact cactataggg aga                                      23

<210> SEQ ID NO 105
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
gaatttaata cgactcacta tagggaga                                 28

<210> SEQ ID NO 106
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 106
taatacgact cactatagg                                           19

<210> SEQ ID NO 107
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 107
gagtcgtatt aatacgactc actatagggg                               30

<210> SEQ ID NO 108
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 108
agtgagtcgt actacgactc actataggg                                30

<210> SEQ ID NO 109
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
gagtcgtatt aatacgactc tctataggg                                30

<210> SEQ ID NO 110
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
taatacgact cactataggg aga                                      23

<210> SEQ ID NO 111
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
ttatacgact cactataggg aga                                      23

<210> SEQ ID NO 112
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
gaatacgact cactataggg aga                                      23

<210> SEQ ID NO 113
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
taatacgtct cactataggg aga                                      23

<210> SEQ ID NO 114
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
tcatacgact cactataggg aga                                          23

<210> SEQ ID NO 115
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
taatacgact cactataggg agaccacaac                                   30

<210> SEQ ID NO 116
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
taattgaact cactaaaggg agaccacagc                                   30

<210> SEQ ID NO 117
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
cgaagtaata cgactcacta ttagggaaga                                   30

<210> SEQ ID NO 118
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
attaaccctc actaaaggga ga                                           22

<210> SEQ ID NO 119
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
```
atttaggtga cactataga						19

<210> SEQ ID NO 120
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 120
acaaacacaa atacacacac taaattaata						30

<210> SEQ ID NO 121
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 121
ccaagcatac aatcaactat ctcatataca						30

<210> SEQ ID NO 122
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 122
gatacaggat acagcggaaa caacttttaa						30

<210> SEQ ID NO 123
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 123
tttcaagcta taccaagcat acaatcaact						30

<210> SEQ ID NO 124
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 124
cctttgcagc ataaattact atacttctat						30

<210> SEQ ID NO 125
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 125
cctttgcagc ataaattact atacttctat                                    30

<210> SEQ ID NO 126
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 126
cctttgcagc ataaattact atacttctat                                    30

<210> SEQ ID NO 127
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 127
cctttgcagc ataaattact atacttctat                                    30

<210> SEQ ID NO 128
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 128
cctttgcagc ataaattact atacttctat                                    30

<210> SEQ ID NO 129
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 129
ttatctactt tttacaacaa atataaaaca                                    30

<210> SEQ ID NO 130
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 130
acaaacacaa atacacacac taaattaata                                    30

<210> SEQ ID NO 131

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
gtttcgaata aacacacata aacaaacaaa                                   30

<210> SEQ ID NO 132
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
accatcaaag gaagctttaa tcttctcata                                   30

<210> SEQ ID NO 133
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
agaacccact gcttactggc ttatcgaaat                                   30

<210> SEQ ID NO 134
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
ggccgttttt ggcttttttg ttagacgaag                                   30

<210> SEQ ID NO 135
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
tgttatagtc gaatacctct ggcggtgata                                   30

<210> SEQ ID NO 136
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
```
ttttggtaca ctccctatca gtgatagaga                                        30

<210> SEQ ID NO 137
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137 cttttggta cactacctct ggcggtgata                                         30

<210> SEQ ID NO 138
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
tacgcaagaa aatggtttgt tatagtcgaa                                        30

<210> SEQ ID NO 139
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
cgtgcgtgtt gataacaccg tgcgtgttga                                        30

<210> SEQ ID NO 140
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
agattgtact aaatcgtata atgacagtga                                        30

<210> SEQ ID NO 141
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
gtgttgatgc ttttatcacc gccagtggta                                        30

<210> SEQ ID NO 142
<211> LENGTH: 30
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 142
agtgtgtgga attgtgagcg gataacaatt                                          30

<210> SEQ ID NO 143
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
acatcttaaa agttttagta tcatattcgt                                          30

<210> SEQ ID NO 144
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
tacgcaagaa aatggtttgt tatagtcgaa                                          30

<210> SEQ ID NO 145
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
atcctccttt agtcttcccc ctcatgtgtg                                          30

<210> SEQ ID NO 146
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
taaaattatg aaatttgcat aaattcttca                                          30

<210> SEQ ID NO 147
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
gtgttgacta ttttacctct ggcggtgata                                          30

```
<210> SEQ ID NO 148
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
gaaatctggc agtttttggt acacgaaagc                                      30

<210> SEQ ID NO 149
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
acaccgtgcg tgttgatata gtcgaataaa                                      30

<210> SEQ ID NO 150
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
aaaattatga aatttgtata aattcttcag                                      30

<210> SEQ ID NO 151
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
ggttcttttt ggtacctctg gcggtgataa                                      30

<210> SEQ ID NO 152
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
tgtaggatcg tacaggtata aattcttcag                                      30

<210> SEQ ID NO 153
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 153
caagaaaatg gtttgttata gtcgaataaa                                    30

<210> SEQ ID NO 154
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
ctatctcatt tgctagtata gtcgaataaa                                    30

<210> SEQ ID NO 155
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
tagtttataa tttaagtgtt ctttaatttc                                    30

<210> SEQ ID NO 156
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
caccttcggg tgggcctttc tgcgtttata                                    30

<210> SEQ ID NO 157
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
aataactctg atagtgctag tgtagatctc                                    30

<210> SEQ ID NO 158
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
caccttcggg tgggcctttc tgcgtttata                                    30

<210> SEQ ID NO 159
<211> LENGTH: 30
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 159
caccttcggg tgggcctttc tgcgtttata                                    30

<210> SEQ ID NO 160
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
ttgacacctg taggatcgta caggtataat                                    30

<210> SEQ ID NO 161
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
caagaaaatg gtttgttata gtcgaataaa                                    30

<210> SEQ ID NO 162
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
cacgcaaaac ttgcgacaaa caataggtaa                                    30

<210> SEQ ID NO 163
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
gttagctttc gaattggcta aaaagtgttc                                    30

<210> SEQ ID NO 164
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
ccattctgct ttccacgaac ttgaaaacgc                                    30
```

<210> SEQ ID NO 165
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
ggccgcgggt tcttttttggt acacgaaagc                                      30

<210> SEQ ID NO 166
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
aagaaaatgg tttgttgata ctcgaataaa                                       30

<210> SEQ ID NO 167
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
gaaaaccttg tcaatgaaga gcgatctatg                                       30

<210> SEQ ID NO 168
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
ttctcgttcg actcatagct gaacacaaca                                       30

<210> SEQ ID NO 169
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
atgacaaaat tgtcat                                                      16

<210> SEQ ID NO 170
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 170
accaatgctg ggaacggcca gggcacctaa                                    30

<210> SEQ ID NO 171
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
ctgaaagcgc ataccgctat ggaggggtt                                     30

<210> SEQ ID NO 172
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
tagatatgcc tgaaagcgca taccgctatg                                    30

<210> SEQ ID NO 173
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
agggaataca agctacttgt tcttttttgca                                   30

<210> SEQ ID NO 174
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
taatacgact cactataggg aga                                           23

<210> SEQ ID NO 175
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gaatttaata cgactcacta tagggaga                                      28

<210> SEQ ID NO 176
<211> LENGTH: 19
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
taatacgact cactatagg                                                     19

<210> SEQ ID NO 177
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
atttaggtga cactataga                                                     19

<210> SEQ ID NO 178
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gagtcgtatt aatacgactc actatagggg                                         30

<210> SEQ ID NO 179
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
agtgagtcgt actacgactc actatagggg                                         30

<210> SEQ ID NO 180
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
gagtcgtatt aatacgactc tctatagggg                                         30

<210> SEQ ID NO 181
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
taatacgact cactataggg aga                                                23
```

<210> SEQ ID NO 182
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
ttatacgact cactataggg aga                                            23

<210> SEQ ID NO 183
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
gaatacgact cactataggg aga                                            23

<210> SEQ ID NO 184
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
taatacgtct cactataggg aga                                            23

<210> SEQ ID NO 185
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
tcatacgact cactataggg aga                                            23

<210> SEQ ID NO 186
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186 atagggaat tgtgagcgga taacaattcc                                      30

<210> SEQ ID NO 187
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 187 atagggaat tgtgagcgga taacaattcc                                30

<210> SEQ ID NO 188
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188 atagggaat tgtgagcgga taacaattcc                                30

<210> SEQ ID NO 189
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189 atagggaat tgtgagcgga taacaattcc                                30

<210> SEQ ID NO 190
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
taatacgact cactataggg agaccacaac                                30

<210> SEQ ID NO 191
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
taattgaact cactaaaggg agaccacagc                                30

<210> SEQ ID NO 192
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
cgaagtaata cgactcacta ttagggaaga                                30

<210> SEQ ID NO 193
<211> LENGTH: 30

<210> SEQ ID NO 194
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 193
ttgtgagcgg ataacaagat actgagcaca                                      30

<210> SEQ ID NO 194
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 194
ttgtgagcgg ataacaattc tgaagaacaa                                      30

<210> SEQ ID NO 195
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 195
ttgtgagcgg ataacaattc tgataaaaca                                      30

<210> SEQ ID NO 196
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 196
ttgtgagcgg ataacatcta accctttaga                                      30

<210> SEQ ID NO 197
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197
ttgtgagcgg ataacatagc agataagaaa                                      30

<210> SEQ ID NO 198
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198
gtttgagcga gtaacgccga aaatcttgca         30

<210> SEQ ID NO 199
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
gtgtgagcga gtaacgacga aaatcttgca         30

<210> SEQ ID NO 200
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
tttgagcgag taacagccga aaatcttgca         30

<210> SEQ ID NO 201
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
tgtgagcgag taacagccga aaatcttgca         30

<210> SEQ ID NO 202
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
ttgtgagcga gtggcaccat taagtacgta         30

<210> SEQ ID NO 203
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
ttgtgagcga gtgacaccat taagtacgta         30

<210> SEQ ID NO 204
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
ttgtgagcga gtaacaccat taagtacgta                                            30

<210> SEQ ID NO 205
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
ttgtgagcga gtaacaccat taagtacgta                                            30

<210> SEQ ID NO 206
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
cagtgagcga gtaacaacta cgctgtttta                                            30

<210> SEQ ID NO 207
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
cagtgagcga gtaacaacta cgctgtttta                                            30

<210> SEQ ID NO 208
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
atgtgagcgg ataacactat aattaataga                                            30

<210> SEQ ID NO 209
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
atgtgagcgg ataacactat aattaataga                                            30

<210> SEQ ID NO 210

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
gaattgtgag cggataacaa ttggatccgg                                        30

<210> SEQ ID NO 211
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
ggaattgtga gcgctcacaa ttggatccgg                                        30

<210> SEQ ID NO 212
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
ggaattgtaa gcgcttacaa ttggatccgg                                        30

<210> SEQ ID NO 213
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
ggaattgtaa acgtttacaa ttggatccgg                                        30

<210> SEQ ID NO 214
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
ggaattgtga acgttcacaa ttggatccgg                                        30

<210> SEQ ID NO 215
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
```
ggaattttga gcgctcaaaa ttggatccgg                                             30

<210> SEQ ID NO 216
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
ggaattatga gcgctcataa ttggatccgg                                             30

<210> SEQ ID NO 217
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
gggacgactg tatacagtcg tcggatccgg                                             30

<210> SEQ ID NO 218
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
ggaattgtga gcgcttacaa ttggatccgg                                             30

<210> SEQ ID NO 219
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
ggaattgtga gcgctcataa ttggatccgg                                             30

<210> SEQ ID NO 220
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
ggaattgtga gctacagtcg tcggatccgg                                             30

<210> SEQ ID NO 221
<211> LENGTH: 30
<212> TYPE: DNA
<213> ORGANISM: Artificial Sequence
<220> FEATURE:

<210> SEQ ID NO 221
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 221
ggaattgtaa gcgctcacaa ttggatccgg                30

<210> SEQ ID NO 222
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
ggaattgtaa gcgttcacaa ttggatccgg                30

<210> SEQ ID NO 223
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 223
ggaattgtaa gcgctcataa ttggatccgg                30

<210> SEQ ID NO 224
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 224
ggaattgtaa gctacagtcg tcggatccgg                30

<210> SEQ ID NO 225
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225
ggaattgtga acgctcataa ttggatccgg                30

<210> SEQ ID NO 226
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 226
ggaattgtga actacagtcg tcggatccgg                30

```
<210> SEQ ID NO 227
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
ggaattatga gcgctcacaa ttggatccgg                                        30

<210> SEQ ID NO 228
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
ggaattgtga gcgctcataa ttggatccgg                                        30

<210> SEQ ID NO 229
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
ggaattgtga gctacagtcg tcggatccgg                                        30

<210> SEQ ID NO 230
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
ggaattgtga acgctcataa ttggatccgg                                        30

<210> SEQ ID NO 231
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
ggaattgtga actacagtcg tcggatccgg                                        30

<210> SEQ ID NO 232
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 232
taaattgtga acgctcataa ttggatccgg                                30

<210> SEQ ID NO 233
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
gaaattgtaa gcgcttacaa ttggatccgg                                30

<210> SEQ ID NO 234
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
gaaattgtaa gcgcttacaa ttggatccgg                                30

<210> SEQ ID NO 235
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
ggaattgtaa gcgcttacaa ttggatccgg                                30

<210> SEQ ID NO 236
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
gccaaattaa acaggattaa caggatccgg                                30

<210> SEQ ID NO 237
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
gccaaattaa acaggattaa caggatccgg                                30

<210> SEQ ID NO 238
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 238
gccaaattaa acaggattaa caggatccgg                                          30

<210> SEQ ID NO 239
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
gccaaattaa acaggattaa caggatccgg                                          30

<210> SEQ ID NO 240
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
gccaaattaa acaggattaa caggatccgg                                          30

<210> SEQ ID NO 241
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
gccaaattaa acaggattaa caggatccgg                                          30

<210> SEQ ID NO 242
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
gccaaattaa acaggattaa caggatccgg                                          30

<210> SEQ ID NO 243
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
gaaattgtaa gcgcttacaa ttggatccgg                                          30
```

<210> SEQ ID NO 244
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 244
taaattgtaa gcgcttacaa ttggatccgg                                    30

<210> SEQ ID NO 245
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 245
gtaattgtaa gcgcttacaa ttggatccgg                                    30

<210> SEQ ID NO 246
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 246
tcaattgtaa gcgcttacaa ttggatccgg                                    30

<210> SEQ ID NO 247
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 247
aaaattgtaa gcgcttacaa ttggatccgg                                    30

<210> SEQ ID NO 248
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 248
caaattgtaa gcgcttacaa ttggatccgg                                    30

<210> SEQ ID NO 249
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

```
<400> SEQUENCE: 249
gaaattgtaa gcgcttacaa ttggatccgg                                          30

<210> SEQ ID NO 250
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
taaattgtaa gcgcttacaa ttggatccgg                                          30

<210> SEQ ID NO 251
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
gtaattgtaa gcgcttacaa ttggatccgg                                          30

<210> SEQ ID NO 252
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
tcaattgtaa gcgcttacaa ttggatccgg                                          30

<210> SEQ ID NO 253
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
aaaattgtaa gcgcttacaa ttggatccgg                                          30

<210> SEQ ID NO 254
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
caaattgtaa gcgcttacaa ttggatccgg                                          30

<210> SEQ ID NO 255
<211> LENGTH: 30
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
gaaattgtaa gcgcttacaa ttggatccgg                                    30

<210> SEQ ID NO 256
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
taaattgtaa gcgcttacaa ttggatccgg                                    30

<210> SEQ ID NO 257
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
gtaattgtaa gcgcttacaa ttggatccgg                                    30

<210> SEQ ID NO 258
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
tcaattgtaa gcgcttacaa ttggatccgg                                    30

<210> SEQ ID NO 259
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
aaaattgtaa gcgcttacaa ttggatccgg                                    30

<210> SEQ ID NO 260
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
caaattgtaa gcgcttacaa ttggatccgg                                    30
```

<210> SEQ ID NO 261
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
gaaattgtaa gcgcttacaa ttggatccgg                                   30

<210> SEQ ID NO 262
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
taaattgtaa gcgcttacaa ttggatccgg                                   30

<210> SEQ ID NO 263
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
gtaattgtaa gcgcttacaa ttggatccgg                                   30

<210> SEQ ID NO 264
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
tcaattgtaa gcgcttacaa ttggatccgg                                   30

<210> SEQ ID NO 265
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
aaaattgtaa gcgcttacaa ttggatccgg                                   30

<210> SEQ ID NO 266
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 266
caaattgtaa gcgcttacaa ttggatccgg     30

<210> SEQ ID NO 267
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
gaaattgtaa gcgcttacaa ttggatccgg     30

<210> SEQ ID NO 268
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
taaattgtaa gcgcttacaa ttggatccgg     30

<210> SEQ ID NO 269
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
gtaattgtaa gcgcttacaa ttggatccgg     30

<210> SEQ ID NO 270
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
tcaattgtaa gcgcttacaa ttggatccgg     30

<210> SEQ ID NO 271
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
aaaattgtaa gcgcttacaa ttggatccgg     30

<210> SEQ ID NO 272
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
caaattgtaa gcgcttacaa ttggatccgg                                   30

<210> SEQ ID NO 273
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
gaaattgtaa gcgcttacaa ttggatccgg                                   30

<210> SEQ ID NO 274
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
taaattgtaa gcgcttacaa ttggatccgg                                   30

<210> SEQ ID NO 275
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
gtaattgtaa gcgcttacaa ttggatccgg                                   30

<210> SEQ ID NO 276
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
tcaattgtaa gcgcttacaa ttggatccgg                                   30

<210> SEQ ID NO 277
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
```
aaaattgtaa gcgcttacaa ttggatccgg    30

<210> SEQ ID NO 278
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
caaattgtaa gcgcttacaa ttggatccgg    30

<210> SEQ ID NO 279
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
gaaattgtaa gcgcttacaa ttggatccgg    30

<210> SEQ ID NO 280
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
taaattgtaa gcgcttacaa ttggatccgg    30

<210> SEQ ID NO 281
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
gtaattgtaa gcgcttacaa ttggatccgg    30

<210> SEQ ID NO 282
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
tcaattgtaa gcgcttacaa ttggatccgg    30

<210> SEQ ID NO 283
<211> LENGTH: 30
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 283
aaaattgtaa gcgcttacaa ttggatccgg                                        30

<210> SEQ ID NO 284
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
caaattgtaa gcgcttacaa ttggatccgg                                        30

<210> SEQ ID NO 285
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
gccaaattaa acaggattaa caggatccgg                                        30

<210> SEQ ID NO 286
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
gccaaattaa acaggattaa caggatccgg                                        30

<210> SEQ ID NO 287
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
caaattatga gcgctcacaa ttggatccgg                                        30

<210> SEQ ID NO 288
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
gtttctccat acccgttttt ttgggctagc                                        30

<210> SEQ ID NO 289
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
tgttatagtc gaatacctct ggcggtgata                                    30

<210> SEQ ID NO 290
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
attacaaact ttcttgtata gatttaacgt                                    30

<210> SEQ ID NO 291
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
atttataaat agtggtgata gatttaacgt                                    30

<210> SEQ ID NO 292
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
tttcttgtat agatttacaa tgtatcttgt                                    30

<210> SEQ ID NO 293
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
tttcttgtag atacttacaa tgtatcttgt                                    30

<210> SEQ ID NO 294
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
```
ctttatgctt ccggctcgta tgttgtgtgg                                          30

<210> SEQ ID NO 295
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295 tttttttgggc tagcaagctt taccatggat                                         30

<210> SEQ ID NO 296
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
tgtttctcca taccgttttt ttgggctagc                                          30

<210> SEQ ID NO 297
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
ttttggtaca ctccctatca gtgatagaga                                          30

<210> SEQ ID NO 298
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298 cttttttggta cactacctct ggcggtgata                                         30

<210> SEQ ID NO 299
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
tacgcaagaa aatggtttgt tatagtcgaa                                          30

<210> SEQ ID NO 300
<211> LENGTH: 30
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 300
gaaaaccttg tcaatgaaga gcgatctatg                                      30

<210> SEQ ID NO 301
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
ctcaaagcgg gccagccgta gccgttacgc                                      30

<210> SEQ ID NO 302
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
ttctcgttcg actcatagct gaacacaaca                                      30

<210> SEQ ID NO 303
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
gttctttaat tatttaagtg ttctttaatt                                      30

<210> SEQ ID NO 304
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
cgtgcgtgtt gataacaccg tgcgtgttga                                      30

<210> SEQ ID NO 305
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
gttacgttta tcgcggtgat tgttacttat                                      30

```
<210> SEQ ID NO 306
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
gcaaaataaa atggaatgat gaaactgggt                                    30

<210> SEQ ID NO 307
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
gttacgttta tcgcggtgat tgttacttat                                    30

<210> SEQ ID NO 308
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
atttcacact gctattgaga taattcacaa                                    30

<210> SEQ ID NO 309
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
agattgtact aaatcgtata atgacagtga                                    30

<210> SEQ ID NO 310
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
gacatctccg gcgcaactga aaataccact                                    30

<210> SEQ ID NO 311
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 311
gaggatgcgc atcgtcggga aactgatgcc                                           30

<210> SEQ ID NO 312
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
catccgggac tgatggcgga ggatgcgcat                                           30

<210> SEQ ID NO 313
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
aacttttata tattgtgcaa tctcacatgc                                           30

<210> SEQ ID NO 314
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
tgttgtccgg tgtacgtcac aattttctta                                           30

<210> SEQ ID NO 315
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
aatggctgtg tgtttttttgt tcatctccac                                          30

<210> SEQ ID NO 316
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
gtgttgatgc ttttatcacc gccagtggta                                           30

<210> SEQ ID NO 317
<211> LENGTH: 30
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 317
agtgtgtgga attgtgagcg gataacaatt                                      30

<210> SEQ ID NO 318
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
atgacaaaat tgtcat                                                     16

<210> SEQ ID NO 319
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
acatcttaaa agttttagta tcatattcgt                                      30

<210> SEQ ID NO 320
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
ctgaaagcgc ataccgctat ggaggggggtt                                     30

<210> SEQ ID NO 321
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
ctgaaagcgc ataccgctat ggagggggtt                                      30

<210> SEQ ID NO 322
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
aacgaatata acaggtggga gatgagagga                                      30
```

```
<210> SEQ ID NO 323
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
aatatttcct cattttccac agtgaagtga                                      30

<210> SEQ ID NO 324
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
tacgcaagaa aatggtttgt tatagtcgaa                                      30

<210> SEQ ID NO 325
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
atttaattgt tttgatcaat tatttttctg                                      30

<210> SEQ ID NO 326
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
attattctgc atttttgggg agaatggact                                      30

<210> SEQ ID NO 327
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
ccttgctgga aggtttaacc tttatcacag                                      30

<210> SEQ ID NO 328
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 328
atgatgtgtc catggatta                                              19

<210> SEQ ID NO 329
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
atgatagacg atgtgcggac aacgtg                                      26

<210> SEQ ID NO 330
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
cattagccgc caccatgggg ttaagtagca                                  30

<210> SEQ ID NO 331
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
atttataaat agtggtgata gatttaacgt                                  30

<210> SEQ ID NO 332
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
ataaagccat cacgagtacc atagaggatc                                  30

<210> SEQ ID NO 333
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
tttgtctttt cttgcttaat aatgttgtca                                  30

<210> SEQ ID NO 334
<211> LENGTH: 30
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
tttgtctttt cttgcttaat aatgttgtca                                    30

<210> SEQ ID NO 335
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
atcctccttt agtcttcccc ctcatgtgtg                                    30

<210> SEQ ID NO 336
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
taaaattatg aaatttgcat aaattcttca                                    30

<210> SEQ ID NO 337
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
gaaatctggc agttttggt acacgaaagc                                     30

<210> SEQ ID NO 338
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
tgccagttct ggcaggtcta aaaagtgttc                                    30

<210> SEQ ID NO 339
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
cacagaactt gcatttatat aaagggaaag                                    30
```

<210> SEQ ID NO 340
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
acaccgtgcg tgttgatata gtcgaataaa                              30

<210> SEQ ID NO 341
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
aaaattatga aatttgtata aattcttcag                              30

<210> SEQ ID NO 342
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342 ggttctttttt ggtacctctg gcggtgataa                             30

<210> SEQ ID NO 343
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
tgtaggatcg tacaggtata aattcttcag                              30

<210> SEQ ID NO 344
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
caagaaaatg gtttgttata gtcgaataaa                              30

<210> SEQ ID NO 345
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 345
ctatctcatt tgctagtata gtcgaataaa					30

<210> SEQ ID NO 346
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
gttacgttta tcgcggtgat tgttacttat					30

<210> SEQ ID NO 347
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
gttacgttta tcgcggtgat tgttacttat					30

<210> SEQ ID NO 348
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
gttacgttta tcgcggtgat tgttacttat					30

<210> SEQ ID NO 349
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
ataaatgctt gactctgtag cgggaaggcg					30

<210> SEQ ID NO 350
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
aaaactggta gtaggactgg agattggtac					30

<210> SEQ ID NO 351
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
gggacacaaa catcaagagg atatgagatt                                        30

<210> SEQ ID NO 352
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
gtcaaaatga ccgaaacggg tggtaacttc                                        30

<210> SEQ ID NO 353
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
agtaatctta tcgccagttt ggtctggtca                                        30

<210> SEQ ID NO 354
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
agtaatctta tcgccagttt ggtctggtca                                        30

<210> SEQ ID NO 355
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
aattctgaac aacatccgta ctcttcgtgc                                        30

<210> SEQ ID NO 356
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
```
tcgataagat taccgatctt acctgaagct                                30

<210> SEQ ID NO 357
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
cgatctattc acctgaaaga gaaataaaaa                                30

<210> SEQ ID NO 358
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
atcgcaacct atttattaca acactagtgc                                30

<210> SEQ ID NO 359
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
aaacgttagt ttgaatggaa agatgcctgc                                30

<210> SEQ ID NO 360
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
tttgcacgaa ccatatgtaa gtatttcctt                                30

<210> SEQ ID NO 361
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
taacacttat ttaattaaaa agaggagaaa                                30

<210> SEQ ID NO 362
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
tagaaacaaa atgtaacatc tctatggaca                                      30

<210> SEQ ID NO 363
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
acaggaaaca gctatgacca tgattacgcc                                      30

<210> SEQ ID NO 364
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
agcgacgtct gatgacgtaa tttctgcctc                                      30

<210> SEQ ID NO 365
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
gttcactcta taccgctgaa ggtgtaatgg                                      30

<210> SEQ ID NO 366
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
tagtttataa tttaagtgtt ctttaatttc                                      30

<210> SEQ ID NO 367
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
cgagcacttc accaacaagg accatagcat                                      30

<210> SEQ ID NO 368

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
caccttcggg tgggcctttc tgcgtttata                                        30

<210> SEQ ID NO 369
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
catggcatgg atgaactata caaataataa                                        30

<210> SEQ ID NO 370
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
caccttcggg tgggcctttc tgcgtttata                                        30

<210> SEQ ID NO 371
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
caccttcggg tgggcctttc tgcgtttata                                        30

<210> SEQ ID NO 372
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
caccttcggg tgggcctttc tgcgtttata                                        30

<210> SEQ ID NO 373
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
```
caccttcggg tgggcctttc tgcgtttata                                30

<210> SEQ ID NO 374
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
caccttcggg tgggcctttc tgcgtttata                                30

<210> SEQ ID NO 375
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
caccttcggg tgggcctttc tgcgtttata                                30

<210> SEQ ID NO 376
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
caccttcggg tgggcctttc tgcgtttata                                30

<210> SEQ ID NO 377
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
caccttcggg tgggcctttc tgcgtttata                                30

<210> SEQ ID NO 378
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
caccttcggg tgggcctttc tgcgtttata                                30

<210> SEQ ID NO 379
<211> LENGTH: 30
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 379
caccttcggg tgggcctttc tgcgtttata                                    30

<210> SEQ ID NO 380
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
caccttcggg tgggcctttc tgcgtttata                                    30

<210> SEQ ID NO 381
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
caccttcggg tgggcctttc tgcgtttata                                    30

<210> SEQ ID NO 382
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
caccttcggg tgggcctttc tgcgtttata                                    30

<210> SEQ ID NO 383
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
caccttcggg tgggcctttc tgcgtttata                                    30

<210> SEQ ID NO 384
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
caccttcggg tgggcctttc tgcgtttata                                    30

<210> SEQ ID NO 385
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 385
tgtttctcca taccgttttt ttgggctagc           30

<210> SEQ ID NO 386
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 386
tgtttctcca taccgttttt ttgggctagc           30

<210> SEQ ID NO 387
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 387
ttttatcgca actctctact gtttctccat           30

<210> SEQ ID NO 388
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 388
gtttctccat tactagagaa agaggggaca           30

<210> SEQ ID NO 389
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 389
caccttcggg tgggcctttc tgcgtttata           30

<210> SEQ ID NO 390
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

```
<400> SEQUENCE: 390
aataactctg atagtgctag tgtagatctc                                    30

<210> SEQ ID NO 391
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
caccttcggg tgggcctttc tgcgtttata                                    30

<210> SEQ ID NO 392
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
caccttcggg tgggcctttc tgcgtttata                                    30

<210> SEQ ID NO 393
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
gggacacaaa catcaagagg atatgagatt                                    30

<210> SEQ ID NO 394
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
ataataagcg aagttagcga gatgaatgcg                                    30

<210> SEQ ID NO 395
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
agttggcaca gatttcgctt tatctttttt                                    30

<210> SEQ ID NO 396
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 396
caagaaaatg gtttgttata gtcgaataaa                                    30

<210> SEQ ID NO 397
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
gtgttgacta ttttacctct ggcggtgata                                    30

<210> SEQ ID NO 398
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
gttagctttc gaattggcta aaaagtgttc                                    30

<210> SEQ ID NO 399
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
ccattctgct ttccacgaac ttgaaaacgc                                    30

<210> SEQ ID NO 400
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
ggccgcgggt tcttttttggt acacgaaagc                                   30

<210> SEQ ID NO 401
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
ttttatcgca actctctact gtttctccat                                    30
```

```
<210> SEQ ID NO 402
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
attattctgc atttttgggg agaatggact                                           30

<210> SEQ ID NO 403
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
attattctgc atttttgggg agaatggact                                           30

<210> SEQ ID NO 404
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
aacgttagtt tgaatggaaa gatgcctgca                                           30

<210> SEQ ID NO 405
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
aagaaaatgg tttgttgata ctcgaataaa                                           30

<210> SEQ ID NO 406
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
aacgcagtcg ttaagttcta caaagtcggt                                           30

<210> SEQ ID NO 407
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 407
gtcggtgaca gataacagga gtaagtaatg					30

<210> SEQ ID NO 408
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
tattggctga ctataataag cgcaaattca					30

<210> SEQ ID NO 409

<400> SEQUENCE: 409

000

<210> SEQ ID NO 410
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
cgaaacggga accctatatt gatctctact					30

<210> SEQ ID NO 411
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
aagttggcac gcatcgtgct ttatacagat					30

<210> SEQ ID NO 412
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
gaggaaacta gacccgccgc caccatggag					30

<210> SEQ ID NO 413
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413

-continued gagtaaccaa aaccaaaaca gatttcaacc                                30

<210> SEQ ID NO 414
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
aaagtaagaa tttttgaaaa ttcaatataa                                30

<210> SEQ ID NO 415
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
atacggtcaa cgaactataa ttaactaaac                                30

<210> SEQ ID NO 416
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
cacaaataca cacactaaat taataactag                                30

<210> SEQ ID NO 417
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
cacaaataca cacactaaat taataactag                                30

<210> SEQ ID NO 418
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
cacaaataca cacactaaat taataactag                                30

<210> SEQ ID NO 419
<211> LENGTH: 30
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 419
atactttaac gtcaaggaga aaaaactata                                    30

<210> SEQ ID NO 420
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
accgttaaga accatatcca agaatcaaaa                                    30

<210> SEQ ID NO 421
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
cttcatatat aaaccgccag aaatgaatta                                    30

<210> SEQ ID NO 422
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
atcttcatac aacaataact accaacctta                                    30

<210> SEQ ID NO 423
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
tttcatacac aatataaacg attaaaagaa                                    30

<210> SEQ ID NO 424
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
aaattccagt aaattcacat attggagaaa                                    30

```
<210> SEQ ID NO 425
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
gggagccaga acgcttctgg tggtgtaaat                                   30

<210> SEQ ID NO 426
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
gcacagactt agattggtat atatacgcat                                   30

<210> SEQ ID NO 427
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
aagtgcaaga aagaccagaa acgcaactca                                   30

<210> SEQ ID NO 428
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
taaaaaaaaa aaaaaaaaaa aaaaaaaaaa                                   30

<210> SEQ ID NO 429
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
ggggcgaggg ccccgcctcc ggaggcgggg                                   30

<210> SEQ ID NO 430
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 430
gaggggacgg ctccggcccc ggggccggag                30

<210> SEQ ID NO 431
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
ggggcgaggg ctccggcccc ggggccggag                30

<210> SEQ ID NO 432
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
gaggggacgg ccccgcctcc ggaggcgggg                30

<210> SEQ ID NO 433
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
tgttatagtc gaatacctct ggcggtgata                30

<210> SEQ ID NO 434
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
gatttaacgt atcagcacaa aaaagaaacc                30

<210> SEQ ID NO 435
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
attacaaact ttcttgtata gatttaacgt                30

<210> SEQ ID NO 436
<211> LENGTH: 30
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 436
tttcttgtat agatttacaa tgtatcttgt                                          30

<210> SEQ ID NO 437
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
tttcttgtag atacttacaa tgtatcttgt                                          30

<210> SEQ ID NO 438
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
actctgtcaa tgatagagtg gattcaaaaa                                          30

<210> SEQ ID NO 439
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
ttttggtaca ctccctatca gtgatagaga                                          30

<210> SEQ ID NO 440
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440 cttttggta cactacctct ggcggtgata                                           30

<210> SEQ ID NO 441
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
aaacctttcg cggtatggca tgatagcgcc                                          30
```

<210> SEQ ID NO 442
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
tattttacct ctggcggtga taatggttgc                                    30

<210> SEQ ID NO 443
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
actctcggca tggacgagct gtacaagtaa                                    30

<210> SEQ ID NO 444
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
ttgtgagcgg ataacaatat gttgagcaca                                    30

<210> SEQ ID NO 445
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
cattgagaca cttgtttgca cagaggatgg                                    30

<210> SEQ ID NO 446
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
ttctcgttcg actcatagct gaacacaaca                                    30

<210> SEQ ID NO 447
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
gaattgtgag cggataacaa ttggatccgg               30

<210> SEQ ID NO 448
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
ggaattgtga gcgctcacaa ttggatccgg               30

<210> SEQ ID NO 449
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
ggaattgtaa gcgcttacaa ttggatccgg               30

<210> SEQ ID NO 450
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
ggaattgtaa acgtttacaa ttggatccgg               30

<210> SEQ ID NO 451
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
ggaattgtga acgttcacaa ttggatccgg               30

<210> SEQ ID NO 452
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
ggaattttga gcgctcaaaa ttggatccgg               30

<210> SEQ ID NO 453
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
ggaattatga gcgctcataa ttggatccgg                                    30

<210> SEQ ID NO 454
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
gggacgactg tatacagtcg tcggatccgg                                    30

<210> SEQ ID NO 455
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
ggaattgtga gcgcttacaa ttggatccgg                                    30

<210> SEQ ID NO 456
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
ggaattgtga gcgctcataa ttggatccgg                                    30

<210> SEQ ID NO 457
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
ggaattgtga gctacagtcg tcggatccgg                                    30

<210> SEQ ID NO 458
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
ggaattgtaa gcgctcacaa ttggatccgg                                    30
```

<210> SEQ ID NO 459
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
ggaattgtaa gcgttcacaa ttggatccgg                                    30

<210> SEQ ID NO 460
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
ggaattgtaa gcgctcataa ttggatccgg                                    30

<210> SEQ ID NO 461
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
ggaattgtaa gctacagtcg tcggatccgg                                    30

<210> SEQ ID NO 462
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
ggaattgtga acgctcataa ttggatccgg                                    30

<210> SEQ ID NO 463
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
ggaattgtga actacagtcg tcggatccgg                                    30

<210> SEQ ID NO 464
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 464
ggaattatga gcgctcacaa ttggatccgg                30

<210> SEQ ID NO 465
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
ggaattgtga gcgctcataa ttggatccgg                30

<210> SEQ ID NO 466
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
ggaattgtga gctacagtcg tcggatccgg                30

<210> SEQ ID NO 467
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
ggaattgtga acgctcataa ttggatccgg                30

<210> SEQ ID NO 468
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
ggaattgtga actacagtcg tcggatccgg                30

<210> SEQ ID NO 469
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
taaattgtga acgctcataa ttggatccgg                30

<210> SEQ ID NO 470
<211> LENGTH: 30

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
gaaattgtaa gcgcttacaa ttggatccgg                                          30

<210> SEQ ID NO 471
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
gaaattgtaa gcgcttacaa ttggatccgg                                          30

<210> SEQ ID NO 472
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
ggaattgtaa gcgcttacaa ttggatccgg                                          30

<210> SEQ ID NO 473
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
gccaaattaa acaggattaa caggatccgg                                          30

<210> SEQ ID NO 474
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
gccaaattaa acaggattaa caggatccgg                                          30

<210> SEQ ID NO 475
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
```
gccaaattaa acaggattaa caggatccgg                                              30

<210> SEQ ID NO 476
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
gccaaattaa acaggattaa caggatccgg                                              30

<210> SEQ ID NO 477
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
gccaaattaa acaggattaa caggatccgg                                              30

<210> SEQ ID NO 478
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
gccaaattaa acaggattaa caggatccgg                                              30

<210> SEQ ID NO 479
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
gccaaattaa acaggattaa caggatccgg                                              30

<210> SEQ ID NO 480
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
gaaattgtaa gcgcttacaa ttggatccgg                                              30

<210> SEQ ID NO 481
<211> LENGTH: 30
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 481
taaattgtaa gcgcttacaa ttggatccgg                                          30

<210> SEQ ID NO 482
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
gtaattgtaa gcgcttacaa ttggatccgg                                          30

<210> SEQ ID NO 483
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
tcaattgtaa gcgcttacaa ttggatccgg                                          30

<210> SEQ ID NO 484
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
aaaattgtaa gcgcttacaa ttggatccgg                                          30

<210> SEQ ID NO 485
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
caaattgtaa gcgcttacaa ttggatccgg                                          30

<210> SEQ ID NO 486
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
gaaattgtaa gcgcttacaa ttggatccgg                                          30

<210> SEQ ID NO 487
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
taaattgtaa gcgcttacaa ttggatccgg                                            30

<210> SEQ ID NO 488
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
gtaattgtaa gcgcttacaa ttggatccgg                                            30

<210> SEQ ID NO 489
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
tcaattgtaa gcgcttacaa ttggatccgg                                            30

<210> SEQ ID NO 490
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
aaaattgtaa gcgcttacaa ttggatccgg                                            30

<210> SEQ ID NO 491
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
caaattgtaa gcgcttacaa ttggatccgg                                            30

<210> SEQ ID NO 492
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
```
gaaattgtaa gcgcttacaa ttggatccgg                                              30

<210> SEQ ID NO 493
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
taaattgtaa gcgcttacaa ttggatccgg                                              30

<210> SEQ ID NO 494
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
gtaattgtaa gcgcttacaa ttggatccgg                                              30

<210> SEQ ID NO 495
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
tcaattgtaa gcgcttacaa ttggatccgg                                              30

<210> SEQ ID NO 496
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
aaaattgtaa gcgcttacaa ttggatccgg                                              30

<210> SEQ ID NO 497
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
caaattgtaa gcgcttacaa ttggatccgg                                              30

<210> SEQ ID NO 498
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 498
gaaattgtaa gcgcttacaa ttggatccgg                                    30

<210> SEQ ID NO 499
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
taaattgtaa gcgcttacaa ttggatccgg                                    30

<210> SEQ ID NO 500
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
gtaattgtaa gcgcttacaa ttggatccgg                                    30

<210> SEQ ID NO 501
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
tcaattgtaa gcgcttacaa ttggatccgg                                    30

<210> SEQ ID NO 502
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
aaaattgtaa gcgcttacaa ttggatccgg                                    30

<210> SEQ ID NO 503
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
caaattgtaa gcgcttacaa ttggatccgg                                    30
```

<210> SEQ ID NO 504
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
gaaattgtaa gcgcttacaa ttggatccgg                                    30

<210> SEQ ID NO 505
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
taaattgtaa gcgcttacaa ttggatccgg                                    30

<210> SEQ ID NO 506
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
gtaattgtaa gcgcttacaa ttggatccgg                                    30

<210> SEQ ID NO 507
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
tcaattgtaa gcgcttacaa ttggatccgg                                    30

<210> SEQ ID NO 508
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
aaaattgtaa gcgcttacaa ttggatccgg                                    30

<210> SEQ ID NO 509
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 509
caaattgtaa gcgcttacaa ttggatccgg                                    30

<210> SEQ ID NO 510
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
gaaattgtaa gcgcttacaa ttggatccgg                                    30

<210> SEQ ID NO 511
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
taaattgtaa gcgcttacaa ttggatccgg                                    30

<210> SEQ ID NO 512
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
gtaattgtaa gcgcttacaa ttggatccgg                                    30

<210> SEQ ID NO 513
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
tcaattgtaa gcgcttacaa ttggatccgg                                    30

<210> SEQ ID NO 514
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
aaaattgtaa gcgcttacaa ttggatccgg                                    30

<210> SEQ ID NO 515
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 515
caaattgtaa gcgcttacaa ttggatccgg                                          30

<210> SEQ ID NO 516
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
gaaattgtaa gcgcttacaa ttggatccgg                                          30

<210> SEQ ID NO 517
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
taaattgtaa gcgcttacaa ttggatccgg                                          30

<210> SEQ ID NO 518
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
gtaattgtaa gcgcttacaa ttggatccgg                                          30

<210> SEQ ID NO 519
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
tcaattgtaa gcgcttacaa ttggatccgg                                          30

<210> SEQ ID NO 520
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
aaaattgtaa gcgcttacaa ttggatccgg                                          30
```

<210> SEQ ID NO 521
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 521
caaattgtaa gcgcttacaa ttggatccgg                                    30

<210> SEQ ID NO 522
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 522
gccaaattaa acaggattaa caggatccgg                                    30

<210> SEQ ID NO 523
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 523
gccaaattaa acaggattaa caggatccgg                                    30

<210> SEQ ID NO 524
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 524
caaattatga gcgctcacaa ttggatccgg                                    30

<210> SEQ ID NO 525
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 525
tgatagagat tccctatcag tgatagagat                                    30

<210> SEQ ID NO 526
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 526
tgatagagat tccctatcag tgatagagat             30

<210> SEQ ID NO 527
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
gttctttaat tatttaagtg ttctttaatt             30

<210> SEQ ID NO 528
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
gttctttaat tatttaagtg ttctttaatt             30

<210> SEQ ID NO 529
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
cgtgcgtgtt gataacaccg tgcgtgttga             30

<210> SEQ ID NO 530
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
gtgttcttta atatttaagt gttctttaat             30

<210> SEQ ID NO 531
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
ggaattgtga gcggataaca atttcacaca             30

<210> SEQ ID NO 532
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
tgtgtgtaat tgtgagcgga taacaattaa                                      30

<210> SEQ ID NO 533
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
ttttacctct ggcggtgata atggttgcag                                      30

<210> SEQ ID NO 534
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
gtgttgatgc ttttatcacc gccagtggta                                      30

<210> SEQ ID NO 535
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
agtgtgtgga attgtgagcg gataacaatt                                      30

<210> SEQ ID NO 536
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536 aggggggtggg ggcgcgttgg cgcgccacac                                     30

<210> SEQ ID NO 537
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
acatcttaaa agtttttagta tcatattcgt                                     30
```

```
<210> SEQ ID NO 538
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
tattttacct ctggcggtga taatggttgc                                    30

<210> SEQ ID NO 539
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
atttataaat agtggtgata gatttaacgt                                    30

<210> SEQ ID NO 540
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
acccttctcg ttcgactcat agctgaacac                                    30

<210> SEQ ID NO 541
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
tgacttatcc gcttcgaaga gagacactac                                    30

<210> SEQ ID NO 542
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
aggtgttaaa ttgatcacgt tttagaccat                                    30

<210> SEQ ID NO 543
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 543
caatttggta aaggctccat catgtaataa                                30

<210> SEQ ID NO 544
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
gagaaacaat ttggtaaagg ctccatcatg                                30

<210> SEQ ID NO 545
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
aacgcgcggg gagaggcggt ttgcgtattg                                30

<210> SEQ ID NO 546
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
cagtgataga gatactgagc acatcagcac                                30

<210> SEQ ID NO 547
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
ttatgcttcc ggctcgtata atgtttcaaa                                30

<210> SEQ ID NO 548
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
ggctcgtatg ttgtgtcgac cgagctgcgc                                30

<210> SEQ ID NO 549
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
aaacctttcg cggtatggca tgatagcgcc                                     30

<210> SEQ ID NO 550
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
atttgtcact gtcgttacta tatcggctgc                                     30

<210> SEQ ID NO 551
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
gtccaatcaa taaccgcttt aatagataaa                                     30

<210> SEQ ID NO 552
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
actttattat caataagtta aatcggtacc                                     30

<210> SEQ ID NO 553
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
gtgttgacta ttttacctct ggcggtgata                                     30

<210> SEQ ID NO 554
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
```
gtgttgacta ttttacctct ggcggtgata                               30

<210> SEQ ID NO 555
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
atacctctgg cggtgatata taatggttgc                               30

<210> SEQ ID NO 556
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
gtgttgacta ttttacctct ggcggtgata                               30

<210> SEQ ID NO 557
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
gaaatctggc agttttggt acacgaaagc                                30

<210> SEQ ID NO 558
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
tgccagttct ggcaggtcta aaaagtgttc                               30

<210> SEQ ID NO 559
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
agcgctcaca atttaatacg actcactata                               30

<210> SEQ ID NO 560
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 560
taataattgt gagcgctcac aattttgaca                                    30

<210> SEQ ID NO 561
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 561
atccctatca gtgatagaga tactgagcac                                    30

<210> SEQ ID NO 562
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 562
ttgtgagcgg ataacaagat actgagcaca                                    30

<210> SEQ ID NO 563
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 563
ggaattgtga gcggataaca atttcacaca                                    30

<210> SEQ ID NO 564
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 564
ggaattgtga gcggataaca atttcacaca                                    30

<210> SEQ ID NO 565
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 565
ggaattgtga gcggataaca atttcacaca                                    30

<210> SEQ ID NO 566

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
agaactgtaa tccctatcag tgatagagat                                          30

<210> SEQ ID NO 567
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
tgttgattta tctaacaccg tgcgtgttga                                          30

<210> SEQ ID NO 568
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
acaccgtgcg tgttgatata gtcgaataaa                                          30

<210> SEQ ID NO 569
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
cctttcgcgg tatggcatga tagcgcccgg                                          30

<210> SEQ ID NO 570
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
cctttcgcgg tatggcatga tagcgcccgg                                          30

<210> SEQ ID NO 571
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
```
cctttcgcgg tatggcatga tagcgcccgg                      30

<210> SEQ ID NO 572
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
ggttcttttt ggtacctctg gcggtgataa                      30

<210> SEQ ID NO 573
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
tgtaggatcg tacaggtata aattcttcag                      30

<210> SEQ ID NO 574
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
ctatctcatt tgctagtata gtcgaataaa                      30

<210> SEQ ID NO 575
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
gtatatatat acagtataat tgcttcaaca                      30

<210> SEQ ID NO 576
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
cacaatgtca attgttatcc gctcacaatt                      30

<210> SEQ ID NO 577
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 577
aattgtgagc ggataacaat ttcacacaga                                    30

<210> SEQ ID NO 578
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
ccggaagaga gtcaattcag ggtggtgaat                                    30

<210> SEQ ID NO 579
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
acggtgacct agatctccga tactgagcac                                    30

<210> SEQ ID NO 580
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
tggaattgtg agcggataaa atttcacaca                                    30

<210> SEQ ID NO 581
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
tagtagataa tttaagtgtt ctttaatttc                                    30

<210> SEQ ID NO 582
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
ccaacgcgtt cacagcgtac aattactagt                                    30
```

```
<210> SEQ ID NO 583
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
aacaaaaaaa cggatcctct agttgcggcc                                    30

<210> SEQ ID NO 584
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
ataaatgctt gactctgtag cgggaaggcg                                    30

<210> SEQ ID NO 585
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
atttcatgat gatacgtgag cggatagaag                                    30

<210> SEQ ID NO 586
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
caaacagaaa gcgttggcgg cagcactggg                                    30

<210> SEQ ID NO 587
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
gtcaaaatga ccgaaacggg tggtaacttc                                    30

<210> SEQ ID NO 588
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 588
agtaatctta tcgccagttt ggtctggtca                                    30

<210> SEQ ID NO 589
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
agtaatctta tcgccagttt ggtctggtca                                    30

<210> SEQ ID NO 590
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
aattctgaac aacatccgta ctcttcgtgc                                    30

<210> SEQ ID NO 591
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
tttacgttat cattcacttt acatcagagt                                    30

<210> SEQ ID NO 592
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
gtttctccat acccgttttt ttgggctagc                                    30

<210> SEQ ID NO 593
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
cgatctattc acctgaaaga gaaataaaaa                                    30

<210> SEQ ID NO 594
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 594
aaacgttagt ttgaatggaa agatgcctgc                                        30

<210> SEQ ID NO 595
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
attgccgaat taatactaag aattattatc                                        30

<210> SEQ ID NO 596
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
acaggaaaca gctatgacca tgattacgcc                                        30

<210> SEQ ID NO 597
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
actggcggtt ataatgagca catcagcagg                                        30

<210> SEQ ID NO 598
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
caccgacaaa caacagataa aacgaaaggc                                        30

<210> SEQ ID NO 599
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
agtgttatta agctactaaa gcgtagtttt                                        30
```

```
<210> SEQ ID NO 600
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
gaataagaag gctggctctg caccttggtg                                          30

<210> SEQ ID NO 601
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
ttagcgactt gatgctcttg atcttccaat                                          30

<210> SEQ ID NO 602
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
acatctaaaa cttttagcgt tattacgtaa                                          30

<210> SEQ ID NO 603
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
ttccgacctc attaagcagc tctaatgcgc                                          30

<210> SEQ ID NO 604
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
caatttttaa acctgtagga tcgtacaggt                                          30

<210> SEQ ID NO 605
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 605
caatttttaa aattaaaggc gttacccaac                              30

<210> SEQ ID NO 606
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
tagtttataa tttaagtgtt ctttaatttc                              30

<210> SEQ ID NO 607
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
gaaaatgtga gcgagtaaca acctcacaca                              30

<210> SEQ ID NO 608
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
caccttcggg tgggcctttc tgcgtttata                              30

<210> SEQ ID NO 609
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
ttttatcgca actctctact gtttctccat                              30

<210> SEQ ID NO 610
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
gtttctccat tactagagaa agagggaca                               30

<210> SEQ ID NO 611
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
caccttcggg tgggcctttc tgcgtttata                                    30

<210> SEQ ID NO 612
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
caccttcggg tgggcctttc tgcgtttata                                    30

<210> SEQ ID NO 613
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
caccttcggg tgggcctttc tgcgtttata                                    30

<210> SEQ ID NO 614
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
aataactctg atagtgctag tgtagatctc                                    30

<210> SEQ ID NO 615
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
caccttcggg tgggcctttc tgcgtttata                                    30

<210> SEQ ID NO 616
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
caccttcggg tgggcctttc tgcgtttata                                    30
```

<210> SEQ ID NO 617
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
ttgtgagcgg ataacaagat actgagcaca                                    30

<210> SEQ ID NO 618
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
actgagcaca tactagagaa agaggagaaa                                    30

<210> SEQ ID NO 619
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
actgagcaca tactagagaa agaggagaaa                                    30

<210> SEQ ID NO 620
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
tcacacatac tagagattaa agaggagaaa                                    30

<210> SEQ ID NO 621
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
ggaattgtga gcggataaca atttcacaca                                    30

<210> SEQ ID NO 622
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 622
ggaattgtga gcggataaca atttcacaca                                           30

<210> SEQ ID NO 623
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
ttgtgagcgg ataacaagat actgagcaca                                           30

<210> SEQ ID NO 624
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
atccctatca gtgatagaga tactgagcac                                           30

<210> SEQ ID NO 625
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
ccgtcataat atgaaccata agttcaccac                                           30

<210> SEQ ID NO 626
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
tattttacct ctggcggtga taatggttgc                                           30

<210> SEQ ID NO 627
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
attgtatgaa aatacaagaa agtttgttga                                           30

<210> SEQ ID NO 628
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
tagtagataa tttaagtgtt ctttaatttc                                        30

<210> SEQ ID NO 629
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
ttgacacctg taggatcgta caggtataat                                        30

<210> SEQ ID NO 630
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
cacgcaaaac ttgcgacaaa caataggtaa                                        30

<210> SEQ ID NO 631
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
gtgttgacta ttttacctct ggcggtgata                                        30

<210> SEQ ID NO 632
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
tagatctcct atagtgagtc gtattaattt                                        30

<210> SEQ ID NO 633
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
```
tactttcaaa gactacattt gtaagatttg                                      30

<210> SEQ ID NO 634
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
cataaagttc atgaaacgtg aactgaaatt                                      30

<210> SEQ ID NO 635
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
ccgtgatact atgaaccata agttcaccac                                      30

<210> SEQ ID NO 636
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
aattttacct ctggcggtga tactggttgc                                      30

<210> SEQ ID NO 637
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
attgtatgat actacaagaa agtttgttga                                      30

<210> SEQ ID NO 638
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
tagtagatac tttaagtgtt ctttaatttc                                      30

<210> SEQ ID NO 639
<211> LENGTH: 30
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 639
tggtcccacg cgcgtgggat actacgtcag                                           30

<210> SEQ ID NO 640
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
attacggtga gatactccca cgcgcgtggg                                           30

<210> SEQ ID NO 641
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
acgcgcgtgg gatactccca cgcgcgtggg                                           30

<210> SEQ ID NO 642
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
gattagattc ataaatttga gagaggagtt                                           30

<210> SEQ ID NO 643
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
acttagattc ataaatttga gagaggagtt                                           30

<210> SEQ ID NO 644
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
ggttagattc ataaatttga gagaggagtt                                           30

<210> SEQ ID NO 645
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
acttagattc ataaatttga gagaggagtt                                    30

<210> SEQ ID NO 646
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
aattagattc ataaatttga gagaggagtt                                    30

<210> SEQ ID NO 647
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
acttagattc ataaatttga gagaggagtt                                    30

<210> SEQ ID NO 648
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
atttagattc ataaatttga gagaggagtt                                    30

<210> SEQ ID NO 649
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
cacgcgcgtg ggaatgttat aatacgtcag                                    30

<210> SEQ ID NO 650
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
```
actgagcaca tactagagaa agaggagaaa				30

<210> SEQ ID NO 651
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
cagtgagcga gtaacaacta cgctgtttta				30

<210> SEQ ID NO 652
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
cagtgagcga gtaacaacta cgctgtttta				30

<210> SEQ ID NO 653
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
atgtgagcgg ataacactat aattaataga			30

<210> SEQ ID NO 654
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
atgtgagcgg ataacactat aattaataga			30

<210> SEQ ID NO 655
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
atttcatgat gatacgtgag cggatagaag			30

<210> SEQ ID NO 656
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 656
ttgtgagcga gtggcaccat taagtacgta                                    30

<210> SEQ ID NO 657
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
ttgtgagcga gtgacaccat taagtacgta                                    30

<210> SEQ ID NO 658
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
ttgtgagcga gtaacaccat taagtacgta                                    30

<210> SEQ ID NO 659
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
ttgtgagcga gtaacaccat taagtacgta                                    30

<210> SEQ ID NO 660
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
agttggcaca gatttcgctt tatctttttt                                    30

<210> SEQ ID NO 661
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
tggaattgtg agcggataac aattaagctt                                    30
```

<210> SEQ ID NO 662
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 662
agtttgttta aacaacaaac taataggtga          30

<210> SEQ ID NO 663
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 663
aatgtgtgta attgtgagcg gataacaatt          30

<210> SEQ ID NO 664
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 664 atagggaat tgtgagcgga taacaattcc           30

<210> SEQ ID NO 665
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 665 atagggaat tgtgagcgga taacaattcc           30

<210> SEQ ID NO 666
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 666 atagggaat tgtgagcgga taacaattcc           30

<210> SEQ ID NO 667
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 667 atagggaat tgtgagcgga taacaattcc                                30

<210> SEQ ID NO 668
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
aaacaaacaa acaaaaaaaa aaaaaaaaaa                                30

<210> SEQ ID NO 669
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
atactttaac gtcaaggaga aaaaactata                                30

<210> SEQ ID NO 670
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
tagatacaat tctattaccc ccatccatac                                30

<210> SEQ ID NO 671
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
ttagtgaacc gtcagatcac tagtctgcag                                30

<210> SEQ ID NO 672
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
ttagtgaacc gtcagatcac tagtctgcag                                30

<210> SEQ ID NO 673
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 673
ggaaaggacg aaacaccgac tagtctgcag                                              30

<210> SEQ ID NO 674
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
attgtttgtg tattttagac tagtctgcag                                              30

<210> SEQ ID NO 675
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
attgtttgtg tattttagac tagtctgcag                                              30

<210> SEQ ID NO 676
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
attgtttgtg tattttagac tagtctgcag                                              30

<210> SEQ ID NO 677
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
ttagtgaacc gtcagatcac tagtctgcag                                              30

<210> SEQ ID NO 678
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
tgttatagtc gaatacctct ggcggtgata                                              30
```

<210> SEQ ID NO 679
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 679
attacaaact ttcttgtata gatttaacgt                                    30

<210> SEQ ID NO 680
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 680
tttcttgtat agatttacaa tgtatcttgt                                    30

<210> SEQ ID NO 681
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 681
tttcttgtag atacttacaa tgtatcttgt                                    30

<210> SEQ ID NO 682
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 682
ttttggtaca ctccctatca gtgatagaga                                    30

<210> SEQ ID NO 683
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 683 cttttggta cactacctct ggcggtgata                                     30

<210> SEQ ID NO 684
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 684
actctcggca tggacgagct gtacaagtaa                              30

<210> SEQ ID NO 685
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
ttctcgttcg actcatagct gaacacaaca                              30

<210> SEQ ID NO 686
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
ggaattgtga gcgctcataa ttggatccgg                              30

<210> SEQ ID NO 687
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
ggaattgtga gctacagtcg tcggatccgg                              30

<210> SEQ ID NO 688
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
ggaattgtga acgctcataa ttggatccgg                              30

<210> SEQ ID NO 689
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
ggaattgtga actacagtcg tcggatccgg                              30

<210> SEQ ID NO 690
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
taaattgtga acgctcataa ttggatccgg                                    30

<210> SEQ ID NO 691
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
gaaattgtaa gcgcttacaa ttggatccgg                                    30

<210> SEQ ID NO 692
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
gaaattgtaa gcgcttacaa ttggatccgg                                    30

<210> SEQ ID NO 693
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
ggaattgtaa gcgcttacaa ttggatccgg                                    30

<210> SEQ ID NO 694
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
gccaaattaa acaggattaa caggatccgg                                    30

<210> SEQ ID NO 695
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
gccaaattaa acaggattaa caggatccgg                                    30
```

```
<210> SEQ ID NO 696
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
gccaaattaa acaggattaa caggatccgg                                       30

<210> SEQ ID NO 697
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
gccaaattaa acaggattaa caggatccgg                                       30

<210> SEQ ID NO 698
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
gccaaattaa acaggattaa caggatccgg                                       30

<210> SEQ ID NO 699
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
gccaaattaa acaggattaa caggatccgg                                       30

<210> SEQ ID NO 700
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
gccaaattaa acaggattaa caggatccgg                                       30

<210> SEQ ID NO 701
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 701
gaaattgtaa gcgcttacaa ttggatccgg                                              30

<210> SEQ ID NO 702
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
taaattgtaa gcgcttacaa ttggatccgg                                              30

<210> SEQ ID NO 703
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
gtaattgtaa gcgcttacaa ttggatccgg                                              30

<210> SEQ ID NO 704
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
tcaattgtaa gcgcttacaa ttggatccgg                                              30

<210> SEQ ID NO 705
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
aaaattgtaa gcgcttacaa ttggatccgg                                              30

<210> SEQ ID NO 706
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
caaattgtaa gcgcttacaa ttggatccgg                                              30

<210> SEQ ID NO 707
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
gaaattgtaa gcgcttacaa ttggatccgg                                    30

<210> SEQ ID NO 708
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
taaattgtaa gcgcttacaa ttggatccgg                                    30

<210> SEQ ID NO 709
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
gtaattgtaa gcgcttacaa ttggatccgg                                    30

<210> SEQ ID NO 710
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
tcaattgtaa gcgcttacaa ttggatccgg                                    30

<210> SEQ ID NO 711
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
aaaattgtaa gcgcttacaa ttggatccgg                                    30

<210> SEQ ID NO 712
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
```

| caaattgtaa gcgcttacaa ttggatccgg | 30 |

<210> SEQ ID NO 713
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713

| gaaattgtaa gcgcttacaa ttggatccgg | 30 |

<210> SEQ ID NO 714
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714

| taaattgtaa gcgcttacaa ttggatccgg | 30 |

<210> SEQ ID NO 715
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715

| gtaattgtaa gcgcttacaa ttggatccgg | 30 |

<210> SEQ ID NO 716
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716

| tcaattgtaa gcgcttacaa ttggatccgg | 30 |

<210> SEQ ID NO 717
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717

| aaaattgtaa gcgcttacaa ttggatccgg | 30 |

<210> SEQ ID NO 718
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 718
caaattgtaa gcgcttacaa ttggatccgg                                          30

<210> SEQ ID NO 719
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 719
gaaattgtaa gcgcttacaa ttggatccgg                                          30

<210> SEQ ID NO 720
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 720
taaattgtaa gcgcttacaa ttggatccgg                                          30

<210> SEQ ID NO 721
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 721
gtaattgtaa gcgcttacaa ttggatccgg                                          30

<210> SEQ ID NO 722
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 722
tcaattgtaa gcgcttacaa ttggatccgg                                          30

<210> SEQ ID NO 723
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 723
aaaattgtaa gcgcttacaa ttggatccgg                                          30

<210> SEQ ID NO 724

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
caaattgtaa gcgcttacaa ttggatccgg                                      30

<210> SEQ ID NO 725
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
gaaattgtaa gcgcttacaa ttggatccgg                                      30

<210> SEQ ID NO 726
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
taaattgtaa gcgcttacaa ttggatccgg                                      30

<210> SEQ ID NO 727
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
gtaattgtaa gcgcttacaa ttggatccgg                                      30

<210> SEQ ID NO 728
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
tcaattgtaa gcgcttacaa ttggatccgg                                      30

<210> SEQ ID NO 729
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
```
aaaattgtaa gcgcttacaa ttggatccgg                                    30

<210> SEQ ID NO 730
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
caaattgtaa gcgcttacaa ttggatccgg                                    30

<210> SEQ ID NO 731
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 731
gaaattgtaa gcgcttacaa ttggatccgg                                    30

<210> SEQ ID NO 732
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
taaattgtaa gcgcttacaa ttggatccgg                                    30

<210> SEQ ID NO 733
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
gtaattgtaa gcgcttacaa ttggatccgg                                    30

<210> SEQ ID NO 734
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
tcaattgtaa gcgcttacaa ttggatccgg                                    30

<210> SEQ ID NO 735
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 735
aaaattgtaa gcgcttacaa ttggatccgg                                    30

<210> SEQ ID NO 736
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 736
caaattgtaa gcgcttacaa ttggatccgg                                    30

<210> SEQ ID NO 737
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
gaaattgtaa gcgcttacaa ttggatccgg                                    30

<210> SEQ ID NO 738
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
taaattgtaa gcgcttacaa ttggatccgg                                    30

<210> SEQ ID NO 739
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
gtaattgtaa gcgcttacaa ttggatccgg                                    30

<210> SEQ ID NO 740
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740
tcaattgtaa gcgcttacaa ttggatccgg                                    30
```

```
<210> SEQ ID NO 741
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
aaaattgtaa gcgcttacaa ttggatccgg                                        30

<210> SEQ ID NO 742
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742
caaattgtaa gcgcttacaa ttggatccgg                                        30

<210> SEQ ID NO 743
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
gccaaattaa acaggattaa caggatccgg                                        30

<210> SEQ ID NO 744
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
gccaaattaa acaggattaa caggatccgg                                        30

<210> SEQ ID NO 745
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
caaattatga gcgctcacaa ttggatccgg                                        30

<210> SEQ ID NO 746
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 746
tgatagagat tccctatcag tgatagagat                                30

<210> SEQ ID NO 747
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
gttctttaat tatttaagtg ttctttaatt                                30

<210> SEQ ID NO 748
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
gttctttaat tatttaagtg ttctttaatt                                30

<210> SEQ ID NO 749
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
cgtgcgtgtt gataacaccg tgcgtgttga                                30

<210> SEQ ID NO 750
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
gtgttcttta atatttaagt gttctttaat                                30

<210> SEQ ID NO 751
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
ggaattgtga gcggataaca atttcacaca                                30

<210> SEQ ID NO 752
<211> LENGTH: 30
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic oligonucleotide"

<400> SEQUENCE: 752
gttacgttta tcgcggtgat tgttacttat                                       30

<210> SEQ ID NO 753
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753
gcaaaataaa atggaatgat gaaactgggt                                       30

<210> SEQ ID NO 754
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 754
aacgcgcggg gagaggcggt ttgcgtattg                                       30

<210> SEQ ID NO 755
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
gtgttgatgc ttttatcacc gccagtggta                                       30

<210> SEQ ID NO 756
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
agtgtgtgga attgtgagcg gataacaatt                                       30

<210> SEQ ID NO 757
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
acatcttaaa agttttagta tcatattcgt                                       30
```

<210> SEQ ID NO 758
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
ctgaaagcgc ataccgctat ggaggggtt                                            30

<210> SEQ ID NO 759
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
tattttacct ctggcggtga taatggttgc                                           30

<210> SEQ ID NO 760
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
atttataaat agtggtgata gatttaacgt                                           30

<210> SEQ ID NO 761
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
atttataaat agtggtgata gatttaacgt                                           30

<210> SEQ ID NO 762
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
gaaatctggc agttttggt acacgaaagc                                            30

<210> SEQ ID NO 763
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
tgccagttct ggcaggtcta aaaagtgttc                                      30

<210> SEQ ID NO 764
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
cacagaactt gcatttatat aaagggaaag                                      30

<210> SEQ ID NO 765
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
agttggcaca gatttcgctt tatctttttt                                      30

<210> SEQ ID NO 766
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
agcgctcaca atttaatacg actcactata                                      30

<210> SEQ ID NO 767
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
ggaattgtga gcggataaca atttcacaca                                      30

<210> SEQ ID NO 768
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
ggaattgtga gcggataaca atttcacaca                                      30

<210> SEQ ID NO 769
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
ggaattgtga gcggataaca atttcacaca                                          30

<210> SEQ ID NO 770
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
agaactgtaa tccctatcag tgatagagat                                          30

<210> SEQ ID NO 771
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
tgttgattta tctaacaccg tgcgtgttga                                          30

<210> SEQ ID NO 772
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 772
acaccgtgcg tgttgatata gtcgaataaa                                          30

<210> SEQ ID NO 773
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 773
ggttcttttt ggtacctctg gcggtgataa                                          30

<210> SEQ ID NO 774
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
tgtaggatcg tacaggtata aattcttcag                                          30
```

<210> SEQ ID NO 775
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 775
ctatctcatt tgctagtata gtcgaataaa                                      30

<210> SEQ ID NO 776
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 776
aattgtgagc ggataacaat ttcacacaga                                      30

<210> SEQ ID NO 777
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
gttacgttta tcgcggtgat tgttacttat                                      30

<210> SEQ ID NO 778
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
acggtgacct agatctccga tactgagcac                                      30

<210> SEQ ID NO 779
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
tggaattgtg agcggataaa atttcacaca                                      30

<210> SEQ ID NO 780
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 780
tagtagataa tttaagtgtt ctttaatttc                                30

<210> SEQ ID NO 781
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
aacaaaaaaa cggatcctct agttgcggcc                                30

<210> SEQ ID NO 782
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
ataaatgctt gactctgtag cgggaaggcg                                30

<210> SEQ ID NO 783
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
atttcatgat gatacgtgag cggatagaag                                30

<210> SEQ ID NO 784
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
gggacacaaa catcaagagg atatgagatt                                30

<210> SEQ ID NO 785
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
gtcaaaatga ccgaaacggg tggtaacttc                                30

<210> SEQ ID NO 786
<211> LENGTH: 30

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
agtaatctta tcgccagttt ggtctggtca                                  30

<210> SEQ ID NO 787
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
agtaatctta tcgccagttt ggtctggtca                                  30

<210> SEQ ID NO 788
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788
aattctgaac aacatccgta ctcttcgtgc                                  30

<210> SEQ ID NO 789
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
cgatctattc acctgaaaga gaaataaaaa                                  30

<210> SEQ ID NO 790
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
aaacgttagt ttgaatggaa agatgcctgc                                  30

<210> SEQ ID NO 791
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
```
acaggaaaca gctatgacca tgattacgcc 30

<210> SEQ ID NO 792
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 792
gttcactcta taccgctgaa ggtgtaatgg 30

<210> SEQ ID NO 793
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 793
tagtttataa tttaagtgtt ctttaatttc 30

<210> SEQ ID NO 794
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 794
gaaaatgtga gcgagtaaca acctcacaca 30

<210> SEQ ID NO 795
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 795
ttttatcgca actctctact gtttctccat 30

<210> SEQ ID NO 796
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 796
gtttctccat tactagagaa agaggggaca 30

<210> SEQ ID NO 797
<211> LENGTH: 30
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 797
aataactctg atagtgctag tgtagatctc                                          30

<210> SEQ ID NO 798
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798
caccttcggg tgggcctttc tgcgtttata                                          30

<210> SEQ ID NO 799
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
caccttcggg tgggcctttc tgcgtttata                                          30

<210> SEQ ID NO 800
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
gtgttgacta ttttacctct ggcggtgata                                          30

<210> SEQ ID NO 801
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
cgaaacggga accctatatt gatctctact                                          30

<210> SEQ ID NO 802
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
accgttaaga accatatcca agaatcaaaa                                          30

<210> SEQ ID NO 803
```

```
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
accgttaaga accatatcca agaatcaaaa                                        30

<210> SEQ ID NO 804
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 804
cacaaataca cacactaaat taataactag                                        30

<210> SEQ ID NO 805
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
atacggtcaa cgaactataa ttaactaaac                                        30

<210> SEQ ID NO 806
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
tagatacaat tctattaccc ccatccatac                                        30

<210> SEQ ID NO 807
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
ggggcgaggg ccccgcctcc ggaggcgggg                                        30

<210> SEQ ID NO 808
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
```
gaggggacgg ctccggcccc ggggccggag         30

<210> SEQ ID NO 809
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
ggggcgaggg ctccggcccc ggggccggag         30

<210> SEQ ID NO 810
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
gaggggacgg ccccgcctcc ggaggcgggg         30

<210> SEQ ID NO 811
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
tttgaattca ccggtcgcca ccatggcc           28

<210> SEQ ID NO 812
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
ttttccggac tacaggaaca ggtggtgg           28

<210> SEQ ID NO 813
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
tttgctagca ccggtcgcca ccatggc            27

<210> SEQ ID NO 814
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 814
tttgcggccg cttagaaggg caccacggag                                      30

<210> SEQ ID NO 815
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 815
ggccgcaaaa agcactctga tttgacaatt aaagcactct gatttgacaa               50

<210> SEQ ID NO 816
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 816
ctttaattgt caaatcagag tgctttaatt gtcaaatcag agtgctt                  47

<210> SEQ ID NO 817
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
ttaaagcact ctgatttgac aattaaagca ctctgatttg acaattaa                 48

<210> SEQ ID NO 818
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
agctttaatt gtcaaatcag agtgctttaa ttgtcaaatc agagtg                   46

<210> SEQ ID NO 819
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
ggccgcaaat caacatcagt ctgataagct atcaacatca gtctgataag               50
```

```
<210> SEQ ID NO 820
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
tgatagctta tcagactgat gttgatagct tatcagactg atgttgattt gc          52

<210> SEQ ID NO 821
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
ctatcaacat cagtctgata agctatcaac atcagtctga taagctaa              48

<210> SEQ ID NO 822
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
agctttagct tatcagactg atgttgatag cttatcagac tgatgt                46

<210> SEQ ID NO 823
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
ccggataact acctgcactg taagcacttt gctacctgca ctgtaagcac            50

<210> SEQ ID NO 824
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
agcaaagtgc ttacagtgca ggtagcaaag tgcttacagt gcaggtagtt at         52

<210> SEQ ID NO 825
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 825
tttgctacct gcactgtaag cactttgcta cctgcactgt aagcactttg a          51

<210> SEQ ID NO 826
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
gatctcaaag tgcttacagt gcaggtagca aagtgcttac agtgcaggt             49

<210> SEQ ID NO 827
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
gatcttaact tccagtcgag gatgtttaca cttccagtcg aggatgttta ca         52

<210> SEQ ID NO 828
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
tggaagtgta aacatcctcg actggaagtg taaacatcct cgactggaag ttaa       54

<210> SEQ ID NO 829
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
cttccagtcg aggatgttta cacttccagt cgaggatgtt tacaggcgcg cct        53

<210> SEQ ID NO 830
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
ctagaggcgc gcctgtaaac atcctcgact ggaagtgtaa acatcctcga c          51

<210> SEQ ID NO 831
<211> LENGTH: 54
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 831
ggccgctaaa ccatctttac cagacagtgt taccatcttt accagacagt gtta          54

<210> SEQ ID NO 832
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
agatggtaac actgtctggt aaagatggta acactgtctg gtaaagatgg tttagc        56

<210> SEQ ID NO 833
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
ccatctttac cagacagtgt taccatcttt accagacagt gttaat                   46

<210> SEQ ID NO 834
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
cgattaacac tgtctggtaa agatggtaac actgtctggt aa                       42

<210> SEQ ID NO 835
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
cgattccata aagtaggaaa cactacatcc ataaagtagg aaacacta                 48

<210> SEQ ID NO 836
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
tggatgtagt gtttcctact ttatggatgt agtgtttcct actttatgga at            52
```

<210> SEQ ID NO 837
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 837
catccataaa gtaggaaaca ctacatccat aaagtaggaa acactacaa         49

<210> SEQ ID NO 838
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 838
agctttgtag tgtttcctac tttatggatg tagtgtttcc tacttta           47

<210> SEQ ID NO 839
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 839
agcttaaccc atggaattca gttctcaaac ccatggaatt cagttctcaa ac      52

<210> SEQ ID NO 840
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 840
ccatgggttt gagaactgaa ttccatgggt ttgagaactg aattccatgg gtta    54

<210> SEQ ID NO 841
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 841
ccatggaatt cagttctcaa acccatggaa ttcagttctc ag                42

<210> SEQ ID NO 842
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 842
tcgactgaga actgaattcc atgggtttga gaactgaatt                             40

<210> SEQ ID NO 843
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
ttgctagcac catgtctaga ctggacaag                                         29

<210> SEQ ID NO 844
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
tttgcggccg cttacccggg gagcatg                                           27

<210> SEQ ID NO 845
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
tttgaattca ccatgtctag actggacaag                                        30

<210> SEQ ID NO 846
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
tttagatctt tacccgggga gcatgtcaag                                        30

<210> SEQ ID NO 847
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
ttgctagcga ggtaccctcc cac                                               23

<210> SEQ ID NO 848
<211> LENGTH: 30
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
tttgcggccg ctcaaacctt cctcttcttc                                  30

<210> SEQ ID NO 849
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
tttgaattcg aggtaccctc ccaccatg                                    28

<210> SEQ ID NO 850
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 850
tttagatctt caaaccttcc tcttcttctt agg                              33

<210> SEQ ID NO 851
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 851
gaagcgcgcg gcgggcggga gtcgagtcgc tgcgttgcct tcgcc                 45

<210> SEQ ID NO 852
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
tttgctagct taccggtcgc caccatggtg agcaag                           36

<210> SEQ ID NO 853
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
ttaaagcttt gcggccgctt acttgtacag ctcgtccatg ccg                   43
```

<210> SEQ ID NO 854
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 854
tttggcgcgc cgaggtgagt atgtgctcgc                                    30

<210> SEQ ID NO 855
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
ttttctagac cctgaggaaa aaaaggaaa caattg                              36

<210> SEQ ID NO 856
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
tttaagcttg aggtgagtat gtgctcgctt cg                                 32

<210> SEQ ID NO 857
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
tttgtcgacc cctgaggaaa aaaaggaaa caattg                              36

<210> SEQ ID NO 858
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
cccgcttgaa gtctttaatt aaaccgcttg aagtctttaa ttaaaccgct tgaagtct     58

<210> SEQ ID NO 859
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 859
ccgggtttaa ttaaagactt caagcggttt aattaaagac ttcaagcggt ttaattaaag    60
acttcaagcg gggtac    76

<210> SEQ ID NO 860
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
tttgctagcc gccaccatgg acgggtccgg g    31

<210> SEQ ID NO 861
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 861
tttgcggccg ctcagcccat cttcttccag    30

<210> SEQ ID NO 862
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
tttgaattcg ctagcatgaa accagtaacg ttatacg    37

<210> SEQ ID NO 863
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
ttttccggat taaagctttt gcggccgctt actagtaacc ttcctcttct tcttag    56

<210> SEQ ID NO 864
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
tttactagtg gatctggcgc caccaacttc tctctgctga agcaggccgg cgacgtgagg    60
agaacccagg cccaatggcg cacgctggga gaacag    96

<210> SEQ ID NO 865
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
tttgcggccg ctcacttgtg gcccagatag gcaccc                              36

<210> SEQ ID NO 866
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
tcattaggat ccaccggtcg ccaccatg                                       28

<210> SEQ ID NO 867
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 867
tcattatgta cagctcgtcc atgccgagag                                     30

<210> SEQ ID NO 868
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 868
gcatgcacag ataaccatct gcggtgataa attatctctg gcggtgttga cataaatacc    60
actggcggtt ataatgagca catcagcagg                                     90

<210> SEQ ID NO 869
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide "

<400> SEQUENCE: 869
gtatgcaaag ga                                                        12

<210> SEQ ID NO 870
<211> LENGTH: 20
<212> TYPE: DNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 870 tatatata tatatata                                                    20

<210> SEQ ID NO 871
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871 tatatata tatata                                                      18

<210> SEQ ID NO 872
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 872
cccccccccc                                                           10

<210> SEQ ID NO 873
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
cccccccccc cc                                                        12
```

MULTIPLE INPUT BIOLOGIC CLASSIFIER CIRCUITS FOR CELLS

CROSS-REFERENCE TO RELATED APPLICATIONS

This is a National Phase Application filed under 35 U.S.C. 371 as a national stage of PCT/US2011/045038, filed on 22 Jul. 2011, an application claiming the benefit under 35 U.S.C. §119(e) from U.S. Provisional Patent Application No. 61/366,787, filed on Jul. 22, 2010, the entire content of each of which is hereby incorporated by reference in its entirety.

GOVERNMENT SUPPORT

This invention was made with Government support under NIGMS Grant GM068763 from the National Institutes of Health and grant W81XWH-09-1-0240 BC085163 from the Department of Defense Congressionally Directed Medical Research Program (CDMRP). The Government has certain rights in the invention.

FIELD OF THE INVENTION

The present invention relates to multi-input engineered genetic circuits for classifying cells.

The Sequence Listing submitted in text format (.txt) filed on Jan. 18, 2013, named "50295PCT.txt", (created on Jan. 8, 2013, 222 KB), is incorporated herein by reference.

BACKGROUND

An important feature of biological pathways is their two-way interaction with the cellular environment in which they operate. Such interaction usually involves (1) sensing of relevant input conditions in the cell, (2) processing those inputs to determine whether and which action to take; and (3) producing a biologically-active output to actuate a physiological effect in the cell. Some engineered analogues of natural pathways with sensing, computational and actuation functionalities (1, 2) have been developed that can augment endogenous processes and enable rational manipulation and control of biological systems. While reporter constructs (3) that transduce cellular inputs into a detectable output, and tissue-specific transgenes controlled transcriptionally and/or posttranscriptionally (4-6) lack complexity, they represent useful components for the development of synthetic circuits. Some synthetic circuits have demonstrated programmed dynamic behavior in cells (oscillators (7-10), memory (11-14), spatial patterns (15), cascades (16) and pulse generators (17)), digital and analog computations (18-20), and complex biosynthetic pathways (21), but the interaction of these circuits with the cellular context has been limited (22, 23). Similarly, molecular network prototypes have demonstrated sensing, computation and actuation (24-28) in cell-free environments, but their utility in cellular contexts has been inadequate.

Hence, engineered biological systems described thus far have lacked the necessary complexity, sophistication, and discriminatory capacities to be functional and responsive to the multitude of inputs that are found in the normal, unmanipulated cellular millieu.

SUMMARY OF THE INVENTION

Described herein are multi-input biological classifier circuits and methods of use thereof developed for processing molecular information in mammalian cells. These classifier circuits use transcriptional and posttranscriptional regulation in order to classify the status of a cell, i.e., determine whether a cell is in a specific state of interest. The biological classifier circuits described herein implement this task by interrogating the state of the cell through simultaneous assessment of multiple inputs, such as the expression levels of a subset of predefined markers, for example, endogenous, mature microRNAs. The classifier circuits described herein are designed to 'compute' whether the expression profile of the markers matches a pre-determined reference profile that characterizes the specific cell state that the classifier circuits are intended to detect. If so, the classifier circuits produce a biological response, such as expression of a reporter molecule. These biological circuits are termed herein as 'classifiers' because they classify individual cells into a number of categories based on processing a multitude of inputs indicative of the cells' internal states, in a manner similar to current practices for characterizing bulk tissue (e.g., biopsy samples) using gene array analysis and computer algorithms (31).

The biological classifier circuits described herein can be used in a variety of applications, such as those requiring precise classification and identification of cell types. In some aspects, described herein are biological classifier circuits for use as therapeutic agents, for example, in highly precise and selective cancer therapy. Many mainstream and experimental drugs exhibit a degree of selectivity toward cancer cells by relying on individual cancer markers (32). However, cancer cells exhibit a complex set of conditions deviating from the normal state of their progenitor tissue (33, 34), and using a single marker to distinguish them from healthy cells is rarely sufficient and often results in harmful side-effects (35). Therefore, sensing and integration of information from multiple markers by a therapeutic agent is crucial for creating next-generation treatments, and for use in a variety of applications, which can include, but are not limited to, identification, sorting, or targeting of stem cells from heterogenous populations of differentiated cells; identification, sorting, or targeting of specific cell types for the treatments of various diseases, such as cancer; identification, sorting, targeting, or detection of cell types at various developmental stages; drug screening assays; and identification, sorting, targeting, or detection of cell types in experimental models to be used in tracking therapeutic treatment responses to a drug or other molecule, such as during a tumor treatment. For example, described herein is an exemplary biological classifier circuit tested in human cell culture that acts as a programmed therapeutic agent that, via identification and processing of a combination of input markers, selectively identifies and triggers apoptosis in a cancer cell line, but not in healthy cells.

Accordingly, provided herein are high-input detector modules for classifying a cell status based on detecting whether an input microRNA is expressed at a specific level or higher than a reference level. Such high-input detector modules comprise a constitutive or inducible promoter sequence operably linked to: (i) a repressor sequence, which encodes a repressor product, and (ii) a sequence which encodes one or more microRNA target sequences, such that the one or more microRNA target sequences comprise target sequences of the one or more input microRNAs the module is designed to detect. In some embodiments, such high-input detector modules can further comprise a repressible promoter sequence operably linked to an output sequence encoding an ouput product, wherein the repressor product is specific for the repressible promoter sequence.

In some embodiments of the high-input detector modules described herein, the high-input detector module can further comprise one or more regulatory units. Such regulatory units comprise a constitutive or inducible promoter sequence operably linked to: (i) a sequence that encodes for a transcriptional activator product, and (ii) a sequence encoding one or more microRNA target sequences, such that the transcriptional activator product activates the inducible promoter sequence operably linked to the repressor sequence and the sequence encoding the one or more microRNA target sequences. In such embodiments, the sequences encoding one or more microRNA target sequences are the same throughout all the units and components of the high-input detector module, i.e., each unit and component of the high-input detector module detects the same input microRNA(s). In some embodiments, the inducible promoter of a second regulatory unit is activated by the transcriptional activator encoded by a first regulatory unit, such that the repressor product of the high-input detector module is expressed only when the transcriptional activator of the second regulatory unit is expressed following activation by the transcriptional activator encoded by the first regulatory unit. In such embodiments, the sequences encoding one or more microRNA target sequences are the same throughout all the units and components of the high-input detector module, i.e., each unit and component of the high-input detector module detects the same input microRNA(s).

In some aspects, described herein are multiple-input biological classifier circuits for classifying a cell status, based on detecting in parallel an expression pattern of a subset of at least two different input microRNAs, each of which is expressed at a specific level or higher than a reference level, such that the biological classifier circuit circuit comprises at least two high-input detector modules as described herein.

In some aspects, described herein are multiple-input biological classifier circuits for classifying a cell status based on detecting in parallel an expression pattern of a subset of at least three different input microRNAs, each of which is expressed at a lower level than a reference expression level. In such aspects, the biological classifier circuit comprises one or more low-input detector modules for detecting the at least three input microRNAs expressed at a lower level than a reference expression level, where the low-input detector module comprises a constitutive or repressible promoter sequence operably linked to: (i) an output sequence that encodes an output product, and (ii) a sequence encoding at least one microRNA target sequence specific for the at least one of the at least three input microRNA having a lower expression level than a reference expression level; and where expression of the output product classifies a cell status.

In some aspects, described herein are multiple-input biological classifier circuits for classifying a cell status based on detecting in parallel an expression pattern of a subset of at least two different input microRNAs, where the biological classifier circuit comprises at least two input detector modules. In such aspects, expression of at least two different input microRNAs are detected by at least two types of input detector modules, such that at least one of the at least two different input microRNAs has a lower expression level than a reference expression level, and at least one of the at least two different input microRNAs has a higher expression level than a reference expression level.

In such multiple-input biological classifier circuits comprising at least two input detector modules, one of the at least two input detector modules is designated a low-input detector module, for detecting the at least one input microRNA expressed at a lower level than a reference expression level. Such low-input detector modules comprise a repressible promoter sequence operably linked to: (i) an output sequence, which encodes an output product, and (ii) a sequence encoding at least one microRNA target sequence specific for the at least one input microRNA having a lower expression level than a reference expression level. In such multiple-input biological classifier circuits, one of the at least two input detector modules is designated a high-input detector module for detecting the at least one input microRNA expressed at a higher level than a reference expression level. Such high-input detector module comprise a constitutive or inducible promoter sequence operably linked to (i) a repressor sequence that encodes for a repressor product, and (ii) a sequence encoding for a microRNA target sequence specific for the at least one input microRNA having a higher expression level than a reference expression level. In such circuits, the repressor product represses the repressible promoter of the low-input detector module. In such circuits, each microRNA target sequence encoded by the low-input detector module(s) and the high-input detector module(s) is different from each other, and expression of the output product classifies a cell status.

In some aspects, multiple-input biological classifier circuits are provided for classifying a cell status based on detecting in parallel an expression pattern of a subset of at least three different input microRNAs. In such aspects, expression of at least three different input microRNAs are detected by at least two input detector modules, such that expression at least one of the three different input microRNAs has a lower expression level than a reference expression level, at least one of the at least three different input microRNAs has a higher expression level than a reference expression level, and wherein one or more of the at least three different input microRNAs has a different expression level (higher or lower) than a reference expression level.

In such multiple-input biological classifier circuits, one of the at least two input detector modules is designated a low-input detector module for detecting each of the different input microRNAs expressed at a lower level than a reference expression level. The low-input detector modules can comprise a repressible promoter sequence operably linked to: (i) an output sequence that encodes an output product and (ii) a sequence encoding one or more microRNA target sequences specific for each of the different input microRNAs having a lower expression level than a reference expression level to be detected. The high-input detector modules can comprise a promoter sequence operably linked to (i) a repressor sequence that encodes for a repressor product and (ii) a sequence encoding a microRNA target sequence, where the microRNA target sequence is specific for one of the different input microRNAs having a higher expression level than a reference expression level, and such that the repressor product represses the repressible promoter of the low-input detector module. In such circuits, each microRNA target sequence encoded by the low-input detector module(s) and the high-input detector module(s) is different from each other, and expression of the output product classifies a cell status. In some circuits, the repressor protein encoded by the high-input detectors are the same, while in other such circuits the repressor protein can be different.

In some embodiments of the multiple-input biological classifier circuits described herein, the promoter sequence operably linked to (i) a repressor sequence and (ii) a sequence encoding a microRNA target sequence, of any of the high-input detector modules, can be an inducible promoter. In some embodiments, such inducible promoters of the high-input detector modules can be activated by a transcriptional activator.

In some embodiments of the multiple-input biological classifier circuits described herein, the high-input detector module can further comprise one or more regulatory units. Such regulatory units comprise a constitutive or inducible promoter sequence operably linked to: (i) a sequence that encodes for a transcriptional activator product, and (ii) a sequence encoding one or more microRNA target sequences, such that the transcriptional activator product activates the inducible promoter sequence operably linked to the repressor sequence and the sequence encoding the one or more microRNA target sequences. In some embodiments, the transcriptional activator encoded by the regulatory unit induces transcription from the promoter sequence operably linked to (i) the repressor sequence and (ii) the sequence encoding the microRNA target sequence of the at least one high-input detector module of the classifier circuit. In such embodiments, the sequences encoding one or more microRNA target sequences are the same throughout all the units and components of the high-input detector module, i.e., each unit and component of the high-input detector module detects the same input microRNA(s).

In some embodiments of the multiple-input biological classifier circuits described herein, the inducible promoter of a second regulatory unit is activated by the transcriptional activator encoded by a first regulatory unit, such that the repressor product of the high-input detector module is expressed only when the transcriptional activator of the second regulatory unit is expressed following activation by the transcriptional activator encoded by the first regulatory unit.

In some embodiments, at least three, at least four, at least five, at least six, at least seven, at least eight, at least nine, at least 10, at least 11, at least 12, at least 13, at least 14, at least 15, at least 16, at least 17, at least 18, at least 19, or at least 20 different input microRNAs are detected by the multiple-input classifier circuit.

In some embodiments, the at least two detector modules comprise at least two, at least three, at least four, at least five, at least six, at least seven, at least eight, at least nine, at least 10, at least 11, at least 12, at least 13, at least 14, at least 15, at least 16, at least 17, at least 18, or at least 19 different high-input detector modules.

In some embodiments, the output sequence of the circuit encoded by a low-input module comprises at least two, at least three, at least four, at least five, at least six, at least seven, at least eight, at least nine, at least 10, at least 11, at least 12, at least 13, at least 14, at least 15, at least 16, at least 17, at least 18, at least 19, or at least 20 different microRNA target sequences. In some embodiments, where the output sequence of the circuit encoded by a high-input module, no target microRNA target sequences are linked to the sequence encoding the output product.

In some embodiments, the repressor sequence of at least one high-input detector module further comprises a sequence encoding a microRNA, such that the microRNA is different from each of the different microRNA inputs detected by the modules of the circuit, and such that the output sequence of the circuit, present in a low-input detector module or in a high-input detector module, further comprises a microRNA target sequence for the microRNA.

In some embodiments of the aspects described herein, the output product is a reporter protein, a transcriptional activator, a transcriptional repressor, a pro-apoptotic protein, a lytic protein, an enzyme, a cytokine, or a cell-surface receptor. In some embodiments, the repressor sequence of at least one high-input detector module further comprises a sequence encoding for a protein or agent that is a functional or physiological inhibitor of the output product of the multiple-input biological classifier circuit.

In other aspects, provided herein are pharmaceutical compositions comprising one or more high-input detector modules and a pharmaceutically acceptable compound.

In other aspects, described herein are pharmaceutical compositions comprising one or more multiple-input biological classifier circuits and a pharmaceutically acceptable compound.

In other aspects, the multiple-input biological classifier circuits described herein are provided for use in identifying a specific target cell, or a cell population in a population of heterogenous cells. In some embodiments of such aspects, the multiple-input biological classifier circuit can be introduced to the heterogenous population of cells using one or more vectors comprising the sequences encoding for the components of the circuits. In some embodiments, the one or more vectors is a lentiviral vector or lentiviral particle. In some embodiments, the cell or population of heterogenous cells is a mammalian cell or a population of heterogenous mammalian cells.

In other aspects, methods are provided for identifying a cell or population of cells based on an expression pattern of at least three different input microRNAs. Such methods comprise introducing any of the high-input detector modules or multiple-input biological classifier circuits described herein into a cell or population of cells, such that expression of an output product by the cell identifies the cell or population of cells. In some embodiments of these aspects, the cell or population of cells is in vitro, ex vivo, or in vivo.

In some aspects, methods are provided for diagnosing a disease or condition in a subject in need thereof. Such methods comprise administering to a subject in need thereof an effective amount of one or more of any of the high-input detector modules or multiple-input biological classifier circuits described herein, wherein expression of one or more output products is indicative that the subject has the disease or condition. In some embodiments of these aspects, the disease or condition can be a cancer, a proliferative disorder, a metabolic disorder, a neurological disorder, an immunological disorder, or an infection.

In some aspects, described herein are methods for treating a disease or condition in a subject in need thereof. Such methods comprise administering to a subject in need thereof an effective amount of one or more of any of the high-input detector modules or multiple-input biological classifier circuits described herein, such that one or more of the output products is a therapeutic agent. In some embodiments of these aspects, the disease or condition can be a cancer, a proliferative disorder, a metabolic disorder, a neurological disorder, an immunological disorder, or an infection.

In some aspects, multiple-input biological classifier circuits are provided for use in diagnosing a disease or condition in a subject in need thereof, such that expression of one or more output products produced by the multiple-input biological classifier circuit is indicative that the subject has the disease or condition. In some embodiments of these aspects, the disease or condition is a cancer, proliferative disorder, metabolic disorder, neurological disorder, immunological disorder, or infection.

In some aspects, provided herein are multiple-input biological classifier circuits for use in treating a disease or condition in a subject in need thereof, such that one or more output products produced by the multiple-input biological classifier circuit is a therapeutic agent. In some embodiments of these aspects, the therapeutic agent is a drug or small molecule that causes cell death or inhibition of cell proliferation. In some embodiments of these aspects, the disease or condition is a cancer, proliferative disorder, metabolic disorder, neurological disorder, immunological disorder, or infection.

BRIEF DESCRIPTION OF THE DRAWINGS

FIG. 1A shows multi-input logic used to selectively identify a specific cell type. FIG. 1B depicts a schematic representation of a HeLa-specific classifier circuit. FIG. 1C shows experimental confirmation of various reporter construct knock-downs by corresponding microRNA markers identified by our bioinformatics analysis in HeLa, HEK293, and MCF7 cell lines. Scatter plots show flow cytometry data measured at 48 hours post-transfection. FIG. 1D depicts the overall knock-down efficiency by the microRNA biomarkers in different cell lines (top). The bars show mean±SD of DsRed/AmCyan values from three independent replicates. The corresponding published microRNA cloning frequencies are shown below, indicating the desired inverse relationship between those frequencies and DsRed reporter levels.

FIG. 2A shows an abstract network diagram for sensing HeLa-low microRNA, whereby an output is directly targeted for degradation by the marker. FIG. 2B depicts a detailed circuit diagram for sensing HeLa-low markers. Output mRNA is knocked down by a corresponding marker via a target sequence fused in this mRNA 3'-UTR. DNA and RNA species are indicated. FIG. 2C shows a coherent type 2 feed-forward motif for sensing HeLa-high microRNAs that enables output expression by down-regulating a repressor (i.e., 'double-inversion' module). FIG. 2D depicts a detailed circuit diagram for a HeLa-high marker sensor. The genes, their promoters and microRNA targets used in module construction are indicated. FIG. 2E depicts a representative schematic of a complete classifier circuit. For simplicity, four adjacent microRNA target sites are shown as a wider box and DNA and RNA species are lumped together as in FIG. 2D. Two double inversion modules for HeLa high markers are shown and rtTA crosstalk is indicated with dotted lines. The logic computed by this classifier circuit is shown. FIG. 2F depicts how, in some embodiments, the circuit of FIG. 2E can be modified to result in apoptotic output production.

FIG. 3A shows that four versions of the circuit with specific microRNA regulatory links interrupted (denoted by stars) can be used to emulate the various combinations of microRNA input levels. FIG. 3B shows output values measured for all 32 input combinations (Tables 52-54 describe the constructs and experimental conditions). The images are overlays of DsRed and AmCyan channels taken ~48 h post-transfection. The bar charts show mean±SD of normalized DsRed intensity obtained from three independent replicates measured by fluorescence-activated cell sorting (FACS) ~48 h post-transfection.

FIG. 5A shows schematics of the circuits and controls. O1, CAGop-driven DsRed with target sites for HeLa-low microRNAs (miRs-HeLa-low). O2, CAGop-driven DsRed without microRNA target sites. R1, CAGop-driven DsRed constitutively repressed by rtTA-activated LacI and engineered intronic miR-FF4 with HeLa-low targets. R2, similar to R1 but without the HeLa-low targets. C1, full classifier circuit. C2, circuit variant without HeLa-low targets. FIG. 5B shows experimental results from a classifier circuit used to distinguish and kill HeLa cells. In addition to the circuits and controls (FIG. 5A) the cells were also transfected with marker CAG-AmCyan. The constructs used in each case are indicated on the X-axis. Each bar represents the mean±SD of DsRed/AmCyan value with three independent replicates measured by FACS 48 h post-transfection. All values are normalized to constitutive output level (O1) in HeLa cells. Representative images of the cell culture obtained in these experiments are overlays of the DsRed and AmCyan channels captured 48 h post-transfection. The constructs used are indicated above the images. FIGS. 5C and 5D show apoptosis assays in HeLa (5C) and HEK293 (5D) cell lines. A complete apoptosis-inducing classifier circuit ('Circuit', FIG. 2F) was co-transfected with the AmCyan marker to determine cell survival due to selective hBax activation. Each bar in the charts represents the mean±SD of the percentage of AmCyan$^+$ cells with three independent replicates measured by FACS 4 days post transfection. The histograms compare gated AmCyan$^+$ populations obtained in FACS measurements from pooled replicas after examining equal number of events in the different pools. FIG. 5E shows a comparison of circuit killing efficiency for two cell lines.

FIG. 6A shows fluorescent reporter assays. The scheme on the left illustrates experimental set-up and data analysis. The histograms on the right show contribution of the two cell types, HeLa and HEK-Cerulean, to the DsRed$^+$ cell population. The inset shows the fraction of DsRed$^+$ cells either transfected with the circuit or with constitutively-repressed output, relative to the constitutively expressed output for each cell type. FIG. 6B shows apoptotic assays in a cell mixture. The scheme at the top of the panel illustrates experimental set-up and data analysis. The scatter plots at the bottom show the contributions of the HeLa-EYFP and HEK293-Cerulean cells to the DsRed$^+$ cell population considered to be surviving cells. The bar chart shows the fraction of surviving cells either transfected with the circuit or with the constitutively-expressed hBax, relative to the number of DsRed$^+$ cells measured without hBax for each cell type.

FIG. 8A shows a simplified dose response of an output to changing concentrations of a repressor in a HeLa-high marker sensor. FIG. 8B depicts a fit of the data shown in FIG. 9A to an exponential output restoration function. The lower and upper bounds of the output amplitude ($O_{OFF}$ and $O_{ON}$) as well as the theoretical upper limit on output intensity ($O_s$) are shown. FIG. 8C shows a dose response of a repressor concentration to changing microRNA input levels. Lower and upper bounds of the repressor concentration are shown. FIG. 8D is a contour plot of the mapping between two hypothetical HeLa-high markers A and B and the output of a two-input circuit that uses them as inputs. Marker concentrations are normalized to their levels in HeLa cells denoted as $A_{HeLa}$ and $B_{HeLa}$ that result in 99% output repression relief. FIG. 8E depicts plots showing predicted output levels in different cell lines from different combinations of microRNA markers relative to the output in HeLa cells. Each marker sensor is assumed to be tuned to relieve 99% output repression in HeLa cells by its cognate input marker. The numbers on the axes are given in cloning frequency (CF) units. Each dot represents one cell type and the contour lines show input combinations that result in 20% output compared to HeLa cells. Dots above the contour line are cell types that generate more than 20% of HeLa output and they represent 'false-positive' cell types for this specific circuit configuration. FIG. 8F shows an analysis of additional microRNA markers not expressed in HeLa cells but highly expressed in cells that can be misidentified based on the profile composed of only miR-21 and miR-17-30a HeLa-high markers. The heat map shows the cloning frequency of selected HeLa-low markers, with blue and red colors indicating low and high CF values, respectively. FIG. 8G depicts simulated output levels in different cell types using a full classifier. From left to right, output levels histogram for a complete set of markers using sensor parameters defined in the text; output levels histogram with the 99% repression relief values for HeLa-high marker sensors doubled compared to their default values; output levels histogram when the 99% repression relief values for the HeLa-high marker sensors are half of the default values.

FIG. 9A shows an effect of a coherent feed-forward motif on sensor performance in response to exogenous siRNA-FF5. Each bar represents the mean±SD of DsRed/AmCyan value with three independent replicates. FIG. 9B shows an effect of LacI dose on sensor performance for highly-expressed endogenous microRNA markers. Each bar represents the mean±SD of DsRed/AmCyan value obtained from three independent replicates. FIG. 9C shows an effect of rtTA dosage on the performance of sensors for highly-expressed endogenous microRNA markers.

FIG. 13A depicts three hypothetical microRNA markers A1, A2 and A3 that are used to determine a specific cell state A. Hypothetical microRNA markers B1, B2 and B3 are used to determine specific cell state B. Cells in state A or B, e.g. two different phases in cancer development, are both intended targets for a multi-purpose therapeutic agent. Two classifier circuits A and B operating in parallel with no crosstalk between them are used to identify cell types A and B, respectively. RA1 and RA2 are 'double-inversion' modules in Circuit A; RB1 is the 'double-inversion' module in Circuit B. FIG. 13B shows output proteins A and B represent two different therapeutic agents for type A and B cells, respectively. Outputs A and B are controlled by circuits A and B that detect profiles characterizing type A and type B cells, respectively.

FIG. 14A shows a schematic flow diagram of high-level operation of a multi-input biological classifier circuit. Different outcomes are shown depending on whether the cell is a stem cell (elimination required) or a differentiated cell (rescue required). The cells that do not receive the classifier circuit will be eliminated due to the presence of antibiotic in the cell culture medium. The outcomes that result depending on the cell type and on whether the cell is transfected or not is summarized. FIG. 14B depicts molecular implementation of the schematic shown in FIG. 14A. The "kill and rescue" output module shown controls a fusion protein that is cleaved to generate a killer protein hBax and a repressor cI-Krab. The repressor inhibits expression of an antibiotic resistance gene. Overall, if the classifier positively identifies a cell as a stem cell, the fusion protein is expressed at a high level, inducing cell death, and inhibiting resistance. If the classifier makes a negative decision, neither the apoptotic protein nor the repressor of the antibiotic resistance is expressed. Therefore, the antibiotic resistance gene permits those cells to survive in selective medium. FIG. 14C depicts a schematic of a full multi-input biological classifier circuit that identified six input microRNAs that comprises a kill and rescue output module.

FIG. 16A depicts schematics of a complete circuit (C1), partially-assembled circuits (P17-30a, P21, R1, C2 and O1) and controls (O2 and R2). FIG. 16B shows results from transfection experiments performed with Effectene transfection reagent. Scatter plots of FACS data measured at 48 hours post-transfection with BD LSRII flow analyzers using a filter set for AmCyan (405 nm Laser, 510/50 emission filter and PMT 230 V) and a filter set for DsRed (561 nm laser, 610/20 emission filter and PMT 290 V for all cell lines except HEK293 (PMT 230V)). FIG. 16C shows results from transfection experiments performed with Nucleofection protocol. Scatter plots of FACS data measured at 48 hours post-transfection with BD LSRII flow analyzers using the same filter sets in FIG. 16B. FIG. 16D shows results from transfection experiments performed with Nucleofection protocol. Scatter plots of FACS data measured at 48 hours post-transfection with BD LSRII flow analyzers using a filter set for AmCyan (405 nm Laser, 525/50 emission filter and PMT 200 V) and a filter set for DsRed (561 nm laser, 582/15 emission filter and PMT 220 V). FIG. 16E is a graph summarizing the results obtained. Each bar represents the mean±SD of DsRed/AmCyan value with at least three independent replicates. All values are normalized to constitutive output level (O1) in HeLa cells.

DETAILED DESCRIPTION

Figures 1A, 1B, 1C, 1D:
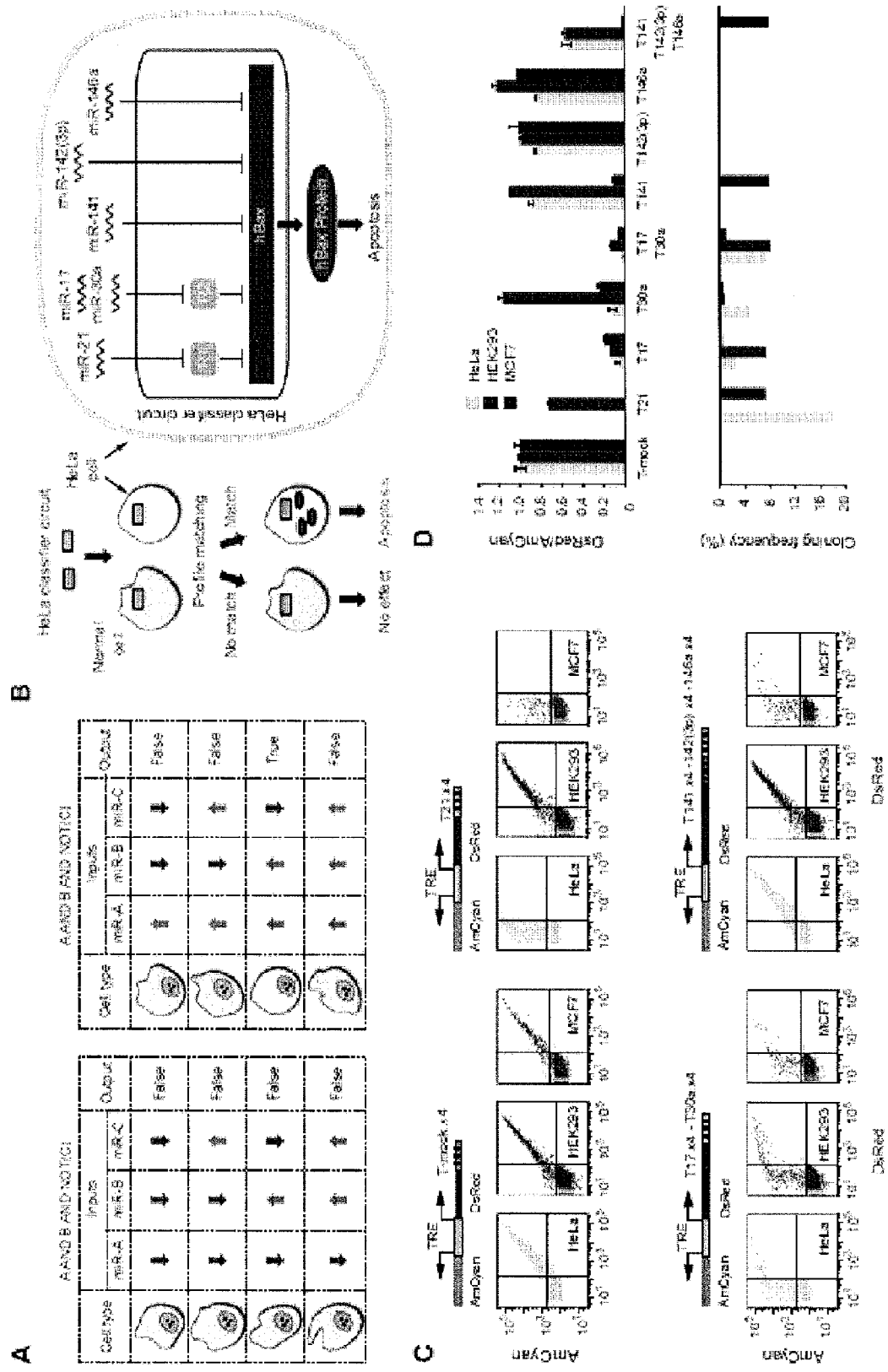
FIGS. 1A-1D show a schematic operation of a cell type classifier.

The high-input detector modules and multi-input biological classifier circuits and systems described herein integrate sophisticated sensing, information processing, and actuation in living cells and permit new directions in basic biology, biotechnology and medicine. The multi-input biological classifier circuits described herein comprise synthetic, scaleable transcriptional/post-transcriptional regulatory circuits that are designed to interrogate the status of a cell by simultaneously sensing expression levels of multiple endogenous inputs, such as microRNAs. The classifier circuits then compute whether to trigger a desired output or response if the expression levels match a pre-determined profile of interest. In other words, when operating in a heterogeneous cell population, the circuits described herein can selectively identify a specific cell population expressing a profile of interest and output a desired response based on the simultaneous interrogation of a multitude of inputs.

A profile of interest that a biological classifier is designed to identify can be based on selecting a small, non-redundant set of inputs that together generate a unique and robust molecular signature for a specific cell type. The classifier circuits described herein are designed to identify molecular signatures or profiles that comprise both high and low/absent inputs using Boolean logic, such as AND-like, OR-like, NOT-like operations, or any combination thereof. For example, a molecular profile to be identified can comprise two different microRNAs that are highly expressed, and three different microRNAs that are low/absent. Such biological classifier circuits can be used, for example, to selectively identify and destroy cancer cells using specific microRNA expression profiles as inputs. Such an approach allows highly-precise cancer treatments with little collateral damage. Numerous other applications can also benefit from accurate single-cell in-vivo identification and classification of highly-complex cell states using the high-input detector modules and biological classifier circuits, and methods of their use thereof described herein, such as drug screening experiments, developmental studies, pharmacokinetics, diagnostic and therapeutic applications, and genetic manipulations.

Accordingly, described herein are multi-input biological classifier circuits and methods of use thereof for the detection of and discrimination between multiple (i.e., at least two) inputs. These multi-input biological classifier circuits use transcriptional and posttranscriptional regulation mechanisms in modular components, such as high-input detector modules, in order to classify the status of a cell, i.e., determine whether a cell is in a specific state of interest defined by a specific subset of two or more markers that serve as inputs for the circuit. The biological classifier circuits described herein implement this task by interrogating the state of the cell through simultaneous assessment of a predefined subset of multiple inputs by modular components using Boolean-like logic, such as AND-like, OR-like, and NOT-like operations. In some embodiments, such circuits can implement a multi-input AND-like logic function, where all inputs must be present at their defined levels simultaneously, in order to identify or classify a cell. In other embodiments, such circuits can implement a multi-input logic function, comprising AND-like, OR-like, or NOT-like operations, or any combination thereof, in order to identify or classify a cell. Examples of such inputs include endogenous mature microRNAs or transcription factors.

Described herein are multiple-input biological classifier circuits for classifying a cell. A multiple-input biological classifier circuit classifies a cell's status based on an expression pattern of a subset of at least two different microRNAs. Such a biological classifier circuit comprises at least two input detector modules, which detect expression of at least two different microRNAs. In some embodiments of the aspects described herein, a multiple-input biological classifier circuit detects at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or more, different microRNAs present in a cell or cellular system.

In some aspects described herein, input detector modules are provided comprising different components, such as promoter sequences, transcriptional activator sequences, transcriptional repressor sequences, microRNA target sequences, and output sequences, to be used as modular components in the biological classifier circuits described herein. Such detector or sensor modules are used to link, for example, intracellular, endogenous microRNA activity to the expression level of an output protein, such as a pharmaceutical agent or a molecule that inpacts cellular activities. Specific combinations of these input detectors are used to implement molecular Boolean logic comprising AND-like, OR-like, NOT-like, or any combination thereof, Boolean operations, such that the circuit expresses a specific output protein only when all Boolean conditions are satisfied. Further, in some embodiments, such input detector modules can be designed such that the biological classifier circuits essentially convert analog input signals into reliable, digital output(s).

Depending on the combination of components used in a biological classifier circuit described herein, an input detector module can be designated as a "low input detector module", for detecting microRNAs inputs expressed at low levels within a cell, or a "high-input detector module," for detecting microRNAs inputs expressed at high levels within a cell. Thus, when a cell or cellular system expresses a particular combination of microRNAs and lacks another combination of microRNAs, i.e., matches a specific microRNA reference profile for a cell type, as detected by a combination of high- and low-input detectors respectively using, for example, AND-like Boolean logic, a classifier circuit designed to detect that specific microRNA profile can express an output product. The ability to modulate the type and number of input detector modules, and their constituent components, provide flexibility in the designs and uses of the multiple-input biological classifier circuits described herein.

The biological classifier circuits described herein can be designed to produce a specific output product, such as a reporter molecule, in response to detecting an appropriate expression profile within a cell or cellular system. Thus, a biological classifier circuit produces an output and classifies a cell only when all the conditions of the circuit are met, i.e., the cell or cellular system is a true positive. These circuits can be further modified to incorporate components or modules that prevent or minimize misclassification of cells, i.e., expression of an output product when a specific microRNA profile is not detected. In preferred embodiments of the aspects described herein, the output level of a biological classifier circuit is at least two, at least three, at least four, at least five, at least six, at least seven, at least eight, at least nine, at least ten, at least eleven, at least twelve, at least thirteen, at least fourteen, at least fifteen, at least twenty, at least twenty five, at least fifty, at least 100×, at least 1000× greater in a cell expressing the appropriate combination of inputs as opposed to a cell not expressing the appropriate combination of inputs.

As used herein, when a biological classifier circuit classifies a cell or cellular system correctly and expresses an output product in a cell or cellular system that matches a specific reference profile, then the cell or cellular system is considered to be a "true positive." As used herein, when a biological classifier circuit classifies a cell or cellular system correctly and does not express an output product in a cell or cellular system that does not match a specific reference profile, then the cell or cellular system is considered to be a "true negative." As used herein, the term "false positive" refers to a cell or cellular system which is classified by a biological classifier circuit as expressing a specific reference profile, i.e., an output product is expressed, when it does not express or match the specific reference profile. As used herein, the term "false negative" refers to a cell or cellular system which is classified by a biological classifier circuit as not expressing a specific reference profile, i.e., an output product is not expressed, when it does express or match the specific reference profile.

High-Input Detector Modules or Double-Inversion Sensor Modules

In some aspects, provided herein are high-input detector modules for use in classifying one or more inputs, such as microRNAs, that are expressed at a specific level or higher in a cell or cellular system in comparison to a reference level.

A "high-input detector module," also referred to herein as a "double-inversion sensor module," comprises a constitutive or inducible promoter sequence operably linked to: (i) a repressor sequence that encodes a repressor product, and (ii) one or more microRNA target sequences, such that the one or more microRNA target sequences comprise target sequences of the one or more input microRNAs the high-input module is designed to detect. In some embodiments, the one or more microRNA target sequences are preferably after the 3' end of the sequence encoding the repressor product. In some embodiments, the one or more microRNA target sequences can be before the 5' end of the sequence encoding the repressor product, in an intronic region within the sequence encoding the repressor product, or within the coding region of the sequence encoding the repressor product.

The expression of the repressor product output of a high-input detector module, in contrast to a low-input detector module, as described herein, occurs when the input condition(s) of the biological classifier circuit is/are not met. Thus, a high-input detector module is designed to be "OFF," i.e., not express the repressor output product, when one or more input, endogenous, mature microRNAs that is/are intended to be expressed at a specific level or higher than a reference level is/are detected in a cell or cellular system. A high-input detector module is designed to be "ON," i.e., express the repressor output product, when one or more input, endogenous, mature microRNAs that is/are intended to be expressed at a specific level or higher than a reference level is not/are not detected in a cell or cellular system.

In such high-input detector modules, the constitutive or inducible promoter drives transcription of the repressor sequence, resulting in an RNA sequence comprising the repressor sequence RNA and the one or more microRNA target sequences. In the absence of the specific level of the input, endogenous microRNA(s) that recognizes the one or more microRNA target sequences encoded by the high-input detector module, translation of the repressor occurs and the module is "ON," and produces the repressor protein. When the input microRNA(s) that recognize(s) or is/are specific for the microRNA target sequence(s) is/are present at a specified level or higher, than when the repressor sequence is transcribed to a repressor RNA and the one or more microRNA target sequences, the input microRNA(s) bind(s) its cognate microRNA target sequence(s) and prevent(s) translation of the repressor product. Thus, production of a repressor product by the high-input detector module in such embodiments is regulated at a post-transcriptional level.

In some aspects, the high-input detector module further comprises an inducible promoter sequence operably linked to an output sequence encoding an output product, such as a reporter output or an apoptosis inducing protein. In such aspects, the inducible promoter sequence is repressed by the repressor product encoded by the high-input detector module, such that when the module is "ON" and produces the repressor product, the output product is not transcribed, i.e., the production of the output product by the high-input detector module in such aspects is regulated at the transcriptional level. Conversely, when the module is "OFF" and does not produce the repressor product, the output product is transcribed. Thus, in such aspects, if the input microRNA(s) that recognize(s) the one or more microRNA target sequences is/are not expressed at the specific level(s) or higher than the reference level(s), the repressor product is expressed, and prevents expression of the ouput product.

In other aspects, the repressor product of a high-input module is specific for the repressible promoter of a low-input module as described herein, such that production of an output product is regulated by both a high-input module and a low-input module.

In further embodiments of the aspects described herein, expression of the repressor product of a high-input detector module is further regulated at the transcriptional level. In such embodiments, the high-input detector modules described herein can further comprise one or more regulatory units. Such "regulatory units," as defined herein, comprise a constitutive or inducible promoter sequence operably linked to: (i) a sequence that encodes for a transcriptional activator product, and (ii) a sequence encoding one or more microRNA target sequences, such that the transcriptional activator product activates the inducible promoter sequence operably linked to the repressor sequence and the sequence encoding the one or more microRNA target sequences of the high-inout module. In such embodiments, the promoter sequence operably linked to: (i) a repressor sequence that encodes a repressor product, and (ii) one or more microRNA target sequences, is an inducible promoter that is induced by one or more transcriptional activators encoded by the regulatory units of the high-input module. In some embodiments, the inducible promoter of a second regulatory unit is activated by the transcriptional activator encoded by a first regulatory unit, such that the repressor product of the high-input detector module is expressed only when the transcriptional activator of the second regulatory unit is expressed following activation by the transcriptional activator encoded by the first regulatory unit. In such embodiments, the sequences encoding one or more microRNA target sequences are the same throughout all the units and components of the high-input detector module, i.e., each unit and component of the high-input detector module detects the same input microRNA(s).

For example, if a reverse tetracycline-controlled transactivator is used, the inducible promoter driving expression of the repressor sequence and the one or more microRNA target sequences comprises a tetracycline response element (TRE). In such embodiments, the one or more microRNA target sequences attached or linked to the transcriptional activator sequence, and the one or more microRNA target sequences attached or linked to the repressor sequence is/are the same, such that the presence of a cognate input endogenous microRNA(s) at a specific level or higher than a reference level(s) in a cell prevents translation of both the transcriptional activator and the repressor product, by binding to its/their cognate microRNA target sequences. Thus, in such embodiments of the high-input detector modules described herein, expression of the repressor product of a high-input detector module is regulated at both the transcriptional level (i.e., requires binding of the transcriptional activator to the promoter driving the repressor product sequence for transcription of mRNA) and at the post-transcriptional level (i.e., binding of the microRNA(s) expressed at the required level(s) to its microRNA target sequence(s) upon transcription of the repressor sequence, prevents translation of the repressor mRNA to repressor protein).

Low-Input Detector Modules

Described herein are low-input detector modules for use as modular components of biological classifier circuits. A "low-input detector module" comprises a repressible promoter sequence operably linked to an output sequence that encodes an output product, and at least one microRNA target sequence. In some embodiments, the at least one microRNA target sequence is preferably after the 3' end of the output sequence encoding the output product. In some embodiments, the at least one microRNA target sequence can be before the 5' end of the sequence encoding the output product, in an intronic region within the sequence encoding the output product, or within the coding region of the sequence encoding the output product.

In such low-input modules, transcription from the repressible promoter results in an output mRNA sequence directly fused at its 3' end with the at least one microRNA target sequence. A low-input detector module is designed to be "OFF," i.e., not express the output product, when an input, endogenous, mature microRNA that is intended to be low or absent in a cell in comparison to a reference level is detected. Accordingly, the output sequence encodes at least one microRNA target sequence that the at least one microRNA intended to be absent or low in a cell specifically recognizes or is cognate for.

In such low-input detector modules, activation or derepression of the repressible promoter results in transcription of the output sequence, resulting in an mRNA of the output sequence fused to at least one microRNA target sequence. If a microRNA specific or cognate for that target sequence is present, then that microRNA binds to the congnate target sequence, thus preventing translation of the output sequence upon transcription from the repressible promoter, i.e., no output product is expressed, and the low-input module remains "OFF." In some embodiments, a low-input detector module comprises an output sequence encoding an output product and two different microRNA target sequences. In such embodiments, only when both microRNAs specific for the microRNA target sequences are absent or expressed at low levels, does translation of the output product occur upon transcription from the repressible promoter. Thus, a low-input detector module comprises at least one microRNA target sequence to compute the absence or low level of at least one microRNA to generate a response or output.

In some embodiments of the aspects described herein, a low-input detector module comprises a sequence encoding at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or more, different microRNA target sequences.

Biological Classifier Circuits

Described herein are multi-input biological classifier circuits and methods of use thereof for the detection of and discrimination between multiple (i.e., at least two) inputs. These multi-input biological classifier circuits use transcriptional and posttranscriptional regulation mechanisms encoded in modular components, such as high-input or low-input detector modules, and components thereof, such as regulatory units, in order to classify the status of a cell, i.e., identify whether a cell is in a specific state of interest as determined by a specific subset of two or more markers that serve as inputs for the circuit. The biological classifier circuits described herein implement this task by interrogating the state of the cell through simultaneous assessment of a predefined subset of multiple inputs by modular components, such as high-input or low-input detector modules that use Boolean-like logic (i.e., AND-like, OR-like, and NOT-like operations).

In some embodiments of the aspects described herein, a biological classifier circuit comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or more, different high-input detector modules, wherein each high-input detector module encodes a different microRNA target sequence or microRNA target sequence. In preferred embodiments of the aspects described herein, each microRNA target sequence encoded by a low-input detector module is different from each microRNA target sequence encoded by each high-input detector module in a biological classifier circuit. For example, a biological classifier circuit can comprise one low-input detector module comprising three different microRNA target sequences, and four different high-input detector modules, each comprising a different microRNA target sequence from each other, and from each of the microRNA target sequences of the low-input module.

In some embodiments of the aspects described herein, each high-input detector module in a biological classifier circuit comprising only high-input detector modules encodes for the same repressor product. In other embodiments of the aspects described herein, different high-input detector modules in a biological classifier circuit encode for different repressor products.

In some embodiments of the aspects described herein, the same or different repressor products of one or more high-input detector modules are all specific for the repressible promoter operably linked to the sequence encoding the output product of a high-input detector module in a biological classifier circuit comprising only high-input modules, and thus prevent transcription of the output product by the circuit. Thus, in such embodiments, unless all the different microRNA inputs that are detected by each of the high-input detectors are present and expressed at the required level, repressor product will be produced by at least one of the high-input detector modules, and repress transcription from the repressible promoter of the high-input detector module encoding for the output product, and prevent generation of the output product of the biological classifier circuit.

In some embodiments, a a biological classifier circuit comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or more, different high-input detector modules, wherein each high-input detector module encodes a different microRNA target sequence, and no low-input modules are included in the circuit. In such embodiments, the biological classifier circuit is designed to detect only microRNA inputs that are at a specific level or higher than a reference level, and no microRNA inputs that are absent. In such embodiments, where no low-input module is present in a circuit, at least one high-input module further comprises an inducible promoter sequence operably linked to an output sequence encoding an output product, such as a reporter output or an apoptosis inducing protein. In such embodiments, the inducible promoter sequence is repressed by the repressor product encoded by the at least one high-input detector module, such that when the module is "ON" and produces the repressor product, the output product is not transcribed, i.e., the production of the output product by the high-input detector module in such aspects is regulated at the transcriptional level. Conversely, when the module is "OFF" and does not produce the repressor product, the output product is transcribed. Thus, in such embodiments of these aspects, if the input microRNA that recognized the at least one microRNA target sequence is not expressed at the specific level or higher than the reference level, the repressor product is expressed, and prevents expression of the ouput product.

In some embodiments of the aspects described herein, each high-input detector module, in a biological classifier circuit comprising both high- and low-input detector modules, encodes for the same repressor product. In other embodiments of the aspects described herein, different high-input detector modules in a biological classifier circuit encode for different repressor products.

In some embodiments of the aspects described herein, the same or different repressor products of one or more high-input detector modules are all specific for the repressible promoter of the low-input detector module in a biological classifier circuit, or the promoter sequence of the output product of the at least one high-input detector module in a biological classifier circuit comprising only high-input detector modules, and thus prevent transcription of the output product by the low-input detector module or the at least one high-input detector module. Thus, in such embodiments, unless all the different microRNA inputs that are detected by each of the high-input detectors are present and expressed at the specific level or higher than a reference level, repressor product will be produced by at least one of the high-input detector modules, and repress transcription from the repressible promoter of the low-input detector module and prevent generation of the output product of the biological classifier circuit.

In some embodiments, a a biological classifier circuit comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or more, different detector modules, wherein each detector module encodes a different microRNA target sequence, and at least one low-input module and at least one high-input module are included in the circuit.

In some embodiments of the aspects described herein, each microRNA target sequence of a low- or high-input detector module is present as two or more multiple, tandem repeats in a sequence. Varying the number of copies or repeats of a microRNA target sequence in a module or classifier circuit adds further flexibility and sensitivity to the amount of input microRNA required to inhibit translation of a given RNA sequence. For example, in a low-input sensor, each microRNA target sequence attached to or linked to the 5' end of the sequence encoding the output product can be present in two or more tandem copies, such as four tandem microRNA target sequence repeats.

Accordingly, in some embodiments, a microRNA target sequence is present as at least two tandem repeats, at least three tandem repeats, at least four tandem repeats, at least five tandem repeats, at least six tandem repeats, at least seven tandem repeats, at least eight tandem repeats, at least nine tandem repeats, or at least ten tandem repeats. In such embodiments, where a specific microRNA target sequence occurs as tandem repeats in a high-input detector module, the number of tandem repeats of a specific microRNA target sequence present in a sequence encoding a transcriptional activator in a high-input detector module is the same as the number of tandem repeats of the specific microRNA target sequence present in the sequence encoding the repressor of that same high-input module.

In further embodiments of the aspects described herein, additional modules, units, components and parts can be added to the biological classifier circuits described herein in order to improve, for example, the sensitivity and the fidelity of a biological classifier circuit. Selectivity of a circuit, i.e., expression of an output product only in cells expressing the appropriate input profile, or the degree of false-positive outputs, for example, increases as the number of input factors that the circuit must detect increases. For example, when the total number of high-input modules increase, i.e., the required number of microRNAs to be detected at high levels increase, the level of repressor protein increases, which prevents transcription of the output product from the promoter of the low-input detector module, which makes it more difficult for a circuit to mis-classify a cell or cellular system.

Accordingly, in some embodiments of the aspects described herein, the sequence encoding the repressor product of a high-input module of a biological classifier circuit can further comprise a sequence encoding an intronic microRNA sequence. In such embodiments, the encoded microRNA is not any of the microRNA inputs being detected by the biological classifier circuit. In such embodiments, the sequence encoding the output product of the low-input module of a biological classifier circuit, or the at least one high-input module of a biological classifier circuit comprising only high-input modules, further comprises a microRNA target sequence specific for the intronic microRNA encoded by the high-input module. In such embodiments, synethesis of the output product is being regulated at both the transcriptional level (by the repressor protein) and at the post-transcriptional level (by the microRNA encoded by the circuit). Examples of biological classifier circuits according to the present invention comprising such additional components can be found at FIG. 4 and FIG. 10, and in the Examples section.

In other embodiments of the biological classifier circuits described herein, the high-input detector modules can further comprise one or more regulatory units. Scuh regulatory units comprise a constitutive or inducible promoter sequence operably linked to: (i) a sequence that encodes for a transcriptional activator product, and (ii) a sequence encoding one or more microRNA target sequences, such that the transcriptional activator product activates the inducible promoter sequence operably linked to the repressor sequence and the sequence encoding the one or more microRNA target sequences of the high-input module of the classifier circuit. In such embodiments, the promoter sequence of the high-input module is an inducible promoter that is induced by one or more transcriptional activators encoded by the regulatory units of the high-input module.

In some embodiments, the inducible promoter of a second regulatory unit is activated by the transcriptional activator encoded by a first regulatory unit, such that the repressor product of the high-input detector module is expressed only when the transcriptional activator of the second regulatory unit is expressed following activation by the transcriptional activator encoded by the first regulatory unit. In such embodiments, the sequences encoding one or more microRNA target sequences are the same throughout all the units and components of the high-input detector module, i.e., each unit and component of the high-input detector module detects the same input microRNA(s).

In other embodiments, an output product can, in addition, be regulated by expression of a known physiological or functional inhibitor of the output product by the circuit. In such embodiments, sequences encoding such inhibitors can be included in at least one high-input detector modules, such that at least one high-input module further comprises an inducible promoter operably linked to a sequence encoding a repressor, an output product inhibitor, and one or more microRNA target sequences. Accordingly, transcription from the promoter results in an RNA sequence for the repressor, output product inhibitor, and the microRNA target sequence. In the absence of the cognate microRNA for the microRNA target sequence, translation of the sequence produces the repressor that prevents transcription of the output product, and the output product inhibitor that functionally inhibits the output product. If such a sequence further comprises a microRNA targeting its cognate microRNA target sequence within the output product sequence, then actuation of the circuit via expression of the output product can designed to be regulated at the transcriptional, post-transcriptional, and functional (post-translational) levels by the high-input detector module.

The biological classifier circuits described herein can be used in various combinations and can be designed to incorporate sensors for additional input types, such as transcription factors, to effect other Boolean-like operations in a cells. For example, expressing two biological classifier circuits that each detect a unique expression profile in a call can be used to effectively achieve an OR-like Boolean operation, i.e., if a cell expresses either of two expression profiles satisfying an AND-like operation, an output product is generated. An exemplary logic operation for such a parallel circuit design could be: (miRNA-A AND miRNA-B AND miRNA-C) AND (NOT miRNA-D AND NOT miRNA-E) OR (miRNA-F AND miRNA-G AND miRNA-H) AND (NOT miRNA-I AND NOT miRNA-J).

Accordingly, in other aspects described herein described herein, two or more biological classifier circuits can be operated in parallel in order to classify, discriminate or distinguish, for example, multiple cell types within a heterogenous population, such as two distinct cell populations in a larger cell population or tissue preparation, using combinations of OR-like and AND-like Boolean operations. In such aspects, the biological classifier circuits operating in parallel can be designed so that there is no cross talk between the circuits. An exemplary depiction of such a parallel set-up is shown in FIG. 13. In some embodiments of such aspects, upon detection of an appropriate expression profile, each circuit produces a different output product. In some embodiments of such aspects, upon detection of an appropriate expression profile, each circuit produces the same output product, such as a therapeutic agent.

The sub-sections below further illustrate and describe exemplary component parts that can be used according to the methods described herein to design biological classifier circuits and low- and high-input detector modules.

MicroRNAs and MicroRNA Target Sequences

The biological classifier circuits, detector modules, and uses thereof described herein, utilize, in part, endogenous expression of multiple, mature microRNAs as inputs. The modules and circuits are designed to incorporate cognate microRNA target sequences that are specific for the mature, endogenous microRNAs being detected. Described herein are references and resources, such as programs and databases found on the World Wide Web, that can be used for obtaining information on microRNAs and their expression patterns, as well as information in regard to cognate microRNA sequences and their properties.

Mature microRNAs (also referred to as miRNAs) are short, highly conserved, endogenous non-coding regulatory RNAs (18 to 24 nucleotides in length), expressed from longer transcripts (termed "pre-microRNAs") encoded in animal, plant and virus genomes, as well as in single-celled eukaryotes. Endogenous miRNAs found in genomes regulate the expression of target genes by binding to complementary sites, termed herein as "microRNA target sequences," in the mRNA transcripts of target genes to cause translational repression and/or transcript degradation. miRNAs have been implicated in processes and pathways such as development, cell proliferation, apoptosis, metabolism and morphogenesis, and in diseases including cancer (S. Griffiths-Jones et al., "miRBase: tools for microRNA genomics." Nuc. Acid. Res., 2007: 36, D154-D158). "Expression of a microRNA target sequence" refers to transcription of the DNA sequence that encodes the microRNA target sequence to RNA. In some embodiments, expression of a microRNA target sequence is operably linked to or driven by a promoter sequence. In some embodiments, a microRNA target sequence comprises part of another sequence that is operably linked to a promoter sequence, such as a sequence encoding an output product or a repressor product, and is said to be linked to, attached to, or fused to, the sequence encoding the output product or a repressor product.

The way microRNA and their targets interact in animals and plants is different in certain aspects. Translational repression is thought to be the primary mechanism in animals, with transcript degradation the dominant mechanism for plant target transcripts. The difference in mechanisms lies in the fact that plant miRNA exhibits perfect or nearly perfect base pairing with the target but in the case of animals, the pairing is rather imperfect. Also, miRNAs in plants bind to their targets within coding regions cleaving at single sites whereas most of the miRNA binding sites in animals are in the 3' un-translated regions (UTR). In animals, functional miRNA:miRNA target sequence duplexes are found to be more variable in structure and they contain only short complementary sequence stretches, interrupted by gaps and mismatches. In animal miRNA: miRNA target sequence interactions, multiplicity (one miRNA targeting more than one gene) and cooperation (one gene targeted by several miRNAs) are very common but rare in the case of plants. All these make the approaches in miRNA target prediction in plants and animals different in details (V. Chandra et al., "MTar: a computational microRNA target prediction architecture for human transcriptome." BMC Bioinformatics 2010, 11(Suppl 1):S2).

Experimental evidence shows that the miRNA target sequence needs enough complementarities in either the 3' end or in the 5' end for its binding to a miRNA. Based on these complementarities of miRNA: miRNA target sequence target duplex, the miRNA target sequence can be divided into three main classes. They are the 5' dominant seed site targets (5' seed-only), the 5' dominant canonical seed site targets (5' dominant) and the 3' complementary seed site targets (3' canonical). The 5' dominant canonical targets possess high complementarities in 5' end and a few complementary pairs in 3' end. The 5' dominant seed-only targets possess high complementarities in 5' end (of the miRNA) and only a very few or no complementary pairs in 3' end. The seed-only sites have a perfect base pairing to the seed portion of 5' end of the miRNA and limited base pairing to 3' end of the miRNA. The 3' complimentary targets have high complementarities in 3' end and insufficient pairings in 5' end. The seed region of the miRNA is a consecutive stretch of seven or eight nucleotides at 5' end. The 3' complementary sites have an extensive base pairing to 3' end of the miRNA that compensate for imperfection or a shorter stretch of base pairing to a seed portion of the miRNA. All of these site types are used to mediate regulation by miRNAs and show that the 3' complimentary class of target site is used to discriminate among individual members of miRNA families in vivo. A genome-wide statistical analysis shows that on an average one miRNA has approximately 100 evolutionarily conserved target sites, indicating that miRNAs regulate a large fraction of protein-coding genes.

At present, miRNA databases include miRNAs for human, *Caenorhabditis elegans*, *D. melanogaster*, *Danio rerio* (zebrafish), *Gallus gallus* (chicken), and *Arabidopsis thaliana*. miRNAs are even present in simple multicellular organisms, such as poriferans (sponges) and cnidarians (starlet sea anemone). Many of the bilaterian animal miRNAs are phylogenetically conserved; 55% of *C. elegans* miRNAs have homologues in humans, which indicates that miRNAs have had important roles throughout animal evolution. Animal miRNAs seem to have evolved separately from those in plants because their sequences, precursor structure and biogenesis mechanisms are distinct from those in plants (Kim V N et al., "Biogenesis of small RNAs in animals." Nat Rev Mol Cell Biol. 2009 February; 10(2): 126-39).

miRNAs useful for designing the modules and circuits described herein can be found at a variety of databases as known by one of skill in the art, such as those described at "miRBase: tools for microRNA genomics." Nuc. Acid. Res., 2007: 36 (Database Issue), D154-D158; "miRBase: microRNA sequences, targets and gene nomenclature." Nuc. Acid. Res., 2006 34 (Database Issue):D140-D144; and "The microRNA Registry." Nuc. Acid. Res., 2004 32 (Database Issue):D109-D111), which are incorporated herein in their entirety by reference.

In some embodiments of the aspects described herein, a microRNA target sequence can be an engineered microRNA target sequence, such as one having full sequence complementarity to an input microRNA of interest. In addition, a number of computational tools are available for animal and plant miRNA target sequence identification. Most of these approaches are based on evolutionary conservation and the presence of miRNA target sites in 3' UTRs of target mRNAs and their relatively better complementarities to 5' end of miRNAs. Tools like miRCheck (Johnes-Rahoades M W and Bartel D P: "Computational identification of Plant microRNAs and their targets, inducing a stress-induced miRNA." Mol Cell 2004, 14:787-799), findmiRNA (Adai A et al., "Computational Prediction of miRNAs in *Arabidopsis thaliana*." Genome Research 2005, 15:78-91), PatScan (Rhoades B et al., "Prediction of Plant microRNA Targets." Cell 2002, 110:513-520), and mirU (Zhang Y. "miRU: an automated plant miRNA target prediction server: Nucleic Acids Res 2005, 33:W701-W704) can be used for rapid prediction of miRNA target sequences in plants where perfect complementarities of miRNA and miRNA target sequences are found.

Target prediction in animal transcriptomes can call for more complex algorithms due to the imperfect complementarities of miRNA: mRNA pairs. Databases, computational programs, and references for use in predicting and obtaining miRNA target sequences for animal cells that can be used in the biological classifier circuits and methods of their use described herein, include, but are not limited to: (i) PicTar (Grun D et al., "microRNA target predictions across seven *Drosophila* species and comparison to mammalian targets." PLoS Comput Biol 2005, 1:e13; Krek et al., "Combinatorial microRNA target predictions." Nat Genet. 2005, 37:495-500; Lall S, et al., "A genome-wide map of conserved microRNA targets in *C. elegans*." Curr Biol 2006, 16:460-471), which predicts miRNA targets in *Drosophila* and other species based on complementarities between miRNA and 3' UTR of mRNA sequence. PicTar uses techniques like seed match, free energy calculation and species conservation. Its false positive rate has been estimated to be 30.0%. (ii) TargetScan (Lewis B P et al. "Prediction of mammalian microRNA targets." Cell 2003, 115:787-798) is a tool used to predict miRNAs which bind to 3' UTRs of vertebrate transcriptomes. TargetScan has been used to predict more than 451 human microRNA targets. TargetSanS, a modified version of TargetScan, omits multiple sites in each target and further filters the targets using thermodynamic stability criterion. Using this modified method more than 5300 human genes and their microRNA target sequences have been predicted as possible targets of miRNAs (Lewis B et al., "Conserved Seed Pairing, Often Flanked by Adenosines, Indicates that Thousands of Human Genes are microRNA Targets." Cell 2005, 120:15-20). The false positive rate varies between 22% to 31%. (iii) MiRanda (John B et al. "Human MicroRNA Targets." PLoS Biol 2004, 2:e363; Enright A J et al. "MicroRNA Targets in *Drosophila*." Genome Biol 2003, 5:R1; Betel D et al., "The microRNA.org resource: targets and expression." Nucleic Acids Res 2008, 36:D149-D153), a target prediction tool, relies on the evolutionary relationships between miRNAs and their targets. This tool focuses on sequence matching of miRNA: miRNA target sequences, by estimating energy of physical interaction. The miRanda algorithm works by scanning for miRNA complementary pairs in the 3' UTR of an mRNA. Using this software, a large number of miRNA target sequences have been identified including protein-coding genes in *Homo sapiens*. The false positive rate was estimated to be 24%. (iv) DIANA-microT (Kiriakidou M et al., "A combined computational-experimental approach predicts human microRNA targets." Genes Dev 2004, 18:1165-1178) is a method based on the rules of single miRNA: mRNA pairing. It predicts targets which contain a single complementary site based on binding energies. (v) MiTarget algorithm (Kim S et al., "MiTarget: miRNA target gene prediction using an SVM." BMC Bioinformatics 2006, 7:441) combines thermodynamics based processing of RNA: RNA duplex interactions with the sequence analysis to predict miRNA target sequences. (vi) RNAhybrid is another computer program for predicting miRNA targets based on complementarities between miRNA and 3' UTR of coding sequence (Rehmsmeier M et al., "Fast and Effective prediction of microRNA/target duplexes." RNA 2004, 10:1507-1517. (vii) MovingTarget (Burgler C and Macdonald P M, "Prediction and verification of microRNA targets by Moving Targets, a highly adaptable prediction method." BMC Bioinformatics 2005, 6:88) is a program used to detect miRNA target sequences satisfying a set of biological constraints. (viii) MicroTar (Thadani R and Tammi M T; "MicroTar: Predicting microRNA targets from RNA duplexes." BMC Bioinformatics 2006, 7(Suppl 5):S20) is a program that has been used to detect target sites in *C. elegans, Drosophila* and mouse by target complementarities and thermodynamic data. This algorithm uses predicted free energies of unbounded mRNA and putative mRNA:miRNA heterodimers, implicitly addressing the accessibility of the mRNA 3' UTR. This software is able to predict both conserved and non-conserved targets. (ix) MTar can identify all known three types of miRNA targets (5' seed-only, 5' dominant, and 3' canonical). MTar uses all these features and also takes into consideration the structural and positional features of miRNA: microRNA target sequences. The method predicts the three types of targets with a prominent accuracy (92.8%), sensitivity (94.5%) and specificity (90.5%). The false positive rate of MTar is 9.5% for MFE≤−17.0 Kcal/mol (V. Chandra et al., "MTar: a computational microRNA target prediction architecture for human transcriptome." BMC Bioinformatics 2010, 11(Suppl 1):S2).

Promoters

Provided herein are promoter sequences for use in the multi-input biological classifier circuits, and component low- and high-input detector modules. In some embodiments of the aspects described herein, the promoters used in the multi-input biological classifier circuits and low- and high-input detector modules drive expression of an operably linked output sequence or repressor sequence, and one or more microRNA target sequences.

The term "promoter" as used herein refers to any nucleic acid sequence that regulates the expression of another nucleic acid sequence by driving transcription of the nucleic acid sequence, which can be a heterologous target gene, encoding a protein or an RNA. Promoters can be constitutive, inducible, activateable, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors. In some embodiments of the aspects, a promoter can drive the expression of a transcription factor that regulates the expression of the promoter itself, or that of another promoter used in another modular component described herein.

A promoter can be said to drive expression or drive transcription of the nucleic acid sequence that it regulates. The phrases "operably linked", "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter" is a promoter in which the nucleic acid sequence is in the reverse orientation, such that what was the coding strand is now the non-coding strand, and vice versa. In addition, in various embodiments described herein, a promoter can or cannot be used in conjunction with an "enhancer", which refers to a cis-acting regulatory sequence involved in the transcriptional activation of a nucleic acid sequence downstream of the promoter. The enhancer can be located at any functional location before or after the promoter, and/or the encoded nucleic acid. A promoter for use in the biological classifier circuits described herein can also be "bidirectional," wherein such promoters can initiate transcription of operably linked sequences in both directions.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, an enhancer can be one naturally associated with a nucleic acid sequence, located either downstream or upstream of that sequence.

Alternatively, certain advantages can be gained by positioning a coding nucleic acid segment under the control of a recombinant or heterologous promoter, which refers to a promoter that is not normally associated with the encoded nucleic acid sequence in its natural environment. A recombinant or heterologous enhancer refers to an enhancer not normally associated with a nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring", i.e., contain different elements of different transcriptional regulatory regions, and/or mutations that alter expression through methods of genetic engineering that are known in the art. In addition to producing nucleic acid sequences of promoters and enhancers synthetically, sequences can be produced using recombinant cloning and/or nucleic acid amplification technology, including PCR, in connection with the biological classifier circuits and modules described herein (see U.S. Pat. No. 4,683,202, U.S. Pat. No. 5,928,906, each incorporated herein by reference). Furthermore, it is contemplated that control sequences that direct transcription and/or expression of sequences within non-nuclear organelles such as mitochondria, chloroplasts, and the like, can be employed as well.

Inducible Promoters

As described herein, an "inducible promoter" is one that is characterized by initiating or enhancing transcriptional activity when in the presence of, influenced by, or contacted by an inducer or inducing agent. An "inducer" or "inducing agent" can be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be a transcriptional repressor protein, such as LacI), which itself can be under the control of an inducible promoter. In some embodiments, an inducible promoter is induced in the absence of certain agents, such as a repressor. In other words, in such embodiments, the inducible promoter drives transcription of an operably linked sequence except when the repressor is present. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

Inducible promoters useful in the biological classifier circuits, methods of use, and systems described herein are capable of functioning in both prokaryotic and eukaryotic host organisms. In some embodiments of the different aspects described herein, mammalian inducible promoters are included, although inducible promoters from other organisms, as well as synthetic promoters designed to function in a prokaryotic or eukaryotic host can be used. One important functional characteristic of the inducible promoters described herein is their ultimate inducibility by exposure to an externally applied inducer, such as an environmental inducer. Appropriate environmental inducers include exposure to heat (i.e., thermal pulses or constant heat exposure), various steroidal compounds, divalent cations (including $Cu^{2+}$ and $Zn^{2+}$), galactose, tetracycline or doxycycline, IPTG (isopropyl-β-D thiogalactoside), as well as other naturally occurring and synthetic inducing agents and gratuitous inducers.

The promoters for use in the biological classifier circuits and low- and high-input modules described herein encompass the inducibility of a prokaryotic or eukaryotic promoter by, in part, either of two mechanisms. In particular embodiments described herein, the biological classifier circuits and their component low- and high-input modules comprise suitable inducible promoters that can be dependent upon transcriptional activators that, in turn, are reliant upon an environmental inducer. In other embodiments, the inducible promoters can be repressed by a transcriptional repressor which itself is rendered inactive by an environmental inducer, such as the product of a sequence driven by another promoter. Thus, unless specified otherwise, an inducible promoter can be either one that is induced by an inducing agent that positively activates a transcriptional activator, or one which is derepressed by an inducing agent that negatively regulates a transcriptional repressor. In such embodiments of the various aspects described herein, where it is required to distinguish between an activating and a repressing inducing agent, explicit distinction will be made.

Inducible promoters that are useful in the biological classifier circuits and methods of use described herein include those controlled by the action of latent transcriptional activators that are subject to induction by the action of environmental inducing agents. Some non-limiting examples include the copper-inducible promoters of the yeast genes CUP1, CRS5, and SOD1 that are subject to copper-dependent activation by the yeast ACE1 transcriptional activator (see e.g. Strain and Culotta, 1996; Hottiger et al., 1994; Lapinskas et al., 1993; and Gralla et al., 1991). Alternatively, the copper inducible promoter of the yeast gene CTT1 (encoding cytosolic catalase T), which operates independently of the ACE1 transcriptional activator (Lapinskas et al., 1993), can be utilized. The copper concentrations required for effective induction of these genes are suitably low so as to be tolerated by most cell systems, including yeast and *Drosophila* cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein that induces mammalian promoters containing GAL4 binding sites (Braselmann et al. (1993) Proc Natl Acad Sci USA 90: 1657-61). These and other inducible promoters responsive to transcriptional activators that are dependent upon specific inducers are suitable for use with the biological classifier circuits described herein.

Inducible promoters useful in the biological classifier circuits and methods of use disclosed herein also include those that are repressed by "transcriptional repressors" that are subject to inactivation by the action of environmental, external agents, or the product of another gene. Such inducible promoters can also be termed "repressible promoters" where it is required to distinguish between other types of promoters in a given module or component of a biological classifier circuit described herein. Examples include prokaryotic repressors that can transcriptionally repress eukaryotic promoters that have been engineered to incorporate appropriate repressor-binding operator sequences. In some embodiments, repressors for use in the circuits described herein are sensitive to inactivation by physiologically benign agent. Thus, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO Operator sequence, treatment of the host cell with tetracycline or doxycycline will cause the dissociation of the tet repressor from the engineered promoter and allow transcription of the sequence downstream of the engineered promoter to occur.

An inducible promoter useful in the methods and systems as disclosed herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent can comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as disclosed herein can be a phage inducible promoter, nutrient inducible promoter, temperature inducible promoter, radiation inducible promoter, metal inducible promoter, hormone inducible promoter, steroid inducible promoter, and/or hybrids and combinations thereof.

Promoters that are inducible by ionizing radiation can be used in certain embodiments, where gene expression is induced locally in a cell by exposure to ionizing radiation such as UV or x-rays. Radiation inducible promoters include the non-limiting examples of fos promoter, c-jun promoter or at least one CArG domain of an Egr-1 promoter. Further non-limiting examples of inducible promoters include promoters from genes such as cytochrome P450 genes, inducible heat shock protein genes, metallothionein genes, hormone-inducible genes, such as the estrogen gene promoter, and such. In further embodiments, an inducible promoter useful in the methods and systems as described herein can be $Zn^{2+}$ metallothionein promoter, metallothionein-1 promoter, human metallothionein IIA promoter, lac promoter, lacO promoter, mouse mammary tumor virus early promoter, mouse mammary tumor virus LTR promoter, triose dehydrogenase promoter, herpes simplex virus thymidine kinase promoter, simian virus 40 early promoter or retroviral myeloproliferative sarcoma virus promoter. Examples of inducible promoters also include mammalian probasin promoter, lactalbumin promoter, GRP78 promoter, or the bacterial tetracycline-inducible promoter. Other examples include phorbol ester, adenovirus E1A element, interferon, and serum inducible promoters.

Inducible promoters useful in the modules and biological classifier circuits as described herein for in vivo uses can include those responsive to biologically compatible agents, such as those that are usually encountered in defined animal tissues or cells. An example is the human PAI-1 promoter, which is inducible by tumor necrosis factor. Further suitable examples include cytochrome P450 gene promoters, inducible by various toxins and other agents; heat shock protein genes, inducible by various stresses; hormone-inducible genes, such as the estrogen gene promoter, and such.

The administration or removal of an inducer or repressor as disclosed herein results in a switch between the "on" or "off" states of the transcription of the operably linked heterologous target gene. Thus, as defined herein the "on" state, as it refers to a promoter operably linked to a nucleic acid sequence, refers to the state when the promoter is actively driving transcription of the operably linked nucleic acid sequence, i.e., the linked nucleic acid sequence is expressed. Several small molecule ligands have been shown to mediate regulated gene expressions, either in tissue culture cells and/or in transgenic animal models. These include the FK1012 and rapamycin immunosupressive drugs (Spencer et al., 1993; Magari et al., 1997), the progesterone antagonist mifepristone (RU486) (Wang, 1994; Wang et al., 1997), the tetracycline antibiotic derivatives (Gossen and Bujard, 1992; Gossen et al., 1995; Kistner et al., 1996), and the insect steroid hormone ecdysone (No et al., 1996). All of these references are herein incorporated by reference. By way of further example, Yao discloses in U.S. Pat. No. 6,444,871, which is incorporated herein by reference, prokaryotic elements associated with the tetracycline resistance (tet) operon, a system in which the tet repressor protein is fused with polypeptides known to modulate transcription in mammalian cells. The fusion protein is then directed to specific sites by the positioning of the tet operator sequence. For example, the tet repressor has been fused to a transactivator (VP16) and targeted to a tet operator sequence positioned upstream from the promoter of a selected gene (Gussen et al., 1992; Kim et al., 1995; Hennighausen et al., 1995). The tet repressor portion of the fusion protein binds to the operator thereby targeting the VP16 activator to the specific site where the induction of transcription is desired. An alternative approach has been to fuse the tet repressor to the KRAB repressor domain and target this protein to an operator placed several hundred base pairs upstream of a gene. Using this system, it has been found that the chimeric protein, but not the tet repressor alone, is capable of producing a 10 to 15-fold suppression of CMV-regulated gene expression (Deuschle et al., 1995).

One example of a repressible promoter useful in the modules and biological classifier circuits described herein is the Lac repressor (lacR)/operator/inducer system of *E. coli* that has been used to regulate gene expression by three different approaches: (1) prevention of transcription initiation by properly placed lac operators at promoter sites (Hu and Davidson, 1987; Brown et al., 1987; Figge et al., 1988; Fuerst et al., 1989; Deuschle et al., 1989; (2) blockage of transcribing RNA polymerase II during elongation by a LacR/operator complex (Deuschle et al. (1990); and (3) activation of a promoter responsive to a fusion between LacR and the activation domain of herpes simples virus (HSV) virion protein 16 (VP16) (Labow et al., 1990; Baim et al., 1991). In one version of the Lac system, expression of lac operator-linked sequences is constitutively activated by a LacR-VP16 fusion protein and is turned off in the presence of isopropyl-β-D-1-thiogalactopyranoside (IPTG) (Labow et al. (1990), cited supra). In another version of the system, a lacR-VP16 variant is used that binds to lac operators in the presence of IPTG, which can be enhanced by increasing the temperature of the cells (Baim et al. (1991), cited supra). Thus, in some embodiments described herein, components of the Lac system are utilized. For example, a lac operator (LacO) can be operably linked to tissue specific promoter, and control the transcription and expression of the heterologous target gene and another repressor protein, such as the TetR. Accordingly, the expression of the heterologous target gene is inversely regulated as compared to the expression or presence of Lac repressor in the system.

Components of the tetracycline (Tc) resistance system of E. coli have also been found to function in eukaryotic cells and have been used to regulate gene expression. For example, the Tet repressor (TetR), which binds to tet operator (tetO) sequences in the absence of tetracycline or doxycycline and represses gene transcription, has been expressed in plant cells at sufficiently high concentrations to repress transcription from a promoter containing tet operator sequences (Gatz, C. et al. (1992) Plant J. 2:397-404). In some embodiments described herein, the Tet repressor system is similarly utilized in the biological classifier circuits and low- and high-input detector modules described herein.

A temperature- or heat-inducible gene regulatory system can also be used in the circuits and modules described herein, such as the exemplary TIGR system comprising a cold-inducible transactivator in the form of a fusion protein having a heat shock responsive regulator, rheA, fused to the VP16 transactivator (Weber et al., 2003a). The promoter responsive to this fusion thermosensor comprises a rheO element operably linked to a minimal promoter, such as the minimal version of the human cytomegalovirus immediate early promoter. At the permissive temperature of 37° C., the cold-inducible transactivator transactivates the exemplary rheO-CMVmin promoter, permitting expression of the target gene. At 41° C., the cold-inducible transactivator no longer transactivates the rheO promoter. Any such heat-inducible or heat-regulated promoter can be used in accordance with the circuits and methods described herein, including but not limited to a heat-responsive element in a heat shock gene (e.g., hsp20-30, hsp27, hsp40, hsp60, hsp70, and hsp90). See Easton et al. (2000) Cell Stress Chaperones 5(4):276-290; Csermely et al. (1998) Pharmacol Ther 79(2): 129-1 68; Ohtsuka & Hata (2000) Int J Hyperthermia 16(3):231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119(2): 185-1 90; Kiang et al. (1998) FASEB J 12(14):1571-16-579), calreticulin (Szewczenko-Pawlikowski et al. (1997) MoI Cell Biochem 177 (1-2): 145-1 52); clusterin (Viard et al. (1999) J Invest Dermatol 112(3):290-296; Michel et al. (1997) Biochem J 328(Pt1):45-50; Clark & Griswold (1997) J Androl 18(3): 257-263), histocompatibility class I gene (HLA-G) (Ibrahim et al. (2000) Cell Stress Chaperones 5(3):207-218), and the Kunitz protease isoform of amyloid precursor protein (Shepherd et al. (2000) Neuroscience 99(2):31 7-325) are upregulated in response to heat. In the case of clusterin, a 14 base pair element that is sufficient for heat-inducibility has been delineated (Michel et al. (1997) Biochem J 328(Pt1):45-50). Similarly, a two sequence unit comprising a 10- and a 14-base pair element in the calreticulin promoter region has been shown to confer heat-inducibility (Szewczenko-Pawlikowski et al. (1997) MoI Cell Biochem 177(1-2): 145-1 52).

Other inducible promoters useful in the biological classifier circuits described herein include the erythromycin-resistance regulon from E. coli, having repressible ($E_{off}$) and inducible ($E_{on}$) systems responsive to macrolide antibiotics, such as erythromycin, clarithromycin, and roxithromycin (Weber et al., 2002). The $E_{off}$ system utilizes an erythromycin-dependent transactivator, wherein providing a macrolide antibiotic represses transgene expression. In the $E_{on}$ system, the binding of the repressor to the operator results in repression of transgene expression. Therein, in the presence of macrolides gene expression is induced.

Fussenegger et al. (2000) describe repressible and inducible systems using a Pip (pristinamycin-induced protein) repressor encoded by the streptogramin resistance operon of Streptomyces coelicolor, wherein the systems are responsive to streptogramin-type antibiotics (such as, for example, pristinamycin, virginiamycin, and Synercid). The Pip DNA-binding domain is fused to a VP16 transactivation domain or to the KRAB silencing domain, for example. The presence or absence of, for example, pristinamycin, regulates the PipON and PipOFF systems in their respective manners, as described therein.

Another example of a promoter expression system useful for the modules and biological classifier circuits described herein utilizes a quorum-sensing (referring to particular prokaryotic molecule communication systems having diffusible signal molecules that prevent binding of a repressor to an operator site, resulting in derepression of a target regulon) system. For example, Weber et al. (2003b) employ a fusion protein comprising the Streptomyces coelicolor quorum-sending receptor to a transactivating domain that regulates a chimeric promoter having a respective operator that the fusion protein binds. The expression is fine-tuned with non-toxic butyrolactones, such as SCB1 and MP133.

In some embodiments, multiregulated, multigene gene expression systems that are functionally compatible with one another are utilized in the modules and biological classifier circuits described herein (see, for example, Kramer et al. (2003)). For example, in Weber et al. (2002), the macrolide-responsive erythromycin resistance regulon system is used in conjunction with a streptogramin (PIP)-regulated and tetracycline-regulated expression systems.

Other promoters responsive to non-heat stimuli can also be used. For example, the mortalin promoter is induced by low doses of ionizing radiation (Sadekova (1997) Int J Radiat Biol 72(6):653-660), the hsp27 promoter is activated by 17-β-estradiol and estrogen receptor agonists (Porter et al. (2001) J MoI Endocrinol 26(1):31-42), the HLA-G promoter is induced by arsenite, hsp promoters can be activated by photodynamic therapy (Luna et al. (2000) Cancer Res 60(6): 1637-1 644). A suitable promoter can incorporate factors such as tissue-specific activation. For example, hsp70 is transcriptionally impaired in stressed neuroblastoma cells (Drujan & De Maio (1999) 12(6):443-448) and the mortalin promoter is up-regulated in human brain tumors (Takano et al. (1997) Exp Cell Res 237(1):38-45). A promoter employed in methods described herein can show selective up-regulation in tumor cells as described, for example, for mortalin (Takano et al. (1997) Exp Cell Res 237(1):38-45), hsp27 and calreticulin (Szewczenko-Pawlikowski et al. (1997) MoI Cell Biochem 177(1-2): 145-1 52; Yu et al. (2000) Electrophoresis 2 1(14):3058-3068)), grp94 and grp78 (Gazit et al. (1999) Breast Cancer Res Treat 54(2): 135-146), and hsp27, hsp70, hsp73, and hsp90 (Cardillo et al. (2000) Anticancer Res 20(6B):4579-4583; Strik et al. (2000) Anticancer Res 20(6B):4457-4552).

In some embodiments, the inducible promoter comprises an Anhydrotetracycline (aTc)-inducible promoter as provided in PLtetO-1 (Pubmed Nucleotide# U66309) with the sequence comprising:

```
                                                      (SEQ ID NO: 1)
GCATGCTCCCTATCAGTGATAGAGATTGACATCCCTATCAGTGATAGAGATACTGAGCACAT

CAGCAGGACGCACTGACCAGGA.
```

In some embodiments, the inducible promoter is an arabinose-inducible promoter $P_{BAD}$ comprising the sequence:

```
                                                      (SEQ ID NO: 2)
AAGAAACCAATTGTCCATATTGCATCAGACATTGCCGTCACTGCGTCTTTTACTGGCTCTTCT

CGCTAACCAAACCGGTAACCCCGCTTATTAAAAGCATTCTGTAACAAAGCGGGACCAAAGC

CATGACAAAAACGCGTAACAAAAGTGTCTATAATCACGGCAGAAAAGTCCACATTGATTAT

TTGCACGGCGTCACACTTTGCTATGCCATAGCATTTTTATCCATAAGATTAGCGGATCCTACC

TGACGCTTTTTATCGCAACTCTCTACTGTTTCTCCATA.
```

In some embodiments, the inducible promoter is an isopropyl β-D-1-thiogalactopyranoside (IPTG) inducible promoter. In one embodiment, the IPTG-inducible promoter comprises the $P_{TAC}$ sequence found in the vector encoded by PubMed Accession ID #EU546824. In one embodiment, the IPTG-inducible promoter sequence comprises the $P_{Trc-2}$ sequence:

```
                                                      (SEQ ID NO: 3)
CCATCGAATGGCTGAAATGAGCTGTTGACAATTAATCATCCGGCTCGTATAATGTGTGGAAT

TGTGAGCGGATAACAATTTCACACAGGA.
```

In some embodiments, the IPTG-inducible promoter comprises the $P_{Trc-2}$ sequence found in the vector encoded by PubMed Accession ID #EU546816.

In some embodiments, the IPTG-inducible promoter comprises the $P_{LlacO-1}$ sequence:

```
                                                      (SEQ ID NO: 4)
ATAAATGTGAGCGGATAACATTGACATTGTGAGCGGATAACAAGATACTGAGCACTCAGCAGG

ACGCACTGACC.
```

In some embodiments, the IPTG-inducible promoter comprises the $P_{A1lacO-1}$ sequence:

```
                                                      (SEQ ID NO: 5)
AAAATTTATCAAAAAGAGTGTTGACTTGTGAGCGGATAACAATGATACTTAGATTCAATTGT

GAGCGGATAACAATTTCACACA.
```

In some embodiments, the IPTG-inducible promoter comprises the $P_{lac/ara-1}$ sequence

```
                                                      (SEQ ID NO: 6)
CATAGCATTTTTATCCATAAGATTAGCGGATCCTAAGCTTTACAATTGTGAGCGCTCACAATT

ATGATAGATTCAATTGTGAGCGGATAACAATTTCACACA.
```

In some embodiments, the inducible promoter sequence comprises the $P_{Ls1con}$ sequence:

```
                                                      (SEQ ID NO: 7)
GCATGCACAGATAACCATCTGCGGTGATAAATTATCTCTGGCGGTGTTGACATAAATACCAC

TGGCGGTtATAaTGAGCACATCAGCAGG//GTATGCAAAGGA
```

Other non-limiting examples of promoters that are useful for use in the low- and high-input detector modules and biological classifier circuits described herein are provided in Tables 1-36.

TABLE 1

Examples of Constitutive *E.coli* $\sigma^{70}$ Promoters

| Name | Description | Promoter Sequence |
| --- | --- | --- |
| BBa_I14018 | SEQ ID NO: 8 P(Bla) | ...gtttatacataggcgagtactctgttatgg |
| BBa_I14033 | SEQ ID NO: 9 P(Cat) | ...agaggttccaactttcaccataatgaaaca |
| BBa_I14034 | SEQ ID NO: 10 P(Kat) | ...taaacaactaacggacaattctacctaaca |
| BBa_I732021 | SEQ ID NO: 11 Template for Building Primer Family Member | ...acatcaagccaaattaaacaggattaacac |
| BBa_I742126 | SEQ ID NO: 12 Reverse lambda cI-regulated promoter | ...gaggtaaaatagtcaacacgcacggtgtta |
| BBa_J01006 | SEQ ID NO: 13 Key Promoter absorbs 3 | ...caggccggaataactccctataatgcgcca |
| BBa_J23100 | SEQ ID NO: 14 constitutive promoter family member | ...ggctagctcagtcctaggtacagtgctagc |
| BBa_J23101 | SEQ ID NO: 15 constitutive promoter family member | ...agctagctcagtcctaggtattatgctagc |
| BBa_J23102 | SEQ ID NO: 16 constitutive promoter family member | ...agctagctcagtcctaggtactgtgctagc |
| BBa_J23103 | SEQ ID NO: 17 constitutive promoter family member | ...agctagctcagtcctagggattatgctagc |
| BBa_J23104 | SEQ ID NO: 18 constitutive promoter family member | ...agctagctcagtcctaggtattgtgctagc |
| BBa_J23105 | SEQ ID NO: 19 constitutive promoter family member | ...ggctagctcagtcctaggtactatgctagc |
| BBa_J23106 | SEQ ID NO: 20 constitutive promoter family member | ...ggctagctcagtcctaggtatagtgctagc |
| BBa_J23107 | SEQ ID NO: 21 constitutive promoter family member | ...ggctagctcagccctaggtattatgctagc |
| BBa_J23108 | SEQ ID NO: 22 constitutive promoter family member | ...agctagctcagtcctaggtataatgctagc |
| BBa_J23109 | SEQ ID NO: 23 constitutive promoter family member | ...agctagctcagtcctagggactgtgctagc |
| BBa_J23110 | SEQ ID NO: 24 constitutive promoter family member | ...ggctagctcagtcctaggtacaatgctagc |
| BBa_J23111 | SEQ ID NO: 25 constitutive promoter family member | ...ggctagctcagtcctaggtatagtgctagc |
| BBa_J23112 | SEQ ID NO: 26 constitutive promoter family member | ...agctagctcagtcctagggattatgctagc |
| BBa_J23113 | SEQ ID NO: 27 constitutive promoter family member | ...ggctagctcagtcctagggattatgctagc |
| BBa_J23114 | SEQ ID NO: 28 constitutive promoter family member | ...ggctagctcagtcctaggtacaatgctagc |
| BBa_J23115 | SEQ ID NO: 29 constitutive promoter family member | ...agctagctcagcccttggtacaatgctagc |
| BBa_J23116 | SEQ ID NO: 30 constitutive promoter family member | ...agctagctcagtcctagggactatgctagc |
| BBa_J23117 | SEQ ID NO: 31 constitutive promoter family member | ...agctagctcagtcctagggattgtgctagc |

TABLE 1-continued

Examples of Constitutive *E.coli* σ[70] Promoters

| Name | Description | Promoter Sequence |
| --- | --- | --- |
| BBa_J23118 | SEQ ID NO: 32 constitutive promoter family member | ...ggctagctcagtcctaggtattgtgctagc |
| BBa_J23119 | SEQ ID NO: 33 constitutive promoter family member | ...agctagctcagtcctaggtataatgctagc |
| BBa_J23150 | SEQ ID NO: 34 1 bp mutant from J23107 | ...ggctagctcagtcctaggtattatgctagc |
| BBa_J23151 | SEQ ID NO: 35 1 bp mutant from J23114 | ...ggctagctcagtcctaggtacaatgctagc |
| BBa_J44002 | SEQ ID NO: 36 pBAD reverse | ...aaagtgtgacgccgtgcaaataatcaatgt |
| BBa_J48104 | SEQ ID NO: 37 NikR promoter, a protein of the ribbon helix-helix family of transcription factors that repress expre | ...gacgaatacttaaaatcgtcatacttattt |
| BBa_J54200 | SEQ ID NO: 38 lacq_Promoter | ...aaaccttttcgcggtatggcatgatagcgcc |
| BBa_J56015 | SEQ ID NO: 39 lacIQ-promoter sequence | ...tgatagcgcccggaagagagtcaattcagg |
| BBa_J64951 | SEQ ID NO: 40 *E. coli* CreABCD phosphate sensing operon promoter | ...ttatttaccgtgacgaactaattgctcgtg |
| BBa_K088007 | SEQ ID NO: 41 GlnRS promoter | ...catacgccgttatacgttgtttacgctttg |
| BBa_K119000 | SEQ ID NO: 42 Constitutive weak promoter of lacZ | ...ttatgcttccggctcgtatgttgtgtggac |
| BBa_K119001 | SEQ ID NO: 43 Mutated LacZ promoter | ...ttatgcttccggctcgtatggtgtgtggac |
| BBa_K137029 | SEQ ID NO: 44 constitutive promoter with (TA)10 between −10 and −35 elements | ...atatatatatatatataatggaagcgtttt |
| BBa_K137030 | SEQ ID NO: 45 constitutive promoter with (TA)9 between −10 and −35 elements | ...atatatatatatatataatggaagcgtttt |
| BBa_K137031 | SEQ ID NO: 46 constitutive promoter with (C)10 between −10 and −35 elements | ...ccccgaaagcttaagaatataattgtaagc |
| BBa_K137032 | SEQ ID NO: 47 constitutive promoter with (C)12 between −10 and −35 elements | ...ccccgaaagcttaagaatataattgtaagc |
| BBa_K137085 | SEQ ID NO: 48 optimized (TA) repeat constitutive promoter with 13 bp between −10 and −35 elements | ...tgacaatatatatatatataatgctagc |
| BBa_K137086 | SEQ ID NO: 49 optimized (TA) repeat constitutive promoter with 15 bp between −10 and −35 elements | ...acaatatatatatatatataatgctagc |
| BBa_K137087 | SEQ ID NO: 50 optimized (TA) repeat constitutive promoter with 17 bp between −10 and −35 elements | ...aatatatatatatatatataatgctagc |
| BBa_K137088 | SEQ ID NO: 51 optimized (TA) repeat constitutive promoter with 19 bp between −10 and −35 elements | ...tatatatatatatatatataatgctagc |
| BBa_K137089 | SEQ ID NO: 52 optimized (TA) repeat constitutive promoter with 21 bp between −10 and −35 elements | ...tatatatatatatatatatataatgctagc |

TABLE 1-continued

Examples of Constitutive E.coli σ⁷⁰ Promoters

| Name | Description | Promoter Sequence |
|---|---|---|
| BBa_K137090 | SEQ ID NO: 53 optimized (A) repeat constitutive promoter with 17 bp between −10 and −35 elements | ...aaaaaaaaaaaaaaaaaatataatgctagc |
| BBa_K137091 | SEQ ID NO: 54 optimized (A) repeat constitutive promoter with 18 bp between −10 and −35 elements | ...aaaaaaaaaaaaaaaaaatataatgctagc |
| BBa_K256002 | SEQ ID NO: 55 J23101:GFP | ...caccttcgggtgggcctttctgcgtttata |
| BBa_K256018 | SEQ ID NO: 56 J23119:IFP | ...caccttcgggtgggcctttctgcgtttata |
| BBa_K256020 | SEQ ID NO: 57 J23119:HO1 | ...caccttcgggtgggcctttctgcgtttata |
| BBa_K256033 | SEQ ID NO: 58 Infrared signal reporter (J23119:IFP:J23119:HO1) | ...caccttcgggtgggcctttctgcgtttata |
| BBa_K292000 | SEQ ID NO: 59 Double terminator + constitutive promoter | ...ggctagctcagtcctaggtacagtgctagc |
| BBa_K292001 | SEQ ID NO: 60 Double terminator + constitutive promoter + Strong RBS | ...tgctagctactagagattaaagaggagaaa |
| BBa_M13101 | SEQ ID NO: 61 M13K07 gene I promoter | ...cctgttttatgttattctctctgtaaagg |
| BBa_M13102 | SEQ ID NO: 62 M13K07 gene II promoter | ...aaatatttgcttatacaatcttcctgtttt |
| BBa_M13103 | SEQ ID NO: 63 M13K07 gene III promoter | ...gctgataaaccgatacaattaaaggctcct |
| BBa_M13104 | SEQ ID NO: 64 M13K07 gene IV promoter | ...ctcttctcagcgtcttaatctaagctatcg |
| BBa_M13105 | SEQ ID NO: 65 M13K07 gene V promoter | ...atgagccagttcttaaaatcgcataaggta |
| BBa_M13106 | SEQ ID NO: M13K07 gene VI promoter | ...ctattgattgtgacaaaataaacttattcc |
| BBa_M13108 | SEQ ID NO: 67 M13K07 gene VIII promoter | ...gtttcgcgcttggtataatcgctgggggtc |
| BBa_M13110 | SEQ ID NO: 68 M13110 | ...ctttgcttctgactataatagtcagggtaa |
| BBa_M31519 | SEQ ID NO: 69 Modified promoter sequence of g3. | ...aaaccgatacaattaaaggctcctgctagc |
| BBa_R1074 | SEQ ID NO: 70 Constitutive Promoter I | ...gccggaataactccctataatgcgccacca |
| BBa_R1075 | SEQ ID NO: 71 Constitutive Promoter II | ...gccggaataactccctataatgcgccacca |
| BBa_S03331 | SEQ ID NO: 72 | ttgacaagcttttcctcagctccgtaaact |

TABLE 2

Examples of Constitutive E. coli σ⁷⁰ Promoters

| Identifier | Sequence | |
|---|---|---|
| BBa_J23119 | SEQ ID NO: 73 ttgacagctagctcagtcctaggtataatgctagc | n/a |
| BBa_J23100 | SEQ ID NO: 74 ttgacggctagctcagtcctaggtacagtgctagc | 1 |
| BBa_J23101 | SEQ ID NO: 75 tttacagctagctcagtcctaggtattatgctagc | 0.70 |

TABLE 2-continued

Examples of Constitutive E. coli σ⁷⁰ Promoters

| Identifier | Sequence | | |
|---|---|---|---|
| BBa_J23102 | SEQ ID NO: 76 | ttgacagctagctcagtcctaggtactgtgctagc | 0.86 |
| BBa_J23103 | SEQ ID NO: 77 | ctgatagctagctcagtcctagggattatgctagc | 0.01 |
| BBa_J23104 | SEQ ID NO: 78 | ttgacagctagctcagtcctaggtattgtgctagc | 0.72 |
| BBa_J23105 | SEQ ID NO: 79 | tttacggctagctcagtcctaggtactatgctagc | 0.24 |
| BBa_J23106 | SEQ ID NO: 80 | tttacggctagctcagtcctaggtatagtgctagc | 0.47 |
| BBa_J23107 | SEQ ID NO: 81 | tttacggctagctcagccctaggtattatgctagc | 0.36 |
| BBa_J23108 | SEQ ID NO: 82 | ctgacagctagctcagtcctaggtataatgctagc | 0.51 |
| BBa_J23109 | SEQ ID NO: 83 | tttacagctagctcagtcctagggactgtgctagc | 0.04 |
| BBa_J23110 | SEQ ID NO: 84 | tttacggctagctcagtcctaggtacaatgctagc | 0.33 |
| BBa_J23111 | SEQ ID NO: 85 | ttgacggctagctcagtcctaggtatagtgctagc | 0.58 |
| BBa_J23112 | SEQ ID NO: 86 | ctgatagctagctcagtcctagggattatgctagc | 0.00 |
| BBa_J23113 | SEQ ID NO: 87 | ctgatggctagctcagtcctagggattatgctagc | 0.01 |
| BBa_J23114 | SEQ ID NO: 88 | tttatggctagctcagtcctaggtacaatgctagc | 0.10 |
| BBa_J23115 | SEQ ID NO: 89 | tttatagctagctcagcccttggtacaatgctagc | 0.15 |
| BBa_J23116 | SEQ ID NO: 90 | ttgacagctagctcagtcctagggactatgctagc | 0.16 |
| BBa_J23117 | SEQ ID NO: 91 | ttgacagctagctcagtcctagggattgtgctagc | 0.06 |
| BBa_J23118 | SEQ ID NO: 92 | ttgacggctagctcagtcctaggtattgtgctagc | 0.56 |

TABLE 3

Examples of Constitutive E. coli σˢ Promoters

| Name | Description | Promoter Sequence |
|---|---|---|
| BBa_J45992 | SEQ ID NO: 93 Full-length stationary phase osmY promoter | ...ggtttcaaaattgtgatctatatttaacaa |
| BBa_J45993 | SEQ ID NO: 94 Minimal stationary phase osmY promoter | ...ggtttcaaaattgtgatctatatttaacaa |

TABLE 4

Examples of Constitutive E. coli σ³² Promoters

| Name | Description | Promoter Sequence |
|---|---|---|
| BBa_J45504 | SEQ ID NO: 95 htpG Heat Shock Promoter | ...tctattccaataaagaaatcttcctgcgtg |

TABLE 5

Examples of Constitutive B. subtilis σ⁴ Promoters

| Name | Description | Promoter Sequence |
|---|---|---|
| BBa_K143012 | SEQ ID NO: 96 Promoter veg a constitutive promoter for B. subtilis | ...aaaaatgggctcgtgttgtacaataaatgt |

TABLE 5-continued

Examples of Constitutive *B. subtilis* σ$^A$ Promoters

| Name | Description | Promoter Sequence |
|---|---|---|
| BBa_K143013 | SEQ ID NO: 97 Promoter 43 a constitutive promoter for *B. subtilis* | ...aaaaaaagcgcgcgattatgtaaaatataa |

TABLE 6

Examples of Constitutive *B. subtilis* σ$^B$ Promoters

| Name | Description | Promoter Sequence |
|---|---|---|
| BBa_K143010 | SEQ ID NO: 98 Promoter ctc for *B. subtilis* | ...atccttatcgttatgggtattgtttgtaat |
| BBa_K143011 | SEQ ID NO: 99 Promoter gsiB for *B. subtilis* | ...taaaagaattgtgagcgggaatacaacaac |
| BBa_K143013 | SEQ ID NO: 100 Promoter 43 a constitutive promoter for *B. subtilis* | ...aaaaaaagcgcgcgattatgtaaaatataa |

TABLE 7

Examples of Constitutive Promoters from Miscellaneous Prokaryotes

| Name | Description | Promoter Sequence |
|---|---|---|
| BBa_K112706 | SEQ ID NO: 101 Pspv2 from Salmonella | ...tacaaaataattcccctgcaaacattatca |
| BBa_K112707 | SEQ ID NO: 102 Pspv from Salmonella | ...tacaaaataattcccctgcaaacattatcg |

TABLE 8

Examples of Constitutive Promoters from bacteriophage T7

| Name | Description | Promoter Sequence |
|---|---|---|
| BBa_I712074 | SEQ ID NO: 103 T7 promoter (strong promoter from T7 bacteriophage) | ...agggaatacaagctacttgttcttttttgca |
| BBa_I719005 | SEQ ID NO: 104 T7 Promoter | taatacgactcactatagggaga |
| BBa_J34814 | SEQ ID NO: 105 T7 Promoter | gaatttaatacgactcactatagggaga |
| BBa_J64997 | SEQ ID NO: 106 T7 consensus -10 and rest | taatacgactcactatagg |
| BBa_K113010 | SEQ ID NO: 107 overlapping T7 promoter | ...gagtcgtattaatacgactcactatagggg |
| BBa_K113011 | SEQ ID NO: 108 more overlapping T7 promoter | ...agtgagtcgtactacgactcactatagggg |
| BBa_K113012 | SEQ ID NO: 109 weaken overlapping T7 promoter | ...gagtcgtattaatacgactctctatagggg |
| BBa_R0085 | SEQ ID NO: 110 T7 Consensus Promoter Sequence | taatacgactcactatagggaga |
| BBa_R0180 | SEQ ID NO: 111 T7 RNAP promoter | ttatacgactcactatagggaga |
| BBa_R0181 | SEQ ID NO: 112 T7 RNAP promoter | gaatacgactcactatagggaga |
| BBa_R0182 | SEQ ID NO: 113 T7 RNAP promoter | taatacgtctcactatagggaga |
| BBa_R0183 | SEQ ID NO: 114 T7 RNAP promoter | tcatacgactcactatagggaga |

TABLE 8-continued

Examples of Constitutive Promoters from bacteriophage T7

| Name | Description | Promoter Sequence |
|---|---|---|
| BBa_Z0251 | SEQ ID NO: 115 T7 strong promoter | ...taatacgactcactatagggagaccacaac |
| BBa_Z0252 | SEQ ID NO: 116 T7 weak binding and processivity | ...taattgaactcactaaagggagaccacagc |
| BBa_Z0253 | SEQ ID NO: 117 T7 weak binding promoter | ...cgaagtaatacgactcactattagggaaga |
|  | SEQ ID NO: 118 T7 14.3 m | attaaccctcactaaagggaga |

TABLE 9

Examples of Constitutive Promoters from bacteriophage SP6

| Name | Description | Promoter Sequence |
|---|---|---|
| BBa_J64998 | SEQ ID NO: 119 consensus -10 and rest from SP6 | atttaggtgacactataga |

TABLE 10

Examples of Constitutive Promoters from Yeast

| Name | Description | Promoter Sequence |
|---|---|---|
| BBa_I766555 | SEQ ID NO: 120 pCyc (Medium) Promoter | ... acaaacacaaatacacacactaaattaata |
| BBa_I766556 | SEQ ID NO: 121 pAdh (Strong) Promoter | ... ccaagcatacaatcaactatctcatataca |
| BBa_I766557 | SEQ ID NO: 122 pSte5 (Weak) Promoter | ... gatacaggatacagcggaaacaactttaa |
| BBa_J63005 | SEQ ID NO: 123 yeast ADH1 promoter | ... tttcaagctataccaagcatacaatcaact |
| BBa_K105027 | SEQ ID NO: 124 cyc100 minimal promoter | ... cctttgcagcataaattactatacttctat |
| BBa_K105028 | SEQ ID NO: 125 cyc70 minimal promoter | ... cctttgcagcataaattactatacttctat |
| BBa_K105029 | SEQ ID NO: 126 cyc43 minimal promoter | ... cctttgcagcataaattactatacttctat |
| BBa_K105030 | SEQ ID NO: 127 cyc28 minimal promoter | ... cctttgcagcataaattactatacttctat |
| BBa_K105031 | SEQ ID NO: 128 cyc16 minimal promoter | ... cctttgcagcataaattactatacttctat |
| BBa_K122000 | SEQ ID NO: 129 pPGK1 | ... ttatctacttttacaacaaatataaaaca |
| BBa_K124000 | SEQ ID NO: 130 pCYC Yeast Promoter | ... acaaacacaaatacacacactaaattaata |
| BBa_K124002 | SEQ ID NO: 131 Yeast GPD (TDH3) Promoter | ... gtttcgaataaacacacataaacaaacaaa |
| BBa_M31201 | SEQ ID NO: 132 Yeast CLB1 promoter region, G2/M cell cycle specific | ... accatcaaaggaagctttaatcttctcata |

TABLE 11

Examples of Constitutive Promoters from Miscellaneous Eukaryotes

| Name | Description | Promoter Sequence |
|---|---|---|
| BBa_I712004 | SEQ ID NO: 133 CMV promoter | ... agaacccactgcttactggcttatcgaaat |
| BBa_K076017 | SEQ ID NO: 134 Ubc Promoter | ... ggccgttttggcttttttgttagacgaag |

TABLE 12

Examples of Cell Signaling Promoters

| Name | Description | | Promoter Sequence |
|---|---|---|---|
| BBa_I1051 | SEQ ID NO: 135 | Lux cassette right promoter | . . . tgttatagtcgaatacctctggcggtgata |
| BBa_I14015 | SEQ ID NO: 136 | P(Las) TetO | . . . ttttggtacactccctatcagtgatagaga |
| BBa_I14016 | SEQ ID NO: 137 | P(Las) CIO | . . . cttttggtacactacctctggcggtgata |
| BBa_I14017 | SEQ ID NO: 138 | P(Rhl) | . . . tacgcaagaaaatggtttgttatagtcgaa |
| BBa_I739105 | SEQ ID NO: 139 | Double Promoter (LuxR/HSL, positive/cI, negative) | . . . cgtgcgtgttgataacaccgtgcgtgttga |
| BBa_I746104 | SEQ ID NO: 140 | P2 promoter in agr operon from S. aureus | . . . agattgtactaaatcgtataatgacagtga |
| BBa_I751501 | SEQ ID NO: 141 | plux-cI hybrid promoter | . . . gtgttgatgcttttatcaccgccagtggta |
| BBa_I751502 | SEQ ID NO: 142 | plux-lac hybrid promoter | . . . agtgtgtggaattgtgagcggataacaatt |
| BBa_J761011 | SEQ ID NO: 143 | CinR, CinL and glucose controlled promoter | . . . acatcttaaaagttttagtatcatattcgt |
| BBa_J06403 | SEQ ID NO: 144 | RhlR promoter repressible by CI | . . . tacgcaagaaaatggtttgttatagtcgaa |
| BBa_J64000 | SEQ ID NO: 145 | rhlI promoter | . . . atcctcctttagtcttcccctcatgtgtg |
| BBa_J64010 | SEQ ID NO: 146 | lasI promoter | . . . taaaattatgaaatttgcataaattcttca |
| BBa_J64067 | SEQ ID NO: 147 | LuxR + 3OC6HSL independent R0065 | . . . gtgttgactattttacctctggcggtgata |
| BBa_J64712 | SEQ ID NO: 148 | LasR/LasI Inducible & RHLR/RHLI repressible Promoter | . . . gaaatctggcagttttggtacacgaaagc |
| BBa_K091107 | SEQ ID NO: 149 | pLux/cI Hybrid Promoter | . . . acaccgtgcgtgttgatatagtcgaataaa |
| BBa_K091117 | SEQ ID NO: 150 | pLas promoter | . . . aaaattatgaaatttgtataaattcttcag |
| BBa_K091143 | SEQ ID NO: 151 | pLas/cI Hybrid Promoter | . . . ggttcttttggtacctctggcggtgataa |
| BBa_K091146 | SEQ ID NO: 152 | pLas/Lux Hybrid Promoter | . . . tgtaggatcgtacaggtataaattcttcag |
| BBa_K091156 | SEQ ID NO: 153 | pLux | . . . caagaaaatggtttgttatagtcgaataaa |
| BBa_K091157 | SEQ ID NO: 154 | pLux/Las Hybrid Promoter | . . . ctatctcatttgctagtatagtcgaataaa |
| BBa_K145150 | SEQ ID NO: 155 | Hybrid promoter: HSL-LuxR activated, P22 C2 repressed | . . . tagtttataatttaagtgttctttaatttc |
| BBa_K266000 | SEQ ID NO: 156 | PAI + LasR -> LuxI (AI) | . . . caccttcgggtgggcctttctgcgtttata |
| BBa_K266005 | SEQ ID NO: 157 | PAI + LasR -> LasI & AI + LuxR --\| LasI | . . . aataactctgatagtgctagtgtagatctc |
| BBa_K266006 | SEQ ID NO: 158 | PAI + LasR -> LasI + GFP & AI + LuxR --\| LasI + GFP | . . . caccttcgggtgggcctttctgcgtttata |
| BBa_K266007 | SEQ ID NO: 159 | Complex QS -> LuxI & LasI circuit | . . . caccttcgggtgggcctttctgcgtttata |
| BBa_R0061 | SEQ ID NO: 160 | Promoter (HSL-mediated luxR repressor) | . . . ttgacacctgtaggatcgtacaggtataat |
| BBa_R0062 | SEQ ID NO: 161 | Promoter (luxR & HSL regulated -- lux pR) | . . . caagaaaatggtttgttatagtcgaataaa |
| BBa_R0063 | SEQ ID NO: 162 | Promoter (luxR & HSL regulated -- lux pL) | . . . cacgcaaaacttgcgacaaacaataggtaa |
| BBa_R0071 | SEQ ID NO: 163 | Promoter (RhlR & C4-HSL regulated) | . . . gttagctttcgaattggctaaaaagtgttc |
| BBa_R0078 | SEQ ID NO: 164 | Promoter (cinR and HSL regulated) | . . . ccattctgctttccacgaacttgaaaacgc |

TABLE 12-continued

Examples of Cell Signaling Promoters

| Name | Description | Promoter Sequence |
|---|---|---|
| BBa_R0079 | SEQ ID NO: 165 Promoter (LasR & PAI regulated) | . . . ggccgcgggttcttttggtacacgaaagc |
| BBa_R1062 | SEQ ID NO: 166 Promoter, Standard (luxR and HSL regulated -- lux pR) | . . . aagaaaatggtttgttgatactcgaataaa |

TABLE 13

Examples of Metal Inducible Promoters

| Name | Description | Promoter Sequence |
|---|---|---|
| BBa_I721001 | SEQ ID NO: 167 Lead Promoter | . . . gaaaaccttgtcaatgaagagcgatctatg |
| BBa_I731004 | SEQ ID NO: 168 FecA promoter | . . . ttctcgttcgactcatagctgaacacaaca |
| BBa_I760005 | SEQ ID NO: 169 Cu-sensitive promoter | atgacaaaattgtcat |
| BBa_I765000 | SEQ ID NO: 170 Fe promoter | . . . accaatgctgggaacggccagggcacctaa |
| BBa_I765007 | SEQ ID NO: 171 Fe and UV promoters | . . . ctgaaagcgcataccgctatggagggggtt |
| BBa_J3902 | SEQ ID NO: 172 PrFe (PI + PII rus operon) | . . . tagatatgcctgaaagcgcataccgctatg |

TABLE 14

Examples of T7 Promoters

| Name | Description | Promoter Sequence |
|---|---|---|
| BBa_I712074 | SEQ ID NO: 173 T7 promoter (strong promoter from T7 bacteriophage) | . . . agggaatacaagctacttgttcttttttgca |
| BBa_I719005 | SEQ ID NO: 174 T7 Promoter | taatacgactcactataggaga |

TABLE 15

Examples of Stress Kit Promoters

| Name | Description | Promoter Sequence |
|---|---|---|
| BBa_K086017 | SEQ ID NO: 193 unmodified Lutz-Bujard LacO promoter | . . . ttgtgagcggataacaagatactgagcaca |
| BBa_K086018 | SEQ ID NO: 194 modified Lutz-Bujard LacO promoter, with alternative sigma factor σ24 | . . . ttgtgagcggataacaattctgaagaacaa |
| BBa_K086019 | SEQ ID NO: 195 modified Lutz-Bujard LacO promoter, with alternative sigma factor σ24 | . . . ttgtgagcggataacaattctgataaaaca |
| BBa_K086020 | SEQ ID NO: 196 modified Lutz-Bujard LacO promoter, with alternative sigma factor σ24 | . . . ttgtgagcggataacatctaacccttaga |
| BBa_K086021 | SEQ ID NO: 197 modified Lutz-Bujard LacO promoter, with alternative sigma factor σ24 | . . . ttgtgagcggataacatagcagataagaaa |
| BBa_K086022 | SEQ ID NO: 198 modified Lutz-Bujard LacO promoter, with alternative sigma factor σ28 | . . . gtttgagcgagtaacgccgaaaatcttgca |
| BBa_K086023 | SEQ ID NO: 199 modified Lutz-Bujard LacO promoter, with alternative sigma factor σ28 | . . . gtgtgagcgagtaacgacgaaaatcttgca |
| BBa_K086024 | SEQ ID NO: 200 modified Lutz-Bujard LacO promoter, with alternative sigma factor σ28 | . . . tttgagcgagtaacagccgaaaatcttgca |

TABLE 15-continued

Examples of Stress Kit Promoters

| Name | Description | Promoter Sequence |
|---|---|---|
| BBa_K086025 | SEQ ID NO: 201 modified Lutz-Bujard LacO promoter, with alternative sigma factor σ28 | . . . tgtgagcgagtaacagccgaaaatcttgca |
| BBa_K086026 | SEQ ID NO: 202 modified Lutz-Bujard LacO promoter, with alternative sigma factor σ32 | . . . ttgtgagcgagtggcaccattaagtacgta |
| BBa_K086027 | SEQ ID NO: 203 modified Lutz-Bujard LacO promoter, with alternative sigma factor σ32 | . . . ttgtgagcgagtgacaccattaagtacgta |
| BBa_K086028 | SEQ ID NO: 204 modified Lutz-Bujard LacO promoter, with alternative sigma factor σ32 | . . . ttgtgagcgagtaacaccattaagtacgta |
| BBa_K086029 | SEQ ID NO: 205 modified Lutz-Bujard LacO promoter, with alternative sigma factor σ32 | . . . ttgtgagcgagtaacaccattaagtacgta |
| BBa_K086030 | SEQ ID NO: 206 modified Lutz-Bujard LacO promoter, with alternative sigma factor σ38 | . . . cagtgagcgagtaacaactacgctgtttta |
| BBa_K086031 | SEQ ID NO: 207 modified Lutz-Bujard LacO promoter, with alternative sigma factor σ38 | . . . cagtgagcgagtaacaactacgctgtttta |
| BBa_K086032 | SEQ ID NO: 208 modified Lutz-Bujard LacO promoter, with alternative sigma factor σ38 | . . . atgtgagcggataacactataattaataga |
| BBa_K086033 | SEQ ID NO: 209 modified Lutz-Bujard LacO promoter, with alternative sigma factor σ38 | . . . atgtgagcggataacactataattaataga |

TABLE 16

Examples of Logic Promoters

| Name | Description | Promoter Sequence |
|---|---|---|
| BBa_I732200 | SEQ ID NO: 210 NOT Gate Promoter Family Member (D00101wt1) | . . . gaattgtgagcggataacaattggatccgg |
| BBa_I732201 | SEQ ID NO: 211 NOT Gate Promoter Family Member (D001011) | . . . ggaattgtgagcgctcacaattggatccgg |
| BBa_I732202 | SEQ ID NO: 212 NOT Gate Promoter Family Member (D001022) | . . . ggaattgtaagcgcttacaattggatccgg |
| BBa_I732203 | SEQ ID NO: 213 NOT Gate Promoter Family Member (D001033) | . . . ggaattgtaaacgtttacaattggatccgg |
| BBa_I732204 | SEQ ID NO: 214 NOT Gate Promoter Family Member (D001044) | . . . ggaattgtgaacgttcacaattggatccgg |
| BBa_I732205 | SEQ ID NO: 215 NOT Gate Promoter Family Member (D001055) | . . . ggaattttgagcgctcaaaattggatccgg |
| BBa_I732206 | SEQ ID NO: 216 NOT Gate Promoter Family Member (D001066) | . . . ggaattatgagcgctcataattggatccgg |
| BBa_I732207 | SEQ ID NO: 217 NOT Gate Promoter Family Member (D001077) | . . . gggacgactgtatacagtcgtcggatccgg |
| BBa_I732270 | SEQ ID NO: 218 Promoter Family Member with Hybrid Operator (D001012) | . . . ggaattgtgagcgcttacaattggatccgg |
| BBa_I732271 | SEQ ID NO: 219 Promoter Family Member with Hybrid Operator (D001016) | . . . ggaattgtgagcgctcataattggatccgg |
| BBa_I732272 | SEQ ID NO: 220 Promoter Family Member with Hybrid Operator (D001017) | . . . ggaattgtgagctacagtcgtcggatccgg |
| BBa_I732273 | SEQ ID NO: 221 Promoter Family Member with Hybrid Operator (D001021) | . . . ggaattgtaagcgctcacaattggatccgg |
| BBa_I732274 | SEQ ID NO: 222 Promoter Family Member with Hybrid Operator (D001024) | . . . ggaattgtaagcgttcacaattggatccgg |

TABLE 16-continued

Examples of Logic Promoters

| Name | Description | Promoter Sequence |
|---|---|---|
| BBa_I732275 | SEQ ID NO: 223 Promoter Family Member with Hybrid Operator (D001026) | . . . ggaattgtaagcgctcataattggatccgg |
| BBa_I732276 | SEQ ID NO: 224 Promoter Family Member with Hybrid Operator (D001027) | . . . ggaattgtaagctacagtcgtcggatccgg |
| BBa_I732277 | SEQ ID NO: 225 Promoter Family Member with Hybrid Operator (D001046) | . . . ggaattgtgaacgctcataattggatccgg |
| BBa_I732278 | SEQ ID NO: 226 Promoter Family Member with Hybrid Operator (D001047) | . . . ggaattgtgaactacagtcgtcggatccgg |
| BBa_I732279 | SEQ ID NO: 227 Promoter Family Member with Hybrid Operator (D001061) | . . . ggaattatgagcgctcacaattggatccgg |
| BBa_I732301 | SEQ ID NO: 228 NAND Candidate (U073026D001016) | . . . ggaattgtgagcgctcataattggatccgg |
| BBa_I732302 | SEQ ID NO: 229 NAND Candidate (U073027D001017) | . . . ggaattgtgagctacagtcgtcggatccgg |
| BBa_I732303 | SEQ ID NO: 230 NAND Candidate (U073022D001046) | . . . ggaattgtgaacgctcataattggatccgg |
| BBa_I732304 | SEQ ID NO: 231 NAND Candidate (U073022D001047) | . . . ggaattgtgaactacagtcgtcggatccgg |
| BBa_I732305 | SEQ ID NO: 232 NAND Candidate (U073022D059046) | . . . taaattgtgaacgctcataattggatccgg |
| BBa_I732306 | SEQ ID NO: 233 NAND Candidate (U073011D002022) | . . . gaaattgtaagcgcttacaattggatccgg |
| BBa_I732351 | SEQ ID NO: 234 NOR Candidate (U037011D002022) | . . . gaaattgtaagcgcttacaattggatccgg |
| BBa_I732352 | SEQ ID NO: 235 NOR Candidate (U035044D001022) | . . . ggaattgtaagcgcttacaattggatccgg |
| BBa_I732400 | SEQ ID NO: 236 Promoter Family Member (U097NUL + D062NUL) | . . . gccaaattaaacaggattaacaggatccgg |
| BBa_I732401 | SEQ ID NO: 237 Promoter Family Member (U097O11 + D062NUL) | . . . gccaaattaaacaggattaacaggatccgg |
| BBa_I732402 | SEQ ID NO: 238 Promoter Family Member (U085O11 + D062NUL) | . . . gccaaattaaacaggattaacaggatccgg |
| BBa_I732403 | SEQ ID NO: 239 Promoter Family Member (U073O11 + D062NUL) | . . . gccaaattaaacaggattaacaggatccgg |
| BBa_I732404 | SEQ ID NO: 240 Promoter Family Member (U061O11 + D062NUL) | . . . gccaaattaaacaggattaacaggatccgg |
| BBa_I732405 | SEQ ID NO: 241 Promoter Family Member (U049O11 + D062NUL) | . . . gccaaattaaacaggattaacaggatccgg |
| BBa_I732406 | SEQ ID NO: 242 Promoter Family Member (U037O11 + D062NUL) | . . . gccaaattaaacaggattaacaggatccgg |
| BBa_I732407 | SEQ ID NO: 243 Promoter Family Member (U097NUL + D002O22) | . . . gaaattgtaagcgcttacaattggatccgg |
| BBa_I732408 | SEQ ID NO: 244 Promoter Family Member (U097NUL + D014O22) | . . . taaattgtaagcgcttacaattggatccgg |
| BBa_I732409 | SEQ ID NO: 245 Promoter Family Member (U097NUL + D026O22) | . . . gtaattgtaagcgcttacaattggatccgg |
| BBa_I732410 | SEQ ID NO: 246 Promoter Family Member (U097NUL + D038O22) | . . . tcaattgtaagcgcttacaattggatccgg |
| BBa_I732411 | SEQ ID NO: 247 Promoter Family Member (U097NUL + D050O22) | . . . aaaattgtaagcgcttacaattggatccgg |

TABLE 16-continued

Examples of Logic Promoters

| Name | Description | Promoter Sequence |
|---|---|---|
| BBa_I732412 | SEQ ID NO: 248 Promoter Family Member (U097NUL + D062O22) | . . . caaattgtaagcgcttacaattggatccgg |
| BBa_I732413 | SEQ ID NO: 249 Promoter Family Member (U097O11 + D002O22) | . . . gaaattgtaagcgcttacaattggatccgg |
| BBa_I732414 | SEQ ID NO: 250 Promoter Family Member (U097O11 + D014O22) | . . . taaattgtaagcgcttacaattggatccgg |
| BBa_I732415 | SEQ ID NO: 251 Promoter Family Member (U097O11 + D026O22) | . . . gtaattgtaagcgcttacaattggatccgg |
| BBa_I732416 | SEQ ID NO: 252 Promoter Family Member (U097O11 + D038O22) | . . . tcaattgtaagcgcttacaattggatccgg |
| BBa_I732417 | SEQ ID NO: 253 Promoter Family Member (U097O11 + D050O22) | . . . aaaattgtaagcgcttacaattggatccgg |
| BBa_I732418 | SEQ ID NO: 254 Promoter Family Member (U097O11 + D062O22) | . . . caaattgtaagcgcttacaattggatccgg |
| BBa_I732419 | SEQ ID NO: 255 Promoter Family Member (U085O11 + D002O22) | . . . gaaattgtaagcgcttacaattggatccgg |
| BBa_I732420 | SEQ ID NO: 256 Promoter Family Member (U085O11 + D014O22) | . . . taaattgtaagcgcttacaattggatccgg |
| BBa_I732421 | SEQ ID NO: 257 Promoter Family Member (U085O11 + D026O22) | . . . gtaattgtaagcgcttacaattggatccgg |
| BBa_I732422 | SEQ ID NO: 258 Promoter Family Member (U085O11 + D038O22) | . . . tcaattgtaagcgcttacaattggatccgg |
| BBa_I732423 | SEQ ID NO: 259 Promoter Family Member (U085O11 + D050O22) | . . . aaaattgtaagcgcttacaattggatccgg |
| BBa_I732424 | SEQ ID NO: 260 Promoter Family Member (U085O11 + D062O22) | . . . caaattgtaagcgcttacaattggatccgg |
| BBa_I732425 | SEQ ID NO: 261 Promoter Family Member (U073O11 + D002O22) | . . . gaaattgtaagcgcttacaattggatccgg |
| BBa_I732426 | SEQ ID NO: 262 Promoter Family Member (U073O11 + D014O22) | . . . taaattgtaagcgcttacaattggatccgg |
| BBa_I732427 | SEQ ID NO: 263 Promoter Family Member (U073O11 + D026O22) | . . . gtaattgtaagcgcttacaattggatccgg |
| BBa_I732428 | SEQ ID NO: 264 Promoter Family Member (U073O11 + D038O22) | . . . tcaattgtaagcgcttacaattggatccgg |
| BBa_I732429 | SEQ ID NO: 265 Promoter Family Member (U073O11 + D050O22) | . . . aaaattgtaagcgcttacaattggatccgg |
| BBa_I732430 | SEQ ID NO: 266 Promoter Family Member (U073O11 + D062O22) | . . . caaattgtaagcgcttacaattggatccgg |
| BBa_I732431 | SEQ ID NO: 267 Promoter Family Member (U061O11 + D002O22) | . . . gaaattgtaagcgcttacaattggatccgg |
| BBa_I732432 | SEQ ID NO: 268 Promoter Family Member (U061O11 + D014O22) | . . . taaattgtaagcgcttacaattggatccgg |
| BBa_I732433 | SEQ ID NO: 269 Promoter Family Member (U061O11 + D026O22) | . . . gtaattgtaagcgcttacaattggatccgg |
| BBa_I732434 | SEQ ID NO: 270 Promoter Family Member (U061O11 + D038O22) | . . . tcaattgtaagcgcttacaattggatccgg |
| BBa_I732435 | SEQ ID NO: 271 Promoter Family Member (U061O11 + D050O22) | . . . aaaattgtaagcgcttacaattggatccgg |
| BBa_I732436 | SEQ ID NO: 272 Promoter Family Member (U061O11 + D062O22) | . . . caaattgtaagcgcttacaattggatccgg |

TABLE 16-continued

Examples of Logic Promoters

| Name | Description | Promoter Sequence |
|---|---|---|
| BBa_I732437 | SEQ ID NO: 273 Promoter Family Member (U049O11 + D002O22) | . . . gaaattgtaagcgcttacaattggatccgg |
| BBa_I732438 | SEQ ID NO: 274 Promoter Family Member (U049O11 + D014O22) | . . . taaattgtaagcgcttacaattggatccgg |
| BBa_I732439 | SEQ ID NO: 275 Promoter Family Member (U049O11 + D026O22) | . . . gtaattgtaagcgcttacaattggatccgg |
| BBa_I732440 | SEQ ID NO: 276 Promoter Family Member (U049O11 + D038O22) | . . . tcaattgtaagcgcttacaattggatccgg |
| BBa_I732441 | SEQ ID NO: 277 Promoter Family Member (U049O11 + D050O22) | . . . aaaattgtaagcgcttacaattggatccgg |
| BBa_I732442 | SEQ ID NO: 278 Promoter Family Member (U049O11 + D062O22) | . . . caaattgtaagcgcttacaattggatccgg |
| BBa_I732443 | SEQ ID NO: 279 Promoter Family Member (U037O11 + D002O22) | . . . gaaattgtaagcgcttacaattggatccgg |
| BBa_I732444 | SEQ ID NO: 280 Promoter Family Member (U037O11 + D014O22) | . . . taaattgtaagcgcttacaattggatccgg |
| BBa_I732445 | SEQ ID NO: 281 Promoter Family Member (U037O11 + D026O22) | . . . gtaattgtaagcgcttacaattggatccgg |
| BBa_I732446 | SEQ ID NO: 282 Promoter Family Member (U037O11 + D038O22) | . . . tcaattgtaagcgcttacaattggatccgg |
| BBa_I732447 | SEQ ID NO: 283 Promoter Family Member (U037O11 + D050O22) | . . . aaaattgtaagcgcttacaattggatccgg |
| BBa_I732448 | SEQ ID NO: 284 Promoter Family Member (U037O11 + D062O22) | . . . caaattgtaagcgcttacaattggatccgg |
| BBa_I732450 | SEQ ID NO: 285 Promoter Family Member (U073O26 + D062NUL) | . . . gccaaattaaacaggattaacaggatccgg |
| BBa_I732451 | SEQ ID NO: 286 Promoter Family Member (U073O27 + D062NUL) | . . . gccaaattaaacaggattaacaggatccgg |
| BBa_I732452 | SEQ ID NO: 287 Promoter Family Member (U073O26 + D062O61) | . . . caaattatgagcgctcacaattggatccgg |

TABLE 17

Examples of Positively Regulated *E. coli* σ70 Promoters

| Name | Description | Promoter Sequence |
|---|---|---|
| BBa_I0500 | SEQ ID NO: 288 Inducible pBad/araC promoter | . . . gtttctccatacccgtttttttgggctagc |
| BBa_I1051 | SEQ ID NO: 289 Lux cassette right promoter | . . . tgttatagtcgaatacctctggcggtgata |
| BBa_I12006 | SEQ ID NO: 290 Modified lamdba Prm promoter (repressed by 434 cI) | . . . attacaaactttcttgtatagatttaacgt |
| BBa_I12007 | SEQ ID NO: 291 Modified lambda Prm promoter (OR-3 obliterated) | . . . atttataaatagtggtgatagatttaacgt |
| BBa_I12036 | SEQ ID NO: 292 Modified lamdba Prm promoter (cooperative repression by 434 cI) | . . . tttcttgtatagatttacaatgtatcttgt |
| BBa_I12040 | SEQ ID NO: 293 Modified lambda P(RM) promoter: −10 region from P(L) and cooperatively repressed by 434 cI | . . . tttcttgtagatacttacaatgtatcttgt |
| BBa_I12210 | SEQ ID NO: 294 plac Or2-62 (positive) | . . . ctttatgcttccggctcgtatgttgtgtgg |
| BBa_I13406 | SEQ ID NO: 295 Pbad/AraC with extra REN sites | . . . ttttttgggctagcaagctttaccatggat |

TABLE 17-continued

Examples of Positively Regulated *E. coli* σ70 Promoters

| Name | Description | Promoter Sequence |
|---|---|---|
| BBa_I13453 | SEQ ID NO: 296 Pbad promoter | . . . tgtttctccataccgttttttttgggctagc |
| BBa_I14015 | SEQ ID NO: 297 P(Las) TetO | . . . ttttggtacactccctatcagtgatagaga |
| BBa_I14016 | SEQ ID NO: 298 P(Las) CIO | . . . cttttggtacactacctctggcggtgata |
| BBa_I14017 | SEQ ID NO: 299 P(Rhl) | . . . tacgcaagaaaatggtttgttatagtcgaa |
| BBa_I721001 | SEQ ID NO: 300 Lead Promoter | . . . gaaaaccttgtcaatgaagagcgatctatg |
| BBa_I723020 | SEQ ID NO: 301 Pu | . . . ctcaaagcgggccagccgtagccgttacgc |
| BBa_I731004 | SEQ ID NO: 302 FecA promoter | . . . ttctcgttcgactcatagctgaacacaaca |
| BBa_I739104 | SEQ ID NO: 303 Double Promoter (LuxR/HSL, positive/P22 cII, negative) | . . . gttctttaattatttaagtgttctttaatt |
| BBa_I739105 | SEQ ID NO: 304 Double Promoter (LuxR/HSL, positive/cI, negative) | . . . cgtgcgtgttgataacaccgtgcgtgttga |
| BBa_I741018 | SEQ ID NO: 305 Right facing promoter (for xylF) controlled by xylR and CRP-cAMP | . . . gttacgtttatcgcggtgattgttacttat |
| BBa_I741019 | SEQ ID NO: 306 Right facing promoter (for xylA) controlled by xylR and CRP-cAMP | . . . gcaaaataaaatggaatgatgaaactgggt |
| BBa_I741020 | SEQ ID NO: 307 promoter to xylF without CRP and several binding sites for xylR | . . . gttacgtttatcgcggtgattgttacttat |
| BBa_I741021 | SEQ ID NO: 308 promoter to xylA without CRP and several binding sites for xylR | . . . atttcacactgctattgagataattcacaa |
| BBa_I746104 | SEQ ID NO: 309 P2 promoter in agr operon from *S. aureus* | . . . agattgtactaaatcgtataatgacagtga |
| BBa_I746360 | SEQ ID NO: 310 PF promoter from P2 phage | . . . gacatctccggcgcaactgaaaataccact |
| BBa_I746361 | SEQ ID NO: 311 PO promoter from P2 phage | . . . gaggatgcgcatcgtcgggaaactgatgcc |
| BBa_I746362 | SEQ ID NO: 312 PP promoter from P2 phage | . . . catccgggactgatggcggaggatgcgcat |
| BBa_I746363 | SEQ ID NO: 313 PV promoter from P2 phage | . . . aacttttatatattgtgcaatctcacatgc |
| BBa_I746364 | SEQ ID NO: 314 Psid promoter from P4 phage | . . . tgttgtccggtgtacgtcacaattttctta |
| BBa_I746365 | SEQ ID NO: 315 PLL promoter from P4 phage | . . . aatggctgtgtgttttttgttcatctccac |
| BBa_I751501 | SEQ ID NO: 316 plux-cI hybrid promoter | . . . gtgttgatgcttttatcaccgccagtggta |
| BBa_I751502 | SEQ ID NO: 317 plux-lac hybrid promoter | . . . agtgtgtggaattgtgagcggataacaatt |
| BBa_I760005 | SEQ ID NO: 318 Cu-sensitive promoter | atgacaaaattgtcat |
| BBa_I761011 | SEQ ID NO: 319 CinR, CinL and glucose controlled promoter | . . . acatcttaaaagttttagtatcatattcgt |
| BBa_I765001 | SEQ ID NO: 320 UV promoter | . . . ctgaaagcgcataccgctatggagggggtt |
| BBa_I765007 | SEQ ID NO: 321 Fe and UV promoters | . . . ctgaaagcgcataccgctatggagggggtt |
| BBa_J01005 | SEQ ID NO: 322 pspoIIE promoter (spo0AJ01004, positive) | . . . aacgaatataacaggtgggagatgagagga |
| BBa_J03007 | SEQ ID NO: 323 Maltose specific promoter | . . . aatatttcctcatttttccacagtgaagtga |
| BBa_J06403 | SEQ ID NO: 324 RhlR promoter repressible by CI | . . . tacgcaagaaaatggtttgttatagtcgaa |
| BBa_J07007 | SEQ ID NO: 325 ctx promoter | . . . atttaattgttttgatcaattattttttctg |
| BBa_J13210 | SEQ ID NO: 326 pOmpR dependent POPS producer | . . . attattctgcatttttggggagaatggact |

TABLE 17-continued

Examples of Positively Regulated *E. coli* σ70 Promoters

| Name | Description | Promoter Sequence |
|---|---|---|
| BBa_J15502 | SEQ ID NO: 327 copA promoter | . . . ccttgctggaaggtttaacctttatcacag |
| BBa_J16101 | SEQ ID NO: 328 BanAp-Banana-induced Promoter | atgatgtgtccatggatta |
| BBa_J16105 | SEQ ID NO: 329 HelPp-"Help" Dependant promoter | atgatagacgatgtgcggacaacgtg |
| BBa_J45503 | SEQ ID NO: 330 hybB Cold Shock Promoter | . . . cattagccgccaccatggggttaagtagca |
| BBa_J58100 | SEQ ID NO: 331 AND-type promoter synergistically activated by cI and CRP | . . . atttataaatagtggtgatagatttaacgt |
| BBa_J61051 | SEQ ID NO: 332 [Psal1] | . . . ataaagccatcacgagtaccatagaggatc |
| BBa_J61054 | SEQ ID NO: 333 [HIP-1] Promoter | . . . tttgtcttttcttgcttaataatgttgtca |
| BBa_J61055 | SEQ ID NO: 334 [HIP-1fnr] Promoter | . . . tttgtcttttcttgcttaataatgttgtca |
| BBa_J64000 | SEQ ID NO: 335 rhlI promoter | . . . atcctccttagtcttcccctcatgtgtg |
| BBa_J64010 | SEQ ID NO: 336 lasI promoter | . . . taaaattatgaaatttgcataaattcttca |
| BBa_J64712 | SEQ ID NO: 337 LasR/LasI Inducible & RHLR/RHLI repressible Promoter | . . . gaaatctggcagtttttggtacacgaaagc |
| BBa_J64800 | SEQ ID NO: 338 RHLR/RHLI Inducible & LasR/LasI repressible Promoter | . . . tgccagttctggcaggtctaaaaagtgttc |
| BBa_J64804 | SEQ ID NO: 339 The promoter region (inclusive of regulator binding sites) of the *B. subtilis* RocDEF operon | . . . cacagaacttgcatttatataaagggaaag |
| BBa_K091107 | SEQ ID NO: 340 pLux/cI Hybrid Promoter | . . . acaccgtgcgtgttgatatagtcgaataaa |
| BBa_K091117 | SEQ ID NO: 341 pLas promoter | . . . aaaattatgaaatttgtataaaattcttcag |
| BBa_K091143 | SEQ ID NO: 342 pLas/cI Hybrid Promoter | . . . ggttcttttggtacctctggcggtgataa |
| BBa_K091146 | SEQ ID NO: 343 pLas/Lux Hybrid Promoter | . . . tgtaggatcgtacaggtataaattcttcag |
| BBa_K091156 | SEQ ID NO: 344 pLux | . . . caagaaaatggtttgttatagtcgaataaa |
| BBa_K091157 | SEQ ID NO: 345 pLux/Las Hybrid Promoter | . . . ctatctcatttgctagtatagtcgaataaa |
| BBa_K100000 | SEQ ID NO: 346 Natural Xylose Regulated Bi-Directional Operator | . . . gttacgtttatcgcggtgattgttacttat |
| BBa_K100001 | SEQ ID NO: 347 Edited Xylose Regulated Bi-Directional Operator 1 | . . . gttacgtttatcgcggtgattgttacttat |
| BBa_K100002 | SEQ ID NO: 348 Edited Xylose Regulated Bi-Directional Operator 2 | . . . gttacgtttatcgcggtgattgttacttat |
| BBa_K112118 | SEQ ID NO: 349 rrnB P1 promoter | . . . ataaatgcttgactctgtagcgggaaggcg |
| BBa_K112320 | SEQ ID NO: 350 {< ftsAZ promoter >} in BBb format | . . . aaaactggtagtaggactggagattggtac |
| BBa_K112322 | SEQ ID NO: 351 {Pdps} in BBb format | . . . gggacacaaacatcaagaggatatgagatt |
| BBa_K112402 | SEQ ID NO: 352 promoter for FabA gene-Membrane Damage and Ultrasound Sensitive | . . . gtcaaaatgaccgaaacgggtggtaacttc |
| BBa_K112405 | SEQ ID NO: 353 Promoter for CadA and CadB genes | . . . agtaatcttatcgccagtttggtctggtca |
| BBa_K112406 | SEQ ID NO: 354 cadC promoter | . . . agtaatcttatcgccagtttggtctggtca |
| BBa_K112701 | SEQ ID NO: 355 has promoter | . . . aattctgaacaacatccgtactcttcgtgc |
| BBa_K112900 | SEQ ID NO: 356 Pbad | . . . tcgataagattaccgatcttacctgaagct |
| BBa_K116001 | SEQ ID NO: 357 nhaA promoter, which can be regulated by pH and nhaR protein. | . . . cgatctattcacctgaaagagaaataaaaa |

TABLE 17-continued

Examples of Positively Regulated E. coli σ70 Promoters

| Name | Description | Promoter Sequence |
|---|---|---|
| BBa_K116401 | SEQ ID NO: 358 external phosphate sensing promoter | . . . atcgcaacctatttattacaacactagtgc |
| BBa_K116500 | SEQ ID NO: 359 OmpF promoter that is activated or repressed by OmpR according to osmolarity. | . . . aaacgttagtttgaatggaaagatgcctgc |
| BBa_K116603 | SEQ ID NO: 360 pRE promoter from λ phage | . . . tttgcacgaaccatatgtaagtatttcctt |
| BBa_K117002 | SEQ ID NO: 361 LsrA promoter (indirectly activated by AI-2) | . . . taacacttatttaattaaaaagaggagaaa |
| BBa_K118011 | SEQ ID NO: 362 PcstA (glucose repressible promoter) | . . . tagaaacaaaatgtaacatctctatggaca |
| BBa_K121011 | SEQ ID NO: 363 promoter (lacI regulated) | . . . acaggaaacagctatgaccatgattacgcc |
| BBa_K135000 | SEQ ID NO: 364 pCpxR (CpxR responsive promoter) | . . . agcgacgtctgatgacgtaatttctgcctc |
| BBa_K136010 | SEQ ID NO: 365 fliA promoter | . . . gttcactctataccgctgaaggtgtaatgg |
| BBa_K145150 | SEQ ID NO: 366 Hybrid promoter: HSL-LuxR activated, P22 C2 repressed | . . . tagtttataatttaagtgttctttaatttc |
| BBa_K180000 | SEQ ID NO: 367 Hybrid promoter (trp & lac regulated--tac pR) | . . . cgagcacttcaccaacaaggaccatagcat |
| BBa_K180002 | SEQ ID NO: 368 tac pR testing plasmid (GFP) | . . . caccttcgggtgggcctttctgcgtttata |
| BBa_K180003 | SEQ ID NO: 369 PTAC testing plasmid (GFP)-basic | . . . catggcatggatgaactatacaaataataa |
| BBa_K180004 | SEQ ID NO: 370 Game of Life-Primary plasmid | . . . caccttcgggtgggcctttctgcgtttata |
| BBa_K180005 | SEQ ID NO: 371 GoL-Primary plasmid (part 1)/RPS-Paper primary plasmid (part 1)[LuxR generator] | . . . caccttcgggtgggcctttctgcgtttata |
| BBa_K180006 | SEQ ID NO: 372 Game of Life-Primary plasmid (part 2)[lux pR, GFP and LacI generator] | . . . caccttcgggtgggcctttctgcgtttata |
| BBa_K180007 | SEQ ID NO: 373 Game of Life-Secondary plasmid[tac pR, LuxI generator] | . . . caccttcgggtgggcctttctgcgtttata |
| BBa_K180010 | SEQ ID NO: 374 Rock-paper-scissors-Rock primary plasmid | . . . caccttcgggtgggcctttctgcgtttata |
| BBa_K180011 | SEQ ID NO: 375 Rock-Primary plasmid (part 1)[RhlR generator] | . . . caccttcgggtgggcctttctgcgtttata |
| BBa_K180012 | SEQ ID NO: 376 Rock-Primary plasmid (part 2)[tac pR, mCherry and LasI generator] | . . . caccttcgggtgggcctttctgcgtttata |
| BBa_K180013 | SEQ ID NO: 377 Rock-paper-scissors-Rock secondary plasmid[rhl pR, LacI generator] | . . . caccttcgggtgggcctttctgcgtttata |
| BBa_K180014 | SEQ ID NO: 378 Rock-paper-scissors-Paper primary plasmid | . . . caccttcgggtgggcctttctgcgtttata |
| BBa_K180015 | SEQ ID NO: 379 Paper-Primary plasmid (part 2)[tac pR, GFP and RhlI generator] | . . . caccttcgggtgggcctttctgcgtttata |
| BBa_K180016 | SEQ ID NO: 380 Rock-paper-scissors-Paper secondary plasmid[lux pR, LacI generator] | . . . caccttcgggtgggcctttctgcgtttata |
| BBa_K180017 | SEQ ID NO: 381 Rock-paper-scissors - Scissors primary plasmid | . . . caccttcgggtgggcctttctgcgtttata |
| BBa_K180018 | SEQ ID NO: 382 Scissors-Primary plasmid (part 1)[LasR generator] | . . . caccttcgggtgggcctttctgcgtttata |
| BBa_K180019 | SEQ ID NO: 383 Scissors-Primary plasmid (part 2)[tac pR, mBanana and LuxI generator] | . . . caccttcgggtgggcctttctgcgtttata |

TABLE 17-continued

Examples of Positively Regulated *E. coli* σ70 Promoters

| Name | Description | Promoter Sequence |
|---|---|---|
| BBa_K180020 | SEQ ID NO: 384 Rock-paper-scissors-Scissors secondary plasmid[las pR, LaI generator] | . . . caccttcgggtgggcctttctgcgtttata |
| BBa_K206000 | SEQ ID NO: 385 pBAD strong | . . . tgtttctccataccgttttttttgggctagc |
| BBa_K206001 | SEQ ID NO: 386 pBAD weak | . . . tgtttctccataccgttttttttgggctagc |
| BBa_K259005 | SEQ ID NO: 387 AraC Rheostat Promoter | . . . ttttatcgcaactctctactgtttctccat |
| BBa_K259007 | SEQ ID NO: 388 AraC Promoter fused with RBS | . . . gtttctccattactagagaaagaggggaca |
| BBa_K266000 | SEQ ID NO: 389 PAI + LasR -> LuxI (AI) | . . . caccttcgggtgggcctttctgcgtttata |
| BBa_K266005 | SEQ ID NO: 390 PAI + LasR -> LasI & AI + LuxR --\| LasI | . . . aataactctgatagtgctagtgtagatctc |
| BBa_K266006 | SEQ ID NO: 391 PAI + LasR -> LasI + GFP & AI + LuxR --\| LasI + GFP | . . . caccttcgggtgggcctttctgcgtttata |
| BBa_K266007 | SEQ ID NO: 392 Complex QS -> LuxI & LasI circuit | . . . caccttcgggtgggcctttctgcgtttata |

TABLE 18

Examples of Positively regulated *E. coli* σS promoters

| Name | Description | Promoter Sequence |
|---|---|---|
| BBa_K112322 | SEQ ID NO: 393 {Pdps} in BBb format | . . . gggacacaaacatcaagaggatatgagatt |

TABLE 19

Examples of Positively regulated *E. coli* σ32 promoters

| Name | Description | Promoter Sequence |
|---|---|---|
| BBa_K112400 | SEQ ID NO: 394 Promoter for grpE gene-Heat Shock and Ultrasound Sensitive | . . . ataataagcgaagttagcgagatgaatgcg |

TABLE 20

Examples of Positively regulated *E. coli* σ54 promoters

| Name | Description | Promoter Sequence |
|---|---|---|
| BBa_J64979 | SEQ ID NO: 395 glnAp2 | . . . agttggcacagatttcgctttatctttttt |

TABLE 21

Examples of Positively regulated *B. subtilis* σA promoters

| Name | Description | Promoter Sequence |
|---|---|---|
| BBa_R0062 | SEQ ID NO: 396 Promoter (luxR & HSL regulated--lux pR) | . . . caagaaaatggtttgttatagtcgaataaa |

TABLE 21-continued

Examples of Positively regulated *B. subtilis* σA promoters

| Name | Description | Promoter Sequence |
|---|---|---|
| BBa_R0065 | SEQ ID NO: 397 Promoter (lambda cI and luxR regulated--hybrid) | . . . gtgttgactattttacctctggcggtgata |
| BBa_R0071 | SEQ ID NO: 398 Promoter (RhlR & C4-HSL regulated) | . . . gttagctttcgaattggctaaaaagtgttc |
| BBa_R0078 | SEQ ID NO: 399 Promoter (cinR and HSL regulated) | . . . ccattctgctttccacgaacttgaaaacgc |
| BBa_R0079 | SEQ ID NO: 400 Promoter (LasR & PAI regulated) | . . . ggccgcgggttcttttggtacacgaaagc |
| BBa_R0080 | SEQ ID NO: 401 Promoter (AraC regulated) | . . . ttttatcgcaactctctactgtttctccat |
| BBa_R0082 | SEQ ID NO: 402 Promoter (OmpR, positive) | . . . attattctgcattttgggggagaatggact |
| BBa_R0083 | SEQ ID NO: 403 Promoter (OmpR, positive) | . . . attattctgcattttgggggagaatggact |
| BBa_R0084 | SEQ ID NO: 404 Promoter (OmpR, positive) | . . . aacgttagtttgaatggaaagatgcctgca |
| BBa_R1062 | SEQ ID NO: 405 Promoter, Standard (luxR and HSL regulated--lux pR) | . . . aagaaaatggtttgttgatactcgaataaa |

TABLE 22

Examples of Miscellaneous Prokaryotic Induced Promoters

| Name | Description | Promoter Sequence |
|---|---|---|
| BBa_J64001 | SEQ ID NO: 406 psicA from Salmonella | . . . aacgcagtcgttaagttctacaaagtcggt |
| BBa_J64750 | SEQ ID NO: 407 SPI-1 TTSS secretion-linked promoter from Salmonella | . . . gtcggtgacagataacaggagtaagtaatg |
| BBa_K112149 | SEQ ID NO: 408 PmgtCB Magnesium promoter from Salmonella | . . . tattggctgactataataagcgcaaattca |
| BBa_K116201 | SEQ ID NO: 409 ureD promoter from *P mirabilis* | |
| BBa_K125100 | SEQ ID NO: 410 nir promoter from *Synechocystis* sp. PCC6803 | . . . cgaaacgggaaccctatattgatctctact |
| BBa_K131017 | SEQ ID NO: 411 p_qrr-4 from *Vibrio harveyi* | . . . aagttggcacgcatcgtgctttatacagat |

TABLE 23

Examples of Yeast Positive (Activatible) Promoters

| Name | Description | Promoter Sequence |
|---|---|---|
| BBa_J63006 | SEQ ID NO: 412 yeast GAL1 promoter | . . . gaggaaactagacccgccgccaccatggag |
| BBa_K284002 | SEQ ID NO: 413 JEN1 Promoter from *Kluyveromyces lactis* | . . . gagtaaccaaaaccaaaacagatttcaacc |
| BBa_K106699 | SEQ ID NO: 414 Gal1 Promoter | . . . aaagtaagaattttgaaaattcaatataa |
| BBa_K165041 | SEQ ID NO: 415 Zif268-HIV binding sites + TEF constitutive yeast promoter | . . . atacggtcaacgaactataattaactaaac |
| BBa_K165034 | SEQ ID NO: 416 Zif268-HIV bs + LexA bs + mCYC promoter | . . . cacaaatacacacactaaattaataactag |
| BBa_K165031 | SEQ ID NO: 417 mCYC promoter plus LexA binding sites | . . . cacaaatacacacactaaattaataactag |
| BBa_K165030 | SEQ ID NO: 418 mCYC promoter plus Zif268-HW binding sites | . . . cacaaatacacacactaaattaataactag |

TABLE 23-continued

Examples of Yeast Positive (Activatible) Promoters

| Name | Description | Promoter Sequence |
|---|---|---|
| BBa_K165001 | SEQ ID NO: 419 pGAL1 + w/XhoI sites | . . . atactttaacgtcaaggagaaaaaactata |
| BBa_K110016 | SEQ ID NO: 420 A-Cell Promoter STE2 (backwards) | . . . accgttaagaaccatatccaagaatcaaaa |
| BBa_K110015 | SEQ ID NO: 421 A-Cell Promoter MFA1 (RtL) | . . . cttcatatataaaccgccagaaatgaatta |
| BBa_K110014 | SEQ ID NO: 422 A-Cell Promoter MFA2 (backwards) | . . . atcttcatacaacaataactaccaaccta |
| BBa_K110006 | SEQ ID NO: 423 Alpha-Cell Promoter MF(ALPHA)1 | . . . tttcatacacaatataaacgattaaaagaa |
| BBa_K110005 | SEQ ID NO: 424 Alpha-Cell Promoter MF(ALPHA)2 | . . . aaattccagtaaattcacatattggagaaa |
| BBa_K110004 | SEQ ID NO: 425 Alpha-Cell Promoter Ste3 | . . . gggagccagaacgcttctggtggtgtaaat |
| BBa_J24813 | SEQ ID NO: 426 URA3 Promoter from *S. cerevisiae* | . . . gcacagacttagattggtatatatacgcat |
| BBa_K284003 | SEQ ID NO: 427 Partial DLD Promoter from *Kluyveromyces lactis* | . . . aagtgcaagaaagaccagaaacgcaactca |

TABLE 24

Examples of Eukaryotic Positive (Activatible) Promoters

| Name | Description | Promoter Sequence |
|---|---|---|
| BBa_I10498 | SEQ ID NO: 428 Oct-4 promoter | . . . taaaaaaaaaaaaaaaaaaaaaaaaaaaaa |
| BBa_J05215 | SEQ ID NO: 429 Regulator for R1-CREBH | . . . ggggcgagggccccgcctccggaggcgggg |
| BBa_J05216 | SEQ ID NO: 430 Regulator for R3-ATF6 | . . . gagggacggctccggccccggggccggag |
| BBa_J05217 | SEQ ID NO: 431 Regulator for R2-YAP7 | . . . ggggcgagggctccggccccggggccggag |
| BBa_J05218 | SEQ ID NO: 432 Regulator for R4-cMaf | . . . gagggacggccccgcctccggaggcgggg |

TABLE 25

Examples of Negatively regulated (repressible) *E. coli* σ70 promoters

| Name | Description | Promoter Sequence |
|---|---|---|
| BBa_I1051 | SEQ ID NO: 433 | Lux cassette right promoter | . . . tgttatagtcgaatacctctggcggtgata |
| BBa_I12001 | SEQ ID NO: 434 | Promoter (PRM+) | . . . gatttaacgtatcagcacaaaaaagaaacc |
| BBa_I12006 | SEQ ID NO: 435 | Modified lamdba Prm promoter (repressed by 434 cI) | . . . attacaaactttcttgtatagatttaacgt |
| BBa_I12036 | SEQ ID NO: 436 | Modified lamdba Prm promoter (cooperative repression by 434 cI) | . . . tttcttgtatagattacaatgtatcttgt |
| BBa_I12040 | SEQ ID NO: 437 | Modified lambda P(RM) promoter: -10 region from P(L) and cooperatively repressed by 434 cI | . . . tttcttgtagatacttacaatgtatcttgt |
| BBa_I12212 | SEQ ID NO: 438 | TetR - TetR-4C heterodimer promoter (negative) | . . . actctgtcaatgatagagtggattcaaaaa |
| BBa_I14015 | SEQ ID NO: 439 | P(Las) TetO | . . . ttttggtacactccctatcagtgatagaga |
| BBa_I14016 | SEQ ID NO: 440 | P(Las) CIO | . . . cttttggtacactacctctggcggtgata |
| BBa_I14032 | SEQ ID NO: 441 | promoter P(Lac) IQ | . . . aaacctttcgcggtatggcatgatagcgcc |

TABLE 25-continued

Examples of Negatively regulated (repressible) *E. coli* σ70 promoters

| Name | Description | Promoter Sequence |
|---|---|---|
| BBa_I714889 SEQ ID NO: 442 | OR21 of PR and PRM | . . . tattttacctctggcggtgataatggttgc |
| BBa_I714924 SEQ ID NO: 443 | RecA_DlexO_DLacO1 | . . . actctcggcatggacgagctgtacaagtaa |
| BBa_I715003 SEQ ID NO: 444 | hybrid pLac with UV5 mutation | . . . ttgtgagcggataacaatatgttgagcaca |
| BBa_I718018 SEQ ID NO: 445 | dapAp promoter | . . . cattgagacacttgtttgcacagaggatgg |
| BBa_I731004 SEQ ID NO: 446 | FecA promoter | . . . ttctcgttcgactcatagctgaacacaaca |
| BBa_I732200 SEQ ID NO: 447 | NOT Gate Promoter Family Member (D001O1wt1) | . . . gaattgtgagcggataacaattggatccgg |
| BBa_I732201 SEQ ID NO: 448 | NOT Gate Promoter Family Member (D001O11) | . . . ggaattgtgagcgctcacaattggatccgg |
| BBa_I732202 SEQ ID NO: 449 | NOT Gate Promoter Family Member (D001O22) | . . . ggaattgtaagcgcttacaattggatccgg |
| BBa_I732203 SEQ ID NO: 450 | NOT Gate Promoter Family Member (D001O33) | . . . ggaattgtaaacgtttacaattggatccgg |
| BBa_I732204 SEQ ID NO: 451 | NOT Gate Promoter Family Member (D001O44) | . . . ggaattgtgaacgttcacaattggatccgg |
| BBa_I732205 SEQ ID NO: 452 | NOT Gate Promoter Family Member (D001O55) | . . . ggaattttgagcgctcaaaattggatccgg |
| BBa_I732206 SEQ ID NO: 453 | NOT Gate Promoter Family Member (D001O66) | . . . ggaattatgagcgctcataattggatccgg |
| BBa_I732207 SEQ ID NO: 454 | NOT Gate Promoter Family Member (D001O77) | . . . gggacgactgtatacagtcgtcggatccgg |
| BBa_I732270 SEQ ID NO: 455 | Promoter Family Member with Hybrid Operator (D001O12) | . . . ggaattgtgagcgcttacaattggatccgg |
| BBa_I732271 SEQ ID NO: 456 | Promoter Family Member with Hybrid Operator (D001O16) | . . . ggaattgtgagcgctcataattggatccgg |
| BBa_I732272 SEQ ID NO: 457 | Promoter Family Member with Hybrid Operator (D001O17) | . . . ggaattgtgagctacagtcgtcggatccgg |
| BBa_I732273 SEQ ID NO: 458 | Promoter Family Member with Hybrid Operator (D001O21) | . . . ggaattgtaagcgctcacaattggatccgg |
| BBa_I732274 SEQ ID NO: 459 | Promoter Family Member with Hybrid Operator (D001O24) | . . . ggaattgtaagcgttcacaattggatccgg |
| BBa_I732275 SEQ ID NO: 460 | Promoter Family Member with Hybrid Operator (D001O26) | . . . ggaattgtaagcgctcataattggatccgg |
| BBa_I732276 SEQ ID NO: 461 | Promoter Family Member with Hybrid Operator (D001O27) | . . . ggaattgtaagctacagtcgtcggatccgg |
| BBa_I732277 SEQ ID NO: 462 | Promoter Family Member with Hybrid Operator (D001O46) | . . . ggaattgtgaacgctcataattggatccgg |
| BBa_I732278 SEQ ID NO: 463 | Promoter Family Member with Hybrid Operator (D001O47) | . . . ggaattgtgaactacagtcgtcggatccgg |
| BBa_I732279 SEQ ID NO: 464 | Promoter Family Member with Hybrid Operator (D001O61) | . . . ggaattatgagcgctcacaattggatccgg |
| BBa_I732301 SEQ ID NO: 465 | NAND Candidate (U073O26D001O16) | . . . ggaattgtgagcgctcataattggatccgg |
| BBa_I732302 SEQ ID NO: 466 | NAND Candidate (U073O27D001O17) | . . . ggaattgtgagctacagtcgtcggatccgg |
| BBa_I732303 SEQ ID NO: 467 | NAND Candidate (U073O22D001O46) | . . . ggaattgtgaacgctcataattggatccgg |
| BBa_I732304 SEQ ID NO: 468 | NAND Candidate (U073O22D001O47) | . . . ggaattgtgaactacagtcgtcggatccgg |

TABLE 25-continued

Examples of Negatively regulated (repressible) *E. coli* σ70 promoters

| Name | Description | Promoter Sequence |
|---|---|---|
| BBa_I732305 SEQ ID NO: 469 (U073022D059046) | NAND Candidate | . . . taaattgtgaacgctcataattggatccgg |
| BBa_I732306 SEQ ID NO: 470 (U073011D002022) | NAND Candidate | . . . gaaattgtaagcgcttacaattggatccgg |
| BBa_I732351 SEQ ID NO: 471 (U037011D002022) | NOR Candidate | . . . gaaattgtaagcgcttacaattggatccgg |
| BBa_I732352 SEQ ID NO: 472 (U035044D001022) | NOR Candidate | . . . ggaattgtaagcgcttacaattggatccgg |
| BBa_I732400 SEQ ID NO: 473 (U097NUL + D062NUL) | Promoter Family Member | . . . gccaaattaaacaggattaacaggatccgg |
| BBa_I732401 SEQ ID NO: 474 (U097011 + D062NUL) | Promoter Family Member | . . . gccaaattaaacaggattaacaggatccgg |
| BBa_I732402 SEQ ID NO: 475 (U085011 + D062NUL) | Promoter Family Member | . . . gccaaattaaacaggattaacaggatccgg |
| BBa_I732403 SEQ ID NO: 476 (U073011 + D062NUL) | Promoter Family Member | . . . gccaaattaaacaggattaacaggatccgg |
| BBa_I732404 SEQ ID NO: 477 (U061011 + D062NUL) | Promoter Family Member | . . . gccaaattaaacaggattaacaggatccgg |
| BBa_I732405 SEQ ID NO: 478 (U049011 + D062NUL) | Promoter Family Member | . . . gccaaattaaacaggattaacaggatccgg |
| BBa_I732406 SEQ ID NO: 479 (U037011 + D062NUL) | Promoter Family Member | . . . gccaaattaaacaggattaacaggatccgg |
| BBa_I732407 SEQ ID NO: 480 (U097NUL + D002022) | Promoter Family Member | . . . gaaattgtaagcgcttacaattggatccgg |
| BBa_I732408 SEQ ID NO: 481 (U097NUL + D014022) | Promoter Family Member | . . . taaattgtaagcgcttacaattggatccgg |
| BBa_I732409 SEQ ID NO: 482 (U097NUL + D026022) | Promoter Family Member | . . . gtaattgtaagcgcttacaattggatccgg |
| BBa_I732410 SEQ ID NO: 483 (U097NUL + D038022) | Promoter Family Member | . . . tcaattgtaagcgcttacaattggatccgg |
| BBa_I732411 SEQ ID NO: 484 (U097NUL + D050022) | Promoter Family Member | . . . aaaattgtaagcgcttacaattggatccgg |
| BBa_I732412 SEQ ID NO: 485 (U097NUL + D062022) | Promoter Family Member | . . . caaattgtaagcgcttacaattggatccgg |
| BBa_I732413 SEQ ID NO: 486 (U097011 + D002022) | Promoter Family Member | . . . gaaattgtaagcgcttacaattggatccgg |
| BBa_I732414 SEQ ID NO: 487 (U097011 + D014022) | Promoter Family Member | . . . taaattgtaagcgcttacaattggatccgg |
| BBa_I732415 SEQ ID NO: 488 (U097011 + D026022) | Promoter Family Member | . . . gtaattgtaagcgcttacaattggatccgg |
| BBa_I732416 SEQ ID NO: 489 (U097011 + D038022) | Promoter Family Member | . . . tcaattgtaagcgcttacaattggatccgg |
| BBa_I732417 SEQ ID NO: 490 (U097011 + D050022) | Promoter Family Member | . . . aaaattgtaagcgcttacaattggatccgg |
| BBa_I732418 SEQ ID NO: 491 (U097011 + D062022) | Promoter Family Member | . . . caaattgtaagcgcttacaattggatccgg |
| BBa_I732419 SEQ ID NO: 492 (U085011 + D002022) | Promoter Family Member | . . . gaaattgtaagcgcttacaattggatccgg |
| BBa_I732420 SEQ ID NO: 493 (U085011 + D014022) | Promoter Family Member | . . . taaattgtaagcgcttacaattggatccgg |

TABLE 25-continued

Examples of Negatively regulated (repressible) *E. coli* σ70 promoters

| Name | Description | Promoter Sequence |
|---|---|---|
| BBa_I732421 SEQ ID NO: 494 (U085011 + D026022) | Promoter Family Member | . . . gtaattgtaagcgcttacaattggatccgg |
| BBa_I732422 SEQ ID NO: 495 (U085011 + D038022) | Promoter Family Member | . . . tcaattgtaagcgcttacaattggatccgg |
| BBa_I732423 SEQ ID NO: 496 (U085011 + D050022) | Promoter Family Member | . . . aaaattgtaagcgcttacaattggatccgg |
| BBa_I732424 SEQ ID NO: 497 (U085011 + D062022) | Promoter Family Member | . . . caaattgtaagcgcttacaattggatccgg |
| BBa_I732425 SEQ ID NO: 498 (U073011 + D002022) | Promoter Family Member | . . . gaaattgtaagcgcttacaattggatccgg |
| BBa_I732426 SEQ ID NO: 499 (U073011 + D014022) | Promoter Family Member | . . . taaattgtaagcgcttacaattggatccgg |
| BBa_I732427 SEQ ID NO: 500 (U073011 + D026022) | Promoter Family Member | . . . gtaattgtaagcgcttacaattggatccgg |
| BBa_I732428 SEQ ID NO: 501 (U073011 + D038022) | Promoter Family Member | . . . tcaattgtaagcgcttacaattggatccgg |
| BBa_I732429 SEQ ID NO: 502 (U073011 + D050022) | Promoter Family Member | . . . aaaattgtaagcgcttacaattggatccgg |
| BBa_I732430 SEQ ID NO: 503 (U073011 + D062022) | Promoter Family Member | . . . caaattgtaagcgcttacaattggatccgg |
| BBa_I732431 SEQ ID NO: 504 (U061011 + D002022) | Promoter Family Member | . . . gaaattgtaagcgcttacaattggatccgg |
| BBa_I732432 SEQ ID NO: 505 (U061011 + D014022) | Promoter Family Member | . . . taaattgtaagcgcttacaattggatccgg |
| BBa_I732433 SEQ ID NO: 506 (U061011 + D026022) | Promoter Family Member | . . . gtaattgtaagcgcttacaattggatccgg |
| BBa_I732434 SEQ ID NO: 507 (U061011 + D038022) | Promoter Family Member | . . . tcaattgtaagcgcttacaattggatccgg |
| BBa_I732435 SEQ ID NO: 508 (U061011 + D050022) | Promoter Family Member | . . . aaaattgtaagcgcttacaattggatccgg |
| BBa_I732436 SEQ ID NO: 509 (U061011 + D062022) | Promoter Family Member | . . . caaattgtaagcgcttacaattggatccgg |
| BBa_I732437 SEQ ID NO: 510 (U049011 + D002022) | Promoter Family Member | . . . gaaattgtaagcgcttacaattggatccgg |
| BBa_I732438 SEQ ID NO: 511 (U049011 + D014022) | Promoter Family Member | . . . taaattgtaagcgcttacaattggatccgg |
| BBa_I732439 SEQ ID NO: 512 (U049011 + D026022) | Promoter Family Member | . . . gtaattgtaagcgcttacaattggatccgg |
| BBa_I732440 SEQ ID NO: 513 (U049011 + D038022) | Promoter Family Member | . . . tcaattgtaagcgcttacaattggatccgg |
| BBa_I732441 SEQ ID NO: 514 (U049011 + D050022) | Promoter Family Member | . . . aaaattgtaagcgcttacaattggatccgg |
| BBa_I732442 SEQ ID NO: 515 (U049011 + D062022) | Promoter Family Member | . . . caaattgtaagcgcttacaattggatccgg |
| BBa_I732443 SEQ ID NO: 516 (U037011 + D002022) | Promoter Family Member | . . . gaaattgtaagcgcttacaattggatccgg |
| BBa_I732444 SEQ ID NO: 517 (U037011 + D014022) | Promoter Family Member | . . . taaattgtaagcgcttacaattggatccgg |
| BBa_I732445 SEQ ID NO: 518 (U037011 + D026022) | Promoter Family Member | . . . gtaattgtaagcgcttacaattggatccgg |

TABLE 25-continued

Examples of Negatively regulated (repressible) *E. coli* σ70 promoters

| Name | Description | Promoter Sequence |
|---|---|---|
| BBa_I732446 SEQ ID NO: 519 (U037011 + D038022) | Promoter Family Member | . . . tcaattgtaagcgcttacaattggatccgg |
| BBa_I732447 SEQ ID NO: 520 (U037011 + D050022) | Promoter Family Member | . . . aaaattgtaagcgcttacaattggatccgg |
| BBa_I732448 SEQ ID NO: 521 (U037011 + D062022) | Promoter Family Member | . . . caaattgtaagcgcttacaattggatccgg |
| BBa_I732450 SEQ ID NO: 522 (U073026 + D062NUL) | Promoter Family Member | . . . gccaaattaaacaggattaacaggatccgg |
| BBa_I732451 SEQ ID NO: 523 (U073027 + D062NUL) | Promoter Family Member | . . . gccaaattaaacaggattaacaggatccgg |
| BBa_I732452 SEQ ID NO: 524 (U073026 + D062061) | Promoter Family Member | . . . caaattatgagcgctcacaattggatccgg |
| BBa_I739101 SEQ ID NO: 525 | Double Promoter (constitutive/ TetR, negative) | . . . tgatagagattccctatcagtgatagagat |
| BBa_I739102 SEQ ID NO: 526 | Double Promoter (cI, negative/ TetR, negative) | . . . tgatagagattccctatcagtgatagagat |
| BBa_I739103 SEQ ID NO: 527 | Double Promoter (lacI, negative/ P22 cII, negative) | . . . gttattaattatttaagtgttattaatt |
| BBa_I739104 SEQ ID NO: 528 | Double Promoter (LuxR/HSL, positive/P22 cII, negative) | . . . gttctttaattatttaagtgttctttaatt |
| BBa_I739105 SEQ ID NO: 529 | Double Promoter (LuxR/HSL, positive/ cI, negative) | . . . cgtgcgtgttgataacaccgtgcgtgttga |
| BBa_I739106 SEQ ID NO: 530 | Double Promoter (TetR, negative/ P22 cII, negative) | . . . gtgttctttaatatttaagtgttctttaat |
| BBa_I739107 SEQ ID NO: 531 | Double Promoter (cI, negative/ LacI, negative) | . . . ggaattgtgagcggataacaatttcacaca |
| BBa_I746665 SEQ ID NO: 532 | Pspac-hy promoter | . . . tgtgtgtaattgtgagcggataacaattaa |
| BBa_I751500 SEQ ID NO: 533 | pcI (for positive control of pcI-lux hybrid promoter) | . . . ttttacctctggcggtgataatggttgcag |
| BBa_I751501 SEQ ID NO: 534 | plux-cI hybrid promoter | . . . gtgttgatgcttttatcaccgccagtggta |
| BBa_I751502 SEQ ID NO: 535 | plux-lac hybrid promoter | . . . agtgtgtggaattgtgagcggataacaatt |
| BBa_I756014 SEQ ID NO: 536 | LexAoperator-MajorLatePromoter | . . . aggggtgggggcgcgttggcgcgccacac |
| BBa_I761011 SEQ ID NO: 537 | CinR, CinL and glucose controlled promoter | . . . acatcttaaaagttttagtatcatattcgt |
| BBa_J05209 SEQ ID NO: 538 | Modified Pr Promoter | . . . tattttacctctggcggtgataatggttgc |
| BBa_J05210 SEQ ID NO: 539 | Modified Prm + Promoter | . . . atttataaatagtggtgatagatttaacgt |
| BBa_J07019 SEQ ID NO: 540 | FecA Promoter (with Fur box) | . . . acccttctcgttcgactcatagctgaacac |
| BBa_J15301 SEQ ID NO: 541 | Pars promoter from *Escherichia coli* chromosomal ars operon. | . . . tgactatccgcttcgaagagagacactac |
| BBa_J22052 SEQ ID NO: 542 | Pcya | . . . aggtgttaaattgatcacgtttagaccat |
| BBa_J22106 SEQ ID NO: 543 | rec A (SOS) Promoter | . . . caatttggtaaaggctccatcatgtaataa |
| BBa_J22126 SEQ ID NO: 544 | Rec A (SOS) promoter | . . . gagaaacaatttggtaaaggctccatcatg |
| BBa_J31013 SEQ ID NO: 545 | pLac Backwards [cf. BBa_R0010] | . . . aacgcgcggggagaggcggtttgcgtattg |
| BBa_J34800 SEQ ID NO: 546 | Promoter tetracycline inducible | . . . cagtgatagagatactgagcacatcagcac |
| BBa_J34806 SEQ ID NO: 547 | promoter lac induced | . . . ttatgcttccggctcgtataatgtgttcaaa |

TABLE 25-continued

Examples of Negatively regulated (repressible) E. coli σ70 promoters

| Name | | Description | Promoter Sequence |
|---|---|---|---|
| BBa_J34809 | SEQ ID NO: 548 | promoter lac induced | . . . ggctcgtatgttgtgtcgaccgagctgcgc |
| BBa_J54016 | SEQ ID NO: 549 | promoter_lacq | . . . aaacctttcgcggtatggcatgatagcgcc |
| BBa_J54120 | SEQ ID NO: 550 | EmrR_regulated promoter | . . . atttgtcactgtcgttactatatcggctgc |
| BBa_J54130 | SEQ ID NO: 551 | BetI_regulated promoter | . . . gtccaatcaataaccgctttaatagataaa |
| BBa_J56012 | SEQ ID NO: 552 includes Ptrc promoter | Invertible sequence of dna | . . . actttattatcaataagttaaatcggtacc |
| BBa_J64065 | SEQ ID NO: 553 | cI repressed promoter | . . . gtgttgactattttacctctggcggtgata |
| BBa_J64067 | SEQ ID NO: 554 | LuxR + 3OC6HSL independent R0065 | . . . gtgttgactattttacctctggcggtgata |
| BBa_J64068 | SEQ ID NO: 555 | increased strength R0051 | . . . atacctctggcggtgatatataatggttgc |
| BBa_J64069 | SEQ ID NO: 556 | R0065 with lux box deleted | . . . gtgttgactattttacctctggcggtgata |
| BBa_J64712 | SEQ ID NO: 557 RHLR/RHLI repressible Promoter | LasR/LasI Inducible & | . . . gaaatctggcagttttggtacacgaaagc |
| BBa_J64800 | SEQ ID NO: 558 LasR/LasI repressible Promoter | RHLR/RHLI Inducible & | . . . tgccagttctggcaggtctaaaaagtgttc |
| BBa_J64981 | SEQ ID NO: 559 regulatory region for Team Challenge03-2007 | OmpR-P strong binding, | . . . agcgctcacaatttaatacgactcactata |
| BBa_J64987 | SEQ ID NO: 560 sigma 70 binding region | LacI Consensus Binding Site in | . . . taataattgtgagcgctcacaattttgaca |
| BBa_J72005 | SEQ ID NO: 561 | {Ptet} promoter in BBb | . . . atccctatcagtgatagagatactgagcac |
| BBa_K086017 | SEQ ID NO: 562 promoter | unmodified Lutz-Bujard LacO | . . . ttgtgagcggataacaagatactgagcaca |
| BBa_K091100 | SEQ ID NO: 563 | pLac_lux hybrid promoter | . . . ggaattgtgagcggataacaatttcacaca |
| BBa_K091101 | SEQ ID NO: 564 | pTet_Lac hybrid promoter | . . . ggaattgtgagcggataacaatttcacaca |
| BBa_K091104 | SEQ ID NO: 565 | pLac/Mnt Hybrid Promoter | . . . ggaattgtgagcggataacaatttcacaca |
| BBa_K091105 | SEQ ID NO: 566 | pTet/Mnt Hybrid Promoter | . . . agaactgtaatccctatcagtgatagagat |
| BBa_K091106 | SEQ ID NO: 567 | LsrA/cI hybrid promoter | . . . tgttgatttatctaacaccgtgcgtgttga |
| BBa_K091107 | SEQ ID NO: 568 | pLux/cI Hybrid Promoter | . . . acaccgtgcgtgttgatatagtcgaataaa |
| BBa_K091110 | SEQ ID NO: 569 | LacI Promoter | . . . ccctttcgcggtatggcatgatagcgcccgg |
| BBa_K091111 | SEQ ID NO: 570 | LacIQ promoter | . . . ccctttcgcggtatggcatgatagcgcccgg |
| BBa_K091112 | SEQ ID NO: 571 | pLacIQ1 promoter | . . . ccctttcgcggtatggcatgatagcgcccgg |
| BBa_K091143 | SEQ ID NO: 572 | pLas/cI Hybrid Promoter | . . . ggttcttttggtacctctggcggtgataa |
| BBa_K091146 | SEQ ID NO: 573 | pLas/Lux Hybrid Promoter | . . . tgtaggatcgtacaggtataaattcttcag |
| BBa_K091157 | SEQ ID NO: 574 | pLux/Las Hybrid Promoter | . . . ctatctcatttgctagtatagtcgaataaa |
| BBa_K093000 | SEQ ID NO: 575 | pRecA with LexA binding site | . . . gtatatatatacagtataattgcttcaaca |
| BBa_K093008 | SEQ ID NO: 576 | reverse BBa_R0011 | . . . cacaatgtcaattgttatccgctcacaatt |
| BBa_K094120 | SEQ ID NO: 577 | pLacI/ara-1 | . . . aattgtgagcggataacaatttcacacaga |
| BBa_K094140 | SEQ ID NO: 578 | pLacIq | . . . ccggaagagagtcaattcagggtggtgaat |
| BBa_K101000 | SEQ ID NO: 579 p22 mnt and TetR | Dual-Repressed Promoter for | . . . acggtgacctagatctccgatactgagcac |
| BBa_K101001 | SEQ ID NO: 580 LacI and LambdacI | Dual-Repressed Promoter for | . . . tggaattgtgagcggataaaatttcacaca |

TABLE 25-continued

Examples of Negatively regulated (repressible) *E. coli* σ70 promoters

| Name | Description | Promoter Sequence |
|---|---|---|
| BBa_K101002 SEQ ID NO: 581 | Dual Repressed Promoter for p22 cII and TetR | . . . tagtagataatttaagtgttctttaatttc |
| BBa_K101017 SEQ ID NO: 582 | MioC Promoter (DNAa-(Repressed Promoter) | . . . ccaacgcgttcacagcgtacaattactagt |
| BBa_K109200 SEQ ID NO: 583 | AraC and TetR promoter (hybrid) | . . . aacaaaaaaacggatcctctagttgcggcc |
| BBa_K112118 SEQ ID NO: 584 | rrnB P1 promoter | . . . ataaatgcttgactctgtagcgggaaggcg |
| BBa_K112318 SEQ ID NO: 585 | {<bolA promoter>} in BBb format | . . . atttcatgatgatacgtgagcggatagaag |
| BBa_K112401 SEQ ID NO: 586 | Promoter for recA gene - SOS and Ultrasound Sensitive | . . . caaacagaaagcgttggcggcagcactggg |
| BBa_K112402 SEQ ID NO: 587 | promoter for FabA gene - Membrane Damage and Ultrasound Sensitive | . . . gtcaaaatgaccgaaacgggtggtaacttc |
| BBa_K112405 SEQ ID NO: 588 | Promoter for CadA and CadB genes | . . . agtaatcttatcgccagtttggtctggtca |
| BBa_K112406 SEQ ID NO: 589 | cadC promoter | . . . agtaatcttatcgccagtttggtctggtca |
| BBa_K112701 SEQ ID NO: 590 | has promoter | . . . aattctgaacaacatccgtactcttcgtgc |
| BBa_K112708 SEQ ID NO: 591 | PfhuA | . . . tttacgttatcattcactttacatcagagt |
| BBa_K113009 SEQ ID NO: 592 | pBad/araC | . . . gtttctccatacccgttttttgggctagc |
| BBa_K116001 SEQ ID NO: 593 | nhaA promoter that can be regulated by pH and nhaR protein. | . . . cgatctattcacctgaaagagaaataaaaa |
| BBa_K116500 SEQ ID NO: 594 | OmpF promoter that is activated or repressed by OmpR according to osmolarity. | . . . aaacgttagtttgaatggaaagatgcctgc |
| BBa_K119002 SEQ ID NO: 595 | RcnR operator (represses RcnA) | . . . attgccgaattaatactaagaattattatc |
| BBa_K121011 SEQ ID NO: 596 | promoter (lacI regulated) | . . . acaggaaacagctatgaccatgattacgcc |
| BBa_K121014 SEQ ID NO: 597 | promoter (lambda cI regulated) | . . . actggcggttataatgagcacatcagcagg |
| BBa_K137046 SEQ ID NO: 598 | 150 bp inverted tetR promoter | . . . caccgacaaacaacagataaaacgaaaggc |
| BBa_K137047 SEQ ID NO: 599 | 250 bp inverted tetR promoter | . . . agtgttattaagctactaaagcgtagtttt |
| BBa_K137048 SEQ ID NO: 600 | 350 bp inverted tetR promoter | . . . gaataagaaggctggctctgcaccttggtg |
| BBa_K137049 SEQ ID NO: 601 | 450 bp inverted tetR promoter | . . . ttagcgacttgatgctcttgatcttccaat |
| BBa_K137050 SEQ ID NO: 602 | 650 bp inverted tetR promoter | . . . acatctaaaacttttagcgttattacgtaa |
| BBa_K137051 SEQ ID NO: 603 | 850 bp inverted tetR promoter | . . . ttccgacctcattaagcagctctaatgcgc |
| BBa_K137124 SEQ ID NO: 604 | LacI-repressed promoter A81 | . . . caattttaaacctgtaggatcgtacaggt |
| BBa_K137125 SEQ ID NO: 605 | LacI-repressed promoter B4 | . . . caattttaaaattaaaggcgttacccaac |
| BBa_K145150 SEQ ID NO: 606 | Hybrid promoter: HSL-LuxR activated, P22 C2 repressed | . . . tagtttataatttaagtgttctttaatttc |
| BBa_K145152 SEQ ID NO: 607 | Hybrid promoter: P22 c2, LacI NOR gate | . . . gaaaatgtgagcgagtaacaacctcacaca |
| BBa_K256028 SEQ ID NO: 608 | placI:CHE | . . . caccttcgggtgggcctttctgcgtttata |
| BBa_K259005 SEQ ID NO: 609 | AraC Rheostat Promoter | . . . ttttatcgcaactctctactgtttctccat |
| BBa_K259007 SEQ ID NO: 610 | AraC Promoter fused with RBS | . . . gtttctccattactagagaaagaggggaca |
| BBa_K266001 SEQ ID NO: 611 | Inverter TetR ->2 LuxR | . . . caccttcgggtgggcctttctgcgtttata |
| BBa_K266003 SEQ ID NO: 612 | POPS -> Lac Inverter -> LasR | . . . caccttcgggtgggcctttctgcgtttata |
| BBa_K266004 SEQ ID NO: 613 | Const Lac Inverter -> LasR | . . . caccttcgggtgggcctttctgcgtttata |

TABLE 25-continued

Examples of Negatively regulated (repressible) *E. coli* σ70 promoters

| Name | | Description | Promoter Sequence |
|---|---|---|---|
| BBa_K266005 | SEQ ID NO: 614 | PAI + LasR -> LasI & AI + LuxR --\| LasI | . . . aataactctgatagtgctagtgtagatctc |
| BBa_K266006 | SEQ ID NO: 615 | PAI + LasR -> LasI + GFP & AI + LuxR --\|LasI + GFP | . . . caccttcgggtgggcctttctgcgtttata |
| BBa_K266007 | SEQ ID NO: 616 | Complex QS -> LuxI & LasI circuit | . . . caccttcgggtgggcctttctgcgtttata |
| BBa_K266008 | SEQ ID NO: 617 | J23100 + Lac inverter | . . . ttgtgagcggataacaagatactgagcaca |
| BBa_K266009 | SEQ ID NO: 618 | J23100 + Lac inverter + RBS | . . . actgagcacatactagagaaagaggagaaa |
| BBa_K266011 | SEQ ID NO: 619 | Lac Inverter and strong RBS | . . . actgagcacatactagagaaagaggagaaa |
| BBa_K292002 | SEQ ID NO: 620 | pLac (LacI regulated) + Strong RBS | . . . tcacacatactagagattaaagaggagaaa |
| BBa_M31370 | SEQ ID NO: 621 | tacI Promoter | . . . ggaattgtgagcggataacaatttcacaca |
| BBa_R0010 | SEQ ID NO: 622 | promoter (lacI regulated) | . . . ggaattgtgagcggataacaatttcacaca |
| BBa_R0011 | SEQ ID NO: 623 | Promoter (lacI regulated, lambda pL hybrid) | . . . ttgtgagcggataacaagatactgagcaca |
| BBa_R0040 | SEQ ID NO: 624 | TetR repressible promoter | . . . atccctatcagtgatagagatactgagcac |
| BBa_R0050 | SEQ ID NO: 625 | Promoter (HK022 cI regulated) | . . . ccgtcataatatgaaccataagttcaccac |
| BBa_R0051 | SEQ ID NO: 626 | promoter (lambda cI regulated) | . . . tattttacctctggcggtgataatggttgc |
| BBa_R0052 | SEQ ID NO: 627 | Promoter (434 cI regulated) | . . . attgtatgaaaatacaagaaagtttgttga |
| BBa_R0053 | SEQ ID NO: 628 | Promoter (p22 cII regulated) | . . . tagtagataaatttaagtgttctttaatttc |
| BBa_R0061 | SEQ ID NO: 629 | Promoter (HSL-mediated luxR repressor) | ttgacacctgtaggatcgtacaggtataat |
| BBa_R0063 | SEQ ID NO: 630 | Promoter (luxR & HSL regulated -- lux pL) | . . . cacgcaaaacttgcgacaaacaataggtaa |
| BBa_R0065 | SEQ ID NO: 631 | Promoter (lambda cI and luxR regulated -- hybrid) | . . . gtgttgactattttacctctggcggtgata |
| BBa_R0073 | SEQ ID NO: 632 | Promoter (Mnt regulated) | . . . tagatctcctatagtgagtcgtattaattt |
| BBa_R0074 | SEQ ID NO: 633 | Promoter (PenI regulated) | . . . tactttcaaagactacatttgtaagatttg |
| BBa_R0075 | SEQ ID NO: 634 | Promoter (TP901 cI regulated) | . . . cataaagttcatgaaacgtgaactgaaatt |
| BBa_R1050 | SEQ ID NO: 635 | Promoter, Standard (HK022 cI regulated) | . . . ccgtgatactatgaaccataagttcaccac |
| BBa_R1051 | SEQ ID NO: 636 | Promoter, Standard (lambda cI regulated) | . . . aattttacctctggcggtgatactggttgc |
| BBa_R1052 | SEQ ID NO: 637 | Promoter, Standard (434 cI regulated) | . . . attgtatgatactacaagaaagtttgttga |
| BBa_R1053 | SEQ ID NO: 638 | Promoter, Standard (p22 cII regulated) | . . . tagtagatactttaagtgttctttaatttc |
| BBa_R2000 | SEQ ID NO: 639 | Promoter, Zif23 regulated, test: between | . . . tggtcccacgcgcgtgggatactacgtcag |
| BBa_R2001 | SEQ ID NO: 640 | Promoter, Zif23 regulated, test: after | . . . attacggtgagatactcccacgcgcgtggg |
| BBa_R2002 | SEQ ID NO: 641 | Promoter, Zif23 regulated, test: between and after | . . . acgcgcgtgggatactcccacgcgcgtggg |
| BBa_R2108 | SEQ ID NO: 642 | Promoter with operator site for C2003 | . . . gattagattcataaatttgagagaggagtt |

TABLE 25-continued

Examples of Negatively regulated (repressible) *E. coli* σ70 promoters

| Name | Description | | Promoter Sequence |
|---|---|---|---|
| BBa_R2109 | SEQ ID NO: 643 | Promoter with operator site for C2003 | . . . acttagattcataaatttgagagaggagtt |
| BBa_R2110 | SEQ ID NO: 644 | Promoter with operator site for C2003 | . . . ggttagattcataaatttgagagaggagtt |
| BBa_R2111 | SEQ ID NO: 645 | Promoter with operator site for C2003 | . . . acttagattcataaatttgagagaggagtt |
| BBa_R2112 | SEQ ID NO: 646 | Promoter with operator site for C2003 | . . . aattagattcataaatttgagagaggagtt |
| BBa_R2113 | SEQ ID NO: 647 | Promoter with operator site for C2003 | . . . acttagattcataaatttgagagaggagtt |
| BBa_R2114 | SEQ ID NO: 648 | Promoter with operator site for C2003 | . . . atttagattcataaatttgagagaggagtt |
| BBa_R2201 | SEQ ID NO: 649 | C2006-repressible promoter | . . . cacgcgcgtgggaatgttataatacgtcag |
| BBa_S04209 | SEQ ID NO: 650 | R0051:Q04121:B0034:C0079:B0015 | . . . actgagcacatactagagaaagaggagaaa |

TABLE 26

Examples of Negatively regulated (repressible) *E. coli* σ^S promoters

| Name | Description | Promoter Sequence |
|---|---|---|
| BBa_K086030 | SEQ ID NO: 651 modified Lutz-Bujard LacO promoter, with alternative sigma factor σ38 | . . . cagtgagcgagtaacaactacgctgtttta |
| BBa_K086031 | SEQ ID NO: 652 modified Lutz-Bujard LacO promoter, with alternative sigma factor σ38 | . . . cagtgagcgagtaacaactacgctgtttta |
| BBa_K086032 | SEQ ID NO: 653 modified Lutz-Bujard LacO promoter, with alternative sigma factor σ38 | . . . atgtgagcggataacactataattaataga |
| BBa_K086033 | SEQ ID NO: 654 modified Lutz-Bujard LacO promoter, with alternative sigma factor σ38 | . . . atgtgagcggataacactataattaataga |
| BBa_K112318 | SEQ ID NO: 655 {<bolA promoter>} in BBb format | . . . atttcatgatgatacgtgagcggatagaag |

TABLE 27

Examples of Negatively regulated (repressible) *E. coli* σ32 promoters

| Name | Description | Promoter Sequence |
|---|---|---|
| BBa_K086026 | SEQ ID NO: 656 modified Lutz-Bujard LacO promoter, with alternative sigma factor σ32 | . . . ttgtgagcgagtggcaccattaagtacgta |
| BBa_K086027 | SEQ ID NO: 657 modified Lutz-Bujard LacO promoter, with alternative sigma factor σ32 | . . . ttgtgagcgagtgacaccattaagtacgta |
| BBa_K086028 | SEQ ID NO: 658 modified Lutz-Bujard LacO promoter, with alternative sigma factor σ32 | . . . ttgtgagcgagtaacaccattaagtacgta |
| BBa_K086029 | SEQ ID NO: 659 modified Lutz-Bujard LacO promoter, with alternative sigma factor σ32 | . . . ttgtgagcgagtaacaccattaagtacgta |

TABLE 28

**Examples of Negatively regulated (repressible) *E. coli* σ54 promoters**

| Name | | Description | Promoter Sequence |
|---|---|---|---|
| BBa_J64979 | SEQ ID NO: 660 | glnAp2 | . . . agttggcacagatttcgctttatcttttt |

TABLE 29

**Examples of Repressible *B. subtilis* σ$^A$ promoters**

| Name | | Description | Promoter Sequence |
|---|---|---|---|
| BBa_K090501 | SEQ ID NO: 661 | Gram-Positive IPTG-Inducible Promoter | . . . tggaattgtgagcggataacaattaagctt |
| BBa_K143014 | SEQ ID NO: 662 | Promoter Xyl for *B. subtilis* | . . . agtttgtttaaacaacaaactaataggtga |
| BBa_K143015 | SEQ ID NO: 663 | Promoter hyper-spank for *B. subtilis* | . . . aatgtgtgtaattgtgagcggataacaatt |

TABLE 30

Examples of T7 Repressible Promoters

| Name | | Description | Promoter Sequence |
|---|---|---|---|
| BBa_R0184 | SEQ ID NO: 664 | T7 promoter (lacI repressible) | . . . atagggaattgtgagcggataacaattcc |
| BBa_R0185 | SEQ ID NO: 665 | T7 promoter (lacI repressible) | . . . atagggaattgtgagcggataacaattcc |
| BBa_R0186 | SEQ ID NO: 666 | T7 promoter (lacI repressible) | . . . atagggaattgtgagcggataacaattcc |
| BBa_R0187 | SEQ ID NO: 667 | T7 promoter (lacI repressible) | . . . atagggaattgtgagcggataacaattcc |

TABLE 31

Examples of Yeast Repressible Promoters

| Name | | Description | Promoter Sequence |
|---|---|---|---|
| BBa_I766558 | SEQ ID NO: 668 | pFig1 (Inducible) Promoter | . . . aaacaaacaaacaaaaaaaaaaaaaaaaaa |
| BBa_I766214 | SEQ ID NO: 669 | pGal1 | . . . atactttaacgtcaaggagaaaaaactata |
| BBa_K165000 | SEQ ID NO: 670 | MET 25 Promoter | . . . tagatacaattctattacceccatccatac |

TABLE 32

Examples of Eukaryotic Repressible Promoters

| Name | | Description | Promoter Sequence |
|---|---|---|---|
| BBa_I756015 | SEQ ID NO: 671 | CMV Promoter with lac operator sites | . . . ttagtgaaccgtcagatcactagtctgcag |
| BBa_I756016 | SEQ ID NO: 672 | CMV-tet promoter | . . . ttagtgaaccgtcagatcactagtctgcag |
| BBa_I756017 | SEQ ID NO: 673 | U6 promoter with tet operators | . . . ggaaaggacgaaacaccgactagtctgcag |
| BBa_I756018 | SEQ ID NO: 674 | Lambda Operator in SV-40 intron | . . . attgtttgtgtattttagactagtctgcag |

TABLE 32-continued

Examples of Eukaryotic Repressible Promoters

| Name | Description | | Promoter Sequence |
|---|---|---|---|
| BBa_I756019 | SEQ ID NO: 675 | Lac Operator in SV-40 intron | . . . attgtttgtgtattttagactagtctgcag |
| BBa_I756020 | SEQ ID NO: 676 | Tet Operator in SV-40 intron | . . . attgtttgtgtattttagactagtctgcag |
| BBa_I756021 | SEQ ID NO: 677 | CMV promoter with Lambda Operator | . . . ttagtgaaccgtcagatcactagtctgcag |

TABLE 33

Examples of Combination Inducible & Repressible E. coli Promoters

| Name | | Description | Promoter Sequence |
|---|---|---|---|
| BBa_I1051 | SEQ ID NO: 678 | Lux cassette right promoter | . . . tgttatagtcgaatacctctggcggtgata |
| BBa_I2006 | SEQ ID NO: 679 | Modified lamdba Prm promoter (repressed by 434 cI) | . . . attacaaactttcttgtatagatttaacgt |
| BBa_I2036 | SEQ ID NO: 680 | Modified lamdba Prm promoter (cooperative repression by 434 cI) | . . . tttcttgtatagatttacaatgtatcttgt |
| BBa_I2040 | SEQ ID NO: 681 | Modified lambda P(RM) promoter: -10 region from P(L) and cooperatively repressed by 434 cI | . . . tttcttgtagatacttacaatgtatcttgt |
| BBa_I14015 | SEQ ID NO: 682 | P(Las) TetO | . . . ttttggtacactccctatcagtgatagaga |
| BBa_I14016 | SEQ ID NO: 683 | P(Las) CIO | . . . cttttggtacactacctctggcggtgata |
| BBa_I714924 | SEQ ID NO: 684 | RecA_DlexO_DLacO1 | . . . actctcggcatggacgagctgtacaagtaa |
| BBa_I731004 | SEQ ID NO: 685 | FecA promoter | . . . ttctcgttcgactcatagctgaacacaaca |
| BBa_I732301 | SEQ ID NO: 686 (U073026D001016) | NAND Candidate | . . . ggaattgtgagcgctcataattggatccgg |
| BBa_I732302 | SEQ ID NO: 687 (U073027D001017) | NAND Candidate | . . . ggaattgtgagctacagtcgtcggatccgg |
| BBa_I732303 | SEQ ID NO: 688 (U073022D001046) | NAND Candidate | . . . ggaattgtgaacgctcataattggatccgg |
| BBa_I732304 | SEQ ID NO: 689 (U073022D001047) | NAND Candidate | . . . ggaattgtgaactacagtcgtcggatccgg |
| BBa_I732305 | SEQ ID NO: 690 (U073022D059046) | NAND Candidate | . . . taaattgtgaacgctcataattggatccgg |
| BBa_I732306 | SEQ ID NO: 691 (U073011D002022) | NAND Candidate | . . . gaaattgtaagcgcttacaattggatccgg |
| BBa_I732351 | SEQ ID NO: 692 (U037011D002022) | NOR Candidate | . . . gaaattgtaagcgcttacaattggatccgg |
| BBa_I732352 | SEQ ID NO: 693 (U035044D001022) | NOR Candidate | . . . ggaattgtaagcgcttacaattggatccgg |
| BBa_I732400 | SEQ ID NO: 694 (U097NUL + D062NUL) | Promoter Family Member | . . . gccaaattaaacaggattaacaggatccgg |
| BBa_I732401 | SEQ ID NO: 695 (U097O11 + D062NUL) | Promoter Family Member | . . . gccaaattaaacaggattaacaggatccgg |
| BBa_I732402 | SEQ ID NO: 696 (U085O11 + D062NUL) | Promoter Family Member | . . . gccaaattaaacaggattaacaggatccgg |
| BBa_I732403 | SEQ ID NO: 697 (U073O11 + D062NUL) | Promoter Family Member | . . . gccaaattaaacaggattaacaggatccgg |
| BBa_I732404 | SEQ ID NO: 698 (U061O11 + D062NUL) | Promoter Family Member | . . . gccaaattaaacaggattaacaggatccgg |

TABLE 33-continued

Examples of Combination Inducible & Repressible *E. coli* Promoters

| Name | Description | Promoter Sequence |
|---|---|---|
| BBa_I732405 SEQ ID NO: 699 (U049O11 + D062NUL) | Promoter Family Member | . . . gccaaattaaacaggattaacaggatccgg |
| BBa_I732406 SEQ ID NO: 700 (U037O11 + D062NUL) | Promoter Family Member | . . . gccaaattaaacaggattaacaggatccgg |
| BBa_I732407 SEQ ID NO: 701 (U097NUL + D002O22) | Promoter Family Member | . . . gaaattgtaagcgcttacaattggatccgg |
| BBa_I732408 SEQ ID NO: 702 (U097NUL + D014O02) | Promoter Family Member | . . . taaattgtaagcgcttacaattggatccgg |
| BBa_I732409 SEQ ID NO: 703 (U097NUL + D026O22) | Promoter Family Member | . . . gtaattgtaagcgcttacaattggatccgg |
| BBa_I732410 SEQ ID NO: 704 (U097NUL + D038O22) | Promoter Family Member | . . . tcaattgtaagcgcttacaattggatccgg |
| BBa_I732411 SEQ ID NO: 705 (U097NUL + D050O22) | Promoter Family Member | . . . aaaattgtaagcgcttacaattggatccgg |
| BBa_I732412 SEQ ID NO: 706 (U097NUL + D06222) | Promoter Family Member | . . . caaattgtaagcgcttacaattggatccgg |
| BBa_I732413 SEQ ID NO: 707 (U097O11 + D002O22) | Promoter Family Member | . . . gaaattgtaagcgcttacaattggatccgg |
| BBa_I732414 SEQ ID NO: 708 (U097O11 + D014O22) | Promoter Family Member | . . . taaattgtaagcgcttacaattggatccgg |
| BBa_I732415 SEQ ID NO: 709 (U097O11 + D026O22) | Promoter Family Member | . . . gtaattgtaagcgcttacaattggatccgg |
| BBa_I732416 SEQ ID NO: 710 (U097O11 + D038O22) | Promoter Family Member | . . . tcaattgtaagcgcttacaattggatccgg |
| BBa_I732417 SEQ ID NO: 711 (U097O11 + D050O22) | Promoter Family Member | . . . aaaattgtaagcgcttacaattggatccgg |
| BBa_I732418 SEQ ID NO: 712 (U097O11 + D062O22) | Promoter Family Member | . . . caaattgtaagcgcttacaattggatccgg |
| BBa_I732419 SEQ ID NO: 713 (U085O11 + D002O22) | Promoter Family Member | . . . gaaattgtaagcgcttacaattggatccgg |
| BBa_I732420 SEQ ID NO: 714 (U085O11 + D014O22) | Promoter Family Member | . . . taaattgtaagcgcttacaattggatccgg |
| BBa_I732421 SEQ ID NO: 715 (U085O11 + D026O22) | Promoter Family Member | . . . gtaattgtaagcgcttacaattggatccgg |
| BBa_I732422 SEQ ID NO: 716 (U085O11 + D038O22) | Promoter Family Member | . . . tcaattgtaagcgcttacaattggatccgg |
| BBa_I732423 SEQ ID NO: 717 (U085O11 + D050O22) | Promoter Family Member | . . . aaaattgtaagcgcttacaattggatccgg |
| BBa_I732424 SEQ ID NO: 718 (U085O11 + D062O22) | Promoter Family Member | . . . caaattgtaagcgcttacaattggatccgg |
| BBa_I732425 SEQ ID NO: 719 (U073O11 + D002O22) | Promoter Family Member | . . . gaaattgtaagcgcttacaattggatccgg |
| BBa_I732426 SEQ ID NO: 720 (U073O11 + D014O22) | Promoter Family Member | . . . taaattgtaagcgcttacaattggatccgg |
| BBa_I732427 SEQ ID NO: 721 (U073O11 + D026O22) | Promoter Family Member | . . . gtaattgtaagcgcttacaattggatccgg |
| BBa_I732428 SEQ ID NO: 722 (U073O11 + D038O22) | Promoter Family Member | . . . tcaattgtaagcgcttacaattggatccgg |
| BBa_I732429 SEQ ID NO: 723 (U073O11 + D050O22) | Promoter Family Member | . . . aaaattgtaagcgcttacaattggatccgg |

TABLE 33-continued

Examples of Combination Inducible & Repressible *E. coli* Promoters

| Name | | Description | Promoter Sequence |
|---|---|---|---|
| BBa_I732430 | SEQ ID NO: 724 (U073O11 + D062O22) | Promoter Family Member | . . . caaattgtaagcgcttacaattggatccgg |
| BBa_I732431 | SEQ ID NO: 725 (U061O11 + D002O22) | Promoter Family Member | . . . gaaattgtaagcgcttacaattggatccgg |
| BBa_I732432 | SEQ ID NO: 726 (U061O11 + D014O22) | Promoter Family Member | . . . taaattgtaagcgcttacaattggatccgg |
| BBa_I732433 | SEQ ID NO: 727 (U061O11 + D026O22) | Promoter Family Member | . . . gtaattgtaagcgcttacaattggatccgg |
| BBa_I732434 | SEQ ID NO: 728 (U061O11 + D038O22) | Promoter Family Member | . . . tcaattgtaagcgcttacaattggatccgg |
| BBa_I732435 | SEQ ID NO: 729 (U061O11 + D050O22) | Promoter Family Member | . . . aaaattgtaagcgcttacaattggatccgg |
| BBa_I732436 | SEQ ID NO: 730 (U061O11 + D062O22) | Promoter Family Member | . . . caaattgtaagcgcttacaattggatccgg |
| BBa_I732437 | SEQ ID NO: 731 (U049O11 + D002O22) | Promoter Family Member | . . . gaaattgtaagcgcttacaattggatccgg |
| BBa_I732438 | SEQ ID NO: 732 (U049O11 + D014O22) | Promoter Family Member | . . . taaattgtaagcgcttacaattggatccgg |
| BBa_I732439 | SEQ ID NO: 733 (U049O11 + D026O22) | Promoter Family Member | . . . gtaattgtaagcgcttacaattggatccgg |
| BBa_I732440 | SEQ ID NO: 734 (U049O11 + D038O22) | Promoter Family Member | . . . tcaattgtaagcgcttacaattggatccgg |
| BBa_I732441 | SEQ ID NO: 735 (U049O11 + D050O22) | Promoter Family Member | . . . aaaattgtaagcgcttacaattggatccgg |
| BBa_I732442 | SEQ ID NO: 736 (U049O11 + D062O22) | Promoter Family Member | . . . caaattgtaagcgcttacaattggatccgg |
| BBa_I732443 | SEQ ID NO: 737 (U037O11 + D002O22) | Promoter Family Member | . . . gaaattgtaagcgcttacaattggatccgg |
| BBa_I732444 | SEQ ID NO: 738 (U037O11 + D014O22) | Promoter Family Member | . . . taaattgtaagcgcttacaattggatccgg |
| BBa_I732445 | SEQ ID NO: 739 (U037O11 + D026O22) | Promoter Family Member | . . . gtaattgtaagcgcttacaattggatccgg |
| BBa_I732446 | SEQ ID NO: 740 (U037O11 + D038O22) | Promoter Family Member | . . . tcaattgtaagcgcttacaattggatccgg |
| BBa_I732447 | SEQ ID NO: 741 (U037O11 + D050O22) | Promoter Family Member | . . . aaaattgtaagcgcttacaattggatccgg |
| BBa_I732448 | SEQ ID NO: 742 (U037O11 + D062O22) | Promoter Family Member | . . . caaattgtaagcgcttacaattggatccgg |
| BBa_I732450 | SEQ ID NO: 743 (U073O26 + D062NUL) | Promoter Family Member | . . . gccaaattaaacaggattaacaggatccgg |
| BBa_I732451 | SEQ ID NO: 744 (U073O27 + D062NUL) | Promoter Family Member | . . . gccaaattaaacaggattaacaggatccgg |
| BBa_I732452 | SEQ ID NO: 745 (U073O26 + D062O61) | Promoter Family Member | . . . caaattatgagcgctcacaattggatccgg |
| BBa_I739102 | SEQ ID NO: 746 | Double Promoter (cI, negative/ TetR, negative) | . . . tgatagagattccctatcagtgatagagat |
| BBa_I739103 | SEQ ID NO: 747 | Double Promoter (lacI, negative/P22 cII, negative) | . . . gttctttaattatttaagtgttctttaatt |
| BBa_I739104 | SEQ ID NO: 748 | Double Promoter (LuxR/HSL, positive/P22 cII, negative) | . . . gttctttaattatttaagtgttctttaatt |

TABLE 33-continued

Examples of Combination Inducible & Repressible E. coli Promoters

| Name | Description | | Promoter Sequence |
|---|---|---|---|
| BBa_I739105 | SEQ ID NO: 749 | Double Promoter (LuxR/HSL, positive/cI, negative) | . . . cgtgcgtgttgataacaccgtgcgtgttga |
| BBa_I739106 | SEQ ID NO: 750 | Double Promoter (TetR, negative/P22 cII, negative) | . . . gtgttctttaatatttaagtgttctttaat |
| BBa_I739107 | SEQ ID NO: 751 | Double Promoter (cI, negative/LacI, negative) | . . . ggaattgtgagcggataacaatttcacaca |
| BBa_I741018 | SEQ ID NO: 752 | Right facing promoter (for xylF) controlled by xylR and CRP-cAMP | . . . gttacgtttatcgcggtgattgttacttat |
| BBa_I741019 | SEQ ID NO: 753 | Right facing promoter (for xylA) controlled by xylR and CRP-cAMP | . . . gcaaataaaatggaatgatgaaactgggt |
| BBa_I742124 | SEQ ID NO: 754 | Reverse complement Lac promoter | . . . aacgcgcggggagaggcggtttgcgtattg |
| BBa_I751501 | SEQ ID NO: 755 | plux-cI hybrid promoter | . . . gtgttgatgcttttatcaccgccagtggta |
| BBa_I751502 | SEQ ID NO: 756 | plux-lac hybrid promoter | . . . agtgtgtggaattgtgagcggataacaatt |
| BBa_I761011 | SEQ ID NO: 757 | CinR, CinL and glucose controlled promoter | . . . acatcttaaaagttttagtatcatattcgt |
| BBa_I765007 | SEQ ID NO: 758 | Fe and UV promoters | . . . ctgaaagcgcataccgctatggaggggtt |
| BBa_J05209 | SEQ ID NO: 759 | Modified Pr Promoter | . . . tattttacctctggcggtgataatggttgc |
| BBa_J05210 | SEQ ID NO: 760 | Modified Prm + Promoter | . . . atttataaatagtggtgatagatttaacgt |
| BBa_J58100 | SEQ ID NO: 761 | AND-type promoter synergistically activated by cI and CRP | . . . atttataaatagtggtgatagatttaacgt |
| BBa_J64712 | SEQ ID NO: 762 | LasR/LasI Inducible & RHLR/RHLI repressible Promoter | . . . gaaatctggcagttttggtacacgaaagc |
| BBa_J64800 | SEQ ID NO: 763 | RHLR/RHLI Inducible & LasR/LasI repressible Promoter | . . . tgccagttctggcaggtctaaaaagtgttc |
| BBa_J64804 | SEQ ID NO: 764 | The promoter region (inclusive of regulator binding sites) of the B. subtilis RocDEF operon | . . . cacagaacttgcatttatataaagggaaag |
| BBa_J64979 | SEQ ID NO: 765 | glnAp2 | . . . agttggcacagatttcgctttatcttttt |
| BBa_J64981 | SEQ ID NO: 766 | OmpR-P strong binding, regulatory region for Team Challenge03-2007 | . . . agcgctcacaatttaatacgactcactata |
| BBa_K091100 | SEQ ID NO: 767 | pLac_lux hybrid promoter | . . . ggaattgtgagcggataacaatttcacaca |
| BBa_K091101 | SEQ ID NO: 768 | pTet_Lac hybrid promoter | . . . ggaattgtgagcggataacaatttcacaca |
| BBa_K091104 | SEQ ID NO: 769 | pLac/Mnt Hybrid Promoter | . . . ggaattgtgagcggataacaatttcacaca |
| BBa_K091105 | SEQ ID NO: 770 | pTet/Mnt Hybrid Promoter | . . . agaactgtaatccctatcagtgatagagat |
| BBa_K091106 | SEQ ID NO: 771 | LsrA/cI hybrid promoter | . . . tgttgatttatctaacaccgtgcgtgttga |
| BBa_K091107 | SEQ ID NO: 772 | pLux/cI Hybrid Promoter | . . . acaccgtgcgtgttgatatagtcgaataaa |
| BBa_K091143 | SEQ ID NO: 773 | pLas/cI Hybrid Promoter | . . . ggttcttttggtacctctggcggtgataa |
| BBa_K091146 | SEQ ID NO: 774 | pLas/Lux Hybrid Promoter | . . . tgtaggatcgtacaggtataaattcttcag |
| BBa_K091157 | SEQ ID NO: 775 | pLux/Las Hybrid Promoter | . . . ctatctcatttgctagtatagtcgaataaa |
| BBa_K094120 | SEQ ID NO: 776 | pLacI/ara-1 | . . . aattgtgagcggataacaatttcacacaga |
| BBa_K100000 | SEQ ID NO: 777 | Natural Xylose Regulated Bi-Directional Operator | . . . gttacgtttatcgcggtgattgttacttat |
| BBa_K101000 | SEQ ID NO: 778 | Dual-Repressed Promoter for p22 mnt and TetR | . . . acggtgacctagatctccgatactgagcac |
| BBa_K101001 | SEQ ID NO: 779 | Dual-Repressed Promoter for LacI and LambdacI | . . . tggaattgtgagcggataaaatttcacaca |

TABLE 33-continued

Examples of Combination Inducible & Repressible *E. coli* Promoters

| Name | Description | Promoter Sequence |
|---|---|---|
| BBa_K101002 | SEQ ID NO: 780 Dual-Repressed Promoter for p22 cII and TetR | . . . tagtagataatttaagtgttctttaatttc |
| BBa_K109200 | SEQ ID NO: 781 AraC and TetR promoter (hybrid) | . . . aacaaaaaaacggatcctctagttgcggcc |
| BBa_K112118 | SEQ ID NO: 782 rrnB P1 promoter | . . . ataaatgcttgactctgtagcgggaaggcg |
| BBa_K112318 | SEQ ID NO: 783 {<bolA promoter>} in BBb format | . . . atttcatgatgatacgtgagcggatagaag |
| BBa_K112322 | SEQ ID NO: 784 {Pdps} in BBb format | . . . gggacacaaacatcaagaggatatgagatt |
| BBa_K112402 | SEQ ID NO: 785 promoter for FabA gene-Membrane Damage and Ultrasound Sensitive | . . . gtcaaaatgaccgaaacgggtggtaacttc |
| BBa_K112405 | SEQ ID NO: 786 Promoter for CadA and CadB genes | . . . agtaatcttatcgccagtttggtctggtca |
| BBa_K112406 | SEQ ID NO: 787 cadC promoter | . . . agtaatcttatcgccagtttggtctggtca |
| BBa_K112701 | SEQ ID NO: 788 hns promoter | . . . aattctgaacaacatccgtactcttcgtgc |
| BBa_K116001 | SEQ ID NO: 789 nhaA promoter, that can be regulated by pH and nhaR protein. | . . . cgatctattcacctgaaagagaaataaaaa |
| BBa_K116500 | SEQ ID NO: 790 OmpF promoter that is activated or repressed by OmpR according to osmolarity. | . . . aaacgttagtttgaatggaaagatgcctgc |
| BBa_K121011 | SEQ ID NO: 791 promoter (lacI regulated) | . . . acaggaaacagctatgaccatgattacgcc |
| BBa_K136010 | SEQ ID NO: 792 fliA promoter | . . . gttcactctataccgctgaaggtgtaatgg |
| BBa_K145150 | SEQ ID NO: 793 Hybrid promoter: HSL-LuxR activated, P22 C2 repressed | . . . tagtttataatttaagtgttctttaatttc |
| BBa_K145152 | SEQ ID NO: 794 Hybrid promoter: P22 c2, LacI NOR gate | . . . gaaaatgtgagcgagtaacaacctcacaca |
| BBa_K259005 | SEQ ID NO: 795 AraC Rheostat Promoter | . . . ttttatcgcaactctctactgtttctccat |
| BBa_K259007 | SEQ ID NO: 796 AraC Promoter fused with RBS | . . . gtttctccattactagagaaagaggggaca |
| BBa_K266005 | SEQ ID NO: 797 PAI + LasR -> LasI & AI + LuxR --\|LasI | . . . aataactctgatagtgctagtgtagatctc |
| BBa_K266006 | SEQ ID NO: 798 PAI + LasR -> LasI + GFP & AI + LuxR --\|LasI + GFP | . . . caccttcgggtgggcctttctgcgtttata |
| BBa_K266007 | SEQ ID NO: 799 Complex QS -> LuxI & LasI circuit | . . . caccttcgggtgggcctttctgcgtttata |
| BBa_R0065 | SEQ ID NO: 800 Promoter (lambda cI and luxR regulated -- hybrid) | . . . gtgttgactattttacctctggcggtgata |

TABLE 34

Examples of Combination Inducible & Repressible Miscellaneous Prokaryotic Promoters

| Name | Description | Promoter Sequence |
|---|---|---|
| BBa_K125100 | SEQ ID NO: 801 nir promoter from *Synechocystis sp.* PCC6803 | . . . cgaaacgggaaccctatattgatctctact |

TABLE 35

Examples of Combination Inducible & Repressible Miscellaneous Yeast Promoters

| Name | Description | Promoter Sequence |
| --- | --- | --- |
| BBa_I766200 | SEQ ID NO: 802 pSte2 | ... accgttaagaaccatatccaagaatcaaaa |
| BBa_K110016 | SEQ ID NO: 803 A-Cell Promoter STE2 (backwards) | ... accgttaagaaccatatccaagaatcaaaa |
| BBa_K165034 | SEQ ID NO: 804 Zif268-HIV bs + LexA bs + mCYC promoter | ... cacaaatacacacactaaattaataactag |
| BBa_K165041 | SEQ ID NO: 805 Zif268-HIV binding sites + TEF constitutive yeast promoter | ... atacggtcaacgaactataattaactaaac |
| BBa_K165043 | SEQ ID NO: 806 Zif268-HIV binding sites + MET25 constitutive yeast promoter | ... tagatacaattctattacccccatccatac |

TABLE 36

Examples of Combination Inducible & Repressible Miscellaneous Eukaryotic Promoters

| Name | Description | Promoter Sequence |
| --- | --- | --- |
| BBa_J05215 | SEQ ID NO: 807 Regulator for R1-CREBH | ... ggggcgagggccccgcctccggaggcgggg |
| BBa_J05216 | SEQ ID NO: 808 Regulator for R3-ATF6 | ... gaggggacggctccggccccggggccggag |
| BBa_J05217 | SEQ ID NO: 809 Regulator for R2-YAP7 | ... ggggcgagggctccggccccggggccggag |
| BBa_J05218 | SEQ ID NO: 810 Regulator for R4-cMaf | ... gaggggacggccccgcctccggaggcgggg |

Output Product Sequences and Output Products

A variety of biological output gene and output product nucleic acid sequences are provided for use in the various low- and high-input detector modules and biological classifier circuits described herein. The biological outputs, or output products, as described herein, refer to products of nucleic acid sequences that can be used as markers of specific states of the low- and high-input detector modules and biological classifier circuits described herein.

An output nucleic acid sequence can encode for a protein or RNA that is used to track or identify the state of the cell upon receiving a specific combination of inputs, as detected by the biological classifier circuits described herein. Such output products can be used to distinguish between various states of a cell or a population of cells, such as a heterogenous population. Representative output products for use with the biological classifier circuits and low- and high-input detector modules described herein include, but are not limited to, reporter proteins, transcriptional repressors, transcriptional activators, selection markers, enzymes, receptor proteins, ligand proteins, RNAs, riboswitches, or short-hairpin RNAs.

Reporter Outputs

In some embodiments of the aspects described herein, an output gene product of a biological classifier circuit or a component high- or low-input module thereof is a "reporter output." As defined herein, reporters refer to proteins or molecules that can be used to produce a measurable signal such as fluorescence, color, or luminescence. Reporter protein coding sequences encode proteins whose presence in the cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product. In some embodiments, reporters are used as output products to identify those cells in a population of cells expressing a specific microRNA expression profile that a biological classifier circuit is designed to detect. In some embodiments, reporters are used to quantify the strength or activity of the signal received by the modules or biological classifier circuits described herein. In some embodiments, reporters can be fused in-frame to other protein coding sequences to identify where a protein is located in a cell or organism.

There are several different ways to measure or quantify a reporter depending on the particular reporter and what kind of characterization data is desired. In some embodiments, microscopy can be a useful technique for obtaining both spatial and temporal information on reporter activity, particularly at the single cell level. In other embodiments, flow cytometers can be used for measuring the distribution in reporter activity across a large population of cells. In some embodiments, plate readers can be used for taking population average measurements of many different samples over time. In other embodiments, instruments that combine such various functions, can be used, such as multiplex plate readers designed for flow cytometers, and combination microscopy and flow cytometric instruments.

Fluorescent proteins are convenient ways to visualize or quantify the output of a module or biological classifier circuit. Fluorescence can be readily quantified using a microscope, plate reader or flow cytometer equipped to excite the fluorescent protein with the appropriate wavelength of light. Since several different fluorescent proteins are available, multiple gene expression measurements can be made in parallel. Non-limiting examples of fluorescent proteins useful for the e biological classifier circuits described herein are provided in Table 37.

TABLE 37

Examples of Fluorescent Protein Reporters

| Name | Protein | Description | Tag | Emission | Excitation | Length |
|---|---|---|---|---|---|---|
| BBa_E0030 | EYFP | enhanced yellow fluorescent protein derived from *A. victoria* GFP | None | 527 | 514 | 723 |
| BBa_E0020 | ECFP | engineered cyan fluorescent protein derived from *A. victoria* GFP | None | 476 | 439 | 723 |
| BBa_E1010 | mRFP1 | highly engineered mutant of red fluorescent protein from *Discosoma striata* (coral) | None | 607 | 584 | 681 |
| BBa_E2050 | mOrange | derivative of mRFP1, yeast-optimized | None | 562 | 548 | 744 |
| BBa_E0040 | GFPmut3b | green fluorescent protein derived from jellyfish *Aequeora victoria* wild-type GFP (SwissProt: P42212 | None | 511 | 501 | 720 |
| BBa_J52021 | | dnTraf6-linker-GFP | | | | 1446 |
| BBa_J52026 | | dnMyD88-linker-GFP | | | | 1155 |
| BBa_I715022 | | Amino Portion of RFP | | | | 462 |
| BBa_I715023 | | Carboxyl portion of RFP | | | | 220 |
| BBa_I712028 | | CherryNLS - synthetic construct monomeric red fluorescent protein with nuclear localization sequence | | | | 733 |
| BBa_K125500 | | GFP fusion brick | | | | 718 |
| BBa_K106000 | | GFP, AarI BD part | | | | 714 |
| BBa_K106004 | | mCherry, Aar1 AB part | | | | 708 |
| BBa_K106005 | | mCherry, Aar1 BD part | | | | 708 |
| BBa_K106028 | | GFP, AarI AB part | | | | 714 |
| BBa_K165005 | | Venus YFP, yeast optimized for fusion | | | | 744 |
| BBa_K157005 | | Split-Cerulean-cCFP | | | | 261 |
| BBa_K157006 | | Split-Cerulean-nCFP | | | | 483 |
| BBa_K157007 | | Split-Venus-cYFP | | | | 261 |
| BBa_K157008 | | Split-Venus-nYFP | | | | 486 |
| BBa_K125810 | | slr2016 signal sequence + GFP fusion for secretion of GFP | | | | 779 |
| BBa_K082003 | GFP | GFP(+LVA) | | | | 756 |
| BBa_K156009 | | OFP (orange fluorescent protein) | | | | 864 |
| BBa_K156010 | | SBFP2 (strongly enhanced blue fluorescent protein) | | | | 720 |
| BBa_K106671 | | GFP, AarI AD part | | | | 714 |
| BBa_K294055 | GFPmut3b | GFP RFP Hybrid | None | 511 | 501 | 720 |
| BBa_K192001 | | CFP + tgt + lva | | | | 858 |
| BBa_K180001 | GFPmut3b | Green fluorescent protein (+LVA) | LVA | | | 754 |
| BBa_K283005 | | lpp_ompA_eGFP_streptavidin | | | | 1533 |
| BBa_K180008 | mCherry | mCherry (rights owned by Clontech) | | | | 708 |
| BBa_K180009 | mBanana | mBanana (rights owned by Clontech) | | | | 708 |

Luminescence can be readily quantified using a plate reader or luminescence counter. Luciferases can be used as output gene products for various embodiments described herein, for example, in samples where background fluorescence might result in an ability to distinguish between cells expressing an output and those that do not, because cells tend to have little to no background luminescence in the absence of a luciferase. Non-limiting examples of luciferases are provided in Table 38.

TABLE 38

Examples of Luciferases

| Name | Description | Length |
|---|---|---|
| BBa_J52011 | dnMyD88-linker-Rluc | 1371 |
| BBa_J52013 | dnMyD88-linker-Rluc-linker-PEST191 | 1872 |
| BBa_I712019 | Firefly luciferase-luciferase from *Photinus pyralis* | 1653 |

In other embodiments, enzymes that produce colored substrates can be quantified using spectrophotometers or other instruments that can take absorbance measurements including plate readers. Like luciferases, enzymes like β-galactosidase tend to amplify low signals.

TABLE 39

Examples of Enzymes that Produce Colored Substrates

| Name | Protein | Description | Length |
|---|---|---|---|
| BBa_I732006 | | lacZ alpha fragment | 234 |
| BBa_I732005 | | lacZ (encoding beta-galactosidase, full-length) | 3075 |
| BBa_K147002 | | xylE | 924 |

Another reporter output product for use in the different aspects described herein includes:

TABLE 40

Examples of Other Reporter Genes

| Name | Protein | Description | Length |
|---|---|---|---|
| BBa_K157004 | | Fluoresceine-A-binding | 522 |

Transcriptional Outputs:

In some embodiments of the different aspects described herein, the output product of a given low- or high-input module or biological classifier circuit is itself a transcriptional activator or repressor, the production of which by a module or circuit can provide additional input signals to subsequent or additional modules or biological classifier circuits. For example, the output product encoded by a high-input detector module can be a transcriptional repressor that prevents transcription from a low-input detector module of a biological classifier circuit.

Transcriptional regulators either activate or repress transcription from cognate promoters. Transcriptional activators typically bind nearby to transcriptional promoters and recruit RNA polymerase to directly initiate transcription. Transcriptional repressors bind to transcriptional promoters and sterically hinder transcriptional initiation by RNA polymerase. Some transcriptional regulators serve as either an activator or a repressor depending on where it binds and cellular conditions. Examples of transcriptional regulators for use as output products in the classifier circuits and high- and low-input modules described herein are provided in Table 41.

TABLE 41

Examples of Transcriptional Regulators

| Name | Protein | Description | Tag | Direction | Uniprot | Length |
|---|---|---|---|---|---|---|
| BBa_C0079 | lasR-LVA | lasR activator from *P. aeruginosa* PAO1(+LVA) | LVA | Forward | P25084 | 756 |
| BBa_C0077 | cinR | cinR activator from *Rhizobium leguminosarum* (+LVA) | LVA | Forward | ~Q84HT2 | 762 |
| BBa_C0179 | lasR | lasR activator from *P. aeruginosa* PAO1 (no LVA) | None | Forward | P25084 | 723 |
| BBa_J07009 | ToxR | toxicity-gene activator from *Vibrio cholerae* | None | Forward | P15795 | 630 |
| BBa_K118001 | | appY coding sequence encoding a DNA-binding transcriptional activator | | | | 753 |
| BBa_K137113 | | rcsA | | | | 624 |
| BBa_K131022 | | LuxO D47E, *Vibrio harveyi* | | | | 1362 |
| BBa_K131023 | | LuxO D47A, *Vibrio harveyi* | | | | 1362 |
| BBa_K082006 | | LuxR-G2F | | | | 753 |
| BBa_K294205 | | This is a coding sequence of heat shock protein from *E. coli* | | | | 402 |
| BBa_S04301 | lasR-LVA | C0079:B0015 | LVA | Forward | P25084 | 918 |
| BBa_K266002 | lasR-LVA | LasR + Term | LVA | Forward | P25084 | 918 |
| BBa_C0012 | LacI | lacI repressor from *E. coli* (+LVA) | LVA | Forward | P03023 | 1128 |
| BBa_C0040 | TetR | tetracycline repressor from transposon Tn10 (+LVA) | LVA | Forward | P04483 | 660 |
| BBa_C0050 | CI HK022 | cI repressor from phage HK022 (+LVA?) | LVA | Forward | P18680 | 744 |
| BBa_C0051 | CI lambda | cI repressor from *E. coli* phage lambda (+LVA) | LVA | Forward | P03034 | 750 |
| BBa_C0052 | CI 434-LVA | cI repressor from phage 434 (+LVA) | LVA | Forward | P16117 | 669 |
| BBa_C0053 | C2 P22 | c2 repressor from *Salmonella* phage P22 (+LVA) | LVA | Forward | P69202 | 687 |
| BBa_C0073 | mnt-weak | mnt repressor (weak) from *Salmonella* phage P22 (+LVA) | LVA | Forward | P03049 | 288 |
| BBa_C0075 | cI TP901 | TP901 cI repressor from phage TP901-1 (+LVA) | LVA | Forward | none | 579 |
| BBa_C0074 | penI | penI repressor from *Bacillus licheniformis* (+LVA) | LVA | Forward | P06555 | 423 |
| BBa_C0072 | mnt | mnt repressor (strong) from *Salmonella* phage P22 (+LVA) | LVA | Forward | P03049 | 288 |
| BBa_C2001 | Zif23-GCN4 | Zif23-GCN4 engineered repressor (+LVA, C2000 codon-optimized for *E. coli*) | LVA | Forward | P03069 | 300 |
| BBa_C0056 | CI 434 | cI repressor from phage 434 (no LVA) | None | Forward | P16117 | 636 |
| BBa_J06501 | LacI-mut2 | LacI repressor (temperature-sensitive mut 265) (+LVA) | LVA | Forward | ~P03023 | 1153 |
| BBa_J06500 | LacI-mut1 | LacI repressor (temperature-sensitive mut 241) (+LVA) | LVA | Forward | ~P03023 | 1153 |
| BBa_C2006 | | MalE.FactorXa.Zif268-GCN4 | | | | 1428 |
| BBa_I715032 | | lacIq reverse | | | | 1128 |
| BBa_I732100 | | LacI | | | | 1086 |
| BBa_I732101 | | LRLa | | | | 1086 |
| BBa_I732105 | | ARL2A0101 | | | | 1086 |
| BBa_I732106 | | ARL2A0102 | | | | 1086 |
| BBa_I732107 | | ARL2A0103 | | | | 1086 |
| BBa_I732110 | | ARL2A0203 | | | | 1086 |
| BBa_I732112 | | ARL2A0301 | | | | 1086 |
| BBa_I732115 | | ARL4A0604 | | | | 1086 |
| BBa_K091001 | | LsrR gene | | Forward | | 954 |
| BBa_K091121 | | LacI wild-type gene | | | | 1083 |
| BBa_K091122 | | LacI_I12 protein | | | | 1083 |
| BBa_K143033 | | LacI (Lva⁻, N-terminal deletion) regulatory protein | | | | 1086 |
| BBa_K142000 | | lacI IS mutant (IPTG unresponsive) R197A | | | | 1128 |
| BBa_K142001 | | lacI IS mutant (IPTG unresponsive) R197F | | | | 1128 |
| BBa_K142002 | | lacI IS mutant (IPTG unresponsive) T276A | | | | 1128 |
| BBa_K142003 | | lacI IS mutant (IPTG unresponsive) T276F | | | | 1128 |
| BBa_K106666 | | Lac Repressor, AarI AB part | | | | 1104 |

TABLE 41-continued

Examples of Transcriptional Regulators

| Name | Protein | Description | Tag | Direction | Uniprot | Length |
|---|---|---|---|---|---|---|
| BBa_K106667 | | Lac Repressor, AarI BD part | | | | 1107 |
| BBa_K142004 | | lacI IS mutant (IPTG unresponsive) R197A T276A | | | | 1128 |
| BBa_K106668 | | Tet Repressor, AarI AB part | | | | 618 |
| BBa_K106669 | | Tet Repressor, AarI BD part | | | | 621 |
| BBa_K142005 | | lacI IS mutant (IPTG unresponsive) R197A T276F | | | | 1128 |
| BBa_K142006 | | lacI IS mutant (IPTG unresponsive) R197F T276A | | | | 1128 |
| BBa_K142007 | | lacI IS mutant (IPTG unresponsive) R197F T276F | | | | 1128 |
| BBa_K082004 | LacI | LacI-wild type | | | | 1083 |
| BBa_K082005 | LacI | LacI-Mutant | | | | 1083 |
| BBa_C0062 | LuxR | luxR repressor/activator, (no LVA?) | None | Forward | P12746 | 756 |
| BBa_C0071 | rhlR-LVA | rhlR repressor/activator from *P. aeruginosa* PA3477 (+LVA) | LVA | Forward | P54292 | 762 |
| BBa_C0080 | araC | araC arabinose operon regulatory protein (repressor/activator) from *E. coli* (+LVA) | LVA | Forward | P0A9E0 | 915 |
| BBa_C0171 | rhlR | rhlR repressor/activator from *P. aeruginosa* PA3477 (no LVA) | None | Forward | P54292 | 729 |
| BBa_K108021 | | Fis | | | | 297 |

Selection Markers

In various embodiments of the aspects described herein, nucleic acid sequences encoding selection markers are used as output product sequences. "Selection markers," as defined herein, refer to output products that confer a selective advantage or disadvantage to a biological unit, such as a cell or cellular system. For example, a common type of prokaryotic selection marker is one that confers resistance to a particular antibiotic. Thus, cells that carry the selection marker can grow in media despite the presence of antibiotic. For example, most plasmids contain antibiotic selection markers so that it is ensured that the plasmid is maintained during cell replication and division, as cells that lose a copy of the plasmid will soon either die or fail to grow in media supplemented with antibiotic. A second common type of selection marker, often termed a positive selection marker, includes those selection markers that are toxic to the cell. Positive selection markers are frequently used during cloning to select against cells transformed with the cloning vector and ensure that only cells transformed with a plasmid containing the insert. Examples of selection markers for use as output products are provided in Table 42.

TABLE 42

Examples of Selection Markers

| Name | Protein | Description | Tag | Direction | UniProt | KEGG | Length |
|---|---|---|---|---|---|---|---|
| BBa_T9150 | PyrF | orotidine 5 | None | Forward | P08244 | eco:b1281; | 741 |
| BBa_J31002 | AadA-bkw | kanamycin resistance backwards (KanB) [cf. BBa_J23012 & BBa_J31003] | | | P0AG05 | none | 816 |
| BBa_J31003 | AadA2 | kanamycin resistance forward (KanF) [cf. BBa_J23012 & BBa_J31002] | | | P0AG05 | none | 816 |
| BBa_J31004 | CAT-bkw | chloramphenicol acetyltransferase (backwards, CmB) [cf. BBa_J31005] | | | P62577 | none | 660 |
| BBa_J31006 | TetA(C)-bkw | tetracycline resistance protein TetA(C) (backwards) [cf. BBa_J31007] | | | P02981 | | 1191 |
| BBa_J31005 | CAT | chloramphenicol acetyltransferase (forwards, CmF) [cf. BBa_J31004] | | | P62577 | none | 660 |
| BBa_J31007 | TetA(C) | tetracycline resistance protein TetA(C) (forward), [cf. BBa_J31006] | | | P02981 | | 1191 |
| BBa_K145151 | | ccdB coding region | | | | | 306 |
| BBa_K143031 | | Aad9 Spectinomycin Resistance Gene | | | | | 771 |
| BBa_K156011 | | aadA (streptomycin 3'-adenyltransferase) | | | | | 789 |

Enzyme Outputs

An output sequence can encode an enzyme for use in different embodiments of the low- and high-input modules and biological classifier circuits described herein. In some embodiments, an enzyme output is used as a response to a particular set of inputs. For example, in response to a particular number of inputs received by one or more biological classifier circuits described herein, a biological classifier circuit can encode as an output product an enzyme that can degrade or otherwise destroy specific products produced by the cell.

In some embodiments, output product sequences encode "biosynthetic enzymes" that catalyze the conversion of substrates to products. For example, such biosynthetic enzymes can be combined together along with or within the modules and biological classifier circuits described herein to construct pathways that produce or degrade useful chemicals and materials, in response to specific signals. These combinations of enzymes can reconstitute either natural or synthetic biosynthetic pathways. These enzymes have applications in specialty chemicals, biofuels, and bioremediation. Descriptions of enzymes useful for the modules and biological classifier circuits described herein are described herein.

N-Acyl Homoserine lactones (AHLs or N-AHLs) are a class of signaling molecules involved in bacterial quorum sensing. Several similar quorum sensing systems exists across different bacterial species; thus, there are several known enzymes that synthesize or degrade different AHL molecules that can be used for the modules and biological classifier circuits described herein.

only in functional groups but also in their basic carbon skeletons. Isoprenoids are synthesized from common prenyl diphosphate precursors through the action of terpene synthases and terpene-modifying enzymes such as cytochrome P450 monooxygenases. Plant terpenoids are used extensively for their aromatic qualities. They play a role in traditional herbal remedies and are under investigation for antibacterial, antineoplastic, and other pharmaceutical functions. Much effort has been directed toward their production in microbial hosts.

There are two primary pathways for making isoprenoids: the mevalonate pathway and the non-mevalonate pathway.

TABLE 44

Examples of Isoprenoids

| Name | Description | Length |
| --- | --- | --- |
| BBa_K118000 | dxs coding sequence encoding 1-deoxyxylulose-5-phosphate synthase | 1866 |
| BBa_K115050 | A-coA -> AA-coA | 1188 |
| BBa_K115056 | IPP -> OPP or DMAPP -> OPP | 552 |
| BBa_K115057 | OPP -> FPP | 903 |
| BBa_K118002 | crtB coding sequence encoding phytoene synthase | 933 |
| BBa_K118003 | crtI coding sequence encoding phytoene dehydrogenase | 1482 |
| BBa_K118008 | crtY coding sequence encoding lycopene B-cyclase | 1152 |

TABLE 43

Examples of AHLs

| Name | Protein | Description | Direction | Uniprot | KEGG | E.C. | Length |
| --- | --- | --- | --- | --- | --- | --- | --- |
| BBa_C0061 | luxI-LVA | autoinducer synthetase for AHL | Forward | P12747 | none | none | 618 |
| BBa_C0060 | aiiA-LVA | autoinducer inactivation enzyme from *Bacillus*; hydrolyzes acetyl homoserine lactone | Forward | Q1WNZ5 | none | 3.1.1.— | 789 |
| BBa_C0070 | rhlI-LVA | autoinducer synthetase for N-butyryl-HSL (BHL) and HHL | Forward | Q02QW5 | none | none | 642 |
| BBa_C0076 | cinI | autoinducer synthetase | Forward | Q1MDW1 | none | none | 702 |
| BBa_C0078 | lasI | autoinducer synthetase for PAI from *Pseudomonas aeruginosa* | Forward | P33883 | pae:PA1432 | none | 642 |
| BBa_C0161 | luxI | autoinducer synthetase for AHL (no LVA) | Forward | P12747 | none | none | 585 |
| BBa_C0170 | rhlI | autoinducer synthetase for N-butyryl-HSL (BHL) and HHL (no LVA) | Forward | Q02QW5 | none | none | 609 |
| BBa_C0178 | lasI | autoinducer synthetase for PAI from *Pseudomonas aeruginosa* (no LVA) | Forward | P33883 | pae:PA1432 | none | 609 |
| BBa_K091109 | | LuxS | | | | | 516 |
| BBa_C0060 | aiiA-LVA | autoinducer inactivation enzyme from *Bacillus*; hydrolyzes acetyl homoserine lactone | Forward | Q1WNZ5 | none | 3.1.1.— | 789 |
| BBa_C0160 | aiiA | autoinducer inactivation enzyme aiiA (no LVA) | Forward | Q1WNZ5 | none | 3.1.1.— | 756 |

Isoprenoids, also known as terpenoids, are a large and highly diverse class of natural organic chemicals with many functions in plant primary and secondary metabolism. Most are multicyclic structures that differ from one another not Odorants are volatile compounds that have an aroma detectable by the olfactory system. Odorant enzymes convert a substrate to an odorant product. Exemplary odorant enzymes are described in Table 45.

TABLE 45

Examples of Odorant Enzymes

| Name | Protein | Description | Uniprot | KEGG | E.C. | Length |
|---|---|---|---|---|---|---|
| BBa_J45001 | SAMT | SAM:salicylic acid carboxyl methyltransferase; converts salicylic acid to methyl salicylate (winter | Q8H6N2 | none | none | 1155 |
| BBa_J45002 | BAMT | SAM:benzoic acid carboxyl methyltransferase; converts benzoic acid to methyl benzoate (floral odor) | Q9FYZ9 | none | 2.1.1.— | 1098 |
| BBa_J45004 | BSMT1 | SAM:benzoic acid/salicylic acid carboxyl methyltransferase I; converts salicylic acid to methyl sali | Q84UB5 | none | none | 1074 |
| BBa_J45008 | BAT2 | branched-chain amino acid transaminase (BAT2); converts leucine to alpha-ketoisocaproate | P47176 | sce:YJR148W | 2.6.1.42 | 1134 |
| BBa_J45014 | ATF1-1148 mutant | alcohol acetyltransferase I; converts isoamyl alcohol to isoamyl acetate (banana odor) | P40353 | sce:YOR377W | 2.3.1.84 | 1581 |
| BBa_J45017 | PchA & PchB | isochorismate pyruvate-lyase and isochorismate synthase (pchBA); converts chorismate to salicylate | | | | 1736 |
| BBa_I742107 | | COMT | | | | 1101 |

The following are exemplary enzymes involved in the biosynthesis of plastic, specifically polyhydroxybutyrate.

TABLE 46

Examples of Plastic Biosynthesis Enzymes

| Name | Description | Length |
|---|---|---|
| BBa_K125504 | phaE BioPlastic polyhydroxybutyrate synthesis pathway (origin PCC6803 slr1829) | 996 |
| BBa_K125501 | phaA BioPlastic polyhydroxybutyrate synthesis pathway (origin PCC6803 slr1994) | 1233 |
| BBa_K125502 | phaB BioPlastic polyhydroxybutyrate synthesis pathway (origin PCC6803 slr1993) | 726 |
| BBa_K125503 | phaC BioPlastic polyhydroxybutyrate synthesis pathway (origin PCC6803 slr1830) | 1140 |
| BBa_K156012 | phaA (acetyl-CoA acetyltransferase) | 1182 |
| BBa_K156013 | phaB1 (acetyacetyl-CoA reductase) | 741 |
| BBa_K156014 | phaC1 (Poly(3-hydroxybutyrate) polymerase) | |

The following are exemplary enzymes involved in the biosynthesis of butanol and butanol metabolism.

TABLE 47

Examples of Butanol Biosynthesis Enzymes

| Name | Description | Length |
|---|---|---|
| BBa_I725011 | B-hydroxy butyryl coA dehydrogenase | 870 |
| BBa_I72512 | Enoyl-coa hydratase | 801 |
| BBa_I725013 | Butyryl CoA dehyrogenase | 1155 |
| BBa_I725014 | Butyraldehyde dehydrogenase | 2598 |
| BBa_I725015 | Butanol dehydrogenase | 1188 |

Bisphenol A is a toxin that has been shown to leech from certain types of plastic. Studies have shown this chemical to have detrimental effects in animal studies and is very likely to be harmful to humans as well. The following exemplary bisphenol A degradation protein coding sequences are from *Sphingomonas bisphenolicum* and can aid in the remediation of bisphenol A contamination.

TABLE 48

Examples of Bisphenol A Biosynthesis Enzymes

| Name | Description | Length |
|---|---|---|
| BBa_K123001 | BisdB | 1284 |
| BBa_K123000 | BisdA | 330 |

Other miscellaneous enzymes for use in the invention are provided in Table 49.

TABLE 49

Examples of Miscellaneous Biosynthetic Enzymes

| Name | Description | Direction | Uniprot | KEGG | E.C. | Length |
|---|---|---|---|---|---|---|
| BBa_K118022 | cex coding sequence encoding *Cellulomonas fimi* exoglucanase | | | | | 1461 |
| BBa_K118023 | cenA coding sequence encoding *Cellulomonas fimi* endoglucanase A | | | | | 1353 |
| BBa_K118028 | beta-glucosidase gene bglX (chu_2268) from *Cytophaga hutchinsonii* | | | | | 2280 |
| BBa_C0083 | aspartate ammonia-lyase | Forward | P0AC38 | eco:b4139 | 4.3.1.1 | 1518 |

TABLE 49-continued

Examples of Miscellaneous Biosynthetic Enzymes

| Name | Description | Direction | Uniprot | KEGG | E.C. | Length |
|---|---|---|---|---|---|---|
| BBa_I15008 | heme oxygenase (ho1) from Synechocystis | Forward | P72849 | syn:sll1184 | 1.14.99.3 | 726 |
| BBa_I15009 | phycocyanobilin:ferredoxin oxidoreductase (PcyA) from synechocystis | Forward | Q55891 | syn:slr0116 | 1.3.7.5 | 750 |
| BBa_T9150 | orotidine 5 | Forward | P08244 | eco:b1281; | 4.1.1.23 | 741 |
| BBa_I716153 | hemB | | | | | 975 |
| BBa_I716154 | hemC | | | | | 942 |
| BBa_I716155 | hemD | | | | | 741 |
| BBa_I716152 | hemA (from CFT703) | | | | | 1257 |
| BBa_I742141 | sam5 (coumarate hydroxylase) coding sequence | | | | | 1542 |
| BBa_I742142 | sam8 (tyrosine-ammonia lyase) coding sequence | | | | | 1536 |
| BBa_I723024 | PhzM | | | | | 1019 |
| BBa_I723025 | PhzS | | | | | 1210 |
| BBa_K137005 | pabA (from pABA synthesis) | | | | | 585 |
| BBa_K137006 | pabB (from pABA synthesis) | | | | | 1890 |
| BBa_K137009 | folB (dihydroneopterin aldolase) | | | | | 354 |
| BBa_K137011 | folKE (GTP Cyclohydrolase I + pyrophosphokinase) | | | | | 1053 |
| BBa_K137017 | Galactose Oxidase | | | | | 1926 |
| BBa_K118015 | glgC coding sequence encoding ADP-glucose pyrophosphorylase | | | | | 1299 |
| BBa_K118016 | glgC16 (glgC with G336D substitution) | | | | | 1299 |
| BBa_K123001 | BisdB | | | | | 1284 |
| BBa_K108018 | PhbAB | | | | | 1997 |
| BBa_K108026 | XylA | | | | | 1053 |
| BBa_K108027 | XylM | | | | | 1110 |
| BBa_K108028 | XylB | | | | | 1101 |
| BBa_K108029 | XylS | | | | | 966 |
| BBa_K147003 | ohbA | | | | | 531 |
| BBa_K123000 | BisdA | | | | | 330 |
| BBa_K284999 | Deletar este | | | | | 1431 |
| BBa_I716253 | HPI, katG | | | | | 2181 |
| BBa_K137000 | katE | | | | | 2265 |
| BBa_K137014 | katE + LAA | | | | | 2298 |
| BBa_K137067 | katG | | | | | 2184 |
| BBa_K078102 | dxnB | | | | | 886 |
| BBa_K078003 | one part of the initial dioxygenase of the dioxin degradation pathway | | | | | 1897 |

Other enzymes of use in the modules and biological classifier circuits described herein include enzymes that phosphorylate or dephosphorylate either small molecules or other proteins, and enzymes that methylate or demethylate other proteins or DNA.

TABLE 50

Examples of Phosphorylation and Methylation-Related Enzymes

| Name | Protein | Description | Direction | Uniprot | KEGG | E.C. | Length |
|---|---|---|---|---|---|---|---|
| BBa_C0082 | tar-envZ | Receptor, tar-envZ | Forward | | | | 1491 |
| BBa_J58104 | | Fusion protein Trg-EnvZ for signal transduction | | | | | 1485 |
| BBa_J58105 | | Synthetic periplasmic binding protein that docks a vanillin molecule | | | | | 891 |
| BBa_I752001 | | CheZ coding sequence (Chemotaxis protein) | | | | | 639 |
| BBa_K091002 | | LsrK gene | Forward | | | | 1593 |
| BBa_K147000 | | cheZ | | | | | 835 |
| BBa_K118015 | | glgC coding sequence encoding ADP-glucose pyrophosphorylase | | | | | 1299 |
| BBa_K118016 | | glgC16 (glgC with G336D substitution) | | | | | 1299 |
| BBa_K094100 | | cheZ gene | | | | | 695 |
| BBa_K136046 | | envZ* | | | | | 1353 |
| BBa_K283008 | chez | chez_Histag | | | | | 713 |

TABLE 50-continued

Examples of Phosphorylation and Methylation-Related Enzymes

| Name | Protein | Description | Direction | Uniprot | KEGG | E.C. | Length |
|---|---|---|---|---|---|---|---|
| BBa_C0024 | CheB | CheB chemotaxis coding sequence (protein glutamate methylesterase) | Forward | P07330 | JW1872 | 3.1.1.61 | 1053 |
| BBa_K108020 | | Dam | | | | | 837 |

Also useful as output products for the purposes described herein are receptors, ligands, and lytic proteins. Receptors tend to have three domains: an extracellular domain for binding ligands such as proteins, peptides or small molecules, a transmembrane domain, and an intracellular or cytoplasmic domain which frequently can participate in some sort of signal transduction event such as phosphorylation. In some embodiments, transporter, channel, or pump gene sequences are used as output product genes. Transporters are membrane proteins responsible for transport of substances across the cell membrane. Channels are made up of proteins that form transmembrane pores through which selected ions can diffuse. Pumps are membrane proteins that can move substances against their gradients in an energy-dependent process known as active transport. In some embodiments, nucleic acid sequences encoding proteins and protein domains whose primary purpose is to bind other proteins, ions, small molecules, and other ligands are used. Exemplary receptors, ligands, and lytic proteins are listed in Table 51.

TABLE 51

Examples of Receptors, Ligands, and Lytic Proteins

| Name | Protein | Description | Tag | Direction | UniProt | Length |
|---|---|---|---|---|---|---|
| BBa_J07009 | ToxR | toxicity-gene activator from *Vibrio cholerae* | None | Forward | P15795 | 630 |
| BBa_K133063 | | (TIR)TLR3 | | | | 453 |
| BBa_K133064 | | (TIR)TLR9 | | | | 585 |
| BBa_K133065 | | (TMTIR)TLR3 | | | | 600 |
| BBa_K133069 | | (TMTIR)TLR3stop | | | | 603 |
| BBa_K133067 | | (TMTIR)TLR4 | | | | 621 |
| BBa_K133060 | | (TMTIR)TLR9 | | | | 645 |
| BBa_K209400 | | AarI B-C part, hM4D | | | | 1434 |
| BBa_K209401 | | AarI B-C part, Rs1.3 | | | | 1407 |
| BBa_I712002 | | CCR5 | | | | 1059 |
| BBa_I712003 | | CCR5-NUb | | | | 1194 |
| BBa_I712010 | | CD4 sequence without signal peptide | | | | 1299 |
| BBa_I712017 | | Chemokine (CXC motif) receptor 4, fused to N-terminal half of ubiquitin. | | | | 1191 |
| BBa_I15010 | Cph8 | cph8 (Cph1/EnvZ fusion) | None | Forward | | 2238 |
| BBa_I728500 | | CPX Terminal Surface Display Protein with Polystyrene-Binding Peptide | | | | 654 |
| BBa_J52035 | | dnMyD88 | | | | 420 |
| BBa_K259000 | | fhuA - Outer membrane transporter for ferrichrome-iron | | | | 2247 |
| BBa_K259001 | | fiu B Outer Membrane Ferric Iron Transporter | | | | 2247 |
| BBa_J58104 | | Fusion protein Trg-EnvZ for signal transduction | | | | 1485 |
| BBa_K137112 | | lamB | | | | 1339 |
| BBa_C0082 | tar-envZ | Receptor, tar-envZ | LVA | Forward | | 1491 |
| BBa_J58105 | | Synthetic periplasmic binding protein that docks a vanillin molecule | | | | 891 |
| BBa_I712012 | | TIR domain of TLR3 | | | | 456 |
| BBa_K143037 | | YtvA Blue Light Receptor for *B. subtilis* | | | | 789 |
| BBa_J07006 | | malE | | | | 1191 |
| BBa_J07017 | | FecA protein | | | | 2325 |
| BBa_K141000 | UCP1 | Ucp1 | | | | 924 |
| BBa_K141002 | | Ucp 175 deleted | | | | 921 |
| BBa_K141003 | | Ucp 76 deleted | | | | 921 |
| BBa_K190028 | | GlpF | | | | 846 |
| BBa_I746200 | | FepA L8T Mutant - Large Diffusion pore for *E. coli* outer membrane. | | | | 2208 |
| BBa_I765002 | | ExbB membrane spanning protein in TonB-ExbB-ExbD complex [*Escherichia coli* K12] | | | | 735 |
| BBa_I765003 | | TonB ferric siderophore transport system, periplasmic binding protein TonB [*Pseudomonas entomophila* | | | | 735 |
| BBa_K090000 | | Glutamate gated K+ channel | | | | 1194 |
| BBa_K284000 | | Lactate Permease from *Kluyveromyces lactis* | | | | 1873 |
| BBa_K284997 | | Deletar este | | | | 1069 |

TABLE 51-continued

Examples of Receptors, Ligands, and Lytic Proteins

| Name | Protein | Description | Tag | Direction | UniProt | Length |
|---|---|---|---|---|---|---|
| BBa_J22101 | | Lac Y gene | | | | 1288 |
| BBa_K079015 | | LacY transporter protein from E. coli | | | | 1254 |
| BBa_K119003 | | RcnA (YohM) | | | | 833 |
| BBa_K137001 | | LacY | | | | 1254 |
| BBa_I712024 | | CD4 | | | | 1374 |
| BBa_K133061 | | CD4 ecto | | | | 1113 |
| BBa_K136046 | | envZ* | | | | 1353 |
| BBa_K157002 | | Transmembrane region of the EGF-Receptor (ErbB-1) | | | | 87 |
| BBa_K227006 | | puc BA coding region of R. sphaeroides | | forward | | 336 |
| BBa_M12067 | | E1 | | | | 264 |
| BBa_I721002 | | Lead Binding Protein | | | | 399 |
| BBa_K126000 | | TE33 Fab L chain | | | | 648 |
| BBa_K133070 | | gyrEC | | | | 660 |
| BBa_K133062 | | gyrHP | | | | 660 |
| BBa_K157003 | | Anti-NIP singlechain Fv-Fragment | | | | 753 |
| BBa_K211001 | | RI7 | | | | 987 |
| BBa_K211002 | | RI7-odr10 chimeric GPCR | | | | 1062 |
| BBa_K103004 | | protein $Z_{SPA-1}$ | | | | 190 |
| BBa_K128003 | | p1025 | | | | 101 |
| BBa_K133059 | | RGD | | | | 9 |
| BBa_K283010 | | Streptavidin | | | | 387 |
| BBa_K103004 | | protein $Z_{SPA-1}$ | | | | 190 |
| BBa_K128003 | | p1025 | | | | 101 |
| BBa_K133059 | | RGD | | | | 9 |
| BBa_K283010 | | Streptavidin | | | | 387 |
| BBa_K112000 | Holin | T4 holin, complete CDS, berkeley standard | | | | 657 |
| BBa_K112002 | Holin | T4 holin, without stop codon, berkeley standard | | | | 654 |
| BBa_K112004 | | a~T4 holin in BBb | | | | 661 |
| BBa_K112006 | | T4 antiholin in BBb | | | | 294 |
| BBa_K112009 | | in BBb | | | | 288 |
| BBa_K112010 | | a~T4 antiholin in BBb | | | | 298 |
| BBa_K112012 | | T4 lysozyme in BBb | | | | 495 |
| BBa_K112015 | | in BBb | | | | 489 |
| BBa_K112016 | | a~T4 lysozyme in BBb | | | | 499 |
| BBa_K117000 | | Lysis gene (promotes lysis in colicin-producing bacteria strain) | | | | 144 |
| BBa_K124014 | | Bacteriophage Holin Gene pS105 | | | | 317 |
| BBa_K108001 | | SRRz | | | | 1242 |
| BBa_K112300 | | {lambda lysozyme} in BBb format | | | | 477 |
| BBa_K112304 | | {a~lambda lysozyme} in BBb format | | | | 481 |
| BBa_K112306 | | {lambda holin} in BBb format | | | | 318 |
| BBa_K112310 | | {a~lambda holin}; adheres to Berkeley standard | | | | 322 |
| BBa_K112312 | | {lambda antiholin}; adheres to Berkeley standard | | | | 324 |
| BBa_K112316 | | {a~lambda antiholin}; adheres to Berkeley standard | | | | 328 |
| BBa_K124017 | | Bacteriophage Lysis Cassette S105, R, and Rz | | | | 1257 |
| BBa_K112806 | | [T4 endolysin] | | | | 514 |
| BBa_K284001 | | Lysozyme from Gallus gallus | | | | 539 |

Uses of Biological Classifier Circuits

The high-input detector modules and biological classifier circuits described herein are useful for identifying and classifying and discriminating between complex phenotypes in cellular systems, such as prokaryotic, eukaryotic (animal or plant), or synthetic cells, as well as in non-cellular systems, including test tubes, viruses and phages. The novel biological classifier circuits described herein can be used to elicit targeted responses in cellular and non-cellular systems, such as the ability to discriminate, identify, mark, target, and/or destroy cells expressing specific complex phenotypes, by identifying and responding to specific input profiles. The biological classifier circuits described herein and cells (e.g., transiently modified cells, transfected cells, or permanently modified cells) containing such circuits have a wide variety of applications, including ones in which the cells are used outside of an organism (ex vivo or in vitro), and ones in which the cells are used within an organism (in vivo), e.g., in a patient. Exemplary applications in which compositions comprising the biological classifier circuits and high- and low-input modules, as well as cells comprising such circuits and modules, can be used are detailed herein and in the following Examples.

In some aspects described herein, a high-input detector module or a biological classifier circuit is provided for use in a cellular system, such as a heterogenous population of mammalian cells, to identify a specific cell type endogenously expressing a distinct microRNA expression profile or pattern, where the microRNA expression profile or pattern is based on the expression or lack of expression of a combination of at least two microRNAs.

In one aspect, a method is provided for identifying a specific cell type based on the expression pattern of at least two unique, endogenous microRNAs. In one embodiment, the method is based on the expression pattern of at least three unique, endogenous microRNAs. In one embodiment, the method is based on the expression pattern of at least four unique, endogenous microRNAs. In one embodiment, the method is based on the expression pattern of at least five unique, endogenous microRNAs. In one embodiment, the method is based on the expression pattern of at least six unique, endogenous microRNAs. In one embodiment, the method is based on the expression pattern of at least seven unique, endogenous microRNAs. In one embodiment, the method is based on the expression pattern of at least eight unique, endogenous microRNAs. In one embodiment, the method is based on the expression pattern of at least nine unique, endogenous microRNAs. In one embodiment, the method is based on the expression pattern of at least ten unique, endogenous microRNAs. In one embodiment, the method is based on the expression pattern of at least eleven unique, endogenous microRNAs. In one embodiment, the method is based on the expression pattern of at least twelve unique, endogenous microRNAs. In one embodiment, the method is based on the expression pattern of at least thirteen unique, endogenous microRNAs. In one embodiment, the method is based on the expression pattern of at least fourteen unique, endogenous microRNAs. In one embodiment, the method is based on the expression pattern of at least fifteen unique, endogenous microRNAs. In one embodiment, the method is based on the expression pattern of at least sixteen unique, endogenous microRNAs. In one embodiment, the method is based on the expression pattern of at least seventeen unique, endogenous microRNAs. In one embodiment, the method is based on the expression pattern of at least eighteen unique, endogenous microRNAs. In one embodiment, the method is based on the expression pattern of at least nineteen unique, endogenous microRNAs. In one embodiment, the method is based on the expression pattern of at least twenty unique, endogenous microRNAs. In some embodiments, the method is based on the expression pattern of at least 20-25, at least 25-30, at least 30-35, at least 35-40, at least 4-45, at least 45-50, at least 50-55, at least 55-60, at least 60-65, at least 65-70, at least 70-75 unique, endogenous microRNAs. Accordingly, in some embodiments of the aspects described herein, a method is provided for identifying a specific cell type based on the expression pattern of at least 2, 3, 4, 5, 6, 7, 8, 9, 10 . . . 13 . . . 17 . . . 23 . . . 32 . . . 41 . . . 55 . . . 69 . . . 75 or more endogenous microRNAs in a cellular or non-cellular system. Such methods comprise introducing a biological classifier circuit comprising at least one low-input and at least one high-input detector modules, or only low-input modules, or only high-input modules, that can detect a specific microRNA profile, into a cellular or non-cellular system for use in identifying an endogenous microRNA expression pattern. In such embodiments, the endogenous microRNA is a mature microRNA, as is understood by one of skill in the art, and as described herein.

The high-input detector modules and biological classifier circuits described herein can be used for a variety of applications and in many different types of methods, including, but not limited to, diagnostics and therapeutic applications, drug screening, genetic manipulations, developmental studies, and pharamcokinetics. For example, in some embodiments, a biological classifier circuit comprises an output product involved in the cell cycle for use in a cellular system. In such embodiments, the output product can be a protein, toxin, or other agent that causes cell death, such that those cells within the cellular system that express the specific microRNA profile the classifier circuit is designed to detect are killed or undergo apoptosis. Such embodiments where a high-input detector module or a biological classifier circuit is coupled to the cell cycle can be useful in diagnostic or therapeutic applications, such as in therapies for cancer or other proliferative disorders.

Diagnostic and Therapeutic Applications

In some aspects, the high-input detector modules and biological classifier circuits described herein can be used in a number of diagnostic and therapeutic applications and methods. For example, in some aspects, the biological classifier circuits can be used in a method for detecting specific microRNA profiles associated with disorders such as, but not limited to, cancer, immunological disorders (e.g., autoimmune diseases), neuronal disorders, cardiovascular disorders, metabolic disorders, or infections. One advantage of the biological classifier circuits described herein in such applications is the ability to identify and target individual cells with precision based on internal molecular cues. In other aspects, the biological classifier circuits can be used in a method for detectingor identifying cells within a heterogenous population, such as identifying cells having cancerous potential, such as teratoma cells, in a population of stem cells, such as induced pluripotent stem cells.

In some embodiments of the aspects described herein, high-input detector modules or biological classifier circuits are introduced into individual cells as a diagnostic molecular probe to identify a specific cell population, in applications such as disease detection or surgical guidance. Upon detecting a particular microRNA expression profile, the high-input detector modules or biological classifier circuits produce a detectable output, such as a reporter, that can be used to discriminate, and select or isolate those cells having the particular microRNA expression profile. In such embodiments, a high-input detector module or biological classifier circuit is being used as a means of labeling or identifying cells. For example, a biological classifier circuit that is specific (i.e., expresses an output product) for a microRNA profile characteristic of a particular cancer type can be introduced into one or more cells from a biopsy from a subject. In such embodiments, the output product can be a fluorescent protein or a enzyme capable of performing a detectable reaction (e.g., β-galactosidase, alkaline phosphatase, or horseradish peroxidase). Thus, all cells expressing the cancer-specific microRNA profile will be differentiated from the non-cancer cells, and aid in early diagnosis modalities. Such detectable outputs can also be useful in treatment of the cancer, by, for example, aiding in precise surgical removal of the cancer or targeted chemotherapy.

In other embodiments of the aspects described herein, the high-input detector modules and biological classifier circuits can be used to identify specific cell populations for isolation, such as different immune cell types, or cells at different stages of differentiation. For example, upon introduction of biological classifier circuits into a cell population, those cells within the population that express a particular microRNA profile can be isolated away from non-labeled cells based on expression of a particular output product by the circuit. In some embodiments, such an output product can be a fluorescent molecule, to allow isolation of the cell using fluorescent cell sorting. In other embodiments, the output product is a cell-surface receptor normally not expressed by any cells in that population which can be used for isolating the cells, using, for example, a antibody specific to that marker. In further embodiments, a therapy can then be applied in a separate step that will target only the labeled or isolated cells. Alternatively, if such labeling is done in vivo or ex vivo, a sample comprising the labeled cells or tissues can be imaged in order to determine the localization of the "labeled" cells; e.g., to guide surgery or radiation therapy.

In some embodiments, the high-input detector modules and biological classifier circuits described herein can be used to identify and select for cells at various stages of differentiation, such as within a stem cell population. For example, a biological classifier circuit can be introduced into a stem cell and produce one or more outputs indicative of different stages of differentiation, in response to a specific microRNA profile indicative of a specific differentiation state.

Tumorigenicity is a safety concern associated with the ultimate in vivo use of stem cell therapies involving human embryonic stem cells or induced pluripotent stem cells, as undifferentiated stem cells have the potential to form teratomas and have tumorigenic potential. It is important to ensure that when stem cells are differentiated into a desired cell type, no undifferentiated or improperly differentiated cells remain either in vivo, if the differentiation is induced in vivo, or in the cell population prior to stem cell therapy and transplantation. Hence, in some embodiments of the aspects described herein, a biological classifier circuit that is specific for a microRNA profile characteristic of a stem cell is introduced into a population of cells, such as a population of cells differentiated from a stem cell population, such as an induced pluripotent stem cell population, to identify the cells having the microRNA profile characteristic or indicative or a stem cell within the heterogenous population of cells (Suhet et al. "Human embryonic stem cells express a unique set of microRNAs." Dev. Biol. 2004, 270: 488-498, and Landgrafet et al. "A mammalian microRNA expression Atlas based on small RNA Library Sequencing." Cell. 2007, 129:1401-1414).

In some further embodiments of these aspects and embodiments, the high-input detector modules or biological classifier circuits described herein can further comprise a constitutive promoter operably linked to a sequence that encodes a protein providing resistance to a selection marker, for example, an antibiotic resistance gene. Accordingly, an output product encoded by such a high-input detector module or biological classifier circuit can comprise a protein or molecule that inihibts or targets the protein providing resistance to the selection marker. In such embodiments, any cell not transfected with the high-input detector module or classifier circuit will be killed or die due to lack of the appropriate resistance product. Further, those transfected cells expressing the microRNA expression profile the biological classifier circuit is specific for will be killed or die due to expression of the output product and inhibition of the transfected resistance molecule.

In some aspects, an in vivo cell or tissue system comprising the high-input detector modules or biological classifier circuits described herein can be administered to a subject. In some embodiments of these aspects, such a method can comprise the following steps: 1) identifying a tissue or cell type of interest and providing a molecular microRNA signature as an indicator for the cell or tissue type; 2) constructing a biological classifier circuit that detects this specific signature; and 3) administering the components of the biological classifier circuit into a subject. In some embodiments, the administration involves transient delivery, or stable incorporation into the subject's genome.

In further embodiments of such aspects, the cell or tissue system comprising the high-input detector modules and biological classifier circuits described herein can be used as a direct therapeutic modality, or as a combination diagnosticic-therapeutic modality for a variety of disorders in which discrimination between different cells type is important, for e.g., cancer or other proliferative disorders, metabolic disorders, neurological disorders, immunological disorders, or infections, such as viral, bacterial, or parasitic infections. Such methods includes the step of delivering to at least one cell in a subject in need thereof any of the biological classifier circuits described herein, wherein one or more outputs is a therapeutic useful in treating, or ameliorating one or more symptoms of the subject in need thereof.

In another aspect, methods of treatment using the high-input detector modules and biological classifier circuits described herein are provides, the methods comprising administering to a mammal in need thereof one or more vectors comprising one or more nucleic acid sequences encoding one or more low-input detector modules or high-input detector modules of any of the biological classifier circuits described herein. In some embodiments of these aspects, a biological classifier circuit, upon detecting the appropriate microRNA profile, triggers the release of a therapeutic agent as the output, such as a protein, an siRNA, an shRNA, a miRNA, a small molecule, or any of the outputs described herein. For example, a protein output can be a reporter such as luciferase, luciferin, green fluorescence protein (GFP), red fluorescence protein (RFP), DsRed, ZsYellow, or an enzyme (e.g., beta-galactosidase, horseradish peroxidase, alkaline phosphatase, or chloramphenicol acetyl transferase (CAT). The output protein can be a selectable marker (e.g., a chemical resistance gene) such as aminoglycoside phosphotransferase (APT) or multidrug resistance protein (MDR). The output protein can also be a pharmaceutical agent (that is an agent with therapeutic ability) or a moiety that triggers the availability of a pharmaceutical agent. The pharmaceutical agent can be, e.g., a small molecule, a protein, or an siRNA (or shRNA).

In such embodiments, the high-input detector modules and biological classifier circuits can be used for local or systemic delivery of one or more therapeutic agents. For example, a biological classifier circuit can be introduced (transfected) into cells. Systemic delivery of one or more therapeutic agents by a classifier circuit can involve, e.g., introducing the circuit into cells, e.g., healthy and/or diseased cells, wherein production and systemic release of one or more therapeutic agents by the classifier circuit is triggered by detection of the appropriate microRNA profile.

For example, a biological classifier circuit can be delivered to a cancer cell, or a heterogenous population of cells comprising cancer cells, wherein the circuit comprises one or more low- and high-input detector modules that can detect and respond to a specific microRNA expression signature or profile characteristic of the cancer cells. Such biological classifier circuits can be designed so that one or more output products of the classifier circuits can modulate a cellular pathway or activity of the cell. For example, the alteration in cellular activity can cause or alter apoptotic cell death, replication (e.g., DNA or cellular replication), cell differentiation, or cell migration. For example, apoptosis can be the result of the expression of a classifier circuit output such as a death receptor (e.g., FasR or TNFR), death receptor ligand (e.g., FasL or TNF), a caspase (e.g., caspase 3 or caspase 9), cytochrome-c, a BH3-containing proapoptotic protein (e.g., BAX, BAD, BID, or BIM), or apoptosis inducing factor (AIF)). Growth arrest can be the result of a circuit output such as p21, p19ARF, p53, or RB protein. Additional non-limiting example of outputs for use with the circuits have been described herein and in the Examples section.

Figure 4:
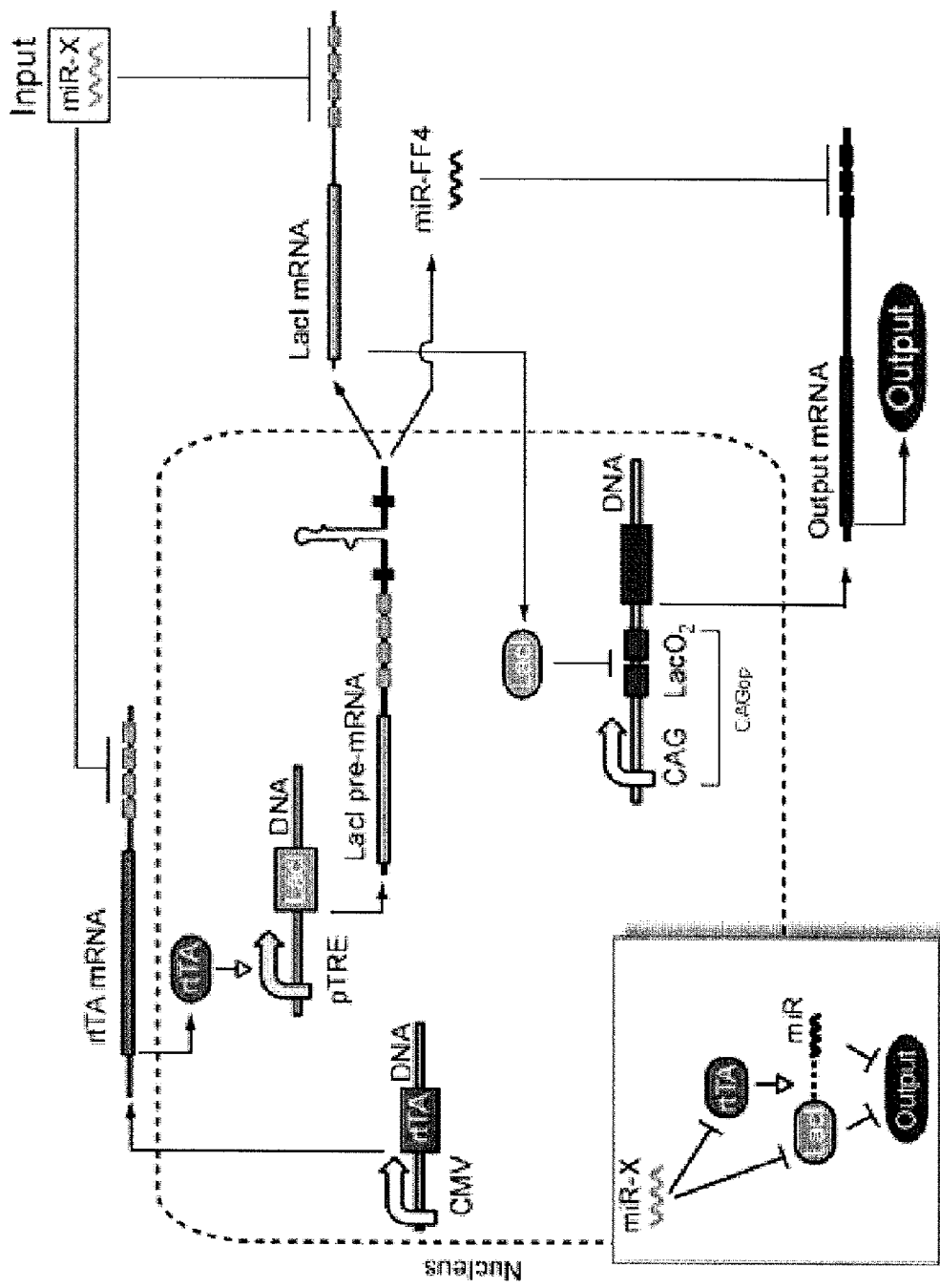
FIG. 4 depicts an optimized sensor configuration for HeLa-high markers. Detailed implementation showing individual DNA and RNA species and a mechanism of operation are shown. The inset depicts a simplified network diagram of a sensing process.

For example, as shown in FIGS. 4, 5, and 6 using HeLa cells as a target cancer cell type, in some embodiments, a biological classifier circuit can be constructed comprising low-input and high-input modules that detects the expression of a total of six distinct microRNAs, wherein 3 microRNAs (expressed at high levels) are detected using two high-input modules, and 3 microRNAs (expressed at low levels) are detected using one low-input module.

In such an embodiment, the biological classifier circuit can further comprise a constitutive promoter driving a reporter protein, such as AmCyan, so that all transfected cells can be identified. In such an embodiment, each high-input module can further comprise a constitutive promoter operably linked to a sequence encoding a transcriptional activator, such as rtTA, and a microRNA target sequence for one of the high microRNAs, wherein the transcriptional activator and another agent, such as doxycycline, induces transcription from the inducible promoter, driving expression of the repressor protein, such as LacI. In such an embodiment, the sequence encoding the repressor high-input module can further comprise an intronic microRNA sequence, such as miR-FF4, that targets a microRNA target sequence in the sequence encoding the output product in the low-input detector module. The additional microRNA target sequence in the output product sequence acts as an additional means to prevent output product leakiness of the biological classifier circuit, by adding a post-transcriptional repression mechanism, in addition to the transcriptional repression mediated by LacI.

In such an embodiment, if a biological classifier circuit does not detect the presence of the three low-input microRNAs, and detects sufficient levels of the three high-input microRNAs, then expression of both the transcriptional activator and the repressor is inhibited, and the repression on the output product is removed, such that an output product is expressed. In such an embodiment, the output product of the biological classifier circuit can comprise a pro-apoptotic gene, such as hBax, such that any cell, such as HeLa cell, expressing the biological classifier circuit undergoes apoptosis.

In such an embodiment, an additional layer of regulation can be added to prevent leakiness of the output product (e.g., hBax), by further engineering the circuit to add a sequence encoding a functional inhibitor of the output product to the sequence encoding the repressor protein and microRNA target sequences in each high-input module. In the example described herein, Bcl2 was used to further minimize leakiness of hBax expression.

In another example, a biological classifier circuit that detects a specific microRNA profile characteristic of a pro-inflammatory response can be introduced into a anatomical site having, suspected of having, or at risk of developing, a pro-inflammatory response (e.g., a joint affected by rheumatoid arthritis). Such circuits could produce anti-inflammatory cytokine outputs (e.g., IL-4, IL-6, IL-10, IL-11, or IL-13).

In some embodiments of the aspects described herein, the high-input detector modules and the biological classifier circuits can trigger the production of one or more siRNA (or shRNA) therapeutic agents. For example, where a cell having a specific microRNA expression profile expresses an aberrant form of a protein, the biological classifier circuit can trigger the production of one or more siRNAs specific for the mRNA encoding the aberrant protein, thereby ablating its translation. In another example, where a cell is infected with a virus, a biological classifier circuit that detects a unique microRNA profile characteristic of a virally infects cell can have as an output product an RNA molecule, such as an siRNA (or shRNA), that interferes with viral viability or propagation within the host cell.

In other embodiments, the high-input detector modules and biological classifier circuits described herein can be used therapeutically to promote, e.g., tissue regeneration, localized production of a secreted protein, and certain types of immune-like responses.

For the clinical use of the methods described herein, administration of the biological classifier circuits or component input detector modules thereof, or vectors comprising nucleic acid sequences encoding the biological classifier circuits or component input detector modules thereof, can include formulation into pharmaceutical compositions or pharmaceutical formulations for parenteral administration, e.g., intravenous; mucosal, e.g., intranasal; ocular, or other mode of administration. In some embodiments, the biological classifier circuits or component input detector modules thereof, or vectors comprising nucleic acid sequences encoding the biological classifier circuits or component input detector modules thereof described herein can be administered along with any pharmaceutically acceptable carrier compound, material, or composition which results in an effective treatment in the subject. Thus, a pharmaceutical formulation for use in the methods described herein can comprise a biological classifier circuit or component input detector module thereof, or one or more vectors comprising nucleic acid sequences encoding the biological classifier circuit or component input detector module thereof as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, a biological classifier circuit or component input detector module thereof, or vectors comprising nucleic acid sequences encoding the biological classifier circuits or component input detector modules thereof. Each carrier must be "acceptable" in the sense of being compatible with the other ingredients of the formulation and not injurious to the patient. The terms "excipient", "carrier", "pharmaceutically acceptable carrier" or the like are used interchangeably herein.

The biological classifier circuits or component input detector modules thereof, or vectors comprising nucleic acid sequences encoding the biological classifier circuits or component input detector modules thereof, described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, biological classifier circuits or component input detector modules thereof, can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

Therapeutic formulations of the biological classifier circuits or component input detector modules thereof, or vectors comprising nucleic acid sequences encoding the biological classifier circuits or component input detector modules thereof described herein can be prepared for storage by mixing a biological classifier circuit or component input detector modules thereof, or vectors comprising nucleic acid sequences encoding the biological classifier circuit or component input detector modules thereof, having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary lyophilized anti-VEGF antibody formulations are described in WO 97/04801, expressly incorporated herein be reference.

Optionally, but preferably, the formulations comprising the compositions described herein contain a pharmaceutically acceptable salt, typically, e.g., sodium chloride, and preferably at about physiological concentrations. Optionally, the formulations described herein can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations described herein can include a pharmaceutically acceptable surfactant at a concentration of 0.005 to 0.02%.

Drug Screening and Pharmacokinetics

In some aspects, the high-input detector modules and biological classifier circuits described herein can be used to report on or classify the physiological state of a cell in drug screening experiments. For example, one or more biological classifier circuits specific for different molecular signatures indicative of specific cell states, such as a microRNA expression profile, can be stably introduced into cells. Such cells can then be tested with various drug and drug combinations to identify those cells in which the specific profile the circuit is designed to detect is altered or modified. In some such embodiments, multiple biological classifier circuits can be introduced in parallel, in order to interrogate multiple pathways simultaneously.

In other embodiments, the biological classifier circuits described herein can be used to monitor the pharmacokinetics of a compound, such as a small molecule compound or a therapeutic protein (e.g., an antibody, a growth factor, chemokine, or cytokine). Such biological classifier circuits could be useful for determining (i) the permeability of a compound (e.g., permeability of a compound through a cell membrane) or (ii) the stability (half-life or clearance) of a compound in a cell. The cell can also be introduced into an animal model (e.g., a rodent model, a canine model, or a non-human primate model), e.g., to test for the half-life of clearance of a compound from the blood of the animal.

Kits

One or more biological classifier circuits or component modules described herein can be provided as a kit, e.g., a package that includes one or more containers. In one example, each component, or genetic material encoding it, can be provided in a different container. In another example, two or more components are combined in a container. Such kits are useful for any of the diagnostic, therapeutic, or protein production modalities described herein.

For example, biological classifier circuits or detector modular components thereof can be provided as a functional part of a kit to identify individual cells with certain complex molecular signatures/phenotypes.

DEFINITIONS

The methods and uses of the biological classifier circuits described herein can involve in vivo, ex vivo, or in vitro systems. The term "in vivo" refers to assays or processes that occur in or within an organism, such as a multicellular animal. In some of the aspects described herein, a method or use can be said to occur "in vivo" when a unicellular organism, such as a bacteria, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing a biological classifier circuit in a non-cellular system, such as a media not comprising cells or cellular systems, such as cellular extracts.

A cell for use with the biological classifier circuits described herein can be any cell or host cell. As defined herein, a "cell" or "cellular system" is the basic structural and functional unit of all known independently living organisms. It is the smallest unit of life that is classified as a living thing, and is often called the building block of life. Some organisms, such as most bacteria, are unicellular (consist of a single cell). Other organisms, such as humans, are multicellular. A "natural cell," as defined herein, refers to any prokaryotic or eukaryotic cell found naturally. A "prokaryotic cell" can comprise a cell envelope and a cytoplasmic region that contains the cell genome (DNA) and ribosomes and various sorts of inclusions.

In some embodiments, the cell is a eukaryotic cell, preferably a mammalian cell. A eukaryotic cell comprises membrane-bound compartments in which specific metabolic activities take place, such as a nucleus. In other embodiments, the cell or cellular system is an artificial or synthetic cell. As defined herein, an "artificial cell" or a "synthetic cell" is a minimal cell formed from artificial parts that can do many things a natural cell can do, such as transcribe and translate proteins and generate ATP.

Cells of use in the various aspects described herein upon transformation or transfection with the biological classifier circuits described herein include any cell that is capable of supporting the activation and expression of the biological classifier circuits. In some embodiments of the aspects described herein, a cell can be from any organism or multi-cell organism. Examples of eukaryotic cells that can be useful in aspects described herein include eukaryotic cells selected from, e.g., mammalian, insect, yeast, or plant cells. The molecular circuits described herein can be introduced into a variety of cells including, e.g., fungal, plant, or animal (nematode, insect, plant, bird, reptile, or mammal (e.g., a mouse, rat, rabbit, hamster, gerbil, dog, cat, goat, pig, cow, horse, whale, monkey, or human)). The cells can be primary cells, immortalized cells, stem cells, or transformed cells. In some preferred embodiments, the cells comprise stem cells. Expression vectors for the components of the biological classifier circuit will generally have a promoter and/or an enhancer suitable for expression in a particular host cell of interest. The present invention contemplates the use of any such vertebrate cells for the biological classifier circuits, including, but not limited to, reproductive cells including sperm, ova and embryonic cells, and non-reproductive cells, such as kidney, lung, spleen, lymphoid, cardiac, gastric, intestinal, pancreatic, muscle, bone, neural, brain, and epithelial cells.

As used herein, the term "stem cells" is used in a broad sense and includes traditional stem cells, progenitor cells, preprogenitor cells, reserve cells, and the like. The term "stem cell" or "progenitor cell" are used interchangeably herein, and refer to an undifferentiated cell which is capable of proliferation and giving rise to more progenitor cells having the ability to generate a large number of mother cells that can in turn give rise to differentiated, or differentiable daughter cells. Stem cells for use with the biological classifier circuits and the methods described herein can be obtained from endogenous sources such as cord blood, or can be generated using in vitro or ex vivo techniques as known to one of skill in the art. For example, a stem cell can be an induced pluripotent stem cell (iPS cell). The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell can derive from a multipotent cell which itself is derived from a multipotent cell, and so on. While each of these multipotent cells can be considered stem cells, the range of cell types each can give rise to can vary considerably. Some differentiated cells also have the capacity to give rise to cells of greater developmental potential. Such capacity can be natural or can be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation".

Exemplary stem cells include, but are not limited to, embryonic stem cells, adult stem cells, pluripotent stem cells, induced pluripotent stem cells (iPS cells), neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including method for isolating and culturing them, can be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96(25):14482 86, 1999; Zuk et al., Tissue Engineering, 7:211 228, 2001 ("Zuk et al."); Atala et al., particularly Chapters 33 41; and U.S. Pat. Nos. 5,559,022, 5,672,346 and 5,827,735. Descriptions of stromal cells, including methods for isolating them, can be found in, among other places, Prockop, Science, 276:7174, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963,489; Phillips B W and Crook J M, Pluripotent human stem cells: A novel tool in drug discovery. BioDrugs. 2010 Apr. 1; 24(2):99-108; Mari Ohnuki et al., Generation and Characterization of Human Induced Pluripotent Stem Cells, Current Protocols in Stem Cell Biology Unit Number: UNIT 4A., September, 2009.

As indicated above, there are different levels or classes of cells falling under the general definition of a "stem cell." These are "totipotent," "pluripotent" and "multipotent" stem cells. The term "totipotency" or "totipotent" refers to a cell with the degree of differentiation describing a capacity to make all of the cells in the adult body as well as the extra-embryonic tissues including the placenta. The fertilized egg (zygote) is totipotent as are the early cleaved cells (blastomeres)

The term "pluripotent" or a "pluripotent state" as used herein refers to a cell with the capacity, under different conditions, to differentiate to cell types characteristic of all three germ cell layers: endoderm (gut tissue), mesoderm (including blood, muscle, and vessels), and ectoderm (such as skin and nerve). Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. In some embodiments, a pluripotent cell is an undifferentiated cell.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and examples of muiltipotent cells include adult stem cells, such as for example, hematopoietic stem cells and neural stem cells. Multipotent means a stem cell can form many types of cells in a given lineage, but not cells of other lineages. For example, a multipotent blood stem cell such as a "hematopoietic stem cells" refers to all stem cells or progenitor cells found inter alia in bone marrow and peripheral blood that are capable of differentiating into any of the specific types of hematopoietic or blood cells, such as erythrocytes, lymphocytes, macrophages and megakaryocytes. The term "multipotency" refers to a cell with the degree of developmental versatility that is less than totipotent and pluripotent.

In the context of cell ontogeny, the adjectives "differentiated", or "differentiating" are relative terms. The term "differentiation" in the present context means the formation of cells expressing markers known to be associated with cells that are more specialized and closer to becoming terminally differentiated cells incapable of further differentiation. The pathway along which cells progress from a less committed cell, to a cell that is increasingly committed to a particular cell type, and eventually to a terminally differentiated cell is referred to as progressive differentiation or progressive commitment. Cell which are more specialized (e.g., have begun to progress along a path of progressive differentiation) but not yet terminally differentiated are referred to as partially differentiated. Differentiation is a developmental process whereby cells assume a specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, we note that in the context of this specification, the terms "differentiation" or "differentiated" refer to cells that are more specialized in their fate or function than at a previous point in their development, and includes both cells that are terminally differentiated and cells that, although not terminally differentiated, are more specialized than at a previous point in their development. The development of a cell from an uncommitted cell (for example, a stem cell), to a cell with an increasing degree of commitment to a particular differentiated cell type, and finally to a terminally differentiated cell is known as progressive differentiation or progressive commitment. A cell that is "differentiated" relative to a progenitor cell has one or more phenotypic differences relative to that progenitor cell. Phenotypic differences include, but are not limited to morphologic differences and differences in gene expression and biological activity, including not only the presence or absence of an expressed marker, but also differences in the amount of a marker and differences in the co-expression patterns of a set of markers.

The term "biological sample" as used herein refers to a cell or population of cells or a quantity of tissue or fluid from a subject. Most often, the sample has been removed from a subject, but the term "biological sample" can also refer to cells or tissue analyzed in vivo, i.e. without removal from the subject. Often, a "biological sample" will contain cells from the animal, but the term can also refer to non-cellular biological material.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, interdisposition, affection. A disease and disorder, includes but is not limited to any condition manifested as one or more physical and/or psychological symptoms for which treatment is desirable, and includes previously and newly identified diseases and other disorders.

In some embodiments of the aspects described herein, the cells for use with the biological classifier circuits described herein are bacterial cells. The term "bacteria" as used herein is intended to encompass all variants of bacteria, for example, prokaryotic organisms and cyanobacteria. In some embodiments, the bacterial cells are gram-negative cells and in alternative embodiments, the bacterial cells are gram-positive cells. Non-limiting examples of species of bacterial cells useful for engineering with the biological classifier circuits described herein include, without limitation, cells from *Escherichia coli, Bacillus subtilis, Salmonella typhimurium* and various species of *Pseudomonas, Streptomyces*, and *Staphylococcus*. Other examples of bacterial cells that can be genetically engineered for use with the biological classifier circuits described herein include, but are not limited to, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., and *Erysipelothrix* spp. In some embodiments, the bacterial cells are *E. coli* cells.

Other examples of organisms from which cells can be transformed or transfected with the biological classifier circuits described herein include, but are not limited to the following: *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides*, cyanobacteria, *Escherichia coli, Helobacter pylori, Selnomonas ruminatium, Shigella sonnei, Zymomonas mobilis, Mycoplasma mycoides*, or *Treponema denticola, Bacillus thuringiensis, Staphlococcus lugdunensis, Leuconostoc oenos, Corynebacterium xerosis, Lactobacillus planta rum, Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Staphylococcus epidermidis, Zymomonas mobilis, Streptomyces phaechromogenes, Streptomyces ghanaenis, Halobacterium* strain GRB, and *Halobaferax* sp. strain Aa2.2.

In other embodiments of the aspects described herein, biological classifier circuits can be introduced into a non-cellular system such as a virus or phage, by direct integration of the biological classifier circuit nucleic acid, for example, into the viral genome. A virus for use with the biological classifier circuits described herein can be a dsDNA virus (e.g. Adenoviruses, Herpesviruses, Poxviruses), a ssDNA viruses ((+)sense DNA) (e.g. Parvoviruses); a dsRNA virus (e.g. Reoviruses); a (+)ssRNA viruses ((+)sense RNA) (e.g. Picornaviruses, Togaviruses); (−)ssRNA virus ((−)sense RNA) (e.g. Orthomyxoviruses, Rhabdoviruses); a ssRNA-Reverse Transcriptase viruses ((+)sense RNA with DNA intermediate in life-cycle) (e.g. Retroviruses); or a dsDNA-Reverse Transcriptase virus (e.g. Hepadnaviruses).

Viruses can also include plant viruses and bacteriophages or phages. Examples of phage families that can be used with the biological classifier circuits described herein include, but are not limited to, Myoviridae (T4-like viruses; P1-like viruses; P2-like viruses; Mu-like viruses; SPO1-like viruses; φH-like viruses); Siphoviridaeλ-like viruses (T1-like viruses; T5-like viruses; c2-like viruses; L5-like viruses; ψM1-like viruses; φC31-like viruses; N15-like viruses); Podoviridae (T7-like viruses; φ29-like viruses; P22-like viruses; N4-like viruses); Tectiviridae (Tectivirus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus); Rudiviridae (Rudivirus); Fuselloviridae (Fusellovirus); Inoviridae (Inovirus, Plectrovirus); Microviridae (Microvirus, Spiromicrovirus, Bdellomicrovirus, Chlamydiamicrovirus); Leviviridae (Levivirus, Allolevivirus) and Cystoviridae (Cystovirus). Such phages can be naturally occurring or engineered phages.

In some embodiments of the aspects described herein, the biological classifier circuits are introduced into a cellular or non-cellular system using a vector or plasmid. As used herein, the term "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors." In general, expression vectors of utility in the methods and biological classifier circuits described herein are often in the form of "plasmids," which refer to circular double stranded DNA loops which, in their vector form are not bound to the chromosome. In some embodiments, all components of a given biological classifier circuit can be encoded in a single vector. For example, a lentiviral vector can be constructed, which contains all components necessary for a functional biological classifier circuit as described herein. In some embodiments, individual components (e.g., a low-input detector modules and one or more high-input detector modules) can be separately encoded in different vectors and introduced into one or more cells separately.

Other expression vectors can be used in different embodiments described herein, for example, but not limited to, plasmids, episomes, bacteriophages or viral vectors, and such vectors can integrate into the host's genome or replicate autonomously in the particular cellular system used. Viral vector include, but are not limited to, retroviral vectors, such as lentiviral vectors or gammaretroviral vectors, adenoviral vectors, and baculoviral vectors. In some embodiments, lentiviral vectors comprising the nucleic acid sequences encoding the high- and low-input modules and biological classifier circuits described herein are used. For example, a lentiviral vector can be used in the form of lentiviral particles. Other forms of expression vectors known by those skilled in the art which serve the equivalent functions can also be used. Expression vectors comprise expression vectors for stable or transient expression encoding the DNA. A vector can be either a self replicating extrachromosomal vector or a vector which integrates into a host genome. One type of vector is a genomic integrated vector, or "integrated vector", which can become integrated into the chromosomal DNA or RNA of a host cell, cellular system, or non-cellular system. In some embodiments, the nucleic acid sequence or sequences encoding the biological classifier circuits and component input detector modules described herein integrates into the chromosomal DNA or RNA of a host cell, cellular system, or non-cellular system along with components of the vector sequence.

In other embodiments, the nucleic acid sequence encoding a biological classifier circuit and component input detector modules directly integrates into chromosomal DNA or RNA of a host cell, cellular system, or non-cellular system, in the absence of any components of the vector by which it was introduced. In such embodiments, the nucleic acid sequence encoding the biological classifier circuits and component input detector modules can be integrated using targeted insertions, such as knock-in technologies or homologous recombination techniques, or by non-targeted insertions, such as gene trapping techniques or non-homologous recombination. The number of copies of a biological classifier circuits and component input detector modules that integrate into the chromosomal DNA or RNA of a cellular or non-cellular system can impact the fidelity of expression and detection, and thus it is preferred that only one copy is integrated per cellular system. Accordingly, in some embodiments of the aspects described herein, only one copy of a biological classifier circuits and its component input detector modules is integrated in the chromosomal DNA or RNA of a cellular or non-cellular system. In some embodiments, the number of copies is less than 10, less than 9, less than 8, less than 7, less than 6, less than 5, less than 4, less than 3, or less than 2.

Another type of vector for use in the methods and biological classifier circuits described herein is an episomal vector, i.e., a nucleic acid capable of extra-chromosomal replication. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. A vector can be a plasmid, bacteriophage, bacterial artificial chromosome (BAC) or yeast artificial chromosome (YAC). A vector can be a single or double-stranded DNA, RNA, or phage vector. In some embodiments, the biological classifier circuits and component input detector modules are introduced into a cellular system using a BAC vector.

The vectors comprising the biological classifier circuits and component input detector modules described herein can be "introduced" into cells as polynucleotides, preferably DNA, by techniques well-known in the art for introducing DNA and RNA into cells. The term "transduction" refers to any method whereby a nucleic acid sequence is introduced into a cell, e.g., by transfection, lipofection, electroporation, biolistics, passive uptake, lipid:nucleic acid complexes, viral vector transduction, injection, contacting with naked DNA, gene gun, and the like. The vectors, in the case of phage and viral vectors can also be introduced into cells as packaged or encapsidated virus by well-known techniques for infection and transduction. Viral vectors can be replication competent or replication defective. In the latter case, viral propagation generally occurs only in complementing host cells. In some embodiments, the biological classifier circuits and component input detector modules are introduced into a cell using other mechanisms known to one of skill in the art, such as a liposome, microspheres, gene gun, fusion proteins, such as a fusion of an antibody moiety with a nucleic acid binding moiety, or other such delivery vehicle.

The biological classifier circuits and component input detector modules or the vectors comprising the biological classifier circuits described herein can be introduced into a cell using any method known to one of skill in the art. The term "transformation" as used herein refers to the introduction of genetic material (e.g., a vector comprising a biological classifier circuit) comprising one or more modules or biological classifier circuits described herein into a cell, tissue or organism. Transformation of a cell can be stable or transient. The term "transient transformation" or "transiently transformed" refers to the introduction of one or more transgenes into a cell in the absence of integration of the transgene into the host cell's genome. Transient transformation can be detected by, for example, enzyme linked immunosorbent assay (ELISA), which detects the presence of a polypeptide encoded by one or more of the transgenes. For example, a biological classifier circuit can further comprise a constitutive promoter operably linked to a second output product, such as a reporter protein. Expression of that reporter protein indicates that a cell has been transformed or transfected with the biological classifier circuit, and is hence being interrogated by the circuit for the presence of the appropriate microRNA profile. Alternatively, transient transformation can be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell can be detected by Southern blot hybridization of genomic DNA of the cell with nucleic acid sequences, which are capable of binding to one or more of the transgenes. Alternatively, stable transformation of a cell can also be detected by the polymerase chain reaction of genomic DNA of the cell to amplify transgene sequences. The term "stable transformant" refers to a cell or cellular, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which can exhibit variable properties with respect to meiotic stability. Transformed cells, tissues, or plants are understood to encompass not only the end product of a transformation process, but also transgenic progeny thereof.

The terms "nucleic acids" and "nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or doublestranded, sense or antisense form. As will also be appreciated by those in the art, many variants of a nucleic acid can be used for the same purpose as a given nucleic acid. Thus, a nucleic acid also encompasses substantially identical nucleic acids and complements thereof. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., ionosin and xanthine, normatural sugars, e.g., 2'-methoxy ribose, or non-natural phosphodiester linkages, e.g., methylphosphonates, phosphorothioates and peptides.

The term "nucleic acid sequence" or "oligonucleotide" or "polynucleotide" are used interchangeably herein and refers to at least two nucleotides covalently linked together. The term "nucleic acid sequence" is also used inter-changeably herein with "gene", "cDNA", and "mRNA". As will be appreciated by those in the art, the depiction of a single nucleic acid sequence also defines the sequence of the complementary nucleic acid sequence. Thus, a nucleic acid sequence also encompasses the complementary strand of a depicted single strand. Unless otherwise indicated, a particular nucleic acid sequence also implicitly encompasses conservatively modified variants thereof (e.g., degenerate codon substitutions) and complementary sequences, as well as the sequence explicitly indicated. As will also be appreciated by those in the art, a single nucleic acid sequence provides a probe that can hybridize to the target sequence under stringent hybridization conditions. Thus, a nucleic acid sequence also encompasses a probe that hybridizes under stringent hybridization conditions. The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. Nucleic acid sequences can be single stranded or double stranded, or can contain portions of both double stranded and single stranded sequence. The nucleic acid sequence can be DNA, both genomic and cDNA, RNA, or a hybrid, where the nucleic acid sequence can contain combinations of deoxyribo- and ribo-nucleotides, and combinations of bases including uracil, adenine, thymine, cytosine, guanine, inosine, xanthine hypoxanthine, isocytosine and isoguanine. Nucleic acid sequences can be obtained by chemical synthesis methods or by recombinant methods. A nucleic acid sequence will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages in the nucleic acid sequence. Other analog nucleic acids include those with positive backbones; non-ionic backbones, and non-ribose backbones, including those described in U.S. Pat. Nos. 5,235,033 and 5,034,506, which are incorporated by reference. Nucleic acid sequences containing one or more non-naturally occurring or modified nucleotides are also included within one definition of nucleic acid sequences. The modified nucleotide analog can be located for example at the 5'-end and/or the 3'-end of the nucleic acid sequence. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH-group can be replaced by a group selected from H. OR, R. halo, SH, SR, NH2, NHR, NR2 or CN, wherein R is C-C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be used; alternatively, mixtures of different nucleic acid analogs, and mixtures of naturally occurring nucleic acids and analogs can be used. Nucleic acid sequences include but are not limited to, a nucleic acid sequence encoding proteins, for example that act as reporters, transcriptional repressors, antisense molecules, ribozymes, small inhibitory nucleic acid sequences, for example but not limited to RNAi, shRNAi, siRNA, micro RNAi (mRNAi), antisense oligonucleotides etc.

The term "oligonucleotide" as used herein refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

In its broadest sense, the term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of 10-22 nucleotides, such as at least 10, 11, 12, 13, 14, 15, 16, 17, 18, 19, 20, 21, 22 or up to 50 nucleotides of a nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence that is "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologues of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions.

As used herein, the term "gene" refers to a nucleic acid sequence comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid sequence can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

The term "operable linkage" or "operably linked" are used interchangeably herein, are to be understood as meaning, for example, the sequential arrangement of a regulatory element (e.g. a promoter) with a nucleic acid sequence to be expressed and, if appropriate, further regulatory elements (such as, e.g., a terminator) in such a way that each of the regulatory elements can fulfill its intended function to allow, modify, facilitate or otherwise influence expression of the linked nucleic acid sequence. The expression can result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly can be any distance, and in some embodiments is less than 200 base pairs, especially less than 100 base pairs, less than 50 base pairs. In some embodiments, the nucleic acid sequence to be transcribed is located behind the promoter in such a way that the transcription start is identical with the desired beginning of the chimeric RNA described herein. Operable linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands). However, further sequences can also be positioned between the two sequences. The insertion of sequences can also lead to the expression of fusion proteins, or serves as ribosome binding sites. In some embodiments, the expression construct, consisting of a linkage of promoter and nucleic acid sequence to be expressed, can exist in a vector integrated form and be inserted into a plant genome, for example by transformation.

The terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for the host cells (e.g., tissue promoters or pathogens like viruses).

If a promoter is an "inducible promoter", as defined herein, then the rate of transcription is modified in response to an inducing agent or inducer. In contrast, the rate of transcription is not regulated by an inducer if the promoter is a constitutive promoter. The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a nucleic acid sequence in substantially any cell and any tissue. In contrast, the term "regulateable" or "inducible" promoter referred to herein is one which is capable of directing a level of transcription of an operably linked nucleic acid sequence in the presence of a stimulus (e.g., heat shock, chemicals, light, agent etc.) which is different from the level of transcription of the operably linked nucleic acid sequence in the absence of the stimulus.

A promoter can be regulated in a tissue-specific or tissue preferred manner such that it is only active in transcribing the associated coding region in a specific tissue type(s). The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter can be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter can be assessed using methods well known in the art, e.g., GUS activity staining or immunohistochemical staining. The term "minimal promoter" as used herein refers to the minimal nucleic acid sequence comprising a promoter element while also maintaining a functional promoter. A minimal promoter can comprise an inducible, constitutive or tissue-specific promoter.

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of a microRNA or RNAi molecule, which refers to expression and transcription of an RNAi agent such as siRNA, shRNA, and antisense DNA but does not require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region can code for a protein of interest but can also code for a functional RNA of interest, for example, microRNA, microRNA target sequence, antisense RNA, dsRNA, or a nontranslated RNA, in the sense or antisense direction. The nucleic acid construct as disclosed herein can be chimeric, meaning that at least one of its components is heterologous with respect to at least one of its other components.

The term "leakiness" or "leaky" as used in reference to "promoter leakiness" refers to some level of expression of the nucleic acid sequence which is operatively linked to the promoter, even when the promoter is not intended to result in expression of the nucleic acid sequence (i.e., when the promoter is in the "off" state, a background level of expression of the nucleic acid sequence which is operatively linked to such promoter exists). In one illustrative example using inducible promoters, for example a Tet-on promoter, a leaky promoter is where some level of the nucleic acid sequence expression (which is operatively linked to the Tet-on promoter) still occurs in the absence of the inducer agent, tetracycline. Typically, most inducible promoters and tissue-specific promoters have approximately 10%-30% or 10-20% unintended or background nucleic acid sequence expression when the promoter is not active, for example, the background of leakiness of nucleic acid sequence expression is about 10%-20% or about 10-30%. As an illustrative example using a tissue-specific promoter, a "leaky promoter" is one in which expression of the nucleic acid sequence occurs in tissue where a tissue-specific promoter is not active, i.e. expression occurs in a non-specific tissue. Stated in another way using a kidney-specific promoter as an example; if at least some level of the nucleic acid sequence expression occurs in at least one tissue other than the kidney, where the nucleic acid sequence is operably linked to a kidney specific promoter, the kidney specific promoter would be considered a leaky promoter The term "enhancer" refers to a cis-acting regulatory sequence involved in the transcriptional activation of a nucleic acid sequence. An enhancer can function in either orientation and can be upstream or downstream of the promoter. As used herein, the term "gene product(s)" is used to refer to include RNA transcribed from a gene, or a polypeptide encoded by a gene or translated from RNA. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof.

The term "nucleic acid construct" as used herein refers to a nucleic acid at least partly created by recombinant methods. The term "DNA construct" refers to a polynucleotide construct consisting of deoxyribonucleotides. The construct can be single or double stranded. The construct can be circular or linear. A person of ordinary skill in the art is familiar with a variety of ways to obtain and generate a DNA construct. Constructs can be prepared by means of customary recombination and cloning techniques as are described, for example, in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands.

The terms "polypeptide", "peptide", "oligopeptide", "polypeptide", "gene product", "expression product" and "protein" are used interchangeably herein to refer to a polymer or oligomer of consecutive amino acid residues.

The term "subject" refers to any living organism from which a biological sample, such as a cell sample, can be obtained. The term includes, but is not limited to, humans; non-human primates, such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" is also intended to include living organisms susceptible to conditions or diseases caused or contributed bacteria, pathogens, disease states or conditions as generally disclosed, but not limited to, throughout this specification. Examples of subjects include humans, dogs, cats, cows, goats, and mice.

The terms "higher" or "increased" or "increase" as used herein in the context of expression or biological activity of a microRNA or protein generally means an increase in the expression level or activity of the microRNA or protein by a statically significant amount relative to a reference level, state or condition. For the avoidance of doubt, a "higher" or "increased", expression of a microRNA means a statistically significant increase of at least about 50% as compared to a reference level or state, including an increase of at least about 60%, at least about 70%, at least about 80%, at least about 90%, at least about 100% or more, including, for example at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90-fold, at least 100-fold, at least 500-fold, at least 1000-fold increase or greater of the level of expression of the microRNA relative to the reference level.

Similarly, the terms "lower", "reduced", or "decreased" are all used herein generally to mean a decrease by a statistically significant amount. However, for avoidance of doubt, "lower", "reduced", "reduction" or "decreased" means a decrease by at least 50% as compared to a reference level, for example a decrease by at least about 60%, or at least about 70%, or at least about 80%, or at least about 90%, or at least about 95%, or up to and including a 100% decrease (i.e. absent level as compared to a reference sample), or any decrease between 50-100% as compared to a reference level.

As used herein, the term "comprising" means that other elements can also be present in addition to the defined elements presented. The use of "comprising" indicates inclusion rather than limitation. Accordingly, the terms "comprising" means "including principally, but not necessary solely". Furthermore, variation of the word "comprising", such as "comprise" and "comprises", have correspondingly the same meanings. The term "consisting essentially of" means "including principally, but not necessary solely at least one", and as such, is intended to mean a "selection of one or more, and in any combination". Stated another way, the term "consisting essentially of" means that an element can be added, subtracted or substituted without materially affecting the novel characteristics described herein. This applies equally to steps within a described method as well as compositions and components therein. In other embodiments, the inventions, compositions, methods, and respective components thereof, described herein are intended to be exclusive of any element not deemed an essential element to the component, composition or method ("consisting of"). For example, a biological classifier circuit that comprises a repressor sequence and a microRNA target sequence encompasses both the repressor sequence and a microRNA target sequence of a larger sequence. By way of further example, a composition that comprises elements A and B also encompasses a composition consisting of A, B and C.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope described herein. Various changes and modifications to the disclosed embodiments, which will be apparent to those of skill in the art, can be made without departing from the spirit and scope described herein. Further, all patents, patent applications, publications, and websites identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Unless otherwise explained, all technical and scientific terms used herein have the same meaning as commonly understood by one of ordinary skill in the art to which this disclosure belongs. Definitions of common terms in molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology can be found in Benjamin Lewin, Genes IX, published by Jones & Bartlett Publishing, 2007 (ISBN-13: 9780763740634); and Kendrew et al. (eds.), The Encyclopedia of Molecular Biology, published by Blackwell Science Ltd., 1994 (ISBN 0-632-02182-9).

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987)); Current Protocols in Molecular Biology (CPMB) (Fred M. Ausubel, et al. ed., John Wiley and Sons, Inc.); Current Protocols in Protein Science (CPPS) (John E. Coligan, et. al., ed., John Wiley and Sons, Inc.); Current Protocols in Immunology (CPI) (John E. Coligan, et. al., ed. John Wiley and Sons, Inc.); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); Animal Cell Culture Methods (Methods in Cell Biology, Vol. 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such can vary. The terminology used herein is for the purpose of describing particular embodiments only, and is not intended to limit the scope described herein, which is defined solely by the claims.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting. The contents of all references cited throughout this application, as well as the figures and tables are incorporated herein by reference.

Examples

The engineered biological systems described herein, which integrate sophisticated sensing, information processing, and actuation in living cells, are useful for new directions in basic biology, biotechnology and medicine. The complexity of the cellular environment requires elaborate sensory and information processing capabilities in individual cells. Herein we demonstrate a multiple-input biological classifier circuit that, in some embodiments, can act as a programmable therapeutic agent that operates in individual cells, diagnose a complex cellular condition, and selectively trigger a therapeutic response using molecular tools analogous to disease profiling arrays and computer algorithms. This programmable therapeutic agent comprises a synthetic, scalable transcriptional/posttranscriptional regulatory circuit—a 'classifier circuit'—designed to sense expression levels of a customizable set of endogenous microRNAs and to compute whether to trigger a response if the expression levels match a pre-determined profile of interest. Specifically, as demonstrated herein, when operating in a heterogeneous cell population, the classifier circuits described herein can identify and selectively destroys cancer cells, such as HeLa cancer cells when using a HeLa-specific microRNA expression profile as a point of reference. The approaches described herein will enable highly-precise cancer treatments with little collateral damage, as well as be useful for numerous other applications that benefit from accurate single-cell in-vivo identification of highly-complex cell states.

A salient feature of biological pathways is their two-way interaction with the cellular environment in which they operate. Such interaction usually involves (1) sensing of relevant input conditions in the cell, (2) 'computing' or processing those inputs to determine whether and which action to take; and (3) producing a biologically-active output to actuate a physiological effect in the cell. Engineered analogues of natural pathways with elaborate sensing, computational and actuation functionalities (1, 2) can augment endogenous processes and enable rational manipulation and control of biological systems for the benefit of basic biological exploration, biotechnology and medical intervention. Reporter constructs (3) that transduce cellular inputs into a detectable output, and tissue-specific transgenes controlled transcriptionally and/or posttranscriptionally (4-6) represent important first steps toward this goal. The discipline of synthetic biology builds on these efforts to create innovative and generally-applicable approaches to molecular sensing, signal integration and actuation, and promises a quantum leap in the complexity and sophistication of engineered biological systems by placing their construction on a rigorous engineering foundation.

Synthetic circuits have already demonstrated basic programmable dynamic behavior in cells (oscillators (7-10), memory (11-14), spatial patterns (15), cascades (16) and pulse generators (17)), digital and analog computations (18-20), and complex biosynthetic pathways (21), but the interaction of these circuits with the cellular context has been limited (22, 23). In parallel, molecular network prototypes have demonstrated sophisticated sensing, computation and actuation (24-28) in cell-free environments, anticipating the benefits of embedding similar networks in cells.

Herein we describe multi-input, genetic classifier circuits that use both transcriptional and posttranscriptional regulation in order to determine, for example, whether a cell of unknown origin is in a specific state of interest. The circuits implement this task by interrogating the state of the host cell through simultaneous assessment of the expression levels of multiple different endogenous mature microRNAs—important regulators and indicators of specific cellular states (30). In some examples, six different microRNAs were used. The circuit 'computes' whether the expression profile of the, for example, six microRNAs matches a pre-determined reference profile that characterizes a cell state that the classifier circuit is intended to detect and if so, produces a biological response. We call this circuit a 'classifier' because it classifies individual cells into a number of categories based on the cells' internal state, in a manner similar to current practices for characterizing bulk tissue (e.g., biopsy samples) using gene array analysis and computer algorithms (31).

The approaches described herein can be used in a variety of applications. In some examples, we chose to develop a multi-input classifier circuit that is applicable for highly precise and selective cancer therapy. Many mainstream and experimental drugs exhibit some degree of selectivity toward cancer cells by relying on individual cancer markers (32). However, cancer cells exhibit a complex set of conditions deviating from the normal state of their progenitor tissue (33, 34), and using a single marker, or even two, to distinguish them from healthy cells is rarely sufficient and often results in harmful side-effects (35). Therefore, sensing and integration of information from multiple markers by a therapeutic agent is crucial for creating next-generation treatments (26). We constructed and tested in human cell culture a programmed therapeutic agent comprising an exemplary multi-input classifier circuit that selectively identifies and triggers apoptosis in HeLa cell line (derived from cervical cancer tissue), but not in healthy cells.

High-Level Operation of a microRNA Classifier Circuit

RNA and protein components of the circuits described herein are expressed from exogenously introduced genes to form a functional network in cells. The functional network is designed to perform a biochemical computation with a pre-defined set of inputs, such as endogenous mature microRNAs. The elementary task of this computation is to determine whether, for example, the microRNA expression profile, i.e. a combination of microRNA expression levels, of a given cell matches a profile of interest, resulting in either 'match' (True) or 'no match' (False) outcome. In our experiments described herein, a positive match classified a cell as a HeLa cancer cell and the circuit generated an output, such as a fluorescent reporter for circuit characterization or an apoptotic protein to trigger biological actuation.

As a first step in designing a classifier circuit that uses microRNA levels as inputs, a microRNA profile for the cell type of interest, the 'reference profile', can be identified by bioinformatics analysis and experimental confirmation. In general, a reference profile for use with the classifier circuits described herein comprises a small number of microRNA markers that are highly expressed in the cell type of interest, but typically not in other cells, together with a few microRNA markers that are not expressed in the cell type of interest but are often highly expressed in others (FIG. 1A). The goal is to identify a small, non-redundant set of markers that generates a unique and robust molecular signature for a specific cell type. We note that multiple sets can exist to uniquely identify any cell type, and the optimal choice is likely to be dictated by practical considerations. For the classifier circuit for classifying HeLa cells described herein, these markers are designated as 'HeLa-high' and 'HeLa-low', respectively.

Once a profile was established, we used a modular design approach to construct a circuit that detects this profile in cells. We have created a number of sensor mechanisms that link intracellular microRNA activity to the expression level of an output protein, and a specific way to combine these sensors in order to implement molecular AND-like logic with the inputs' expression levels. The AND logic abstraction is inspired by a similar abstraction in computer engineering and describes in a simplified fashion the general properties of the circuit. We discuss the underlying 'analog' properties of the circuit components and overall capacity of the circuit to convert analog input signals to reliable, near-digital output. Some components of the sensors designed to detect high marker expression, e.g., HeLa-high markers, comprise specially-designed 'double-inversion' modules. These modules efficiently repress an output in the absence of their cognate microRNA inputs, while the repression is largely relieved and the output reaches high levels in cells that express this marker at or above its level in HeLa cells. Sensors for HeLa-low markers comprise short micoRNA target sequences directly fused to mRNA of the output gene (4, 29). The sensors for detecting low-marker expression efficiently knock down output protein expression when microRNA level is high, but the knock-down is weak and the output level is high when the microRNA is present at low levels typical of HeLa cells.

The AND-type logic behavior of the classifier circuits described herein is achieved by fine tuning sensor responses to their cognate microRNA inputs and by properly integrating the sensors in the classifier circuit. Output expression is programmed to trigger actuation only in cells with HeLa-high markers present at or above their levels in HeLa cells and HeLa-low markers present at or below their levels in HeLa cells.

Selection of microRNA Markers for Use with HeLa Cell Classifier Circuit

Construction of a circuit involves, in part: (a) determination of a reference profile; (b) construction, testing and optimization of sensors for individual markers of the profile; (c) assembly and fine-tuning of an integrated logic network; and (d) fine-tuning an output response and actuation. Accordingly, as described herein, we first set out to determine whether there exists a small set of markers expessed at 'high' and 'low' levels that can be used to distinguish HeLa cancer cell line from healthy cells and tissues (but not necessarily other cancer cell lines) (37, 38) using the microRNA Atlas database (39).

We first focused on HeLa-high markers first and found two promising candidates: miR21 and a compound marker that adds the expression levels of miR-17 and miR-30a (miR17-30a). Our analysis suggested that a properly-tuned circuit that uses these two markers should provide a substantial, five-fold difference between the output level in HeLa cells and the output levels in all but a few other healthy cell types. We then analyzed markers highly expressed in potentially misclassified cell types and unexpressed in HeLa and converged on the set comprising miR-141, miR-142(3p) and miR-146a. These markers are also expressed at high levels in many other healthy cell types, contributing to the overall circuit robustness (36). This collection of markers results in a unique HeLa reference profile of "HeLa-high markers: miR-21, miR-17-30a; and HeLa-low markers: miR-141, miR-142(3p), miR-146a". This profile corresponds to a high level circuit wiring diagram shown in FIG. 1B and the following abstract logic: miR-21 AND miR-17-30a AND NOT(miR-141) AND NOT(miR-142(3p)) AND NOT(miR-146a)

According to our computational analysis, a classifier circuit based on this profile generates at least a 7-fold output increase in HeLa cells relative to the closest other cell type USSC-7d (unrestricted somatic stem cells cultured for 7 days), and on average about 350-fold increase relative to the rest of the cells. This analysis takes into account the analog intermediate input values observed in all cell types considered. The separation of the classifier output in HeLa compared to all other cells can be optimized further with additional sensor fine-tuning (FIG. 8G).

Following the bioinformatics analysis, we assayed how well the chosen markers knock down reporter expression in HeLa cells as well as in human embryonic kidney 293 cell line (HEK293) and breast cancer cell line MCF7 that represent 'other tissues' in our experiments. We chose MCF7 cells as a model of non-cancer MCF10 cells that are difficult to transfect, because expression levels of the HeLa profile microRNA markers in MCF10 cells are similar to those in MCF7 cells. Our fluorescent reporters were fused to appropriate microRNA targets to measure knock-down efficiencies. We observed knock-down of the miR-21 reporter in HeLa and MCF7 but not in HEK293 cells, while knock-down by a combination of miR-17 and 30a was detected in all three cell lines (FIGS. 1C and 1D). In addition, reporter knock-down by miR-141 was observed in MCF7 cells. Note that fewer than six inputs are required if our goal were to distinguish only between HeLa, HEK293 and MCF7. However, we use all six inputs here to demonstrate that the system can scale to this size and that the classifier circuit operates correctly when we artificially vary all marker levels, implying that HeLa cells can be distinguished from all healthy tissues profiled in the MicroRNA Atlas report.

Building the Classifier Circuit

The exemplary HeLa cell classifier described herein uses two sensors for HeLa-high inputs miR-21 and a combination of miR-17 and 30a, and three sensors for HeLa-low inputs miR-141, 142(3p) and 146a. The sensors for HeLa-low markers are implemented by fusing four tandem repeats (5) of the corresponding target sites directly into the 3'-UTR of the output driven by a constitutive promoter (FIGS. 2A and 2B).

The construction of 'double-inversion' sensor modules for HeLa-high markers was much more elaborate. A minimal module comprises a microRNA-targeted transcriptional repressor and an output-driving promoter efficiently controlled by this repressor. We explored this arrangement using siRNA-targeted transcriptional repressor LacI in combination with LacI-controlled promoter CAGop (29) (chimeric promoter CAG (40) harboring two Lac operator binding sites) and measured ON:OFF ratios of ~2-4 fold. These proved insufficient for our purposes. We incorporated reverse tetracycline-controlled transactivator (rtTA) to regulate LacI expression in the presence of doxycycline to form a coherent type 2 feed-forward motif (41, 42) (FIG. 2C). Both rtTA and LacI mRNAs are fused with microRNA targets for the HeLa-high markers. In the absence of the HeLA-high microRNA markers, constitutively expressed rtTA induces LacI via the PTA-controlled tetracycline responsive element promoter (pTRE); LacI in turn represses the output. Highly-expressed microRNA reduces the level of PTA, greatly weakening LacI expression, and also targets LacI directly reducing its level even further and relieving repression of the CAGop-driven output (FIG. 2D). This sensor optimization resulted in an ON:OFF ratio of ~8-10 fold in both 'double-inversion' modules (FIG. 9).

Figures 2A, 2B, 2C, 2D, 2E, 2F:
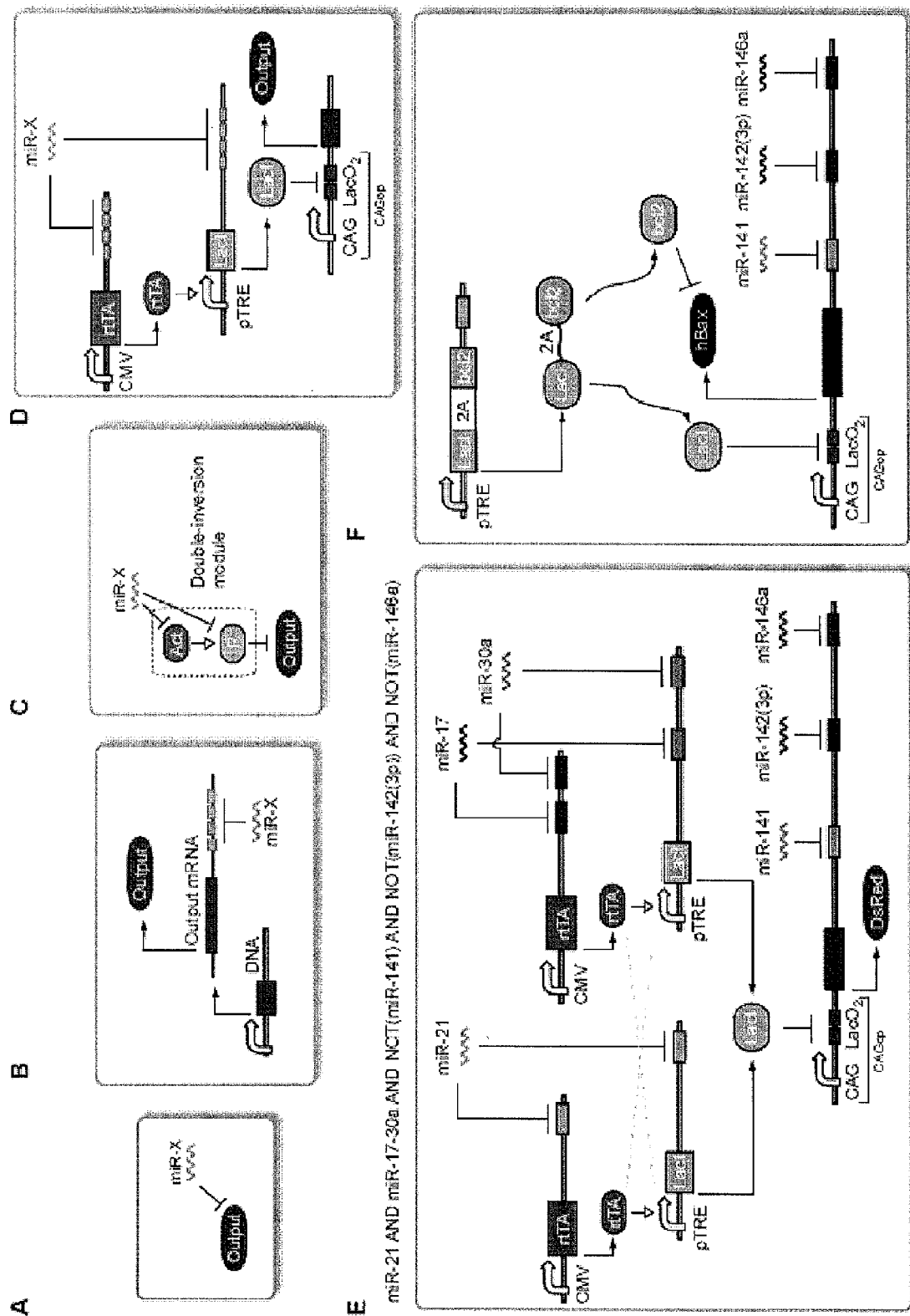
FIGS. 2A-2F depict the schematics of a classifier circuit.

Next, we proceeded to construct, test and optimize the complete HeLa cell classifier circuit (FIG. 2E). The construction amounts to incorporating all HeLa-low sensors in tandem in the output 3'-UTR, placing the output gene under LacI-controlled promoter CAGop, and adding the genes encoding HeLa-high marker sensors. After circuit construction, we first assayed for correct logic operation of the classifier in response to all possible combinations of ON (i.e., saturating) and OFF (i.e., near-zero) input values.

We used the DsRed-Express red fluorescent protein (DsRed for short) as output and analyzed whether it is generated only when levels of miR-21 and the added levels of miR-17 and 30a are at or above their levels in HeLa cells, AND levels of miRs 141, 142(3p) and 146a are below detection threshold. With five inputs, this assay requires $2^5=32$ different input combinations. Ideally one would need 32 different cell lines each expressing a unique combination of the input microRNAs with each input being either low or above saturation. Since such collection of cell lines is hardly feasible, we used a different but equivalent approach. Specifically, we performed all experiments in HeLa cells with their high expression of miR-21 and miR-17-30a and negligible expression of miR-141, 142(3p) and 146a. The 32 input combinations were generated in HeLa cells by mutating target sites for HeLa-high markers to emulate artificial low levels, and transfecting microRNA mimics of HeLa-low markers to emulate high levels (FIG. 3A).

Figures 3A, 3B:
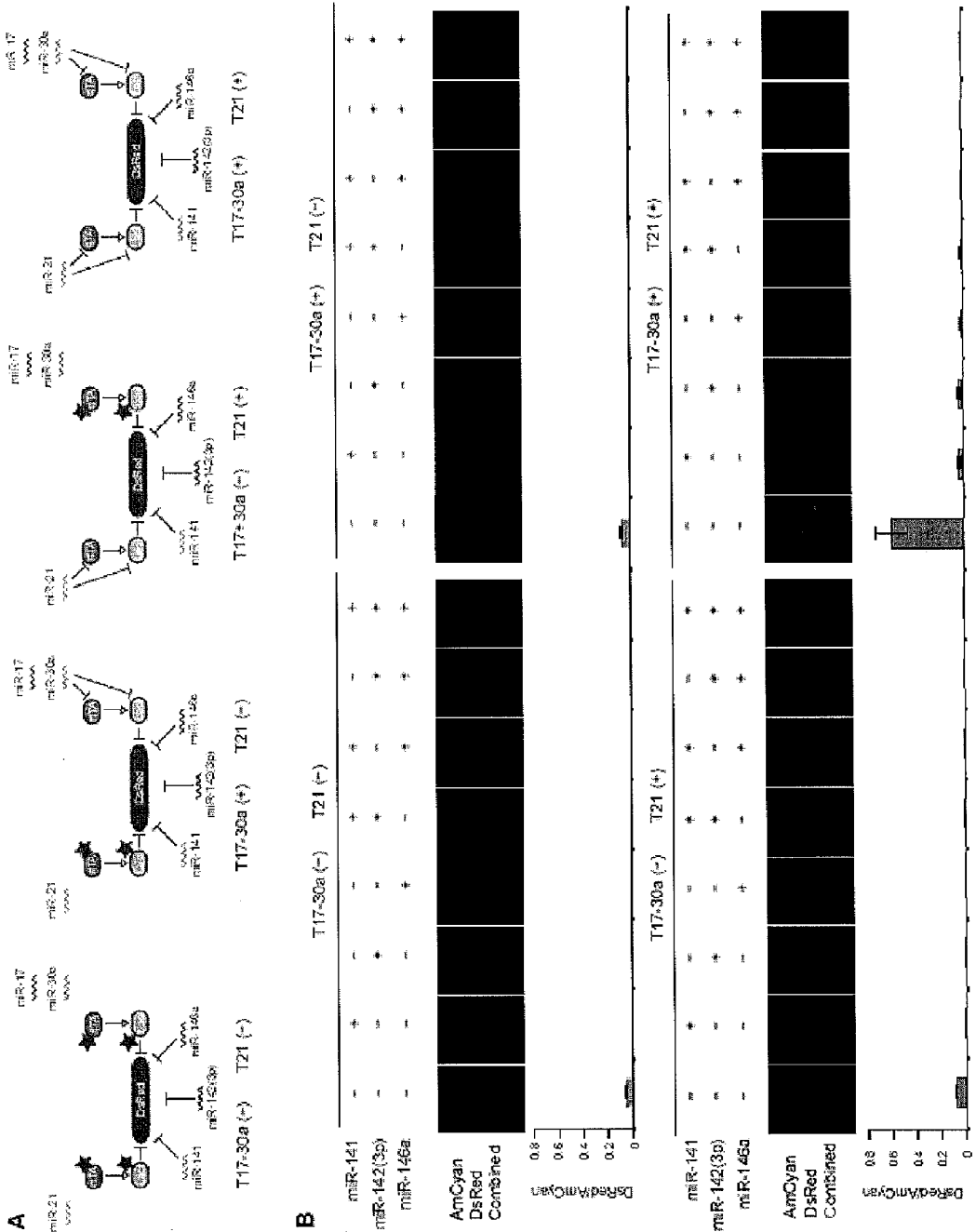
FIGS. 3A-3B depict extensive validation of a classifier circuit's logic operation.
Figure 10:
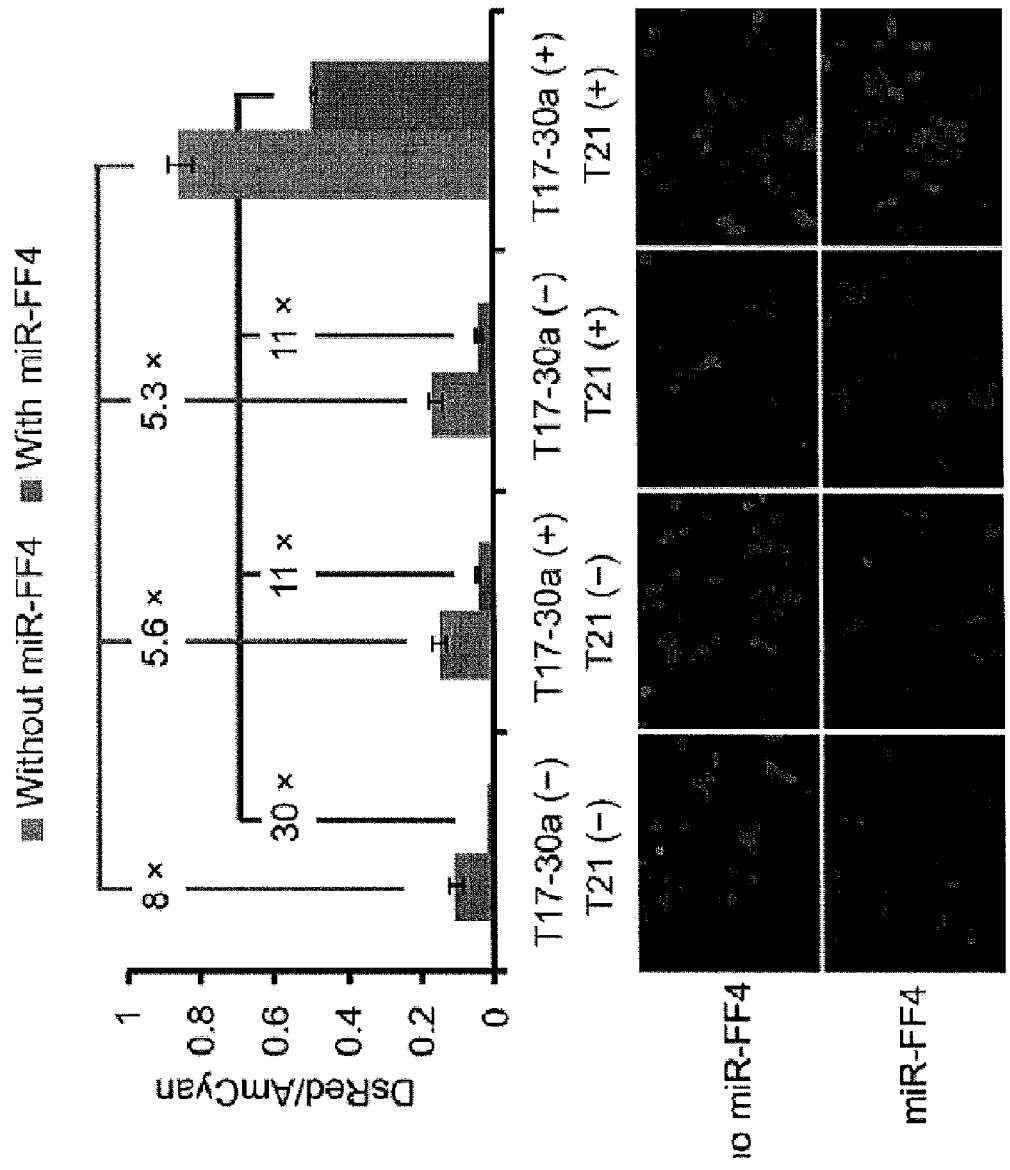
FIG. 10 shows a representative circuit optimization with engineered intronic microRNA miR-FF4. Transfection protocol is described in Table 58. Four versions of the circuit (FIG. 2E), with specific microRNA regulatory links interrupted (denoted as "−") or functional (denoted as "+"), are used to emulate four different combinations of input levels for two HeLa-high microRNA markers (FIG. 3A). The bar charts show mean±SD of DsRed/AmCyan values from three independent replicates measured by FACS ~48 h post-transfection. The ON:OFF ratio is calculated by dividing the DsRed/AmCyan ratio of the ON state (the last category) by the value in the OFF state (the first three categories). The images are overlays of DsRed and AmCyan channels taken ~48 h post-transfection.

The results demonstrating correct operation of the circuit under all 32 conditions are shown in FIG. 3B. We detected undesirably high output levels in the three cases where one of the HeLa-high markers was set to OFF and microRNA mimics for the HeLa-low markers were absent. In order to further reduce the insufficiently-low OFF levels in cases when only one of the two sensors for HeLa-high markers is triggered (43, 44) and combined transcriptional repression by LacI with posttranscriptional repression by engineered intronic microRNA (FIG. 4). Using this approach, we observed a modest reduction in the ON state that was more than compensated for by a significantly-improved OFF state, increasing the ON:OFF ratio of the classifier circuit from ~5-8 fold to ~11-30 fold (FIG. 10). The output reduction in the ON state could occur because of additional output repression by residual intronic microRNA.

Figures 5A, 5B:
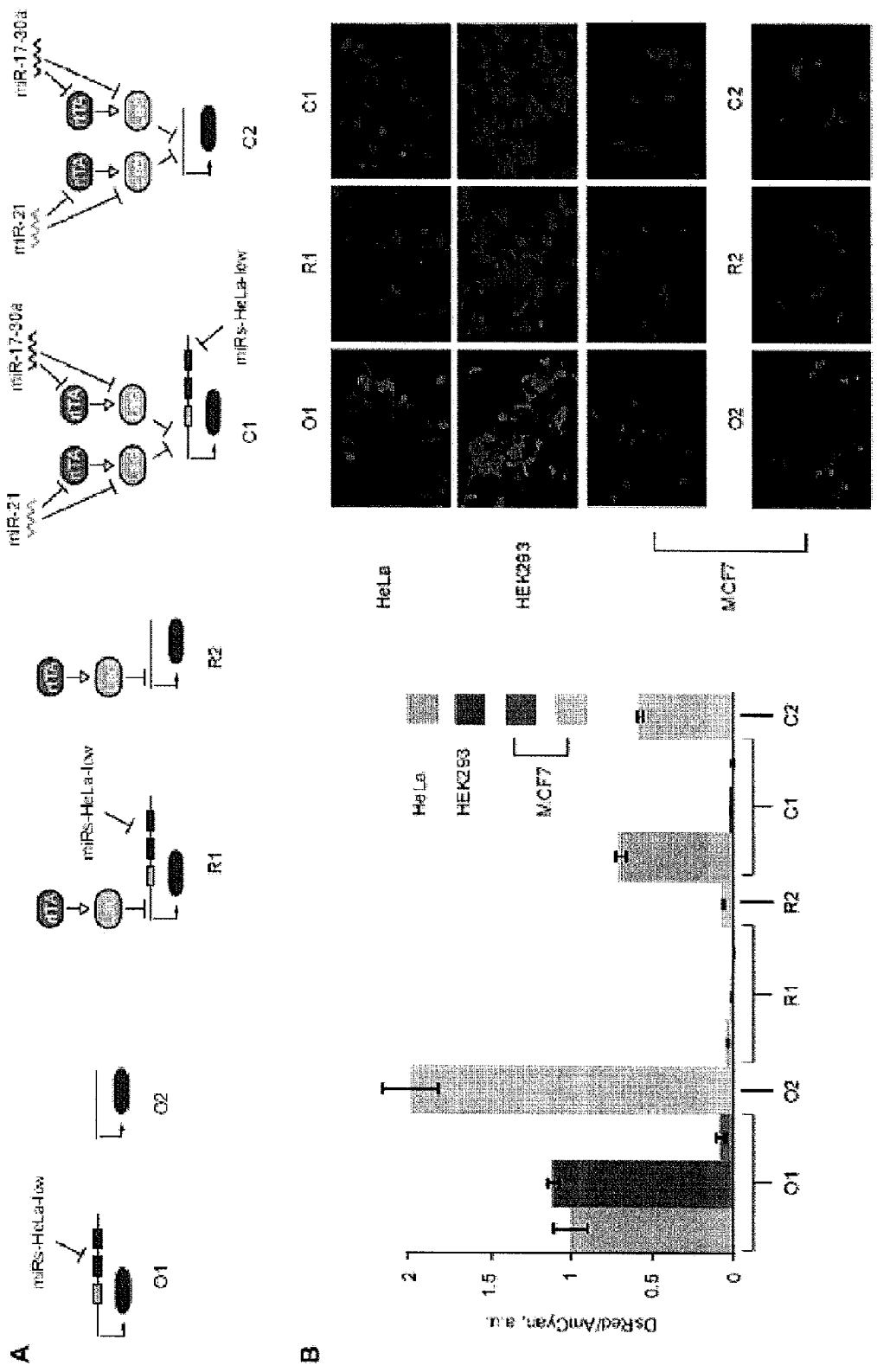
FIGS. 5A-5E show that a classifier circuit can be used to distinguish and specifically kill HeLa cells. Plasmids encoding the circuits and transfection protocols are listed in Tables 55 and 56. Fluorescent reporter assays are shown in FIGS. 5A and 5B.

We then constructed a new multi-input classifier circuit that uses the above optimized sensors for HeLa-high markers and analyzed how well it distinguishes between HeLa cells and the cell lines HEK293 and MCF7. The results show that the optimized circuit indeed generates a strong fluorescent signal in HeLa cells but not in HEK293 and MCF7 cells, and that the differences are due to classifier circuit operation rather than differential promoter activity (FIGS. 5A and 5B). As additional evidence that the circuit operates consistently with our design, we constructed partial networks that only respond to a subset of microRNA markers and observed that they behave as expected. These results also show that two markers (miR-21 and miR-141) are sufficient for distinguishing between our three cell lines, yet the full set of markers has much better properties when expanding the assays to larger cell collections.

Figures 5C, 5D, 5E:
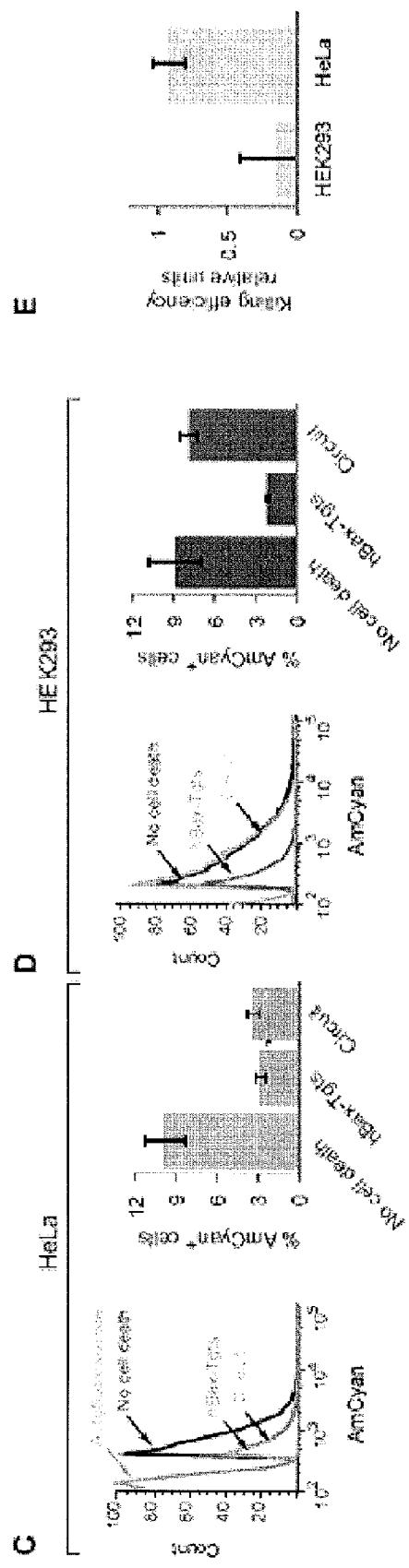

Next, we tested whether a multi-input classifier circuit can selectively trigger useful biological actuation, such as induction of apoptosis by human Bcl-2-associated X protein hBax (45). Programmed apoptotic actuation was tested in HeLa and HEK293 but not in MCF7 cells that proved resistant to hBax using our cell killing protocol. To quantify circuit-induced cell death, constitutively-expressed AmCyan fluorescent protein driven by CAG promoter and the apoptosis-inducing classifier circuit (FIG. 2F) were co-transfected into cells. We reasoned that after an amount of time sufficient for circuit operation elapsed, the fraction of cells expressing the AmCyan in this experiment would range between the fraction of AmCyan$^+$ cells measured in a separate experiment using a circuit without hBax (indicating no apoptosis), and zero in the case of fully-efficient apoptosis. As shown in FIGS. 5C and 5D, in a control experiment constitutively expressed hBax reduces the number of AmCyan$^+$ cells to ~25% (HeLa) and ~23% (HEK293) of the number measured in the absence of hBax 4 days post-transfection. The apoptosis-inducing classifier circuit inflicts almost the same degree of cell death in HeLa cells but causes little cell death in HEK293 cells, indicating highly-selective actuation (FIGS. 5C and 5D). Based on comparison of cell death when regulated by the classifier to cell death under constitutive hBax, we observe roughly 92% HeLa cells killing efficiency and 14% undesired HEK293 cell death (FIG. 5E).

Figures 6A, 6B:
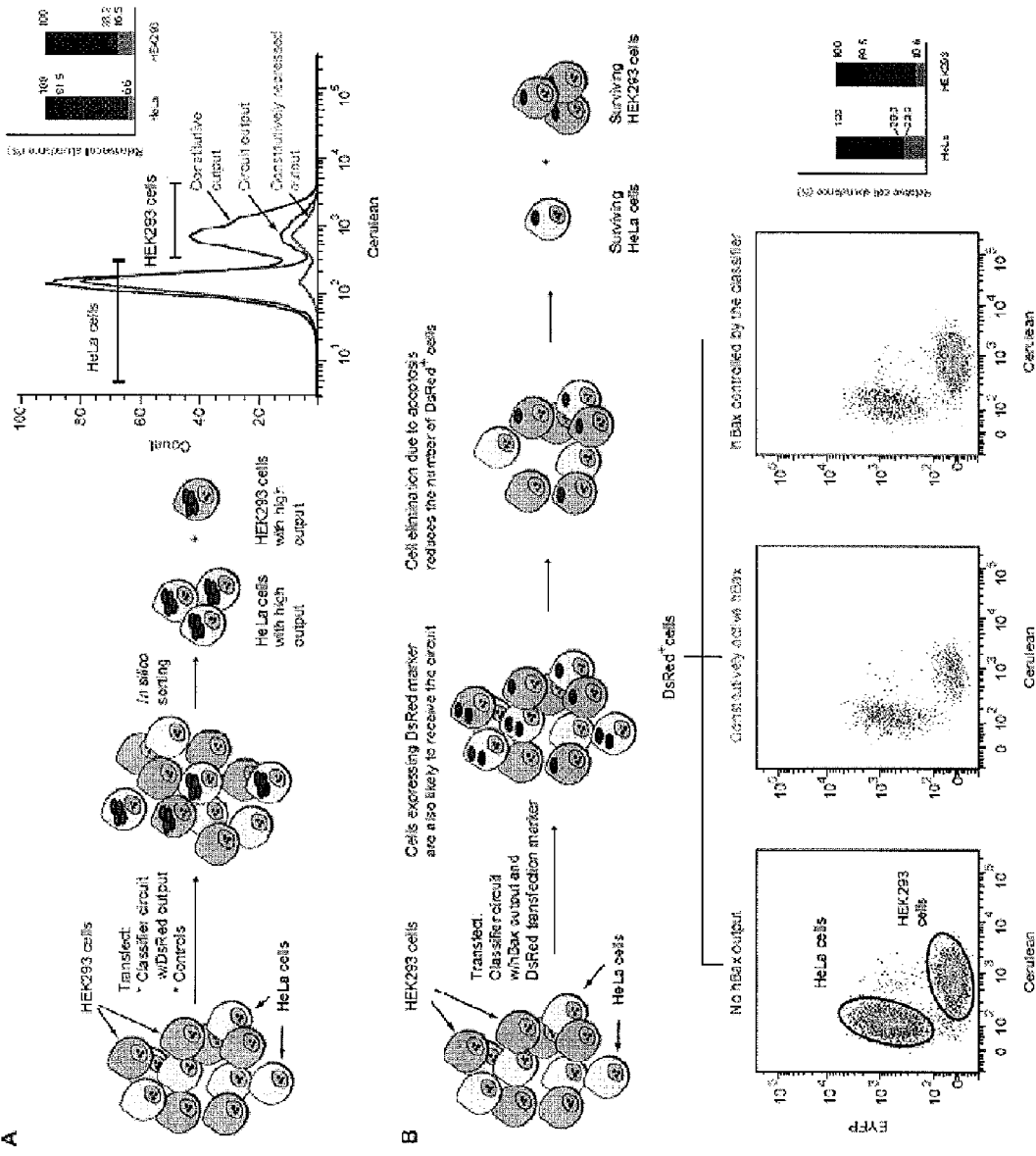
FIGS. 6A-6B show fluorescent reporter assays and killing experiments in cell mixtures. Transfection protocols are listed in Table 57.
Figure 12:
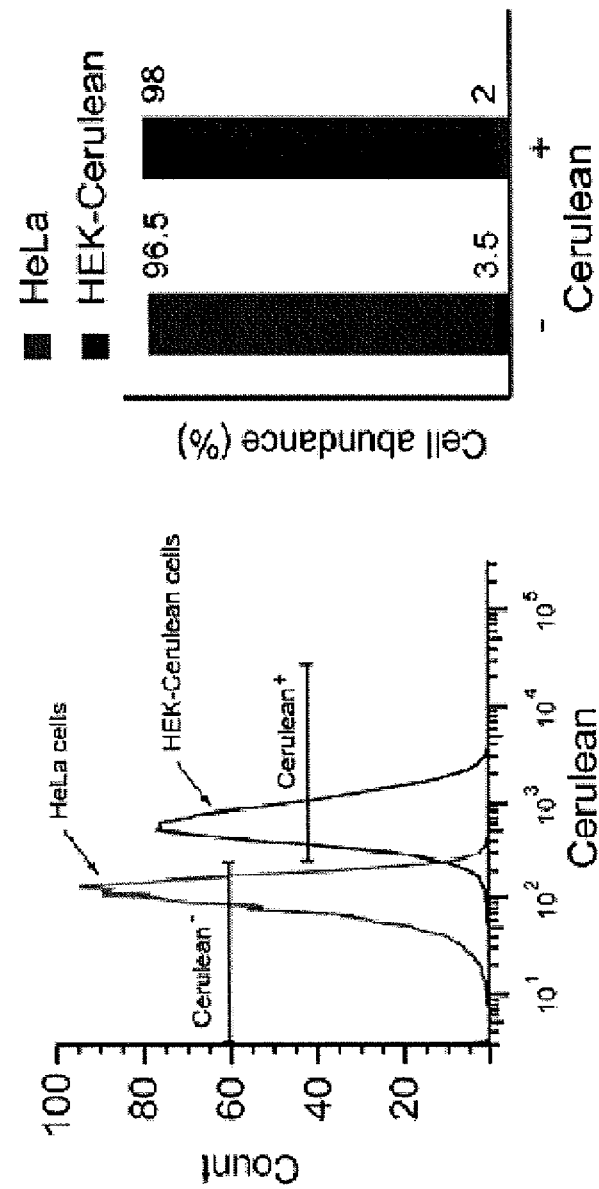
FIG. 12 shows a separation of HEK-Cerulean cells from HeLa cells using Cerulean fluorescent channel. The histograms on the left show contributions of the two cell types, HeLa and HEK-Cerulean to Cerulean-negative (Cerulean$^-$) and Cerulean-positive (Cerulean$^+$) cells. The chart on the right show the relative percentage of HeLa and HEK-Cerulean in Cerulean$^-$ and Cerulean$^+$ cells respectively.

An important measure of circuit performance is specificity and selectivity when operating in heterogeneous cell populations. To enable quantification of different cell lines in a mixture, we stably integrated a Cerulean fluorescent marker in HEK293 cells (HEK293-Cerulean), that is adequate for separating between HeLa and HEK293 cells using the Cerulean fluorescence channel (FIG. 12). Next, we transfected co-cultured HEK293-Cerulean and HeLa cells with various circuits expressing DsRed output (FIG. 6A). In a control experiment where we transfected constitutively-expressed DsRed, HEK923 and HeLa cells contribute to the DsRed$^+$ population in roughly equal proportions. When we transfect the mixture with the classifier circuit, the DsRed$^+$ population consists predominantly of HeLa cells as expected. Repression of the output by mutant 'double-inversion' modules that are insensitive to HeLa-high microRNA markers results in substantial but not full reduction in the numbers of DsRed$^+$ cells from both HeLa and HEK293 origin, representing a baseline for mis-identifying cells due to leaky expression under maximal output repression. The classifier circuit's selectivity can be approximated by its ability to induce DsRed above this leaky expression.

To test selective induction of HeLa cell death in a cell mixture, CAG-driven DsRed was co-transfected with the apoptosis-inducing classifier circuit to co-cultured HEK293-Cerulean and HeLa-EYFP cells (FIG. 6B). In one control experiment without hBax, the DsRed$^+$ population comprises of roughly the same number of HeLa-EYFP and HEK293-Cerulean cells. In a second control experiment, constitutive expression of hBax results in significant reduction in both numbers. In comparison, the classifier circuit with hBax results in significant apoptosis of HeLa-EYFP cells but not of HEK293-Cerulean cells. While the results confirm that programmed apoptosis operates correctly in the cell mixture, the observed degree of false-positive cell death as well as false-negative cell survival warrants continuing circuit and DNA delivery optimization, e.g., using lentiviruses.

The examples described herein demonstrate engineered synthetic biological networks that diagnose complex intracellular conditions and execute programmed biological actuation by sensing and computing with multiple endogenous signals. In other embodiments, the classifier circuits can incorporate components and features to eliminate false-positives and false-negatives, increase the efficiency of programmed apoptosis, and ensure uniform operation of the circuit in noisy environments across different cell lines and tissue types. The circuit design framework itself can be expanded, in some embodiments, by developing sensors for non-microRNA markers, such as transcription factors, scaling-up the computation to implement a "cocktail" approach to address heterogeneous cancer populations (FIG. 13), and by including additional controls for actuation timing and intensity.

Apart from the technological advances, our experience with the synthetic constructs developed here sheds light on a number of important basic questions pertaining to biological regulation in general and RNAi in particular. Recent research has uncovered microRNA regulation complexities that include fan-out control of multiple genes by the same microRNA, fan-in control of a gene by multiple microRNAs (46), and complex feedback and feed-forward interactions between microRNA and transcription factors (47). MicroRNAs were also identified as key players in complex regulatory networks (48, 49) and as stabilizing regulators of cell fate (50). Our circuits implement such regulatory modalities in a synthetic context, confirming by construction that microRNA can be integrated with transcriptional regulation in a complex fashion. Furthermore, because of the synthetic construction and orthogonality of some of the circuit modules, we were able to quantify the individual contribution of various components and the interplay of transcriptional and posttranscriptional regulation in complex regulatory schemes. In some aspects, our systems and circuits can also be used to guide further basic biological inquiry. For example, while it is possible to engineer highly-efficient repression by microRNA, such efficiency is not normally observed in mammalian cells (51). Our data that show residual repression activity of microRNA-targeted LacI (FIG. 3 and FIG. 9) suggest that even highly-efficient microRNA triggered knock-down can be insufficient and inferior to transcriptional regulation, explaining the above observation. Thus, in some aspects and embodiments 'near-perfect' knock-down can be achieved by hybrid regulatory networks that amplify the microRNA effect, as with our sensors for HeLa-high markers. The figures are described in more detail below.

FIG. 1 shows a schematic operation of a cell type classifier. FIG. 1A shows multi-input logic used to selectively identify a specific cell type. Three hypothetical microRNA markers A, B and C are expressed at different levels in different cell types. Only cells with high expression of markers A and B and low expression of C represent a specific type of cancer, i.e., when the logic formula A AND B AND NOT(C) is satisfied. FIG. 1B depicts a schematic representation of a HeLa-specific classifier circuit. Synthetic transcriptional/posttranscriptional regulatory circuits (rectangles) were created that implement logic integration of multiple microRNA markers and programmed actuation. These circuits are delivered into heterogeneous populations of cells comprising both healthy and HeLa cells. The circuit operates separately in each cell and determines whether the cell is HeLa based on a HeLa-specific microRNA expression profile. If the profiles match, the cell is targeted for apoptosis. Otherwise, the cell is classified as 'healthy' and is not affected. The circuit senses the levels of six endogenous input microRNAs and combines transcriptional and post-transcriptional regulation to control output protein expression (e.g., hBax) based on those levels. Both miR-21 and the sum of miR-17 and 30a concentrations (miR-17-30a) must be present at high levels and markers miR-141, 142(3p) and 146a must not be present for high hBax protein expression. Lines with bars indicate down-regulation. R1 and R2 represent intermediate circuit elements needed to invert microRNA activity. The entire network implements a multi-input AND logic function (where all inputs must be present at their prescribed levels simultaneously) for identification and selective killing of HeLa cells. FIG. 1C shows experimental confirmation of various reporter construct knock-downs by corresponding microRNA markers identified by our bioinformatics analysis in HeLa, HEK293, and MCF7 cell lines. Transiently-transfected bidirectional constructs include DsRed reporter with fused microRNA targets (four tandem repeats of the same target fully complementary to the corresponding mature microRNA sequences), and an internal reference reporter AmCyan. Scatter plots show flow cytometry data measured at 48 hours post-transfection. FIG. 1D depicts the overall knock-down efficiency by the microRNA biomarkers in different cell lines (top). The bars show mean±SD of DsRed/AmCyan values from three independent replicates. The corresponding published microRNA cloning frequencies are shown below, indicating the desired inverse relationship between those frequencies and DsRed reporter levels.

FIG. 2 depicts the schematics of a classifier circuit. FIG. 2A shows an abstract network diagram for sensing HeLa-low microRNA, whereby an output is directly targeted for degradation by the marker. FIG. 2B depicts a detailed circuit diagram for sensing HeLa-low markers. Output mRNA is knocked down by a corresponding marker via a target sequence fused in this mRNA 3'-UTR. DNA and RNA species are indicated. FIG. 2C shows a coherent type 2 feed-forward motif for sensing HeLa-high microRNAs that enables output expression by down-regulating a repressor (i.e., 'double-inversion' module). The microRNA effect was amplified by targeting a repressor R and an auxiliary activator Act that regulates repressor expression. FIG. 2D depicts a detailed circuit diagram for a HeLa-high marker sensor. DNA and RNA species are lumped together, with transcriptional regulation occurring at the DNA level and posttranscriptional regulation by microRNAs occurring at the mRNA level, respectively. The genes, their promoters and microRNA targets used in module construction are indicated. FIG. 2E depicts a representative schematic of a complete classifier circuit. For simplicity, four adjacent microRNA target sites are shown as a wider box and DNA and RNA species are lumped together as in FIG. 2D. Two double inversion modules for HeLa high markers are shown and rtTA crosstalk is indicated with dotted lines. Sensors for HeLa-low markers are fused in tandem into the 3'-UTR of the output gene. The logic computed by this classifier circuit is shown. FIG. 2F depicts how, in some embodiments, the circuit of FIG. 2E can be modified to result in apoptotic output production. For example, DsRed output is replaced with a gene for hBax protein, and LacI protein in the double-inversion modules is co-translated with an hBax inhibitor bcl2 using a 2A linker (only one LacI construct is shown). hBax and bcl2 are in some embodiments counter-regulated by the circuit such that residual hBax in the OFF state is inhibited by highly-expressed bcl2, implementing an additional safety mechanism.

FIG. 3 depicts extensive validation of a classifier circuit's logic operation. FIG. 3A shows that four versions of the circuit with specific microRNA regulatory links interrupted (denoted by stars) can be used to emulate the various combinations of microRNA input levels. Specifically, in order to emulate low miR-21 and miR-17-30a levels, the target sites for both those markers were eliminated from the circuit, resulting in a modified configuration denoted as T17-30a (−) T21 (−). Target elimination disrupts RNAi even with highly-expressed markers, and therefore is equivalent to including the correct targets in the circuit but with markers not expressed. The other three base cases for HeLa-high markers are also shown, indicating which links were interrupted in the circuit variants. To measure the operation of each of the above variants under high levels of miRs 141, 142(3p) and/or 146a, commercial microRNA mimics were transfected into HeLa cells as appropriate. FIG. 3B shows output values measured for all 32 input combinations (Tables 53 and 54 describe the constructs and experimental conditions). DsRed fluorescent protein is the output and AmCyan protein serves as a transfection marker. The images are overlays of DsRed and AmCyan channels taken ~48 h posttransfection. The bar charts show mean±SD of normalized DsRed intensity obtained from three independent replicates measured by fluorescence-activated cell sorting (FACS) ~48 h post-transfection.

FIG. 4 depicts an optimized sensor configuration for HeLa-high markers. rtTA activates expression of a LacI-miR-FF4 pre-mRNA that is spliced to produce LacI mRNA further translated into LacI repressor, and miR-FF4 microRNA that target the output transcriptionally and posttranscriptionally, respectively. HeLa-high marker miR-X targets rtTA and LacI mRNA but not the intron-encoded miR-FF4. Detailed implementation showing individual DNA and RNA species and a proposed mechanism of operation are shown. The inset depicts a simplified network diagram of a sensing process.

Figure 11:
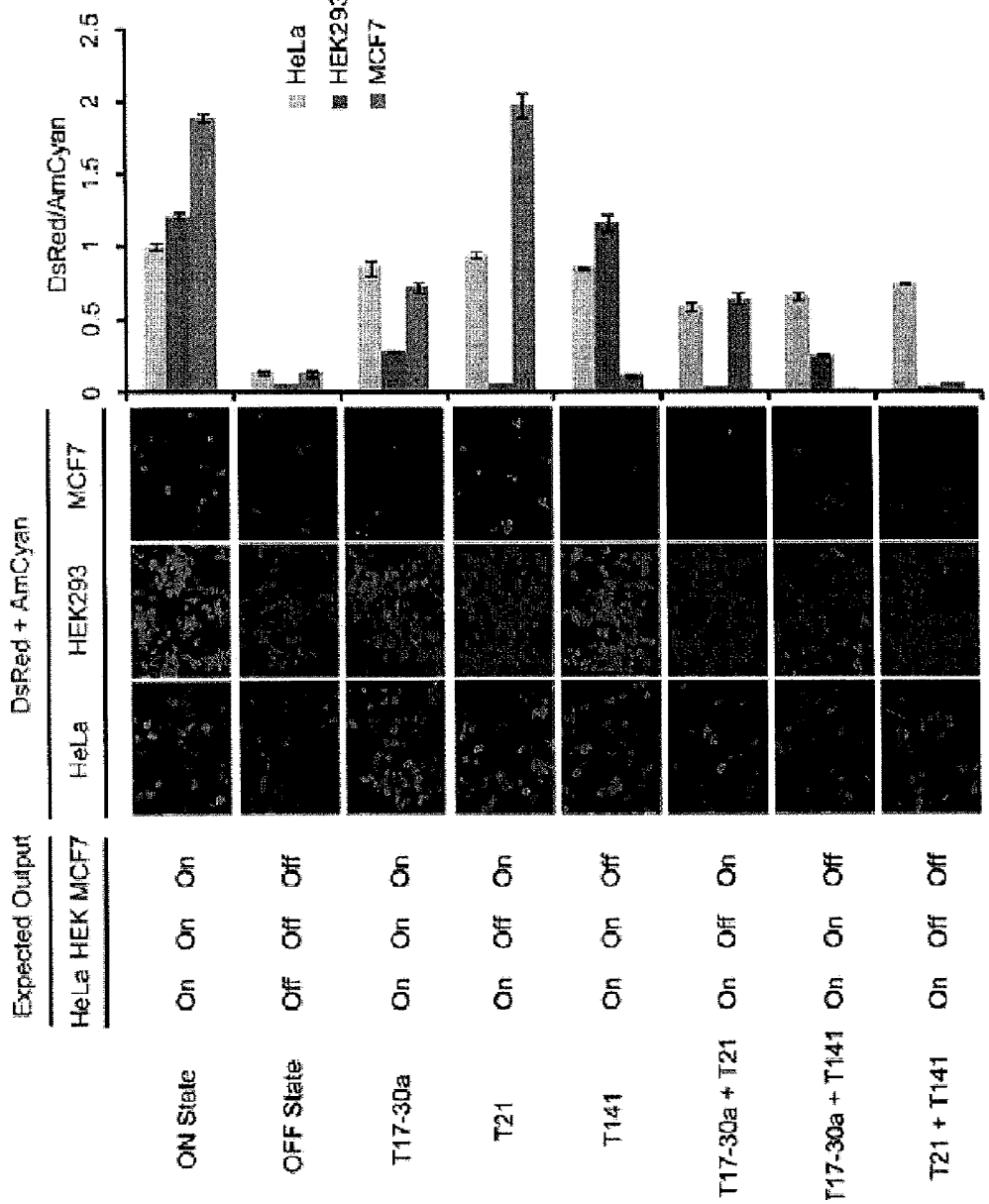
FIG. 11 shows an operation of partially-assembled circuits in HeLa, HEK293 and MCF7 cell lines. Transfection protocol is described in Table 58. ON State, no repression of DsRed output; OFF state, constitutive repression on DsRed output; T17-30a, only sensor for miR-17-30a is used; T21, only sensor for miR-2 1 is used; T1 41, only sensor for miR-141 is used; "+" represents a combination of sensors. The bar charts show mean±SD of DsRed/AmCyan values from three independent replicates measured by FACS ~48 h posttransfection. All DsRed/AmCyan values are normalized to that of HeLa cells at the ON state. Images are overlays of DsRed and AmCyan channels taken ~48 h post-transfection.

FIG. 5 shows that a classifier circuit can be used to distinguish and specifically kill HeLa cells. Plasmids encoding the circuits and transfection protocols are provided in the tables. Fluorescent reporter assays are shown in FIGS. 5A and 5B. FIG. 5A shows schematics of the circuits and controls. O1, CAGop-driven DsRed with target sites for HeLa-low microRNAs (miRs-HeLa-low). O2, CAGop-driven DsRed without microRNA target sites. R1, CAGop-driven DsRed constitutively repressed by rtTA-activated LacI and engineered intronic miR-FF4 with HeLa-low targets. R2, similar to R1 but without the HeLa-low targets. C1, full classifier circuit. C2, circuit variant without HeLa-low targets. Experiments with O2 and R2 constructs in HeLa and HEK293 cells do not provide any additional information due to the lack of specific RNAi by HeLa-low microRNAs in those cells (FIG. 1D and FIG. 11). FIG. 5B shows experimental results from a classifier circuit used to distinguish and kill HeLa cells. In addition to the circuits and controls (FIG. 5A) the cells were also transfected with marker CAG-AmCyan. The constructs used in each case are indicated on the X-axis. Each bar represents the mean±SD of DsRed/AmCyan value with three independent replicates measured by FACS 48 h post-transfection. All values are normalized to constitutive output level (O1) in HeLa cells. Representative images of the cell culture obtained in these experiments are overlays of the DsRed and AmCyan channels captured 48 h post-transfection. The constructs used are indicated above the images. FIGS. 5C and 5D show apoptosis assays in HeLa (5C) and HEK293 (5D) cell lines. The CAG-AmCyan transfection marker indicates cell survival. AmCyan$^+$ fraction, the percentage of AmCyan-positive cells gated using untransfected cells as a reference, was measured 4 days post-transfection by FACS. The percentage of AmCyan$^+$ cells in the absence of cell death ('No cell death') was measured by co-ransfecting the cells with constitutive DsRed-expressing control (O1). The number of AmCyan$^+$ cells surviving after maximal induction of hBax was measured by co-transfecting an hBax-expressing version of O1 ('hBax-Tgts'). A complete apoptosis-inducing classifier circuit ('Circuit', FIG. 2F) was co-transfected with the AmCyan marker to determine cell survival due to selective hBax activation. Each bar in the charts represents the mean±SD of the percentage of AmCyan$^+$ cells with three independent replicates measured by FACS 4 days post transfection. The histograms compare gated AmCyan$^+$ populations obtained in FACS measurements from pooled replicas after examining equal number of events in the different pools. FIG. 5E shows a comparison of circuit killing efficiency for two cell lines.

FIG. 6 shows fluorescent reporter assays and killing experiments in cell mixtures. Transfection protocols are listed in Table 57. FIG. 6A shows fluorescent reporter assays. The scheme on the left illustrates experimental set-up and data analysis. The histograms on the right show contribution of the two cell types, HeLa and HEK-Cerulean, to the DsRed$^+$ cell population. The inset shows the fraction of DsRed$^+$ cells either transfected with the circuit or with constitutively-repressed output, relative to the constitutively expressed output for each cell type. The classifier circuit used here is able to identify most transfected HeLa cells in the mixture, while most transfected HEK293 cells are not classified as HeLa (especially after normalizing to fully-repressed DsRed transfection). FIG. 6B shows apoptotic assays in a cell mixture. The scheme at the top of the panel illustrates experimental set-up and data analysis. The scatter plots at the bottom show the contributions of the HeLa-EYFP and HEK293-Cerulean cells to the DsRed$^+$ cell population considered to be surviving cells. The bar chart shows the fraction of surviving cells either transfected with the circuit or with the constitutively-expressed hBax, relative to the number of DsRed$^+$ cells measured without hBax for each cell type. In the cell mixture experiment using a classifier circuit, the classifier circuit is almost as efficient in killing HeLa cells as constitutive hBax expression, while at the same time the HEK293 cell population survives transfection by apoptosis-inducing classifier much better than the HeLa cell population.

Figure 7:
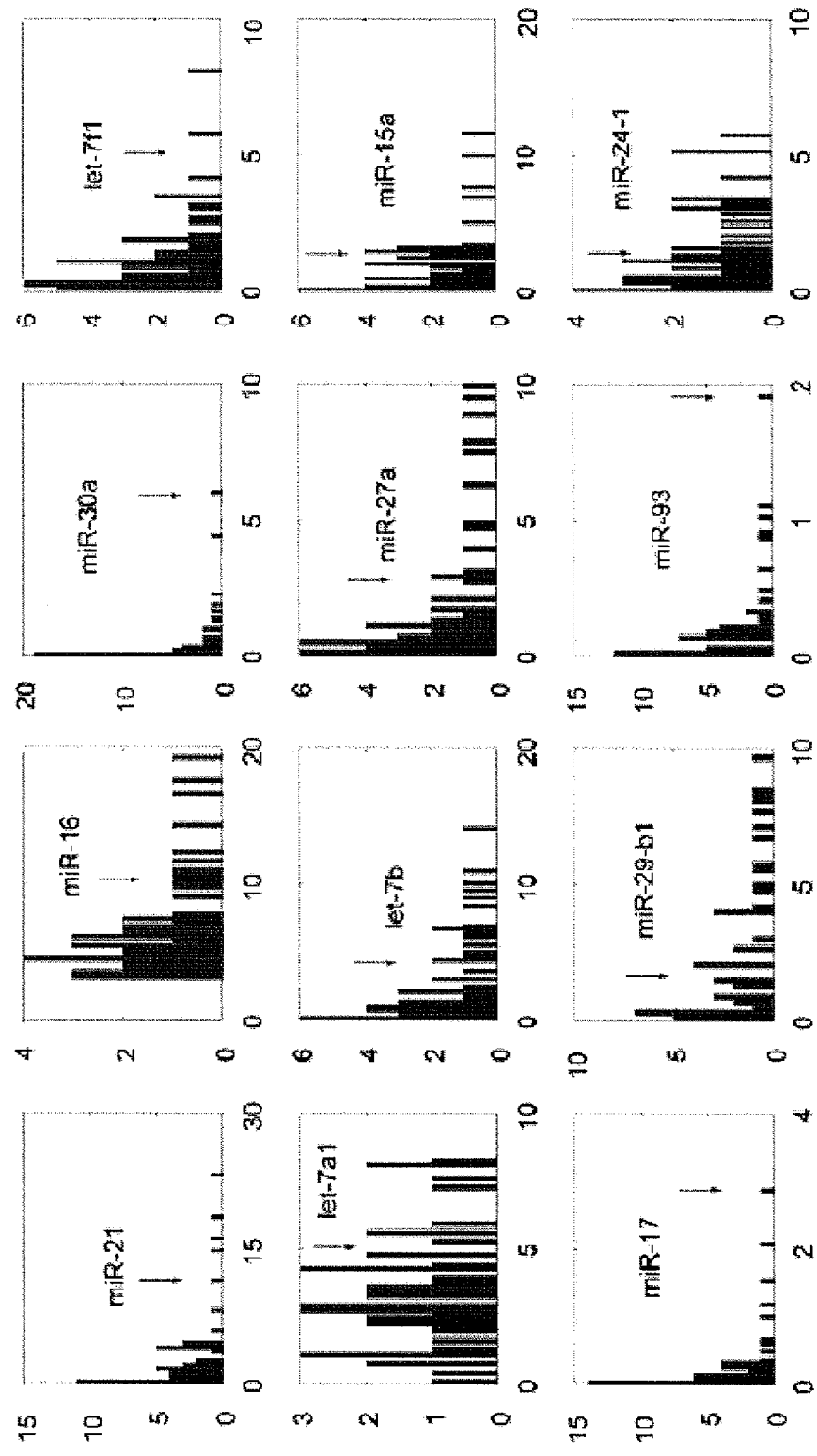
FIG. 7 depicts initial marker screening. Expression histograms for the top 12 HeLa microRNAs, ranked in descending order according to their cloning frequency (CF). Expression levels in HeLa cells are indicated by an arrow in each histogram. Horizontal axes show cloning frequency in percent units.

Analysis of a Classifier Circuit Operation in an Analog Regime and Determination of HeLa-Specific microRNA Profile In order to determine a HeLa reference profile, expression data from the microRNA Atlas was analyzed (51). We first searched for 'HeLa-high' microRNAs expressed at high levels in HeLa cells (so that they can be efficiently detected by the sensors), but not expressed in the majority of other tissues (FIG. 7). Of the markers considered, miR-21, miR-30a, let-7f1 and miR-17 represented good candidates for inclusion in the profile due to a combination of both properties. We decided to include miR-21 in the profile due to its exceptionally high expression level based on the cloning frequency estimates (51).

Figures 8A, 8B, 8C, 8D:
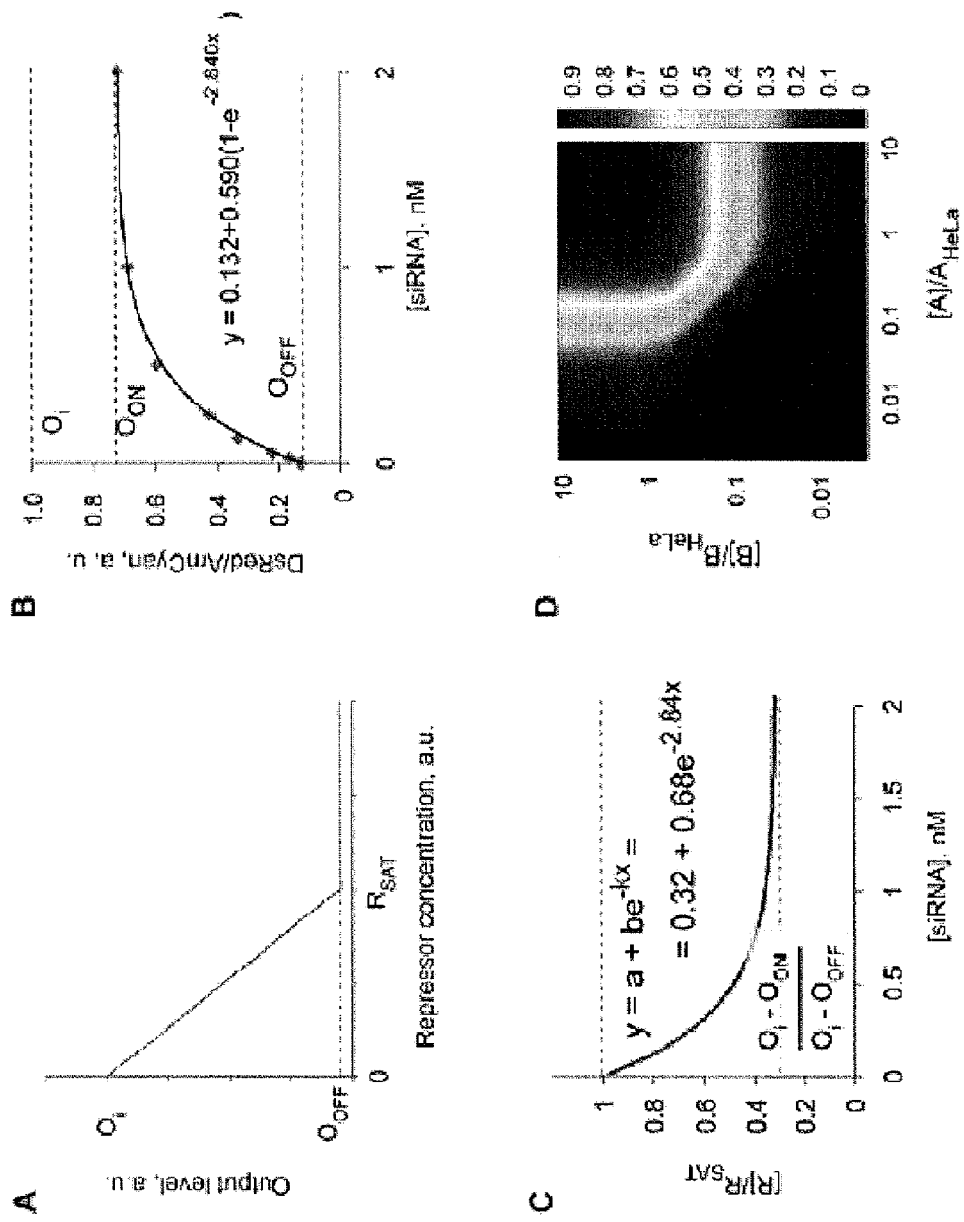
FIGS. 8A-8G depict a circuit performance analysis and profile determination.
Figures 8E, 8F, 8G:
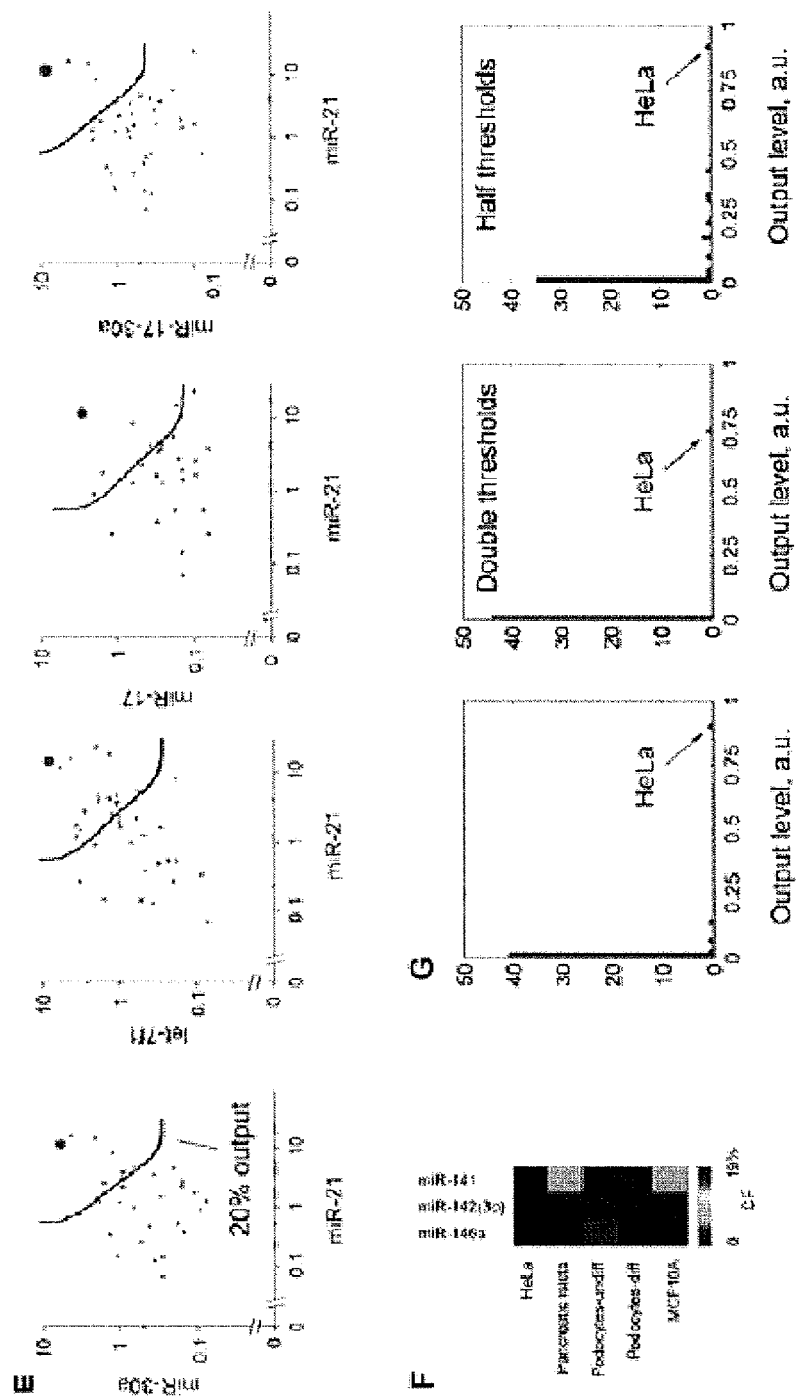
Figures 9A, 9B:
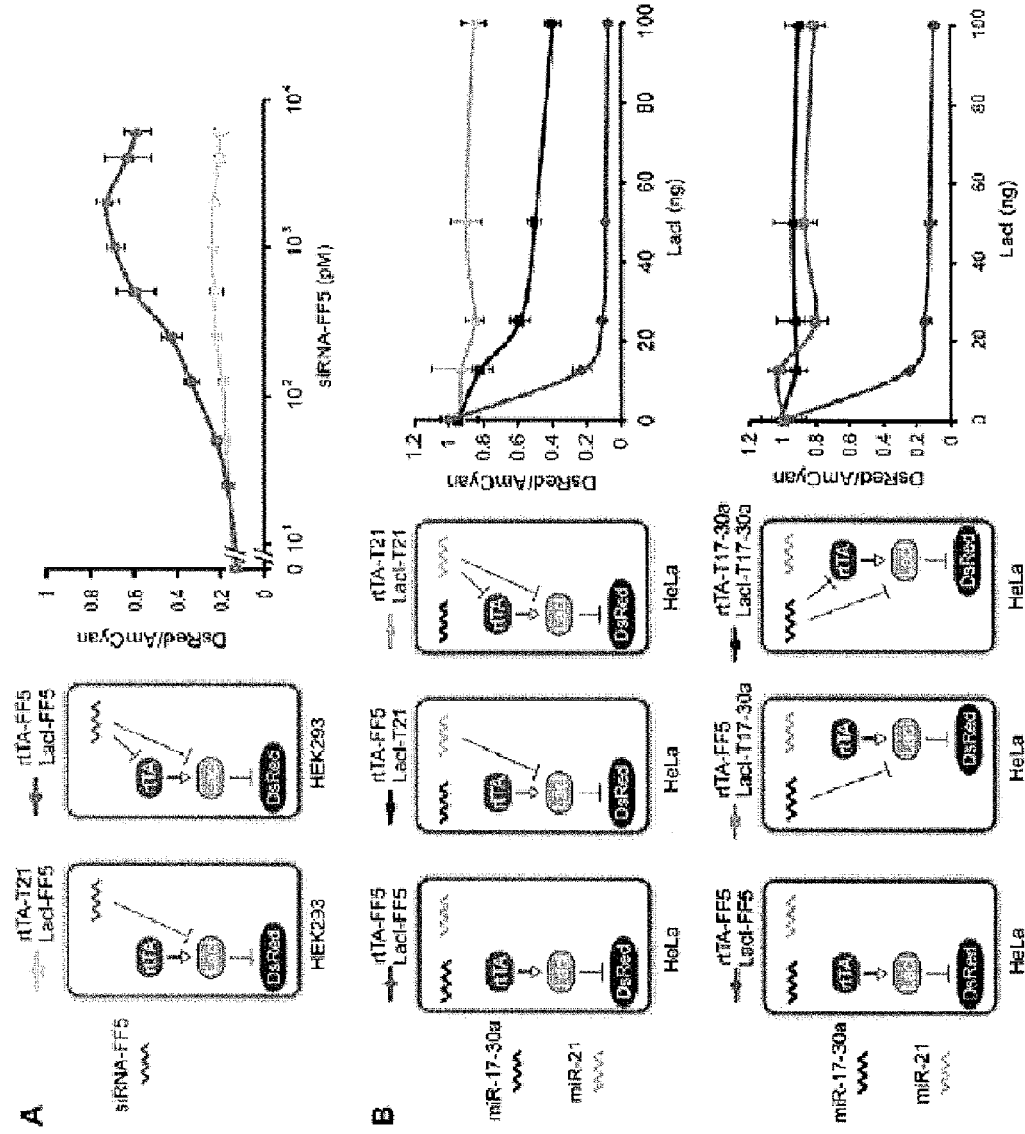
FIGS. 9A-9C show optimization of sensors for highly expressed markers. Transcriptional activator rtTA and repressor LacI are fused to indicated targets for either exogenous siRNA-FF5 or endogenous microRNAs. FF5, target for siRNA-FF5; T21, target for miR-21; T17-30a, targets for miR-17 and 30a. Left panels show the schematics of different sensor variants. Charts on the right show quantitative results measured by FACS 48 h post-transfection.

To determine which candidate markers besides miR-21 should be included in the profile, the relationship between increasing HeLa-high microRNA input concentrations and increasing circuit output needed to be described. This increase is brought about by the corresponding 'double-inversion' sensor module's decreasing capacity to repress the output. We measured the dose-response curve of this module (FIG. 2D, a version without miR-FF4 intron) by constructing a sensor for an engineered siRNA (siRNA-FF5), transfecting different concentrations of siRNA-FF5 as a proxy for endogenous microRNA input, and observing the levels of CAGop-driven DsRed reporter output (FIG. 9A). In order to incorporate this dose response into our analysis, we make two simplifying assumptions about the 'double-inversion' module. First, we approximate output response to the intracellular concentration of the module's repressor R as a linear decrease up to a point where repression is maximal, and by a constant output level at repressor concentrations above this saturation point ('leakage', or OFF level):

$$O([R]) = \begin{cases} O_{OFF}, & \text{if } [R] > R_{SAT} \\ O_{OFF} + (O_i - O_{OFF})\left(1 - \frac{1}{R_{SAT}}[R]\right) & \text{if } [R] \leq R_{SAT} \end{cases} \quad (1)$$

where $O_i$ is the unrepressed output level, $O_{OFF}$ is the leakage, $O([R])$ is the observed output in the presence of a repressor at a concentration $[R]$, and $R_{SAT}$ is the repressor saturation concentration (FIG. 8A). Second, we assume that for a given module the initial repressor concentration used in the circuit is fine-tuned to be close to its saturation point RSAT. Under these two assumptions, we can use the siRNA input dose response to derive the dose response of the 'double-inversion' module's repressor R to siRNA input A:

$$O([A])=O_{OFF}+(O_{ON}-O^{OFF})(1-e^{-k[A]}) \quad (2)$$

where $O_{OFF}$ is the same as above, i.e., promoter leakage in the absence of siRNA input, $O_{ON}$ is the maximal output measured in the presence of saturating siRNA input such that $O_{ON} \leq O_i$, [A] is the siRNA input concentration and k is a constant (FIG. 8B).

From eq. (1) we deduce how repressor levels depend on the output levels by deriving an inverse function, under the assumption that the repressor in a single module is never above the saturation point $R_{SAT}$:

$$\frac{R(O)}{R_{SAT}} = \frac{O_i - O}{O_i - O_{OFF}} \quad (3)$$

where O is the observed output level and R(O) is the inferred repressor level corresponding to this output.

We now substitute eq. (2) into eq. (3) and derive a dependency of the normalized repressor activity on siRNA levels, which is assumed to apply for microRNA as well:

$$\frac{R([A])}{R_{SAT}} = \frac{O_i - O_{ON}}{O_i - O_{OFF}} + \frac{O_{ON} - O_{OFF}}{O_i - O_{OFF}} e^{-k[A]} \equiv a + be^{-k[A]} \quad (4)$$

with $a = \frac{O_i - O_{ON}}{O_i - O_{OFF}}$ and $b = \frac{O_{ON} - O_{OFF}}{O_i - O_{OFF}}$

[A] is the siRNA concentration and the rest of the terms have been defined previously. We calculate this curve using the data measured with siRNA-FF5 and find that a=0.32, b=0.68 and k=-2.84. This siRNA-FF5 sensor exhibits somewhat high output leakage $O_{OFF}$ in the absence of input and fails to fully relieve repression for saturating input. We describe the ratio between the output observed at sensor saturation and the maximally-possible output by a parameter we call 'yield' or Y, with $Y=O_{ON}/O_i$. While it is desirable to have both parameters optimized such that $O_{OFF}=0$ and Y=1, reducing the leakage is a top priority because high leakage levels will cause mis-classification and mis-actuation by the circuit. We performed extensive tuning of the double-inversion module and among other things introduced posttranscriptional repression by engineered intronic microRNA FF4 in order to dramatically reduce this parameter, resulting in $O_{OFF} \approx 0$ (FIGS. 4, 5A and 10). When $O_{OFF}=0$, the repressor dependency on the input becomes $$\frac{R([A])}{R_{SAT}} = \frac{O_i - O_{ON}}{O_i} + \frac{O_{ON}}{O_i} e^{-k[A]} = (1-Y) + Ye^{-k[A]} \quad (5)$$

Setting the value of Y aside for a moment, we focus on the response parameter k which shows how quickly the sensor responds to changing input levels. We set the value of the response parameter by requiring that the repression be relieved to a pre-determined extent α (α<1), when marker A is present at concentrations observed in HeLa cells($A_{HeLa}$). The resulting repression level would then be 1−αY instead of the theoretical limit 1−Y. We solve this equation and obtain:

$$(1-Y) + Ye^{-k_A[A_{HeLa}]} = 1 - \alpha Y \quad (6)$$

$$Ye^{-k_A[A_{HeLa}]} = (1-\alpha)Y$$

$$e^{-k_A[A_{HeLa}]} = (1-\alpha)$$

$$k_A = -\frac{\ln(1-\alpha)}{A_{HeLa}} = -\frac{\ln(1-\alpha)}{A_\alpha}$$

where Aα is a general notation for the marker level resulting in repression relief of α (in percent units). This derivation shows that the value of k does not depend on sensor yield.

Having constructed the dose response function of individual sensors, we proceeded to construct the response function of a composite circuit with two sensors. In one classifier circuit, two sensor modules converge at the expression of transcriptional protein repressor LacI and posttranscriptional microRNA repressor miR-FF4 (whose combination is denoted as 'repressor' from here on, FIG. 2E and FIG. 4), and generate a combined repressor level in the absence of both HeLa-high markers that is double the amount needed for full repression. A single input marker present at intermediate levels in non-HeLa cells can reduce the contribution of its corresponding module to the combined repressor level, but an increase in circuit output will only be observed when repressor level decreases below the amount needed for full repression, or $R_{SAT}$. There are many combinations of intermediate marker levels that do not lead to measurable output, and there are input combinations that lead to partial increase in output. In order to estimate composite circuit response to varying input levels, we make a simplifying assumption that the 'double-inversion' modules act additively on the output. In practice, our modules are not fully insulated because the activator component rtTA of each module can also regulate the repressor component of the other module. This causes each module in a composite circuit to generate more repressor than would be anticipated were this module operating alone, resulting in more input combinations that do not trigger output formation. Hence, the following conservative analysis underestimates the total repressor levels and overestimates output levels for any input combination.

In a two-sensor configuration where the sensors for markers A and B have identical yields Y and response parameters kA and kB, input combinations that do not trigger output expression satisfy inequality (7):

$$\frac{R_{tot}}{R_{SAT}} = \frac{[R_A] + [R_B]}{R_{SAT}} =$$

$$\frac{R_A([A]) + R_B([B])}{R_{SAT}} = (1-Y) + Ye^{-k_A[A]} + (1-Y) + Ye^{-k_B[B]} \geq 1$$

$$e^{-k_A[A]} + e^{-k_B[B]} \geq 2 - \frac{1}{Y}$$

Since Y≤1 and $e^{-kx}$ is a monotonously decreasing function, more input combinations will not trigger output expression with decreasing Y. In reality Y is strictly less than 1, and by assuming Y=1 we perform a conservative estimation of those combinations and false positive circuit classification. We estimate the values of the parameter k by requiring that 99% of the repression be relieved by a marker level in the cell type we are interested in classifying, that is, $A_{HeLa}=A_{99}$ and $B_{HeLa}=B_{99}$ in our case. Substituting these values into eq. (6) gives $$k_A = -\frac{\ln(1-0.99)}{A_{HeLa}} = -\frac{\ln(0.01)}{A_{HeLa}} \quad (8)$$

$$k_B = -\frac{\ln(1-0.99)}{B_{HeLa}} = -\frac{\ln(0.01)}{B_{HeLa}}$$

We can now estimate the output generated by a classifier for any two input combinations in terms of their '99%' concentrations, substituting eq. (7) into eq. (1):

$$\frac{O}{O_i} = \begin{cases} 0 & \text{if } e^{-k_A[A]} + e^{-k_B[B]} \geq 1 \\ \left(1 - e^{-\ln(0.01)[A]/A_{HeLa}} - e^{-\ln(0.01)[B]/B_{HeLa}}\right) & \text{if } e^{-k_A[A]} + e^{-k_B[B]} < 1 \end{cases} \quad (9)$$

A contour plot of this function is shown in FIG. 8D. It shows input combinations where the output levels are low and do not depend on the inputs, and a general AND-like behavior with high output levels obtained only when both inputs are high.

Using the above function, we evaluated the performance of various HeLa-high marker pairs with respect to their selectivity toward HeLa cells. For this we carefully examined the number of non-HeLa cells that have undesirably high classifier output levels of at least 20% compared to the classifier output in HeLa cells. Note that this performance reflects and intermediate circuit architecture with only two sensors for HeLa-high markers. We describe in detail below how a fully-assembled circuit with more inputs improves this performance significantly. To compute expected output levels in different cell lines for different marker pairs, we first calculate the sensors' response parameter k for different candidate markers. We use equation (8) and the markers' expression levels in HeLa cells and calculate the following k values:

$k_{miR-21}=0.399$, $k_{miR-30a}=0.767$, $k_{let7f1}=0.795$ and $k_{miR-17}=1.588$ We then solve the equation $$\frac{O}{O_i} = 0.2 = (1 - e^{-k_A[A]} - e^{-k_B[B]}) \quad (10)$$

$$e^{-k_A[A]} + e^{-k_B[B]} = 0.8$$

to estimate combinations of input values that result in 20% output activation. These 'contour lines' are overlaid with the observed microRNA levels in different cell types as shown in FIG. 8E. Cells above this line are likely to generate more than 20% output and cause false-positive classification with a two-input classifier. The first three diagrams examine marker pairs miR21/miR-30a, miR-21/let-7f1 and miR-21/miR-17. Using miR-17 results in a small number of false-positive cell classifications, but we reasoned that its low absolute expression level can require overly challenging sensor optimization. MiR-30a also results in a few false-positives, while the use of let-7f1 results in too many false-positives. Note, however, that simple arithmetic addition of markers miR-30a and miR-17 into a single compound marker (miR-17-30a, kmiR-17-30a=0.5 16) reduces the number of false-positives compared to using miR-21 with miR-30a alone. This pairing also has the advantage of higher absolute expression in comparison to miR-21/miR17. The four cell types with high classifier output using a combination of miR-21 and miR-17-30a are MCF10 cells, pancreatic islets and differentiated and undifferentiated Moins podocytes.

Next we searched for markers highly-expressed in these four false-positive cell lines and unexpressed in HeLa cells (FIG. 8F). We found that adding miR-141 as a marker to the profile excludes MCF10 and pancreatic islets from misclassification, and miR-146a excludes differentiated podocytes. The latter is also modestly expressed in undifferentiated podocytes. We reasoned that this marker alone can not be enough to exclude undifferentiated podocytes from misclassification and added another modestly-expressed marker miR-142(3p). Marker miR142(3p) is an especially good candidate because it is also highly expressed in more than half of all healthy cell types, increasing the robustness of the molecular profile. This collection of markers results in reference profile that uniquely identifies HeLa cells using "HeLa-high markers: miR-21, miR-17-30a; and HeLa-low markers: miR-141, miR-142(3p), miR-146a", which can be described by a logic function
miR-21 AND miR-17-30a AND NOT(miR-141) AND NOT(miR-142(3p)) AND NOT(miR-146a)

We then analyzed how well this profile classifies HeLa cells. First, we estimated dose response behavior for HeLa-low markers. The response function of a sensor directly incorporated into the output mRNA is described by exponential decay (2):

$$O([X])=O_{OFF}+(O_i-O_{OFF})e^{-k[X]} \quad (11)$$

where $O([X])$ is the output obtained with input concentration $[X]$, $O_i$ is the original output level and $O_{OFF}$ is the residual output level at maximal knock-down. With our sensors we observed very efficient knock-down and hence assume that $O_{OFF}=0$. Similarly to our treatment of HeLahigh marker sensors, we require that a HeLa-low marker result in 99% of theoretically possible knock-down at levels observed in cell types whose mis-classification should be avoided. If the same marker is used to exclude a number of cell types, its lowest expression among these cells should set the value of the response parameter. For example, miR-141 is used to exclude pancreatic islets and MCF10, but its cloning frequency (CF) is 5.7 in the former and 13.3 in the latter. Accordingly, 99% repression should be observed with 5.7% CF; for simplicity we set this value to 5, which results in sensor parameter $k_{miR-141}=0.921$ Similarly, for miR-146a the threshold is about 3% CF. Since miR-142(3p) is used mostly as a 'robustness' marker, we set its 99% knockdown value arbitrarily to 3% CF. Therefore $k_{miR-146a}=k_{miR-142(3p)}=1.535$ With these parameter values for different sensors, we proceed to estimate the functional form of the full multi-sensor integration. To assess the improvement of the circuit performance due to the HeLa-low marker sensors for miR-141, miR-142(3p) and miR-146a (denoted C, D and E below to shorten the notation), we first approximate that the sensors' individual knock-down contributions combine to act as a product:

$$O([C],[D],[E])=O_i e^{-k_C[C]} e^{-k_D[D]} e^{-k_E[E]} = O_i e^{-(k_C[C]+k_D[D]+k_E[E])} \quad (12)$$

We combine this dependency with the effect of HeLa-high sensors to obtain the following mapping of the five inputs to the circuit output:

$$O = \begin{cases} 0 & \text{if } e^{-k_A[A]} + e^{-k_B[B]} \geq 1 \\ \left(1 - e^{-k_A[A]} - e^{-k_B[B]}\right) e^{-(k_C[C]+k_D[D]+k_E[E])} & \text{if } e^{-k_A[A]} + e^{-k_B[B]} < 1 \end{cases} \quad (13)$$

where A and B represent miR-2 1 and miR-1 7-30a, respectively. For our specific classifier circuit we obtain equation 14:

$$O_i = \begin{cases} 0 & \text{if } e^{-0.39[A]} + e^{-0.52[B]} \geq 1 \\ \left(1 - e^{-0.39[A]} - e^{-0.52[B]}\right) e^{-(0.92[C]+1.54[D]+1.54[E])} & \text{if } e^{-0.39[A]} + e^{-0.52[B]} < 1 \end{cases}$$

With this function, we calculate the anticipated output in each cell type based on corresponding marker levels. As shown in FIG. 8G, the full classifier provides clear separation between the output in HeLa cells and the rest of the cells. The HeLa classifier output level is 7-fold higher than in the closest cell type USSC-7d (unrestricted somatic stem cells cultured for 7 days), and on average is about 350-fold higher than the rest of the cells.

We emphasize that the response function is sensitive to parameter values. For example, if we choose the input values resulting in 99% repression relief for the highly-expressed markers to be twice their level in HeLa cells (as opposed to being exactly those levels), the resulting separation between HeLa and the rest of the cell types improves dramatically. However, if 99% relief occurs at half the original values, the significant separation between the cell types disappears (FIG. 8G, 'Half thresholds' histogram). This effect is intuitive, because if the sensors respond too quickly to low input values, in many cell types inputs are transduced into full (false-positive) activation of the sensor. Another factor that will affect the response is the total number of double inversion modules, because the excess repressor level will grow with their increasing number making it increasingly more difficult for the circuit to trigger mis-classification with intermediate inputs.

The operation of the circuit as a reliable system that takes in analog input marker values and produces digital ON:OFF output values for a given set of cell types requires that the sensors' response curves separate effectively between the values observed in the cell type of interest and the values observed in most other cell types. In a sense it suggests that in designing the sensors it is preferable to err on the higher side of the parameter values, i.e., make them saturate slower rather than faster. In our experiments we observed that it is generally not trivial to make sensors respond quickly to low microRNA levels, and we chose highly-expressed markers in the first place. Therefore, while we did not explicitly tune the parameter k for the sensors and instead focused on optimizing the end points of the curves to achieve robust ON:OFF ratios, we speculate that out particular sensors are not overly sensitive, complying with the above conclusion.

Optimization of Sensors for HeLa-High microRNA Markers

We implement a coherent type 2 feed-forward motif in the sensors for HeLa-high microRNA markers by fusing microRNA targets to both PTA activator and PTA-inducible LacI repressor that in turn represses DsRed output (FIGS. 2C and 2D). Therefore, in principle, DsRed level remains low in the absence of microRNA marker, while high microRNA level is expected to relieve the repression and lead to a high level of DsRed output.

We first tested the response of the sensor to different amounts of exogenous siRNA (siRNA-FF5) in HEK293 cells. A target for endogenous microRNA miR-21 (T21) is used as a mock target in this experiment because miR-21 is undetectable by functional assays in HEK293 cells (FIG. 1). As shown in FIG. 9A, when correct targets are present in both rtTA and LacI, the sensor (blue line) shows a robust response to a wide range of siRNA-FF5 concentrations. The ON:OFF ratio reaches ~5.5 fold by comparing the value in each ON state with varying amounts of siRNA-FF5 to that in the OFF state without siRNA-FF5. However, when siRNA-FF5 target is replaced with T21 to disrupt the repression of rtTA by siRNA-FF5, the performance of the mutant sensor (orange line) is dramatically reduced.

Figure 9C:
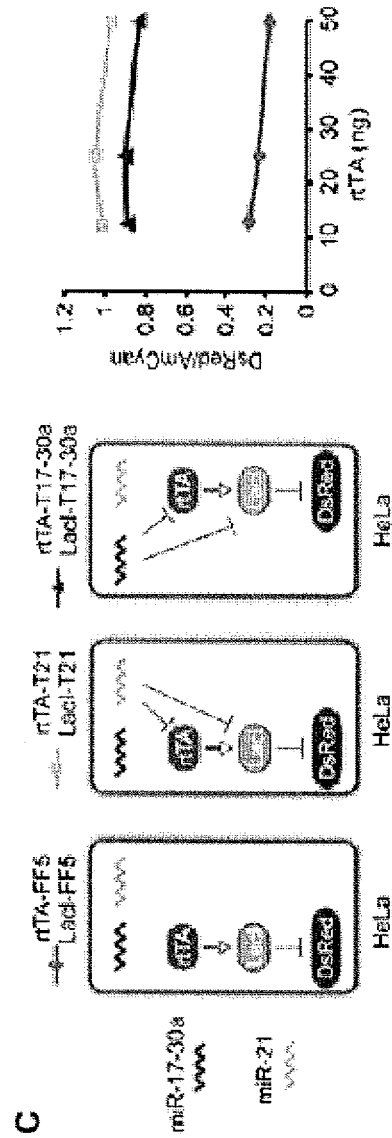

Next we calibrated the miR-21 and miR-17-30a sensors in HeLa cells that express both these markers at high levels by varying the amount of LacI with fixed amount of 50 ng rtTA. Adding FF5 sequences does not affect output expression in HeLa cells (FIGS. 1C and 1D, T-mock) and it is used as a mock target. The results show that the motif with both rtTA and LacI targeted by a microRNA almost doubles the ON:OFF ratio of the miR-21 sensor, but only moderately increases the ON:OFF ratio of the miR-17-30a sensor (FIG. 9B) compared to the motif where rtTA knock-down is eliminated. This difference might be explained by different knockdown efficiency of rtTA and LacI by miR-21 and miR-17-30a, respectively. Based on these results, we determine that the minimum amount of LacI needed for high ON:OFF ratio for both sensors is ~50 ng. Next we measured sensor performance with varying amounts of rtTA (12.5 ng-50 ng) and observed the best ON:OFF ratio with 50 ng of rtTA (FIG. 9C). We decided to use a combination of 40-50 ng rtTA and 40-50 ng LacI for each sensor in all other experiments in this study.

Materials and Methods

Reagents, Enzymes and Small RNAs

Restriction endonucleases, polynucleotide kinase (PNK), T4 DNA ligase and Klenow DNA polymerase (Klenow in what follows) were purchased from New England Biolabs. Shrimp alkaline phosphatase was ordered from Promega. Pfu Ultra II Fusion HS DNA polymerase (Agilent Technologies) and dNTPs (Invitrogen) were used in PCR amplification.

Oligonucleotides were made by Integrated DNA Technologies. Doxycycline was purchased from Clontech. siRNA-FF5 was designed to target a firefly luciferase gene (53), and RNA mimics of the human microRNAs miR-141, miR-142-3p and miR-146a were purchased from Dharmacon RNAi Technologies. Silencer Negative Control siRNA (Ambion) was used as a control that does not target any transcript used in this study.

Plasmid DNA Constructs for Single-Cell microRNA Profiling

When required, equal molar amounts of oligonucleotides were annealed in 1×PNK buffer by heating to 95° C. and gradually cooling down (−1° C. per min) to 37° C., and then 1 μM of annealed product was phosphorylated by 0.5 unit/μL PNK in presence of 0.5 mM ATP (Invitrogen).

All bi-directional constructs were derived from pTRE-tight-BI (Clontech). pAmCyan-TRE-DsRed was cloned by sequentially inserting the AmCyan-containing fragment from pAmCyan-C1 (Clontech) using AgeI and BglII, and the DsRed-Express containing fragment from RNAi-Ready pSIREN-DNR-DsRed Express template (Clontech) using NheI and NotI into pTRE-tight-B pAmCyan-TRE-DsRed2 was cloned by sequentially inserting the DsRed-containing fragment amplified with 5'-TTTGAATTCACCGGTCGC- CACCATGGCC-3'(SEQ ID NO: 811) and 5'-TTTTCCG-GACTACAGGAACAGGTGGTGG-3' (SEQ ID NO: 812) from RNAi-Ready pSIREN-DNR-DsRed Express DNA template and digested using EcoRI and BspEI, and the AmCyan-containing fragment amplified with 5'-TTT-GCTAGCACCGGTCGCCACCATGGC-3'(SEQ ID NO: 813), 5'-TTTGCGGCCGCTTAGAAGGGCACCACG-GAG-3' (SEQ ID NO: 814) from pAmCyan-C1 DNA template and subcloned using NheI and NotI into pTRE-tight-BI.

pAmCyan-TRE-DsRed-FF5, containing 4 repeats of 22-nt mock target FF5 based on firefly luciferase gene (53) in 3'-UTR of DsRed gene, was constructed using a modified cloning protocol. Briefly, equal molar amounts of two pairs of pre-annealed oligonucleotides (5'-GGCCG-CAAAAAGCACTCTGATTTGACAATTAAAGCACTCT-GATTTGACAA-3'(SEQ ID NO: 815) annealed with 5'-CTTTAATTGTCAAATCAGAGTGCTTTAATTGT-CAAATCAGAGTGCTT3' (SEQ ID NO: 816) and 5'-TTAAAGCACTCTGATTTGACAATTAAAGCACTCT-GATTTGACAATTAA-3' (SEQ ID NO: 817) annealed with 5'-AGCTTTAATTGTCAAATCAGAGTGCTTTAATTGT-CAAATCAGAGTG3' (SEQ ID NO: 818) were incubated with 5 units of T4 DNA ligase for 2 h, and then the ligated product was used as the DNA insert for subcloning into pAmCyan-TRE-DsRed using NotI and HindIII.

pAmCyan-TRE-DsRed-T21 harboring 4 repeats of miR-21 targets in 3'-UTR of DsRed gene, was made by inserting the ligated product of two pairs of pre-annealed oligonucleotides (5'-GGCCGCAAATCAACATCAGTCTGATAAGC-TATCAACATCAGTCTGATAAG-3' (SEQ ID NO: 819) annealed with 5'-TGATAGCTTATCAGACTGATGTTGA-TAGCTTATCAGACTGATGTTGATTTGC-3' (SEQ ID NO: 820) and 5'-CTATCAACATCAGTCTGATAAGCTAT-CAACATCAGTCTGATAAGCTAA-3'(SEQ ID NO: 821) annealed with 5'-AGCTTTAGCTTATCAGACTGATGTT-GATAGCTTATCAGACTGATGT-3' (SEQ ID NO: 822) into pAmCyan-TRE-DsRed using NotI and HindIII.

pDsRed-TRE-AmCyan-T17 that contains 4 repeats of miR-17 targets and pDsRed-TRE-AmCyan-T30a that has 4 repeats of miR-30a targets in 3'-UTR of AmCyan gene, were made by inserting the ligated product of two pairs of pre-annealed oligonucleotides (5'-CCGGATAAACTACCTG-CACTGTAAGCACTTTGCTACCTGCACTGTAAGCAC-3' (SEQ ID NO: 823) annealed with 5'-AGCAAAGTGCT-TACAGTGCAGGTAGCAAAGTGCTTACAGTGCAGG-TAGTTAT-3' (SEQ ID NO: 824) and 5'-TTTGCTACCTG-CACTGTAAGCACTTTGCTACCTGCACTG-TAAGCACTTTGA-3'(SEQ ID NO: 825) annealed with 5' GATCTCAAAGTGCTTACAGTGCAGGTAGCAAAGT-GCTTACAGTGCAGGT-3'(SEQ ID NO: 826)) using BglII and BspEI, and the ligated product of two pairs of pre-annealed oligonucleotides (5'-GATCTTAACTTCCAGTC-GAGGATGTTTACACTTCCAGTCGAGGATGTTTACA-3' (SEQ ID NO: 827) annealed with 5'-TGGAAGTGTAAACATCCTCGACTGGAAGTG-TAAACATCCTCGACTGGAAGTTAA-3' (SEQ ID NO: 828) and 5'-CTTCCAGTCGAGGATGTTTACACTTCCA-GTCGAGGATGTTTACAGGCGCGCCT-3'(SEQ ID NO: 829) annealed with 5' CTAGAGGCGCGCCTG-TAAACATCCTCGACTGGAAGTGTAAACATCCTC-GAC-3'(SEQ ID NO: 830)) using BglII and XbaI into pAmCyan-TRE-DsRed, respectively.

pDsRed-TRE-AmCyan-T17-T30a was made by replacing the AmCyan in pDsRed TRE-AmCyan-T30a with AmCyan-T17 from pDsRed-TRE-AmCyan-T17 using EcoRI and BglII.

AmCyan-TRE-DsRed-T17-T30a was made by replacing the entire DsRed-TREAmCyan fragment in pDsRed-TRE-AmCyan-T17-T30a with AmCyan-TRE-DsRed fragment obtained from pAmCyan-TRE-DsRed2 using BspEI and NotI to digest both the recipient and the donor vectors.

pAmCyan-TRE-DsRed-T141 with 4 repeats of miR-141 targets in 3'-UTR of DsRed gene was produced by inserting the ligated product of two pairs of pre-annealed oligonucleotides (5-GGCCGCTAAACCATCTTTACCAGACAGT-GTTACCATCTTTACCAGACAGTGTTA3' (SEQ ID NO: 831) annealed with 5'-AGATGGTAACACTGTCTGG-TAAAGATGGTAACACTGTCTGGTAAAGATGGTT-TAGC3' (SEQ ID NO: 832) and 5'-CCATCTTTACCA-GACAGTGTTACCATCTTTACCAGACAGTGTTAAT-3' (SEQ ID NO: 833) annealed with 5'-CGATTAACACT-GTCTGGTAAAGATGGTAACACTGTCTGGTAA-3' (SEQ ID NO: 834))
pAmCyan-TRE-DsRed using NotI and ClaI.

pAmCyan-TRE-DsRed-T142(3p) with 4 repeats of miR-142(3p) targets in 3'-UTR of DsRed gene was produced by inserting the ligated product of two pairs of pre-annealed oligonucleotides (5'-CGATTCCATAAAGTAGGAAACAC-TACATCCATAAAGTAGGAAACACTA-3'(SEQ ID NO: 835) annealed with 5'-TGGATGTAGTGTTTCCTACTT-TATGGATGTAGTGTTTCCTACTTTATGGAAT-3' (SEQ ID NO: 836) and 5'-CATCCATAAAGTAGGAAACACTA-CATCCATAAAGTAGGAAACACTACAA-3' (SEQ ID NO: 837) annealed with 5'-AGCTTTGTAGTGTTTC-CTACTTTATGGATGTAGTGTTTCCTACTTTA3'(SEQ ID NO: 838)) into pAmCyan-TRE-DsRed using ClaI and HindIII.

pAmCyan-TRE-DsRed-T146a with 4 repeats of miR-146a targets in 3'-UTR of DsRed gene was prepared by inserting the ligated product of two pairs of preannealed oligonucleotides (5'-AGCTTAACCCATGGAATTCAGT-TCTCAAACCCATGGAATTCAGTTCTCAAAC (SEQ ID NO: 839)-annealed with 5'-CCATGGGTTTGAGAACT-GAATTCCATGGGTTTGAGAACTGAATTC-CATGGGTTA-3' (SEQ ID NO: 840) and 5'-CCATGGAAT-TCAGTTCTCAAACCCATGGAATTCAGTTCTCAG-3' (SEQ ID NO: 841) annealed with 5' TCGACTGAGAACT-GAATTCCATGGGTTTGAGAACTGAATT-3'(SEQ ID NO: 842)) into pAmCyanTRE DsRed using HindIII and SalI.

pAmCyan-TRE-DsRed-T141-T142(3p) was produced by replacing the DsRed in pAmCyan-TRE-DsRed-T1 42(3p) with DsRed-T1 41 from pAmCyan-TRE-DsRed-T141 using NheI and ClaI.

pAmCyan-TRE-DsRed-T141-T142(3p)-T146a was prepared by replacing the DsRed in pAmCyan-TRE-DsRed-T146a with DsRed-T141-T142(3p) from pAmCyan-TRE-DsRedT141-T142(3p) using NheI and HindIII.

Circuit Construction pTET-ON-Advanced that contains rtTA activator driven by CMV promoter was purchased from Clontech.

pAmCyan-TRE-rtTA was produced by amplifying the rtTA fragment from the pTETON-Advanced DNA template with 5'-TTGCTAGCACCATGTCTAGACTGGACAAG-3' (SEQ ID NO: 843) and 5'-TTTGCGGCCGCTTAC-CCGGGGAGCATG-3'(SEQ ID NO: 844), and then cloning it into pAmCyan-TREDsRed using NheI and NotI.

prtTA-TRE-DsRed was produced by amplifying the rtTA fragment from the pTETON-Advanced DNA template with 5'-TTTGAATTCACCATGTCTAGACTGGACAAG-3' (SEQ ID NO: 845) and 5'-TTTAGATCTTTAC- CCGGGGAGCATGTCAAG-3'(SEQ ID NO: 846), and then cloning it into pAmCyanTRE-DsRed using EcoRI and BglII.

pAmCyan-TRE-LacI was prepared by amplifying LacI from CMV-LacI-FF4×33 DNA template with 5'-TTGCTAGCGAGGTACCCTCCCAC-3'(SEQ ID NO: 847) and 5'-TTTGCGGCCGCTCAAACCTTCCTCTTCTTC-3' (SEQ ID NO: 848), and then cloning it into pAmCyan-TREDsRed using NheI and NotI.

pDsRed-TRE-LacI was prepared by amplifying LacI from CMV-LacI-FF4×33 DNA template with 5'-TTTGAATTCGAGGTACCCTCCCACCATG-3'(SEQ ID NO: 849) and 5'-TTTAGATCTTCAAACCTTCCTCTTCTTCTTAGG-3'(SEQ ID NO: 850), and then cloning it into pAmCyanTRE-DsRed using EcoRI and BglII.

pAmCyan-TRE-rtTA-FF5 was prepared by subcloning the 4 repeats of the mock target FF5 from pAmCyan-TRE-DsRed-FF5 using NotI and PciI into pAmCyan-TRE-rtTA.

pAmCyan-TRE-rtTA-T21 was prepared by subcloning the 4 repeats of the miR-21 target T21 from pAmCyan-TRE-DsRed-T21 into pAmCyan-TRE-rtTA using NotI and PciI.

pAmCyan-TRE-LacI-FF5 was prepared by subcloning the 4 repeats of the mock target FF5 from pAmCyan-TRE-DsRed-FF5 using NotI and PciI into pAmCyan-TRE-LacI.

pAmCyan-TRE-LacI-T21 was prepared by subcloning the 4 repeats of the miR-21 target T21 from pAmCyan-TRE-DsRed-T21 into pAmCyan-TRE-LacI.

pCMV-rtTA-FF5 was made by subcloning rtTA-FF5 fragment from pAmCyan-TRErtTA-FF5 into pAmCyan-C1 (Clontech) using NheI and HindIII.

pCMV-rtTA-T21 was made by subcloning the rtTA-T21 fragment from pAmCyan TRE-rtTA-T21 into pAmCyan-C1 using NheI and HindIII.

pTRE-LacI-FF5 was prepared by self-ligation of a pAmCyan-TRE-LacI-FF5 vector digested with EcoRI and BglII followed by filling sticky ends with Klenow in the presence of 50.tM dNTPs and gel purification.

pTRE-LacI-T21 was prepared by self-ligation of a pAmCyan-TRE-LacI-T21 vector digested with EcoRI and BglII followed by filling sticky ends with Klenow in the presence of 50.tM dNTPs and gel purification.

pCMV-C1 was made by deleting AmCyan in pAmCyan-C1 with NheI and HindIII followed by filling sticky ends with Klenow and circulization.

pCMV-rtTA-T17-T30a was made according to the following steps. pDsRed-TREAmCyan-T17-T30a was digested with BspEI, sticky ends were filled with Klenow, digested again with EcoRI and gel-purified as the vector backbone. prtTA-TRE-DsRed was digested with BglII, sticky ends were filled with Klenow, digested again with EcoRI and rtTA containing fragment was gel-purified to serve as an insert. The insert was cloned into the above vector backbone using T4 ligase. The resulting construct was digested with AscI, sticky ends were filled with Klenow, digested again with EcoRI and the DNA fragment containing rtTA-T17-30a was gel-purified to serve as an insert. pCMV-C1 was digested with BamHI followed by filling sticky ends with Klenow, then digested again by EcoRI and gel-purified as backbone. The rtTA-T17-30a insert was cloned into the above vector backbone with T4 ligase.

pTRE-LacI-T17-T30a was made according to the following steps. pDsRed-TREAmCyan-T17-T30a was digested with BspEI, sticky ends were filled with Klenow, digested again with EcoRI and the large band was gel-purified to serve as the vector backbone. pDsRedTRE-LacI was digested with BglII, sticky ends were with Klenow, digested again by EcoRI and the LacI containing band was gel-purified as the insert. The insert was cloned into the above vector backbone using T4 ligase. DsRed was removed from pDsRed-TRE-LacI using NheI and HindIII followed by filling sticky ends with Klenow, and the vector backbone was self-ligated using T4 ligase.

pCAGop-DsRed was produced according to the following steps. Neo-FF6 in pCAGopNeo-FF6 (54) was replaced with ZsYellow from pZsYellow-C1 (Clontech) using NheI and MluI enzymes, making pCAGop-ZsYellow. DsRed from pAmCyan-TRE-DsRed was subcloned into pCAGop-ZsYellow using NheI and HindIII enzymes, producing pCAGop-DsRed.

pCAGop-DsRed-FF5 was prepared by inserting DsRed-FF5 from pAmCyan-TREDsRed-FF5 into pCAGop-DsRed using NheI and HindIII enzymes.

pCAGop-DsRed-T141-T142(3p)-T146a was prepared according to the following steps. pCAGop-DsRed-FF5 was digested with HindIII, sticky ends were filled with Klenow, digested again withNheI and the large band was gel-purified as the vector backbone. pAmCyan-TREDsRed-T141-T142(3p)-T146a was digested by SalI, sticky ends were filled with Kleno and digested again by NheI. DsRed-containing band was gel-purified to serve as the insert. The insert was cloned into the above vector backbone using T4 ligase.

pCAG-DsRed-FF5 containing DsRed-FF5 driven by CAG promoter (55), was made by first subcloning the CAGop promoter containing LacO sites in the 5'-UTR downstream of the CAG promoter into a cloning vector pUBI-linker-NOS containing the f1 filamentous phage origin of replication (56), producing pCAGop. Then two LacO sites in 5'-UTR downstream of the CAG promoter in pCAGop were deleted using 5'-GAAGCGCGCGGCGGGCGGGAGTCGAGTCGCTGCGTTGCCTTCGCC-3'(SEQ ID NO: 851) as described (57), resulting in pCAG. Lastly, CAGop promoter in pCAGop-DsRed-FF5 was replaced with the CAG promoter from pCAG using PacI and NheI, producing the desired construct pCAG-DsRedFF5.

pCAG-AmCyan reference construct was made by replacing DsRed-FF5 in pCAGDsRed-FF5 with AmCyan in pAmCyan-TRE-DsRed2 using NheI and HindIII. pCMV-Brainbow-1.1 containing EYFP and Cerulean (58) was purchased from Addgene. pCAG-EYFP was produced, first, by digesting pCMV-Brainbow-1.1 with BamHI and gel-purification of the 1 140-bp DNA fragment containing EYFP. EYFP was PCR-amplified using the above gel-purified DNA template using primers 5'-TTTGCTAGCTTACCGGTCGCCACCATGGTGAGCAAG-3' (SEQ ID NO: 852) and 5'-TTAAAGCTTTGCGGCCGCTTACTTGTACAGCTCGTCCATGCCG-3' (SEQ ID NO: 853), and used to replace DsRed-FF5 in pCAG-DsRed-FF5 by using NheI and HindIII.

Circuit Optimization Constructs pTRE-LacI-T17-T30a-miR-FF4, a LacI repressor gene fused with a microRNAcontaining intron, was prepared by amplifying a microRNA FF4-containing intron from pRheoAmCyan-miR-FF4 (54) as the DNA template with 5' TTTGGCGCGCCGAGGTGAGTATGTGCTCGC-3'(SEQ ID NO: 854) and 5'-TTTTCTAGACCCTGAGGAAAAAAAAGGAAACAATTG-3'(SEQ ID NO: 855), and then subcloning the amplicon downstream of LacI-T17-T30a using AscI and XbaI.

pTRE-LacI-FF5-miR-FF4 and pTRE-LacI-T21-miR-FF4 were prepared similarly by amplifying the miR-FF4-containing intron from pRheo-AmCyan-miR-FF4 using 5'-TTTAAGCTTGAGGTGAGTATGTGCTCGCTTCG-3' (SEQ ID NO: 856) and 5'-TTTGTCGACCCCTGAG-GAAAAAAAAGGAAACAATTG-3'(SEQ ID NO: 857), and then subcloning the PCR product into pTRE-LacI-FF5 and pTRE-LacI-T21 respectively using HindIII and SalI. pCAGop-DsRed-FF5-FF4 and pCAGop-DsRed-T141-T142 (3p)-T146a-FF4 were made by subcloning a pair of annealed oligos (5'-CCCGCTTGAAGTCTTTAATTAAACCGCTT-GAAGTCTTTAATTAAACCGCTTGAAGTCTTTAAT-TAAAC-3' (SEQ ID NO: 858) and 5'-CCGGGTTTAAT-TAAAGACTTCAAGCGGTTTAATTAAAGACTTCAA-GCGGTTTAATTA AAGACTTCAAGCGGGGTAC-3' (SEQ ID NO: 859)) containing three repeats of FF4 target (53) into pCAGopDsRed-FF5 and pCAGop-DsRed-T141-T142(3p)-T146a respectively using KpnI and XmaI.

pCAGop-DsRed-T141-FF4 was made by replacing DsRed-FF5 in pCAGop-DsRed-FF5-FF4 with DsRed-T141 from pAmCyan-TRE-DsRed-T141 using NheI and HindIII.

Plasmid DNA Constructs for hBax-Induced Apoptosis phBax-C3-EGFP that contains human Bax gene (NM_13 87761) (59) was purchased from Addgene.

pAmCyan-TRE-hBax-T141-T142(3p)-T146a was prepared by PCR amplification of the hBax fragment from phBax-C3-EGFP using 5'-TTTGCTAGCCGCCACCATG-GACGGGTCCGGG-3' (SEQ ID NO: 860) and 5'-TTT-GCGGCCGCTCAGCCCATCTTCTTCCAG-3' (SEQ ID NO: 861) and replacing the DsRed fragment in pAmCyan-TRE-DsRed-T141-T142(3p)-T146a with this PCR product using NheI and NotI.

pCAGop-hBax-T141-T142(3p)-T146a-FF4: pCAGop-DsRed-FF5-FF4 was digested with HindIII, and the sticky ends were filled by Klenow in the presence of 50 µM dNTPs, digested by NheI and the larger band was gel-purified as the vector backbone for cloning. pAmCyan-TRE-hBax-T141-T142(3p)-T146a was digested by NheI and EcoRV, and the hBax containing band was gel-purified to serve as an insert. The insert was cloned into the above vector backbone using T4 DNA ligase.

pCAGop-hBax-FF5-FF4 was prepared according to the following steps. pCAGop-hBax-T141-T142(3p)-T146a-FF4 was digested by NotI and the larger band was gel-purified. The purified fragment was dephosphorylated using shrimp alkaline phosphatase and gel-purified as the vector backbone. pCAGop-DsRed-FF5-FF4 was digested by NotI and FF5-FF4 containing fragment was gel-purified to serve as an insert. The insert was cloned into the above vector backbone using T4 ligase.

Bicistronic expression vectors co-expressing Bcl2 with LacI: Plasmid DNA pCMV6-XL4-Bcl2 (SC 125546) containing the full-length Bcl2 cDNA (NM_000633.2) was purchased from OriGene Technologies. pAmCyan-TRE-DsRed-T17-T30a was digested with NheI and HindIII, and the sticky ends were filled with Klenow in the presence of 50 µM dNTP. Then the larger band was gel-purified and self-ligated with T4 DNA ligase, giving pTRE-DsRed-T17-T30a. LacI was PCR-amplified using the primers 5'-TTT-GAATTCGCTAGCATGAAACCAGTAACGTTATACG-3' (SEQ ID NO: 862) and 5'-TTTTCCGGATTAAAGCTTTT-GCGGCCGCTTACTAGTAACCTTCCTCTTCTTCTTAG-3'(SEQ ID NO: 863) from pTRE-LacI-FF5 DNA template, and then subcloned into pTRE-DsRed-T17-T30a using EcoRI and BspEI, producing pTRE-LacI-linker-T17-T30a. In this vector, the stop codon of the LacI is deleted and replaced with a linker containing restriction enzyme sites (SpeI-NotI-HindIIIBspEI) downstream of LacI coding sequence. Bcl2 was amplified using the primers 5'-TT-TACTAGTGGATCTGGCGCCACCAACTTCTCTCT-GCTGAAGCAGGCCGGCGACGTGAGGAG AACCCA-GGCCCAATGGCGCACGCTGGGAGAACAG-3'(SEQ ID NO: 864) and 5'-TTTGCGGCCGCTCACTTGTGGCCCA-GATAGGCACCC-3' (SEQ ID NO: 865) from pCMV6-XL4-Bcl2 DNA template. The gel-purified PCR product that harbours a P2A tag10 upstream of Bcl2 was inserted into pTRE-LacI-linker-T17-T30a using NotI and SpeI, producing pTRE-LacI-2A-Bcl2-T17-T30a. To make pTRE-LacI-2A-Bcl2-T21-miR-FF4, LacI in pTRE-LacI-T21-miR-FF4 was replaced with LacI-2A-Bcl2 using NheI and NotI. To make pTRE-LacI-2A-Bcl2-T17-T30amiR-FF4, the DNA fragment containing miR-FF4 in a synthetic intron of pTRE-LacI-T17-T30a-miR-FF4 was inserted in the 3'UTR of LacI-2A-Bcl2 cDNA in pTRE-LacI-2A-Bcl2-T17-T30a downstream of T17 and T30a targets using XbaI and AscI.

Construction of Stable Cell Lines

The lentiviral plasmid pFUGW1 1 (Addgene) contains human polyubiquitin promoter-C (UbC), the EGFP gene, and WPRE (woodchuck hepatitis virus posttranscriptional regulatory element). To create pFHGUBW, pFUGW was modified in the following way: UbC promoter was replaced with human elongation factor 1 alpha promoter hEF1a from pLV-hEF1a-IRES2-Puro (a gift from Sairam Subramanian), using PacI and BamHI; UbC promoter driving expression of blasticidin resistance gene was cloned downstream of EGFP using EcoRI. EYFP and Cerulean genes were PCR-amplified using the gel-purified DNA fragments of digested pCMV-Brainbow-1.1 with XmnI and primers (5'-TCATT-AGGATCCACCGGTCGCCACCATG-3' (SEQ ID NO: 866) and 5'-TCATTATGTACAGCTCGTCCATGCCGA-GAG-3'(SEQ ID NO: 867)). Then EYFP and Cerulean were inserted into pFHGUBW using BamHI and BsrGI, producing pFHYUBW and pFHCUBW, respectively.

For production of lentiviral particles, $\sim 8 \times 10^5$ HEK293 cells in 3 mL of DMEM complete media were plated into gelatin-coated 60 mm dishes (Corning Incorporated) and grown for ~24 h. Then cells were co-transfected with the expression vector (pFHYUBW or pFHCUBW), the packaging plasmid pCMV-dR8.2 (Addgene) and the envelope plasmid pCMV-VSV-G (Addgene), as described (61) using Superfect reagent (Qiagen) by following manufacturer's protocol. Media containing viral particles produced from transfected HEK293 cells were harvested ~48 h post-transfection and filtered through a 0.45-3 L syringe filter. 1.5 mL of the filtrate and 10 3 g/mL of polybrene (Millipore) were added to ~20% confluent HEK293 or HeLa in 12-well plate seeded 24 h prior transfection. After 48 h, Blasticidin (InvivoGen) was added into media to a final concentration of 10 3 g/mL and the cells were grown for another 6 days. Fluorescent-activated cell sorting (FACS) analysis confirmed stable integration of the desired genes (~80% of HEK293-Cerulean cells were Cerulean positive and ~95% of HeLa-EYFP cells were EYFP positive (data not shown)). To enrich Cerulean positive cells in HEK293-Cerulean stable cell line, $\sim 5 \times 10^6$ cells were trypsinized and centrifuged at 250 g for 5 min HEK293-Cerulean cells were resuspended in 1×PBS (Invitrogen) with 10% FBS (Invitrogen) and 1% sodium pyruvate (Invitrogen). HEK293-Cerulean cells were sorted on a Beckman Coulter MoFlo Legacy equipped with a Coherent Innova 170 C Spectrum laser tuned to 457 nm for the excitation wavelength with a 530/40 bandpass filter in FL-6. The top 10% of Cerulean positive HEK293-Cerulean cells were collected in 1×PBS (Invitrogen), and centrifuged at 250 g for 5 min Cells were resuspended in DMEM complete media and plated into collagen-coated 12-well plate (Becton Dickinson Labware) and grew at 37° C., 100% humidity and 5% CO2. FACS analysis confirmed that ~97% enriched HEK293-Cerulean cells are Cerulean positive while ~97% HeLa cells were Cerulean negative (FIG. 12). HeLa-EYFP was used directly in FIG. 6B without sorting.

Cell Culture and Transfection

HEK293 (293-H) cell line was purchased from Invitrogen. HeLa (CCL.2) and MCF7 (HTB-22) cell lines were originally obtained from ATCC. HEK293 and HeLa cells were cultured in DMEM complete media (Dulbecco's modified Eagle's medium (DMEM), 0.045 units/mL of penicillin and 0.045 µg/mL streptomycin and 10% FBS (Invitrogen)) at 37° C., 100% humidity and 5% CO2. MCF7 cells were grown in high-glucose-DMEM complete media (high glucose Dulbecco's modified eagle medium (DMEM, 4.5 g'L D-glucose, no phenol red), 0.045 units/mL of penicillin and 0.045 µg/mL streptomycin and 10% FBS (Invitrogen)) at 37° C., 100% humidity and 5% CO2.

Effectene transfection reagent (Qiagen) was used in transfection experiments as described in the manual with certain optimizations. In transfection experiments with individual cell lines in each well, ~8×10$^4$ HEK293 cells or ~1.5×10$^5$ HeLa cells in 1 mL of DMEM complete media, or ~8×10$^4$ MCF7 cells in 1 mL of high-glucose-DMEM complete media were seeded into each well of 12-well uncoated glass-bottom (MatTek) plates and grown for ~24 h. In transfection experiments with cell line mixtures, ~2.5×10$^4$ HEK293-Cerulean cells were mixed with ~7.5×10$^4$ HeLa cells (experiments described in FIG. 6A) or HeLa-EYFP cells (experiments described in FIG. 6B) in 1 mL of DMEM complete media, then the mixture was seeded into each well of 12-well uncoated glass-bottom (MatTek) plates and grown for 24 h. Shortly before transfection, the medium was replaced with fresh DMEM complete media for HEK239, HeLa cells or mixtures, or fresh high-glucose-DMEM complete media for MCF7 cells. A 75-µL sample mixture was prepared by mixing the required amounts of plasmid DNAs and/or small RNAs in EC buffer (Qiagen). pUBI-linker-NOS (56) that contains a maize ubiquitin promoter (UBI) followed by a NOS terminator with no protein-coding sequences between UBI and NOS was used to ensure an equal amount of plasmid DNAs. Then 2.4 µL Enhancer and 6 µL Effectene (Qiagen) were sequentially added to each sample mixture as described in the manual, followed by adding 400 µL DMEM complete media (for transfection experiments with HEK293, HeLa cells or mixtures) or high-glucose-DMEM complete media (for transfection experiments with MCF7 cells). Doxycycline was added to each well to a final concentration of 1 µg/mL. After 3-h incubation, media containing transfection complexes were replaced with fresh DMEM complete media or high-glucose-DMEM complete media plus 1 µg/mL doxycycline. Cells with fluorescent output were incubated for 2 days before the analysis. For cell apoptosis experiments in FIGS. 5C and 5D, and FIG. 6B, cells were trypsinized with 0.5 mL 0.25% trypsin-EDTA at 48 h after transfection. ~25% of the cells were plated again in 1 mL fresh DMEM complete media (for HEK293, HeLa cells or mixtures) or high-glucose-DMEM complete media (for MCF7 cells), plus 1 µg/mL doxycycline, and incubated for another 2 days before the analysis. The cells were prepared as described for FACS analysis (53).

The amount of plasmid DNAs and/or small RNAs used to obtain the data presented in the figures are listed in the following tables: Table 52 for FIG. 1; Tables 53 and 54 for FIG. 3; Tables 55 and 56 for FIG. 5; Table 57 for FIG. 6; Table 58 for FIG. 10; and Table 59 for FIG. 11.

Microscope Measurements and Image Processing

All microscopy images of live cells were taken in glass-bottom 12-well plates using Zeiss Axiovert 200 microscope equipped with shutter filter wheels, as described (53) with modifications. The imaging settings for the fluorophores were S430/25x (excitation) and S470/30m (emission) filters for AmCyan, and S565/25x (excitation) and S650/70m (emission) for DsRed. A dichroic mirror 86004v2bs (Chroma) was used for AmCyan. The dichroic mirror 8602 lbs (Chroma) was used for DsRed. Exposure times were 200 ms for AmCyan, and 300 ms for DsRed. Data collection and processing were performed using Metamorph 7.0 software (Molecular Devices).

FACS Measurement

BD LSRII flow analyzer (BD Biosciences) was used for FACS measurements. EYFP was measured using a 488 nm Laser, a 505 nm Longpass filter and a 530/30 emission filter with a PMT 220 V. AmCyan and Cerulean were measured with a 405 nm Laser, a 460 nm Longpass filter and a 480/40 emission filter using PMT 225 V. DsRed was measured using 561 nm laser and a 585/20 emission filter with a PMT 210 V. The numbers of cell events collected by BD LSRII flow analyzer were ~1×10$^5$ for HEK293, ~1×10$^5$ for HeLa, and 3×10$^4$ for MCF7. Data were analyzed using FloJo software (FlowJo LLC).

Data Analysis

In FIG. 1 and FIG. 3, the bar charts were generated as follows. In each sample, the value of DsRed/AmCyan was calculated using the formula:

$$\frac{DsRed}{AmCyan} = \frac{Ave(DsRed) \times Freq(DsRed)}{Ave(AmCyan) \times Freq(AmCyan)}$$

where Ave(DsRed) and Ave(AmCyan) are the average intensity of DsRed-positive cells and AmCyan-positive cells, respectively, and Freq(DsRed) and Freq(AmCyan) are the frequency of DsRed-positive cells and the frequency of AmCyan-positive cells among all cells collected, respectively. This ratio therefore represents the total DsRed signal from the sample normalized by the internal transfection marker to account for sample-to-sample variability. Additionally, the DsRed/AmCyan value for each sample obtained with a given cell line was normalized to the DsRed/AmCyan value in the positive control sample in the same cell line in which both DsRed and AmCyan were constitutively expressed, resulting in a scale from zero to one for all experimental samples for different cell lines.

In FIG. 5B data analysis was performed as described above, but all the DsRed/AmCyan ratios obtained with different cell lines were normalized to the positive control value obtained with HeLa cells in order to enable direct comparison between different cell lines.

In FIGS. 5C and 5D, raw FACS data was used to derive the percentage of AmCyan$^+$ cells and to compute the distributions of the AmCyan levels in AmCyan$^+$ cell fraction. The overlapping distributions for different cell lines were normalized using the FloJo software while maintaining their relative shapes. The killing efficiency in FIG. 5E is calculated by dividing the difference between the percentage of AmCyan$^+$ cells of the 'No cell death' control sample and that of the circuit sample by the difference between the percentage of AmCyan$^+$ cells of the 'No cell death' control sample and that of the hBax-Tgts sample.

In FIG. 6A, raw FACS data was used to gate DsRed$^+$ cells using untransfected HEK293-Cerulean and HeLa cells as references. The resulted fraction was used to compute the distributions of the Cerulean+ (classified as HEK293) and Cerulean (classified as HeLa) cells in DsRed+ cells. The percentage of classified HEK293 or HeLa cells in the constitutively repressed sample and the circuit sample was normalized to that of classified HEK293 or HeLa cells among the 'constitutive output' sample respectively.

In FIG. 6B, DsRed and EYFP data were compensated in FlowJo before analysis and used to gate DsRed+ cells using untransfected HEK293-Cerulean and HeLa-EYFP cells as references. The resulted fraction was used to compute the distributions of the Cerulean+/EYFP− (interpreted as HEK293) and Cerulean−/EYFP+ (interpreted as HeLa) cells in DsRed+ cell fraction. The percentage of classified HEK293 or HeLa cells in the 'constitutively-active hBax' sample and the 'hBax controlled by the classifier' sample was normalized to that of classified HEK293 or HeLa cells in the 'no hBax output' sample respectively.

FIG. 7 depicts initial marker screening. Expression histograms for the top 12 HeLa microRNAs, ranked in descending order according to their cloning frequency (CF). Expression levels in HeLa cells are indicated by a red arrow in each histogram. Horizontal axes show cloning frequency in percent units.

FIG. 8 depicts a circuit performance analysis and profile determination. FIG. 8A shows simplified dose response of an output to changing concentrations of a repressor in a HeLa-high marker sensor. FIG. 8B depicts a fit of the data shown in FIG. 9A to an exponential output restoration function. The lower and upper bounds of the output amplitude ($O_{OFF}$ and $O_{ON}$) as well as the theoretical upper limit on output intensity ($O_s$) are shown. FIG. 8C shows a dose response of a repressor concentration to changing microRNA input levels. Lower and upper bounds of the repressor concentration are shown. FIG. 8D is a contour plot of the mapping between two hypothetical HeLa-high markers A and B and the output of a two-input circuit that uses them as inputs. Marker concentrations are normalized to their levels in HeLa cells denoted as $A_{HeLa}$ and $B_{HeLa}$ that result in 99% output repression relief. FIG. 8E depicts plots showing predicted output levels in different cell lines from different combinations of microRNA markers relative to the output in HeLa cells. Each marker sensor is assumed to be tuned to relieve 99% output repression in HeLa cells by its cognate input marker. The numbers on the axes are given in cloning frequency (CF) units. Each dot represents one cell type and the contour lines show input combinations that result in 20% output compared to HeLa cells (red dots). Dots above the contour line are cell types that generate more than 20% of HeLa output and they represent 'false-positive' cell types for this specific circuit configuration. FIG. 8F shows an analysis of additional microRNA markers not expressed in HeLa cells but highly expressed in cells that can be misidentified based on the profile composed of only miR-21 and miR-17-30a HeLa-high markers. The heat map shows the cloning frequency of selected HeLa-low markers, with blue and red colors indicating low and high CF values, respectively. FIG. 8G depicts simulated output levels in different cell types using a full classifier. From left to right, output levels histogram for a complete set of markers using sensor parameters defined in the text; output levels histogram with the 99% repression relief values for HeLa-high marker sensors doubled compared to their default values; output levels histogram when the 99% repression relief values for the HeLa-high marker sensors are half of the default values.

FIG. 9 shows optimization of sensors for highly expressed markers. Transcriptional activator rtTA and repressor LacI are fused to indicated targets for either exogenous siRNA-FF5 or endogenous microRNAs. FF5, target for siRNA-FF5 (blue wave line); T21, target for miR-21 (green wave line); T17-30a, targets for miR-17 and 30a (red wave line). For simplicity, only one red wave line is drawn representing both miR-17 and 30a. rtTA is driven by a constitutive CMV promoter. LacI is driven by pTRE promoter that is induced by rtTA plus 1 µg/mL doxycycline. DsRed output is driven by CAGop promoter that is repressed by LacI. AmCyan driven by a constitutive CMV promoter is used as a transfection reference in all experiments. Left panels show the schematics of different sensor variants. Charts on the right show quantitative results measured by FACS 48 h post-transfection. FIG. 9A shows an effect of a coherent feed-forward motif on sensor performance in response to exogenous siRNA-FF5. ~100 ng pCAGop-dsRed-FF5 was co-transfected with rtTA and LacI fused with indicated targets and increasing amount of siRNA-FF5 into HEK293 cells. Silencer Negative Control siRNA (Ambion) was used to ensure equal molar amount of siRNA used in each sample. Each bar represents the mean±SD of DsRed/AmCyan value with three independent replicates. FIG. 9B shows an effect of LacI dose on sensor performance for highly-expressed endogenous microRNA markers. ~100 ng pCAGop-DsRed was co-transfected with 50 ng rtTA and increasing amount of LacI fused with indicated targets into HeLa cells. Each bar represents the mean±SD of DsRed/AmCyan value obtained from three independent replicates. FIG. 9C shows an effect of rtTA dosage on the performance of sensors for highly-expressed endogenous microRNA markers. ~100 ng pCAGop-DsRed was transfected into HeLa cells with increasing amount of rtTA and 50 ng LacI fused with indicated targets.

FIG. 10 shows a circuit optimization with engineered intronic microRNA miR-FF4. Transfection protocol is described in Table 58. Four versions of the circuit (FIG. 2E), with specific microRNA regulatory links interrupted (denoted as "−") or functional (denoted as "+"), are used to emulate four different combinations of input levels for two HeLa-high microRNA markers (FIG. 3A). Each variant is tested with or without engineered miR-FF4 regulation (FIG. 4). The output is DsRed fluorescent protein and the CAG-driven AmCyan serves as a transfection reference. The bar charts show mean±SD of DsRed/AmCyan values from three independent replicates measured by FACS ~48 h post-transfection. The ON:OFF ratio is calculated by dividing the DsRed/AmCyan ratio of the ON state (the last category) by the value in the OFF state (the first three categories). The images are overlays of DsRed and AmCyan channels taken ~48 h post-transfection.

FIG. 11 shows an operation of partially-assembled circuits in HeLa, HEK293 and MCF7 cell lines Transfection protocol is described in Table 59. The output is DsRed fluorescent protein and the protein AmCyan driven by constitutive CAG promoter serves as a transfection reference. ON State, no repression of DsRed output; OFF state, constitutive repression on DsRed output; T17-30a, only sensor for miR-17-30a is used; T21, only sensor for miR-2 1 is used; T1 41, only sensor for miR-141 is used; "+" represents a combination of sensors. Sensors for miR-21 and miR17-30a contain engineered miR-FF4 regulation (shown in FIG. 4). The bar charts show mean±SD of DsRed/AmCyan values from three independent replicates measured by FACS ~48 h posttransfection. All DsRed/AmCyan values are normalized to that of HeLa cells at the ON state. Images are overlays of DsRed and AmCyan channels taken ~48 h post-transfection.

FIG. 11 shows a separation of HEK-Cerulean cells from HeLa cells using Cerulean fluorescent channel. HEKCerulean and HeLa cells are grown separately in DMEM complete media. Raw data of $10^5$ events for both HeLa cells and HEK-Cerulean cells are obtained by FACS and used for analysis. The histograms on the left show contributions of the two cell types, HeLa (green line) and HEK-Cerulean (blue line) to Cerulean-negative (Cerulean⁻) and Cerulean-positive (Cerulean⁺) cells. The chart on the right show the relative percentage of HeLa (green bar) and HEK-Cerulean (blue bar) in Cerulean⁻ and Cerulean⁺ cells respectively.

Figures 13A, 13B:
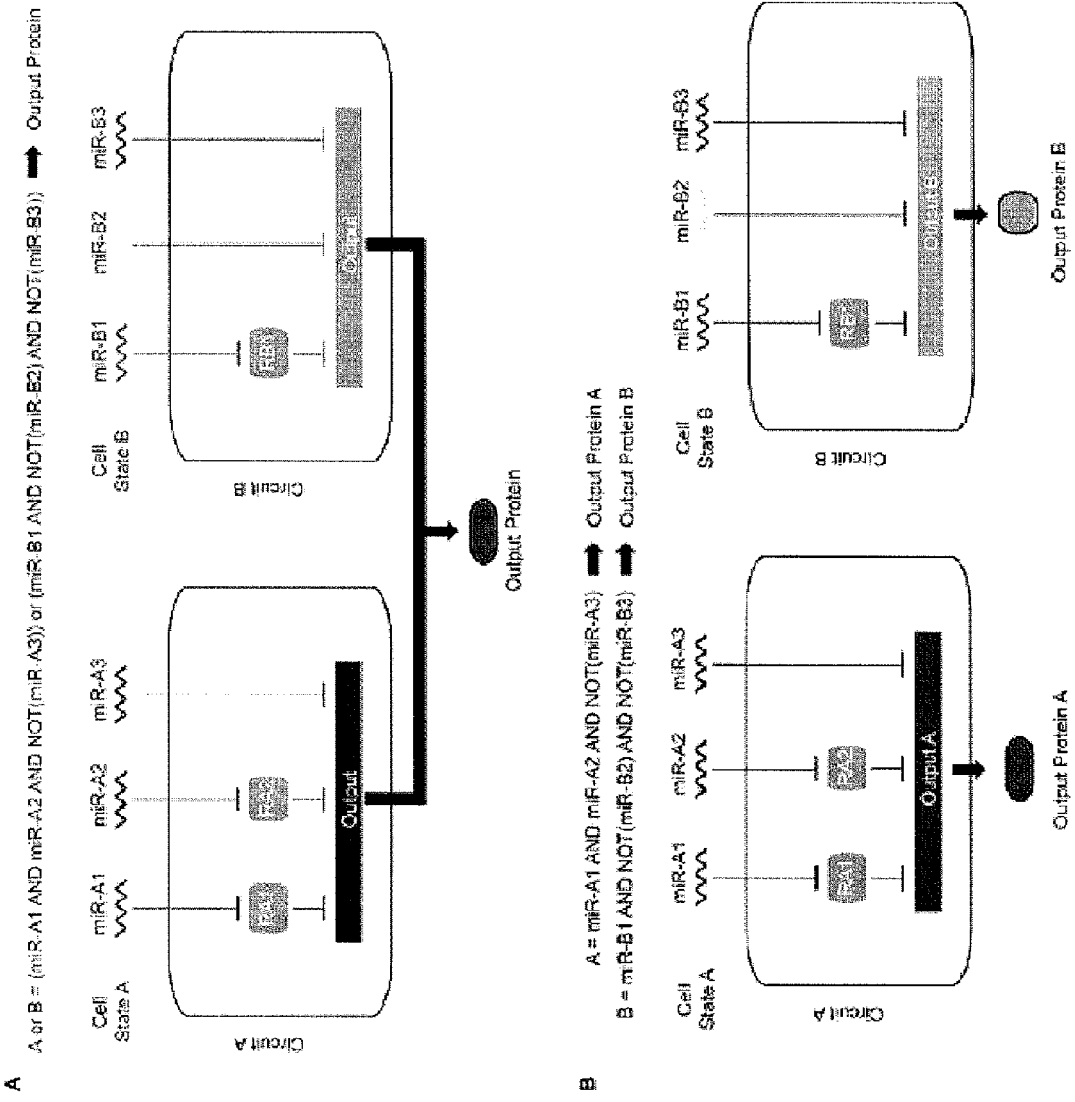
FIGS. 13A-13B show an exemplary parallel operation of classifier circuits.
Figure 14A:
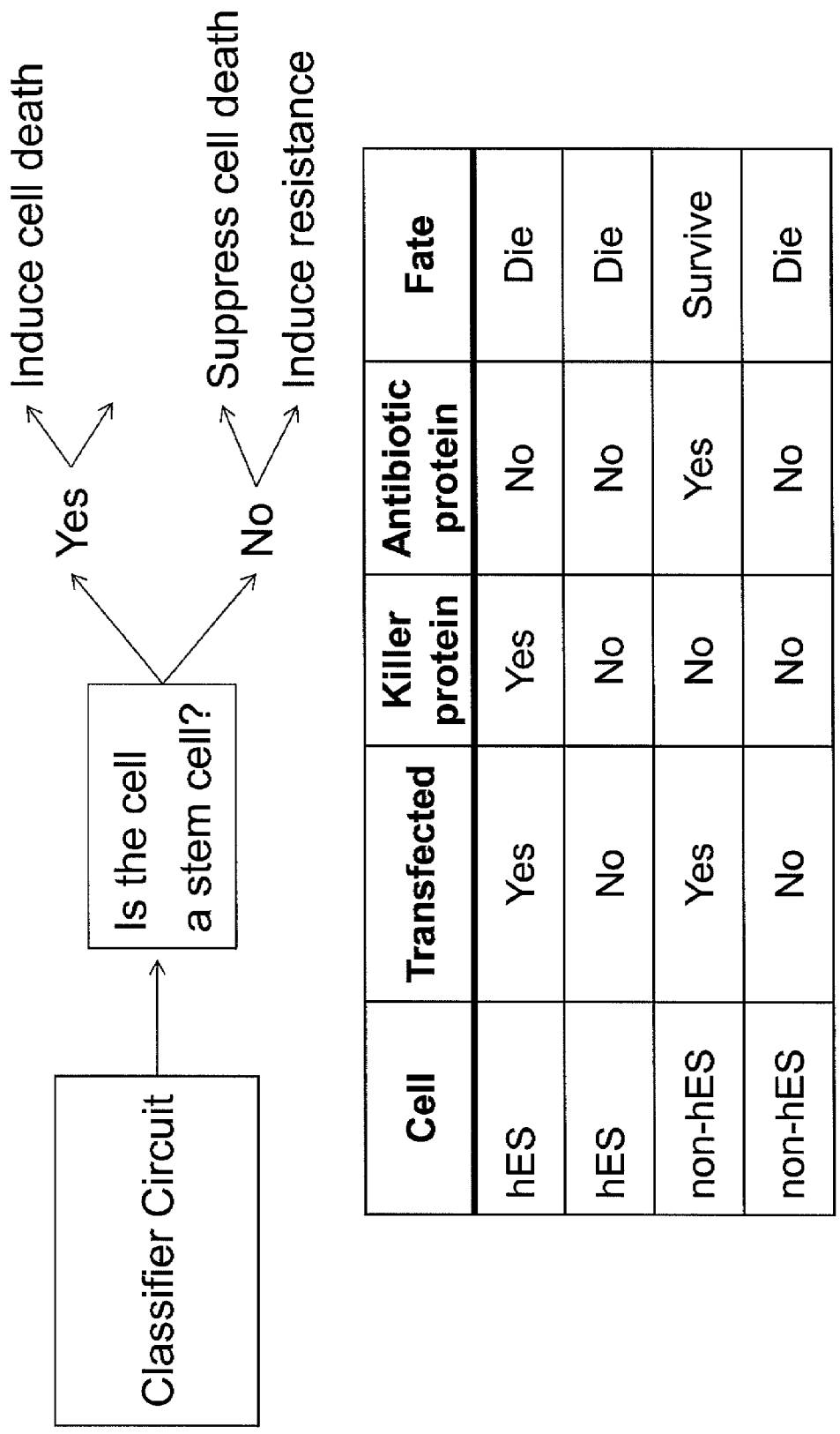
FIGS. 14A-14C show exemplary operational decisions that can be executed by a multi-input biological classifier circuit comprising an embodiment of a "kill and rescue" output module as described herein.
Figure 14B:
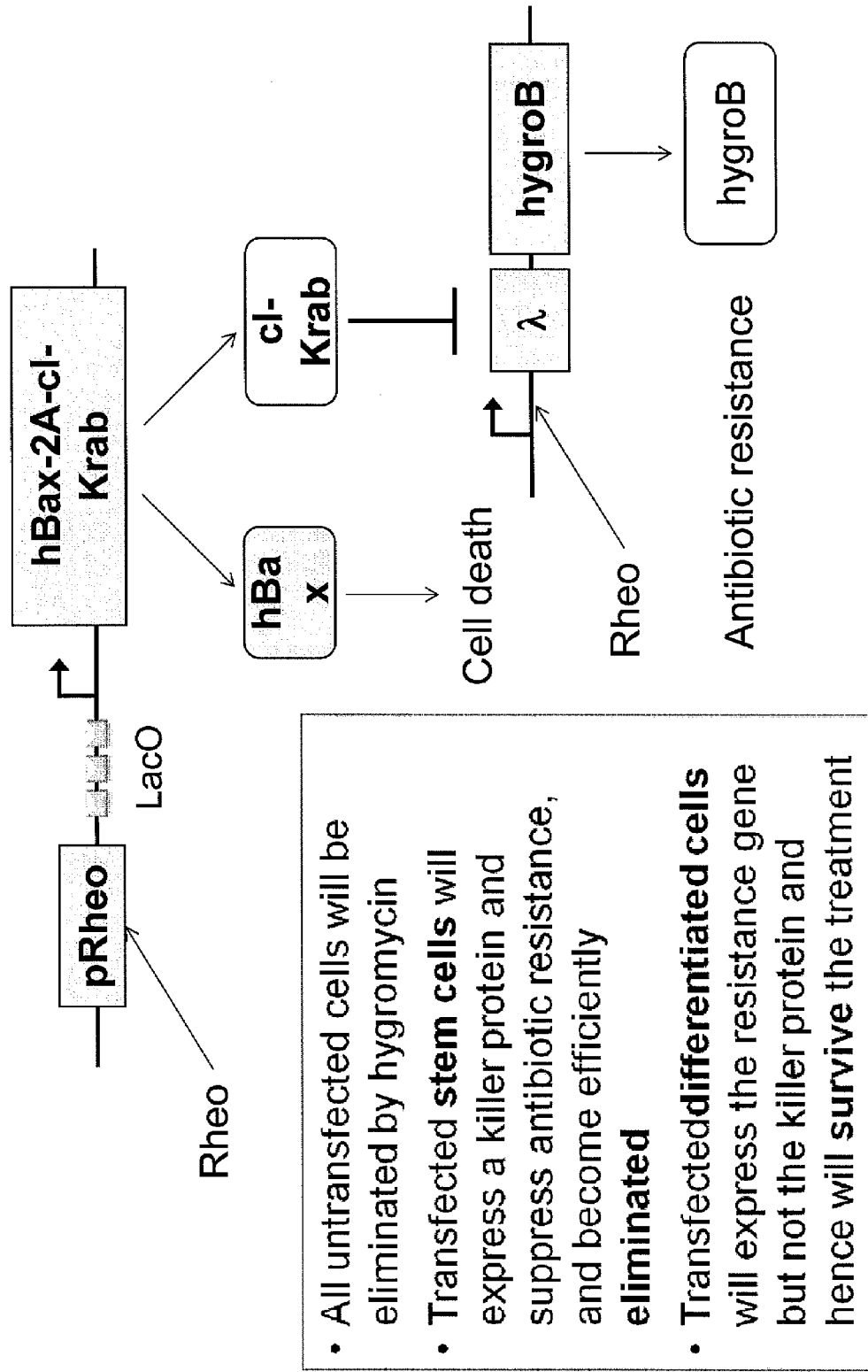
Figure 14C:
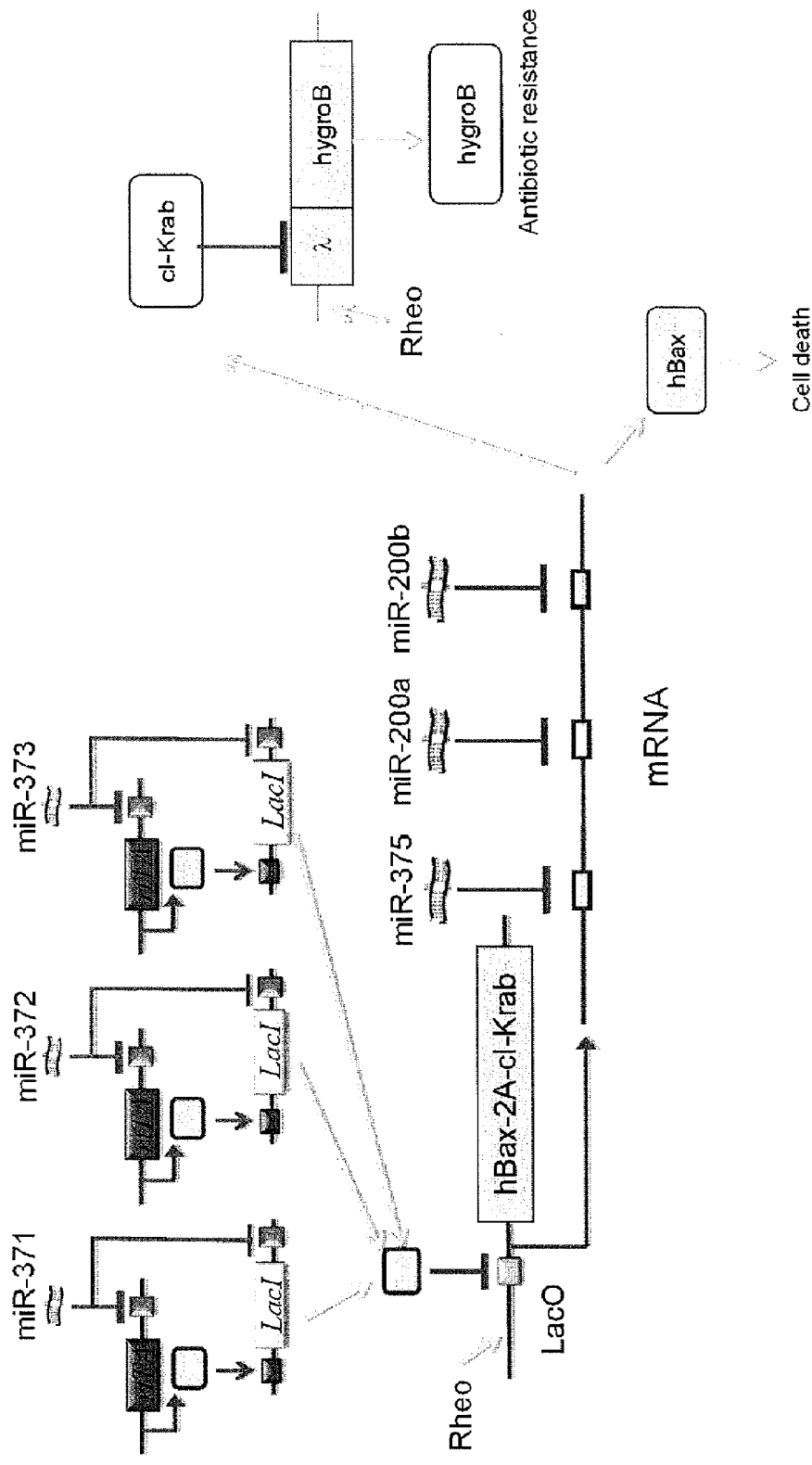

FIG. 13 shows an exemplary parallel operation of classifier circuits. FIG. 13A depicts three hypothetical microRNA markers A1, A2 and A3 that are used to determine a specific cell state A. Hypothetical microRNA markers B1, B2 and B3 are used to determine specific cell state B. Cells in state A or B, e.g. two different phases in cancer development, are both intended targets for a multi-purpose therapeutic agent. Two classifier circuits A and B operating in parallel with no crosstalk between them are used to identify cell types A and B, respectively. RA1 and RA2 are 'double-inversion' modules in Circuit A; RB1 is the 'double-inversion' module in Circuit B. FIG. 13B shows output proteins A and B represent two different therapeutic agents for type A and B cells, respectively. Outputs A and B are controlled by circuits A and B that detect profiles characterizing type A and type B cells, respectively. Output A is high for cells of type A that have high expression of markers A1 and A2 and low expression of A3; output B is high when the cells are of type B with high expression of marker B1 and low expression of B2 and B3.

Figure 15:
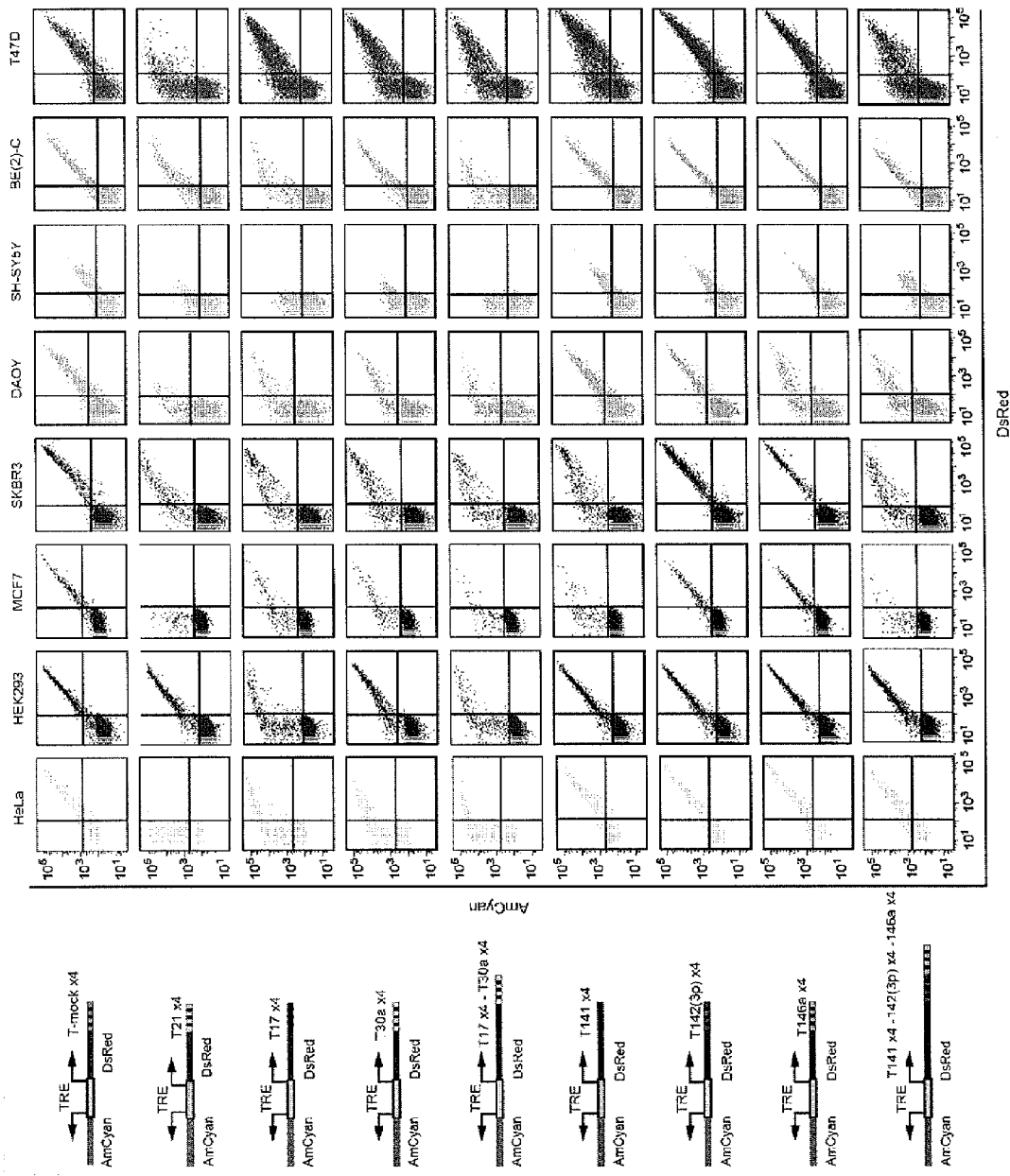
FIG. 15 shows experimental confirmation of microRNA markers in various cell lines. Transiently-transfected bidirectional constructs include DsRed reporter with fused microRNA targets (four tandem repeats of the same target fully complementary to the corresponding mature microRNA sequences), and an internal reference reporter AmCyan. Schematics diagrams for bidirectional reporters are shown in the left panel. Transfection experiments were performed with Effectene transfection reagent for all cell lines except for SH-SY5Y and T47D. FACS data for HEK293, HeLa and MCF7 cells were measured at 48 hours post-transfection with BD LSRII flow analyzers using a filter set for AmCyan (405 nm Laser, 460 nm Longpass filter, 480/40 emission filter and PMT 225 V) and a filter set for DsRed (561 nm Laser, 585/20 emission filter and PMT 210 V). FACS data for SKBR3, DAOY, SH-SY5Y and BE(2)-C were measured at 48 hours post-transfection with BD LSRII flow analyzers using a filter set for AmCyan (405 nm Laser, 510/50 emission filter and PMT 230 V) and a filter set for DsRed (561 nm laser, 610/20 emission filter and PMT 230 V). Scatter plots of raw FACS data are shown in the right panel.
Figures 16A, 16B:
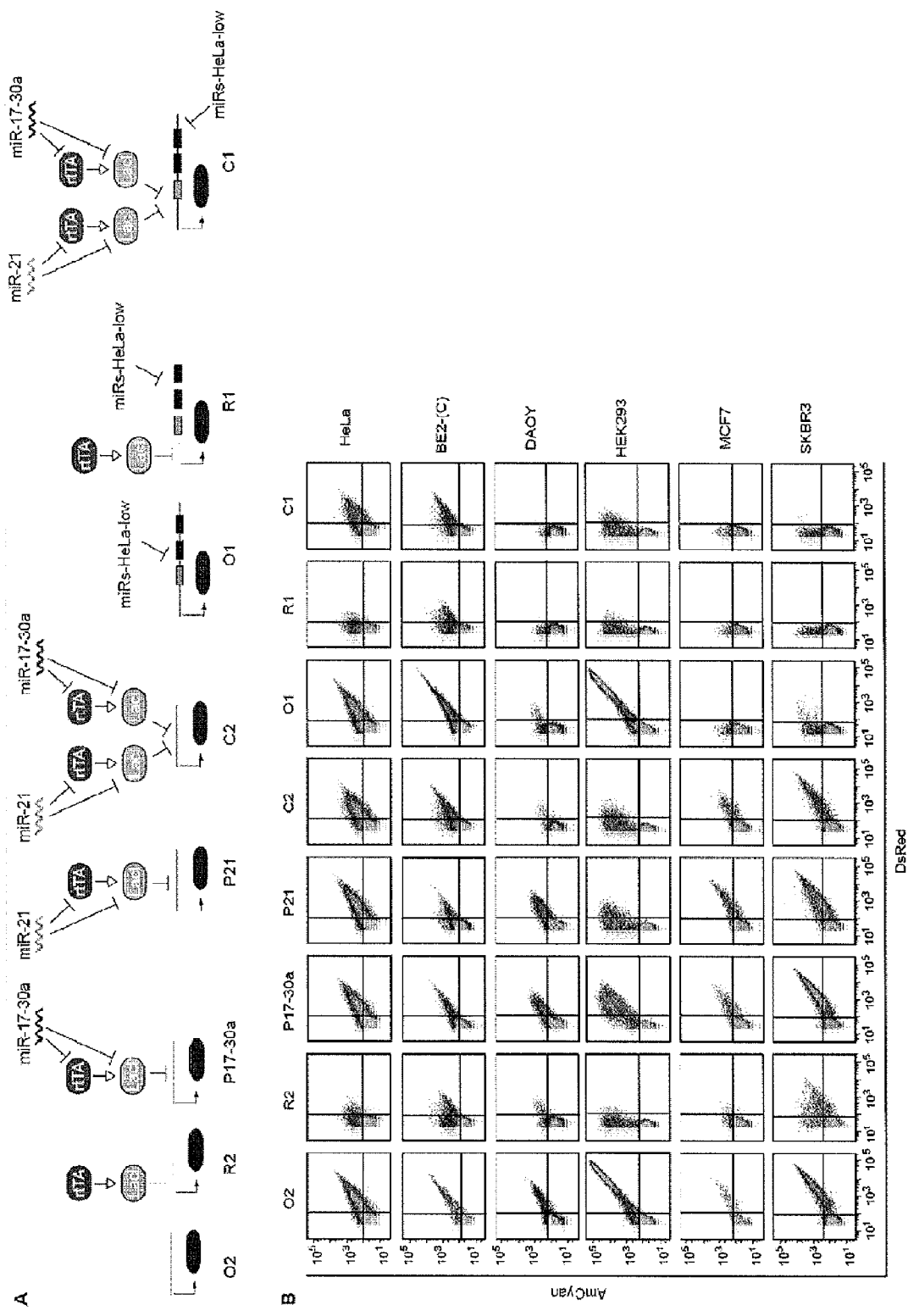
FIGS. 16A-16E demonstrate operation of circuits in variant cells. CAG-AmCyan was co-transfected in all cases as an internal control.
Figures 16C, 16D, 16E:
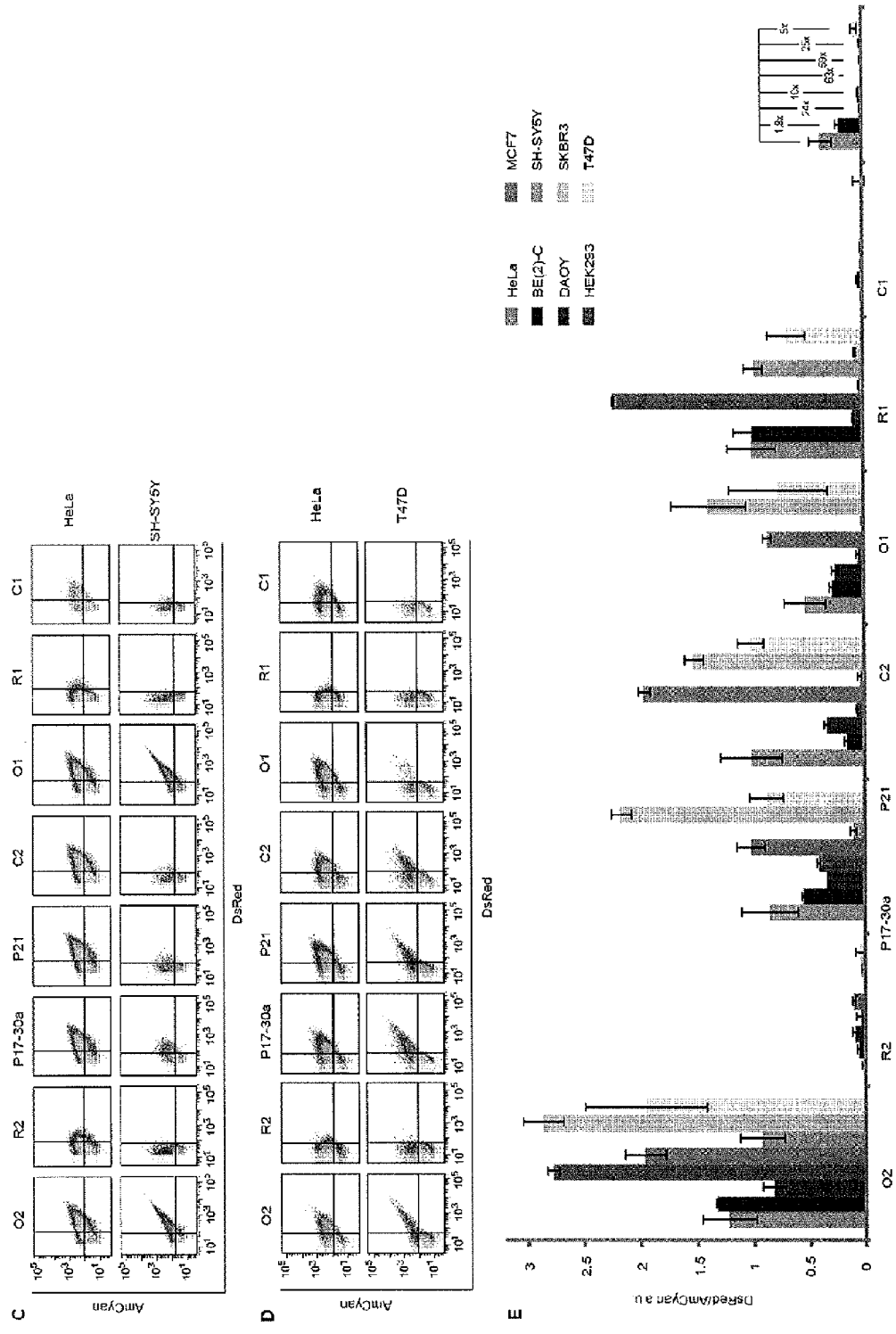

HeLa and a number of control cell lines were chosen for experimental tests. Most of the control cells are cancer cell lines that were used as a proxy for healthy cells with comparable marker levels. First, we confirmed microRNA activity in HeLa and control cells using DsRed-Express fluorescent reporter (DsRed) fused with appropriate microRNA targets (FIG. 15). Measured activities generally agreed with previously-published data in microRNA Atlas database (P. Landgraf et al., Cell 129, 1401 (June, 2007)).

Optimized sensors were incorporated with the miR-FF4 synthetic microRNA in one embodiment of a classifier circuit and the complete circuit analyzed (FIG. 16A, "C1" circuit) to determine how well it distinguishes between HeLa and other cell lines. It was observed that the fluorescent output was at least 5-fold higher in HeLa than in six other cell lines and 1.8-fold higher than that in BE(2)-cells (FIGS. 16B, 16C, 16D and 16E). Partial circuits (FIG. 16A, "P17-30a", "P21", "R1", "C2" and "O1") that only respond to subsets of microRNA markers behaved as expected (FIGS. 16B, 16C, 16D and 16E), further validating our mechanistic model. Overall, the results confirm that strong output suppression in non-HeLa cells can be expected in two cases: either a large difference from HeLa profile in at least one of the markers, or a combination of intermediate differences in a few markers. When there is an intermediate or small difference in only one marker, as in the case of BE(2)-C, the suppression becomes less efficient.

TABLE 52

Transfection configuration for samples used to generate data shown in FIGS. 1A-1D. Nanogram amounts of plasmids are indicated.

|  | T-mock | T21 | T17 | T30a | T17-30a | T141 | T142 (3p) | T146a | T1 41 142 (3p) 146a |
|---|---|---|---|---|---|---|---|---|---|
| pTET-ON-Advanced | 50 | 50 | 50 | 50 | 50 | 50 | 50 | 50 | 50 |
| pAmCyan-TRE-DsRed-FF5 | 100 | | | | | | | | |
| pAmCyan-TRE-DsRed-T21 | | 100 | | | | | | | |
| pAmCyan-TRE-DsRed-T17 | | | 100 | | | | | | |
| pAmCyan-TRE-DsRed-T30a | | | | 100 | | | | | |
| pAmCyan-TRE-DsRed-T17- | | | | | 100 | | | | |
| pAmCyan-TRE-DsRed-T141 | | | | | | 100 | | | |
| pAmCyan-TRE-DsRed-T1 42(3p) | | | | | | | 100 | | |
| pAmCyan-TRE-DsRed-T146a | | | | | | | | 100 | |
| pAmCyan-TRE-DsRedT141- | | | | | | | | | 100 |

TABLE 53

The plasmids used to construct different circuit variants for the experiments shown in FIGS. 3A-3B.

| T17-30a (−) T21 (−) | T17-30a (i−) T21 (−) | T17-30a (−) T21 (i−) | T17-30a (i−) T21 (i−) |
|---|---|---|---|
| pCAGop-DsRed-T1 41-T1 42(3p)-T1 46a | pCAGop-DsRed-T1 41-T1 42(3p)-T1 46a | pCAGop-DsRed-T1 41-T1 42(3p)-T1 46a | pCAGop-DsRed-T1 41-T1 42(3p)-T1 46a |
| pCMV-rtTA-FF5 | pCMV-rtTA-FF5 | pCMV-rtTA-FF5 | pCMV-rtTA-T1 7-T30a |

TABLE 53-continued

The plasmids used to construct different circuit variants for the experiments shown in FIGS. 3A-3B.

| T17-30a (−) T21 (−) | T17-30a (i−) T21 (−) | T17-30a (−) T21 (i−) | T17-30a (i−) T21 (i−) |
|---|---|---|---|
| pTRE-LacI-FF5 | pTRE-LacI-FF5<br>pCMV-rtTA-T1 7-T30a<br>pTRE-LacI-T1 7-T30a | pTRE-LacI-FF5<br>pCMV-rtTA-T21<br>pTRE-LacI-T21 | pTRE-LacI-T1 7-T30a<br>pCMV-rtTA-T21<br>pTRE-LacI-T21 |

TABLE 54

Transfection configuration for the experiments shown in FIGS. 3A-3B. Nanogram plasmid amounts are shown unless indicated otherwise.

| T17-30a (−) T21 (−) | | | | | | | | |
|---|---|---|---|---|---|---|---|---|
| pAmCyan-C1 | 100 | 100 | 100 | 100 | 100 | 100 | 100 | 100 |
| pCAGop-DsRed-T141 - T142(3p)-T146a | 100 | 100 | 100 | 100 | 100 | 100 | 100 | 100 |
| pCMV-rtTA-FF5 | 100 | 100 | 100 | 100 | 100 | 100 | 100 | 100 |
| pTRE-LacI-FF5 | 100 | 100 | 100 | 100 | 100 | 100 | 100 | 100 |
| Mimic miR-141 (pmol) | | 1 | | | 1 | 1 | | 1 |
| Mimic miR-142(3p) (pmol) | | | 1 | | 1 | | 1 | 1 |
| Mimic miR-146a (pmol) | | | | 1 | | 1 | 1 | 1 |
| Control siRNA (pmol) | 3 | 2 | 2 | 2 | 1 | 1 | 1 | |
| T17-30a (i−) T21 (−) | | | | | | | | |
| pAmCyan-C1 | 100 | 100 | 100 | 100 | 100 | 100 | 100 | 100 |
| pCAGop-DsRed-T141 - T142(3p)-T146a | 100 | 100 | 100 | 100 | 100 | 100 | 100 | 100 |
| pCMV-rtTA-FF5 | 50 | 50 | 50 | 50 | 50 | 50 | 50 | 50 |
| pTRE-LacI-FF5 | 50 | 50 | 50 | 50 | 50 | 50 | 50 | 50 |
| pCMV-rtTA-T17-T30a | 50 | 50 | 50 | 50 | 50 | 50 | 50 | 50 |
| pTRE-LacI-T17-T30a | 50 | 50 | 50 | 50 | 50 | 50 | 50 | 50 |
| Mimic miR-141 (pmol) | | 1 | | | 1 | 1 | | 1 |
| Mimic miR-142(3p) (pmol) | | | 1 | | 1 | | 1 | 1 |
| Mimic miR-146a (pmol) | | | | 1 | | 1 | 1 | 1 |
| Control siRNA (pmol) | 3 | 2 | 2 | 2 | 1 | 1 | 1 | |
| T17-30a (−) T21 (+) | | | | | | | | |
| pAmCyan-C1 | 100 | 100 | 100 | 100 | 100 | 100 | 100 | 100 |
| pCAGop-DsRed-T141 - T142(3p)-T146a | 100 | 100 | 100 | 100 | 100 | 100 | 100 | 100 |
| pCMV-rtTA-FF5 | 50 | 50 | 50 | 50 | 50 | 50 | 50 | 50 |
| pTRE-LacI-FF5 | 50 | 50 | 50 | 50 | 50 | 50 | 50 | 50 |
| pCMV-rtTA-T21 | 50 | 50 | 50 | 50 | 50 | 50 | 50 | 50 |
| pTRE-LacI-T21 | 50 | 50 | 50 | 50 | 50 | 50 | 50 | 50 |
| Mimic miR-141 (pmol) | | 1 | | | 1 | 1 | | 1 |
| Mimic miR-142(3p) (pmol) | | | 1 | | 1 | | 1 | 1 |
| Mimic miR-146a (pmol) | | | | 1 | | 1 | 1 | 1 |
| Control siRNA (pmol) | 3 | 2 | 2 | 2 | 1 | 1 | 1 | |
| T17-30a (+) T21 (+) | | | | | | | | |
| pAmCyan-C1 | 100 | 100 | 100 | 100 | 100 | 100 | 100 | 100 |
| pCAGop-DsRed-T141 - T142(3p)-T146a | 100 | 100 | 100 | 100 | 100 | 100 | 100 | 100 |
| pCMV-rtTA-T17-T30a | 50 | 50 | 50 | 50 | 50 | 50 | 50 | 50 |
| pTRE-LacI-T17-T30a | 50 | 50 | 50 | 50 | 50 | 50 | 50 | 50 |
| pCMV-rtTA-T21 | 50 | 50 | 50 | 50 | 50 | 50 | 50 | 50 |
| pTRE-LacI-T21 | 50 | 50 | 50 | 50 | 50 | 50 | 50 | 50 |
| Mimic miR-141 (pmol) | | 1 | | | 1 | 1 | | 1 |
| Mimic miR-142(3p) (pmol) | | | 1 | | 1 | | 1 | 1 |
| Mimic miR-146a (pmol) | | | | 1 | | 1 | 1 | 1 |
| Control siRNA (pmol) | 3 | 2 | 2 | 2 | 1 | 1 | 1 | |

TABLE 55

The plasmids used to construct different circuit variants for the experiments shown in FIGS. 5A-5E.

| Circuit with DsRed output fused to targets for unexpressed miRs (C1) | Circuit with DsRed output without the targets for unexpressed miRs (C2) | Apoptosis-inducing circuit |
|---|---|---|
| pCAGop-DsRed-T1 41-T1 42(3p)-T1 46a-FF4 | pCAGop-DsRed-FF5-FF4 | pCAGop-hBax-T1 41-T1 42(3p)-T1 46a-FF4 |
| pCMV-rtTA-T1 7-T30a | pCMV-rtTA-T1 7-T30a | pCMV-rtTA-T1 7-T30a |
| pTRE-LacI-T1 7-T30a-miR-FF4 | pTRE-LacI-T1 7-T30a-miR-FF4 | pTRE-LacI-2A-Bcl2-T1 7-T30amiR-FF4 |
| pCMV-rtTA-T21 | pCMV-rtTA-T21 | pCMV-rtTA-T21 |
| pTRE-LacI-T21-miR-FF4 | pTRE-LacI-T21-miR-FF4 | pTRE-LacI-2A-Bcl2-T21-miRFF4 |

TABLE 56

Transfection configuration for the experiments shown in FIGS. 5A-5E. Nanogram amounts for all plasmids are shown.

| FIG. 5B for HeLa, HEK293 and MCF7 (DsRed output with targets for unexpressed miRs) | Constitutive output levels (O1) | Constitutively repressed output levels (R1) | Circuit ( |
|---|---|---|---|
| pUBI-linker-NOS | 160 | | |
| pCAG-AmCyan | 100 | 100 | 100 |
| pCAGop-DsRed-T1 41-T1 42(3p)-T146a-FF4 | 100 | 100 | 100 |
| pCMV-rtTA-FF5 | | 80 | |
| pTRE-LacI-FF5-miR-FF4 | | 80 | |
| pCMV-rtTA-T1 7-T30a | | | 40 |
| pTRE-LacI-T1 7-T30a-miR-FF4 | | | 40 |
| pCMV-rtTA-T21 | | | 40 |
| pTRE-LacI-T21-miR-FF4 | | | 40 |

| FIG. 5B for MCF7 (DsRed output without targets for unexpressed miRs) | Constitutive output levels (O2) | Constitutively repressed output levels (R2) | Circuit ( |
|---|---|---|---|
| pUBI-linker-NOS | 160 | | |
| pCAG-AmCyan | 100 | 100 | 100 |
| pCAGop-DsRed-FF5-FF4 | 100 | 100 | 100 |
| pCMV-rtTA-FF5 | | 80 | |
| pTRE-LacI-FF5-miR-FF4 | | 80 | |
| pCMV-rtTA-T1 7-T30a | | | 40 |
| pTRE-LacI-T1 7-T30a-miR-FF4 | | | 40 |
| pCMV-rtTA-T21 | | | 40 |
| pTRE-LacI-T21-miR-FF4 | | | 40 |

| FIG. 5, C and D | No cell death | hBax-Tgts | Circuit |
|---|---|---|---|
| pUBI-linker-NOS | 160 | 160 | |
| pCAG-AmCyan | 100 | 100 | 100 |
| pCAGop-DsRed-T141-T142(3p)-T146a-FF4 | 80 | | |
| pCAGop-hBax-T1 41-T1 42(3p)-T1 46a-FF4 | | 80 | 80 |
| pCMV-rtTA-T1 7-T30a | | | 40 |
| pTRE-LacI-2A-Bcl2-T1 7-T30a-miR-FF4 | | | 40 |
| pCMV-rtTA-T21 | | | 40 |
| pTRE-LacI-2A-Bcl2-T21-miR-FF4 | | | 40 |

TABLE 57

Transfection configuration for the experiments shown in FIGS. 6A-6B. Nanogram amounts for all plasmids are shown.

| FIG. 6A in the cell mixture (HeLa:HEK293-Cerulean, 3:1) | Constitutive output | Constitutively repressed output | Circuit output |
|---|---|---|---|
| pUBI-linker-NOS | 160 | | |
| pCAG-EYFP | 100 | 100 | 100 |
| pCAGop-DsRed-T141-T142(3p)-T1 46a-FF4 | 100 | 100 | 100 |
| pCMV-rtTA-FF5 | | 80 | |
| pTRE-LacI-FF5-miR-FF4 | | 80 | |
| pCMV-rtTA-T1 7-T30a | | | 40 |
| pTRE-LacI-T1 7-T30a-miR-FF4 | | | 40 |
| pCMV-rtTA-T21 | | | 40 |
| pTRE-LacI-T2 1-miR-FF4 | | | 40 |

| FIG. 6B in the cell mixture (HeLaEYFP:HEK293-Cerulean, | Baseline | hBax-Tgts | Circuit |
|---|---|---|---|
| pUBI-linker-NOS | 200 | 160 | |
| pCAG-DsRed-FF5 | 150 | 150 | 150 |
| pCAGop-hBax-T141-T142(3p)-T1 46a-FF4 | | 50 | 50 |
| pCMV-rtTA-T1 7-T30a | | | 40 |
| pTRE-LacI-2A-Bcl2-T1 7-T30a-miR-FF4 | | | 40 |
| pCMV-rtTA-T21 | | | 40 |
| pTRE-LacI-2A-Bcl2-T21-miR-FF4 | | | 40 |

TABLE 58

Transfection configuration for the experiments shown in FIG. 10. Nanogram amounts for all plasmids are shown.

| | T17-30a (−) T21 (−) | | T17-30a (~) T21 (−) | | T17-30a (−) T21 (~) | | T17-30a (~) T21 (~) | |
|---|---|---|---|---|---|---|---|---|
| pCAG-AmCyan | 100 | 100 | 100 | 100 | 100 | 100 | 100 | 100 |
| pCAGop-DsRed-T1 41-T1 42(3p)-T1 46a-FF4 | 100 | 100 | 100 | 100 | 100 | 100 | 100 | 100 |
| pCMV-rtTA-FF5 | 80 | 80 | 40 | 40 | 40 | 40 | | |

TABLE 58-continued

Transfection configuration for the experiments shown in FIG. 10. Nanogram amounts for all plasmids are shown.

| | T17-30a (−) T21 (−) | T17-30a (~) T21 (−) | T17-30a (−) T21 (~) | T17-30a (~) T21 (~) |
|---|---|---|---|---|
| pTRE-LacI-FF5 | 80 | 40 | 40 | |
| pTRE-LacI-FF5-miR-FF4 | | 80 | 40 | 40 |
| pCMV-rtTA-T17-T30a | | 40 | 40 | 40 40 |
| pTRE-LacI-T17-T30a | | 40 | | 40 |
| pTRE-LacI-T17-T30a-miR-FF4 | | 40 | | 40 |
| pCMV-rtTA-T21 | | | 40 40 | 40 40 |
| pTRE-LacI-T21 | | | 40 | 40 |
| pTRE-LacI-T21-miR-FF4 | | | 40 | 40 |

TABLE 59

Transfection configuration for the experiments shown in FIG. 11. Nanogram amounts for all plasmids are shown.

| | ON State | OFF State | T17-30a | T21 | T141 | T17-30a~T21 | T17-30a~T141 | T21~T141 |
|---|---|---|---|---|---|---|---|---|
| pUBI-linker-NOS | 160 | 80 | 80 | 80 | 160 | | 80 | 80 |
| pCAG-AmCyan | 100 | 100 | 100 | 100 | 100 | 100 | 100 | 100 |
| pCAGop-DsRed-FF5-FF4 | 100 | 100 | 100 | 100 | | 100 | | |
| pCAGop-DsRed-T141-FF4 | | | | | 100 | | 100 | 100 |
| pCMV-rtTA-FF5 | | 40 | | | | | | |
| pTRE-LacI-FF5-miR-FF4 | | 40 | | | | | | |
| pCMV-rtTA-T17-T30a | | | 40 | | | 40 | 40 | |
| pTRE-LacI-T17-T30a-miR-FF4 | | | 40 | | | 40 | 40 | |
| pCMV-rtTA-T21 | | | | 40 | | 40 | | 40 |
| pTRE-LacI-T21-miR-FF4 | | | | 40 | | 40 | | 40 |

LIST OF ABBREVIATIONS

RNAi: RNA interference
3'-UTR: 3'-untranslated region
LacI: Lac repressor
rtTA: reverse tetracycline-controlled transactivator
TRE: tetracycline responsive element
hBax: human Bcl-associated X protein
CAG: hybrid promoter combing CMV-IE promoter, chicken f3-actin promoter, 5' flanking sequence and the first intron sequence with a modified splice acceptor sequence derived from the rabbit f3-globin gene
AmCyan: engineered *Anemonia majano* cyan fluorescent protein
DsRed: DsRed-Express, engineered *Discosoma* sp. red fluorescent protein with a reduced tendency to aggregate
EYFP: enhanced yellow fluorescent protein
CMV: cytomegalovirus immediate-early enhancer
CAGop: CAG promoter with two LacO sites in the intron
FACS: fluorescence activated cell sorting
siRNA: small interfering RNA
UBI: maize ubiquitin promoter
NOS: transcription terminator derived from nopalin synthase gene from *Agrobacterium tumefaciens*
DMEM: Dulbecco's modified Eagle's medium
FBS: fetal bovine serum
HeLa: a cervical cancer cell line derived from cells taken from Henrietta Lacks MCF7: a breast cancer cell line isolated in 1970 from a 69-year-old Caucasian woman
HEK293: human embryonic kidney 293 cell line

REFERENCES

1. D. Baker et al., *Scientific American* 294, 44 (June, 2006).
2. E. Shapiro, Y. Benenson, *Scientific American* 294, 44 (Can, 2006).
3. J. Zhang, R. E. Campbell, A. Y. Ting, R. Y. Tsien, *Nature Reviews Molecular Cell Biology* 3, 906 (December, 2002).
4. J. H. Mansfield et al., *Nature Genetics* 36, 1079 (October, 2004).
5. B. D. Brown et al., *Nature Biotechnology* 25, 1457 (2007).
6. C. X. Wu et al., *Molecular Therapy* 17, 2058 (December, 2009).
7. M. B. Elowitz, S. Leibler, *Nature* 403, 335 (January, 2000).
8. J. Stricker et al., *Nature* 456, 516 (November, 2008).
9. M. Tigges, T. T. Marquez-Lago, J. Stelling, M. Fussenegger, *Nature* 457, 309 (2009).
10. T. Damino, O. Mondragon-Palomino, L. Tsimring, J. Hasty, *Nature* 463, 326 (January, 2010).
11. T. S. Gardner, C. R. Cantor, J. J. Collins, *Nature* 403, 339 (January, 2000).
12. B. P. Kramer et al., *Nature Biotechnology* 22, 867 (July, 2004).
13. C. M. Ajo-Franklin et al., *Genes & Development* 21, 2271 (September, 2007).
14. A. E. Friedland et al., *Science* 324, 1199 (Can, 2009).
15. S. Basu, Y. Gerchman, C. H. Collins, F. H. Arnold, R. Weiss, *Nature* 434, 1130 (April, 2005).
16. S. Hooshangi, S. Thiberge, R. Weiss, *Proceedings of the National Academy of Sciences of the United States of America* 102, 3581 (2005).

17. S. Basu, R. Mehreja, S. Thiberge, M. T. Chen, R. Weiss, *Proceedings of the National Academy of Sciences of the United States of America* 101, 6355 (2004).
18. R. Weiss, G. E. Homsy, T. F. Knight, in *Evolution as Computation: DIMACS Workshop*, L. F. Landweber, E. Winfree, Eds. (Springer, 1999), pp. 275-295.
19. B. P. Kramer, C. Fischer, M. Fussenegger, *Biotechnology and Bioengineering* 87, 478 (August, 2004).
20. M. N. Win, C. D. Smolke, *Science* 322, 456 (October, 2008)
21. V. J. J. Martin, D. J. Pitera, S. T. Withers, J. D. Newman, J. D. Keasling, *Nature Biotechnology* 21, 796 (July, 2003).
22. H. Kobayashi et al., *Proceedings of the National Academy of Sciences of the United States of America* 101, 8414 (June, 2004).
23. J. C. Anderson, E. J. Clarke, A. P. Arkin, C. A. Voigt, *Journal of Molecular Biology* 355, 619 (2006).
24. Y. Benenson et al., *Nature* 414, 430 (November, 2001).
25. M. N. Stojanovic, D. Stefanovic, *Nature Biotechnology* 21, 1069 (September, 2003).
26. Y. Benenson, B. Gil, U. Ben-Dor, R. Adar, E. Shapiro, *Nature* 429, 423 (Can, 2004).
27. G. Seelig, D. Soloveichik, D. Y. Zhang, E. Winfree, *Science* 314, 1585 (December, 2006).
28. Z. Xie, S. J. Liu, L. Bleris, Y. Benenson, *Nucleic Acids Research*, (2010).
29. K. Rinaudo et al., *Nature Biotechnology* 25, 795 (July, 2007).
30. D. P. Bartel, *Cell* 136, 215 (2009).
31. X. W. Zhang, Y. L. Yap, D. Wei, F. Chen, A. Danchin, *European Journal of Human Genetics* 13, 1303 (December, 2005).
32. T. W. Hambley, *Cancer Research* 69, 1259 (2009).
33. T. R. Golub et al., *Science* 286, 531 (October, 1999).
34. D. T. Ross et al., *Nature Genetics* 24, 227 (March, 2000).
35. E. Kusumi et al., *Leukemia* 18, 1138 (June, 2004).
36. J. Lu et al., *Nature* 435, 834 (June, 2005).
37. N. Rosenfeld et al., *Nature Biotechnology* 26, 462 (April, 2008).
38. P. Landgraf et al., *Cell* 129, 1401 (2007).
39. H. Niwa, K. Yamamura, J. Miyazaki, *Gene* 108, 193 (1991).
40. S. Mangan, U. Alon, *Proceedings of the National Academy of Sciences of the United States of America* 100, 11980 (2003).
41. A. Re, D. Cora, D. Taverna, M. Caselle, *Molecular Biosystems* 5, 854 (2009).
42. T. L. Deans, C. R. Cantor, J. J. Collins, *Cell* 130, 363 (2007).
43. D. Greber, M. D. El-Baba, M. Fussenegger, *Nucleic Acids Research* 36, (2008).
44. S. L. Lowe et al., *Gene Therapy* 8, 1363 (September, 2001).
45. M. Peter, *Oncogene*, 1 (2010).
46. E. Hornstein, N. Shomron, *Nature Genetics* 38, S20 (2006).
47. K. A. O'Donnell, E. A. Wentzel, K. I. Zeller, C. V. Dang, J. T. Mendell, *Nature* 435, 839 (2005).
48. J. Tsang, J. Zhu, A. van Oudenaarden, *Mol Cell* 26, 753 (2007).
49. C. Melton, R. L. Judson, R. Blelloch, *Nature* 463, 621 (February, 2010).
50. S. Yekta, I. H. Shih, D. P. Bartel, *Science* 304, 594 (2004)
51. Landgraf, P. et al. *Cell* 129, 1401 (2007).
52. Miyagishi, M., Hayashi, M. & Taira, K. *Antisense & Nucleic Acid Drug Development* 13, 1 (2003).
53. Rinaudo, K. et al. *Nat Biotechnol* 25, 795 (2007).
54. Leisner, M., Bleris, L., Lohmueller, J., Xie, Z. & Benenson, Y. Submitted to Nat Nanotechnology (2010).
55. Niwa, H., Yamamura, K. & Miyazaki, J. *Gene* 108, 193 (1991).
56. Zhang, Z. et al. *Plant Physiol* 134, 1500 (2004).
57. Kunkel, T., Roberts, J. & Zakour, R. *Methods Enzymol* 154, 367 (1987)
58. Livet, J. et al. *Nature* 450, 56 (2007)
59. Nechushtan, A., Smith, C., Hsu, Y. & Youle, R. *EMBO J.* 18, 2330 (1999).
60. Szymczak, A. et al. *Nat Biotechnol* 22, 589 (2004).
61. Lois, C., Hong, E., Pease, S., Brown, E. & Baltimore, D. *Science* 295, 868 (2002).

We claim:

1. A high-input detector module for classifying a cell status based on detecting whether an input microRNA is expressed at a specific level or higher than a reference level, said high-input detector module comprising:
   (a) an inducible promoter sequence operably linked to:
      (i) a repressor sequence encoding a repressor product, and
      (ii) one or more target sequences for microRNA, said one or more target sequences for microRNA are the target sequences of the one or more input microRNAs the module is designed to detect;
   (b) a repressible promoter sequence operably linked to an output sequence encoding an output product, said repressor product being specific for the repressible promoter sequence; and
   (c) one or more regulatory units, comprising a constitutive or inducible promoter sequence operably linked to:
      (i) a sequence encoding a transcriptional activator product, said transcriptional activator product activates the inducible promoter sequence operably linked to the repressor sequence and the one or more target sequences for microRNA of the module, and
      (ii) one or more target sequences for microRNA, said one or more target sequences for microRNA are the target sequences of the one or more input microRNAs the module is designed to detect.

2. The high-input detector module of claim 1, wherein said transcriptional activator product activates the inducible promoter sequence operably linked to:
   (i) the sequence encoding the transcriptional activator product, and
   (ii) the one or more target sequences for microRNA of the one or more regulatory units.

3. A multiple-input biological classifier circuit for classifying a cell status based on detecting in parallel an expression pattern of a subset of at least two different input microRNAs, each of which is expressed at a specific level or higher than a reference level, the biological classifier circuit comprising at least two high-input detector modules according to claim 1.

4. The multiple-input biological classifier circuit of claim 3, wherein the output product is a reporter protein, a transcriptional activator, a transcriptional repressor, a pro-apoptotic protein, a lytic protein, an enzyme, a cytokine, or a cell-surface receptor.

5. The multiple-input biological classifier circuit of claim 3, wherein the repressor sequence of at least one of the high-input detector module further comprises a sequence encoding for a protein or agent that is a functional or physiological inhibitor of the output product of the multiple-input biological classifier circuit.

6. A pharmaceutical composition comprising the high-input detector module of claim 1 and a pharmaceutically acceptable compound.

7. A pharmaceutical composition comprising the multiple-input biological classifier circuit of claim 3 and a pharmaceutically acceptable compound.

8. A method for identifying a cell or population of cells in vitro, ex vivo, or in vivo based on an expression pattern of at least three different input microRNAs, the method comprising introducing the multiple-input biological classifier circuit of claim 3 into a cell or population of cells, wherein expression of an output product by the cell identifies the cell or population of cells.

9. A method for identifying a cell or population of cells in vitro, ex vivo, or in vivo based on an expression pattern of at least three different input microRNAs, the method comprising introducing the multiple-input biological classifier circuit of claim 3 into a cell or population of cells, wherein expression of an output product by the cell identifies the cell or population of cells.

10. A multiple-input biological classifier circuit for classifying a cell status based on detecting in parallel an expression pattern of a subset of at least two different input microRNAs, the biological classifier circuit comprising:
at least two types of input detector modules detecting expression of at least two different input microRNAs, at least one of the at least two different input microRNAs having a lower expression level than a reference expression level, and at least one of the at least two different input microRNAs having a higher expression level than the reference expression level, and
  (a) one of the at least two input detector modules is a low-input detector module for detecting the at least one input microRNA expressed at a lower level than the reference expression level, said low-input detector module comprises a repressible promoter sequence operably linked to:
    (i) an output sequence encoding an output product, and
    (ii) at least one target sequence for microRNA specific for the at least one input microRNA having a lower expression level than the reference expression level; and
  (b) one of the at least two input detector modules is a high-input detector module for detecting the at least one input microRNA expressed at a higher level than the reference expression level, said high-input detector module comprises a constitutive or inducible promoter sequence operably linked to:
    (i) a repressor sequence that encodes for a repressor product, said repressor product represses the repressible promoter of the low input detector module, and
    (ii) one or more target sequences for microRNA specific for the one or more input microRNAs having a higher expression level than the reference expression level;
wherein each of the at least one microRNA target sequences of each low-input detector module are different from each of the at least one microRNA target sequences of each high-input detector module; and wherein expression of the output product classifies the cell status.

11. The multiple-input biological classifier circuit of claim 10, wherein the constitutive or inducible promoter sequence of the at least one high-input detector module is an inducible promoter sequence.

12. The multiple-input biological classifier circuit of claim 11, wherein the at least one of the high-input detector modules further comprises one or more regulatory units, the one or more regulatory units comprising a constitutive or inducible promoter sequence operably linked to:
  (i) a sequence encoding a transcriptional activator product, said transcriptional activator product activates the inducible promoter sequence operably linked to the repressor sequence and the one or more target sequences for microRNA of the high-input module, and
  (ii) the one or more target sequences for microRNA.

13. The multiple-input biological classifier circuit of claim 12, wherein said transcriptional activator product activates the inducible promoter sequence operably linked to:
  (i) the sequence encoding a transcriptional activator product, and
  (ii) the one or more target sequences for microRNA of one or more regulatory units.

14. The multiple-input biological classifier circuit of claim 10, wherein the repressor sequence of at least the one high-input detector module further comprises a sequence encoding a microRNA, wherein said microRNA is different from each different microRNA inputs detected by the circuit, and wherein the output sequence of the at least one low-input detector module further comprises a microRNA target sequence for the microRNA.

15. The multiple-input biological classifier circuit of claim 10, wherein the output product is a reporter protein, a transcriptional activator, a transcriptional repressor, a pro-apoptotic protein, a lytic protein, an enzyme, a cytokine, or a cell-surface receptor.

16. The multiple-input biological classifier circuit of claim 10, wherein the repressor sequence of the at least one high-input detector module further comprises a sequence encoding for a protein or agent that is a functional or physiological inhibitor of the output product of the multiple-input biological classifier circuit.

17. A pharmaceutical composition comprising the high-input detector module of claim 10 and a pharmaceutically acceptable compound.

18. A multiple-input biological classifier circuit for classifying a cell status based on detecting in parallel an expression pattern of a subset of at least three different input microRNAs, the biological classifier circuit comprising:
at least two types of input detector modules detecting expression of at least three different input microRNAs, at least one of the at least three different input microRNAs having a lower expression level than a reference expression level, at least one of the at least three different input microRNAs having a higher expression level than the reference expression level, and a third or more of the at least three different input microRNAs having a different expression level than the reference expression level, and:
  (a) one of said at least two input detector modules is a low-input detector module for detecting each of the different input microRNAs expressed at a lower level than the reference expression level, said low-input detector module comprises a repressible promoter sequence operably linked to:

(i) an output sequence encoding an output product, and
(ii) one or more target sequences for microRNA specific for each of the different input microRNAs having a lower expression level than the reference expression level; and
(b) at least one of said at least two input detector modules is a high-input detector module for detecting one of the different input microRNAs expressed at a higher level than the reference expression level, wherein said high-input detector module comprises a promoter sequence operably linked to:
(i) a repressor sequence that encodes for a repressor product, said repressor product represses the repressible promoter of the low-input detector module, and
(ii) one or more target sequences for microRNA, said one or more microRNA target sequences are specific for the at least one of the different input microRNAs having a higher expression level than the reference expression level;
wherein each of the one or more microRNA target sequences of the low-input detector module is different from each microRNA target sequence of each high-input detector module; and
wherein expression of the output product classifies the cell status.

19. The multiple-input biological classifier circuit of claim 18, wherein the constitutive or inducible promoter sequence of the at least on high-input detector module is an inducible promoter sequence.

20. The multiple-input biological classifier circuit of claim 19, wherein the at least one of the high-input detector modules further comprises one or more regulatory units, the one or more regulatory units comprising a constitutive or inducible promoter sequence operably linked to:
(i) a sequence encoding a transcriptional activator product, said transcriptional activator product activates the inducible promoter sequence operably linked to the repressor sequence and the one or more target sequences for microRNA of the high-input module, and
(ii) the one or more target sequences for microRNA.

21. The multiple-input biological classifier circuit of claim 20, wherein said transcriptional activator product activates the inducible promoter sequence operably linked to:
(i) the sequence encoding a transcriptional activator product, and
(ii) the one or more target sequences for microRNA of one or more regulatory units.

* * * * *